(12) United States Patent
Zhou et al.

(10) Patent No.: US 11,920,129 B2
(45) Date of Patent: Mar. 5, 2024

(54) LIGATION AND/OR ASSEMBLY OF NUCLEIC ACID MOLECULES

(71) Applicant: National University of Singapore, Singapore (SG)

(72) Inventors: Kang Zhou, Singapore (SG); Xiaoqiang Ma, Singapore (SG); Hong Liang, Singapore (SG)

(73) Assignee: National University of Singapore, Singapore (SG)

( * ) Notice: Subject to any disclaimer, the term of this patent is extended or adjusted under 35 U.S.C. 154(b) by 475 days.

(21) Appl. No.: 16/758,933

(22) PCT Filed: Oct. 24, 2018

(86) PCT No.: PCT/SG2018/050528
§ 371 (c)(1),
(2) Date: Apr. 24, 2020

(87) PCT Pub. No.: WO2019/083449
PCT Pub. Date: May 2, 2019

(65) Prior Publication Data
US 2020/0308574 A1    Oct. 1, 2020

(30) Foreign Application Priority Data
Oct. 25, 2017    (SG) .............. 10201708764U

(51) Int. Cl.
*C12N 15/10*    (2006.01)
*C12N 15/11*    (2006.01)

(52) U.S. Cl.
CPC .......... *C12N 15/1065* (2013.01); *C12N 15/11* (2013.01); *C12N 2310/531* (2013.01)

(58) Field of Classification Search
CPC .................................. C12N 15/11; C12N 15/10
See application file for complete search history.

(56) References Cited

U.S. PATENT DOCUMENTS

| | | | |
|---|---|---|---|
| 2002/0192769 A1 | 12/2002 | Park et al. | |
| 2008/0166773 A1* | 7/2008 | Mead .................. | C12N 15/70 435/320.1 |
| 2011/0319290 A1* | 12/2011 | Raymond ............ | C12Q 1/6869 506/7 |
| 2012/0259607 A1 | 10/2012 | Hillson | |
| 2016/0083736 A1 | 3/2016 | Li et al. | |
| 2016/0195598 A1 | 7/2016 | Reitsma | |
| 2017/0226498 A1* | 8/2017 | Zheng ............ | C12Y 605/01001 |

FOREIGN PATENT DOCUMENTS

| | | | |
|---|---|---|---|
| CN | 104212791 A | | 12/2014 |
| CN | 104212791 B | * | 3/2019 |
| DE | 10209071 | | 9/2003 |
| WO | WO-00/18967 | | 4/2000 |
| WO | WO-2014/077782 | | 5/2014 |
| WO | WO-2016/195598 | | 12/2016 |
| WO | WO-2016/195963 | | 12/2016 |
| WO | WO-2017/112731 | | 6/2017 |

OTHER PUBLICATIONS

Wei, Hua, et al. "Production of dumbbell probe through hairpin cleavage-ligation and increasing RCA sensitivity and specificity by circle to circle amplification." Scientific reports 6.1 (2016): 1-9. (Year: 2016).*
Jiang, Xiaoou, and Volker Patzel. "Advanced Design of Minimalistic Dumbbell-shaped Gene Expression Vectors." Bio-protocol 7.15 (2017): e2425-e2425. (Year: 2017).*
Phosphorothioate-based BioBrick cloning (Potsdam) Standard, Document Version 1.0, Oct. 26, 2012 (Year: 2012).*
Li, Ji Gang, et al. "Improvement of TA cloning method to facilitate direct directional cloning of PCR products." Applied Mechanics and Materials. vol. 565. Trans Tech Publications Ltd, 2014. (Year: 2014).*
Baumann and Müller, "Phosphorothioate-based BioBrick cloning (Potsdam) Standard," The BioBricks Foundation, 6 pages (Oct. 26, 2012) Retrieved online from: <http://2012.igem.org/wiki/images/9/98/UP12_BBF_RFC_91_phosphorothioate_based_cloning.pdf>.
Chen et al., "The MASTER (methylation-assisted tailorable ends rational) ligation method for seamless DNA assembly," Nucleic Acids Res., 41(8):e93, 9 pages (2013).
International Search Report and Written Opinion for International PCT Application No. PCT/SG2018/050528, dated Jan. 10, 2019 (12 pages).
Ajikumar et al., "Isoprenoid Pathway Optimization for Taxol Precursor Overproduction in *Escherichia coli*," Science, 330, pp. 70-74 (2010).
Anilionyte et al., "Short, auto-inducible promoters for well-controlled protein expression in *Escherichia coli*," Applied Microbiology and Biotechnology, 102, pp. 7007-7015 (2018).
Banks et al., "Proteins interacting with cloning scars: a source of false positive protein-protein interactions," Scientific Reports, 5(8530), 7 pages (2015).

(Continued)

*Primary Examiner* — Weihua Fan
(74) *Attorney, Agent, or Firm* — Mintz, Levin, Cohn, Ferris, Glovsky and Popeo, P.C

(57) ABSTRACT

The present invention relates to ligation and/or assembly of nucleic acid molecules. Particularly, a double-stranded target nucleic acid having overhangs of at least one nucleotide is ligated with another nucleic acid molecule capable of forming a stem-loop structure with an overhang of at least one nucleotide. The invention is suitable for tagging nucleic acid molecules. In specific embodiments, the overhangs can be produced by chemical cleavage of phosphorothioate-modified nucleic acid molecules. The invention further relates to the amplification of the ligated product, and using the resultant amplicon for assembly of multiple nucleic acid fragments.

17 Claims, 25 Drawing Sheets
Specification includes a Sequence Listing.

(56) References Cited

OTHER PUBLICATIONS

Bassalo et al., "Rapid and Efficient One-Step Metabolic Pathway Integration in *E. coli*," ACS Synth. Biol., 5, pp. 561-568 (2016).
Bitinaite et al., "USER™ friendly DNA engineering and cloning method by uracil excision," Nucleic Acids Research, 35(6), pp. 1992-2002 (2007).
Casini et al., "Bricks and blueprints: methods and standards for DNA assembly," Nat. Rev. Mol. Cell Biol., 16(9), pp. 568-576 (2015).
Casini et al., "One-pot DNA construction for synthetic biology: the Modular Overlap-Directed Assembly with Linkers (MODAL) strategy," Nucleic Acids Research, 42(1), e7, 13 pages (2014).
Chen and Zhang, "Why Are Genes Encoded on the Lagging Strand of the Bacterial Genome?" Genome Biol. Evol., 5(12), pp. 2436-2439 (2013).
Chen et al., "The MASTER (methylation-assisted tailorable ends rational) ligation method for seamless DNA assembly," Nucleic Acids Research, 41(8), e93, 9 pages (2013).
Coussement et al., "One step DNA assembly for combinatorial metabolic engineering," Metabolic Engineering, 23, pp. 70-77 (2014).
Crook et al., "Re-engineering multicloning sites for function and convenience," Nucleic Acids Research, 39(14), e92, 10 pages (2011).
Danino et al., "Programmable probiotics for detection of cancer in urine," Sci. Transl. Med., 7(289), 289ra84, 12 pages (2015).
Eisenstein, "Living Factories of the future," Nature, 531, pp. 401-403 (2016).
Engler et al., "A One Pot, One Step, Precision Cloning Method with High Throughput Capability," PLOS One, 3(11), e3647, 7 pages (2008).
Engler et al., "Golden Gate Shuffling: A One-Pot DNA Shuffling Method Based on Type IIs Restriction Enzymes," PLOS One, 4(5), e5553, 9 pages (2009).
Fernandez-Rodriguez et al., "Engineering RGB color vision into *Escherichia coli*," Nature Chemical Biology, 13, pp. 706-708, 5 pages (2017).
Fowler and Koffas, "Biosynthesis and biotechnological production of flavanones: current state and perspectives," Appl. Microbiol. Biotechnol., 83, pp. 799-808 (2009).
Gao et al., "Identification of a heterologous cellulase and its N-terminus that can guide recombinant proteins out of *Escherichia coli*," Microbial Cell Factories, 14(49), 8 pages (2015).
Gibson et al., "Enzymatic assembly of DNA molecules up to several hundred kilobases," Nature Methods, 6(5), pp. 343-345, 5 pages (2009).
Green and Sambrook, Molecular Cloning: A Laboratory Manual, Cold Spring Harbor Laboratory Press, New York, vol. 1, Fourth Edition, List of Tables, Preface, and Acknowledgments, 34 pages (2012).
Hayden, "Synthetic biology called to order: Meeting launches effort to develop standards for fast-moving field," Nature, 142(520), pp. 141-142 (2015).
Hillson et al., "j5 DNA Assembly Design Automation Software," ACS Synth. Biol., 1, pp. 14-21 (2012).
Jendresen et al., "Highly Active and Specific Tyrosine Ammonia-Lyases from Diverse Origins Enable Enhanced Production of Aromatic Compounds in Bacteria and *Saccharomyces cerevisiae*," Applied and Environmental Microbiology, 81(13), pp. 4458-4476 (2015).
Jiang et al., "Multigene Editing in the *Escherichia coli* Genome via the CRISPR-Cas9 System," Applied and Environmental Microbiology, 81(7), pp. 2506-2514 (2015).
Jinek et al., "A Programmable Dual-RNA-Guided DNA Endonuclease in Adaptive Bacterial Immunity," Science, 337, pp. 816-821 (2012).
Kang et al., "Artificial biosynthesis of phenylpropanoic acids in a tyrosine overproducing *Escherichia coli* strain," Microbial Cell Factories, 11(153), 9 pages (2012).
Kim et al., "Metabolic engineering of *Escherichia coli* for the enhanced production of L-tyrosine," Biotechnology and Bioengineering, 115, pp. 2554-2564 (2018).
Kosuri and Church "Large-scale de novo DNA synthesis: technologies and applications," Nature Methods, 11(5), pp. 499-507 (2014).
Li and Elledge, "Harnessing homologous recombination in vitro to generate recombinant DNA via SLIC," Nature Methods, 4(3), pp. 251-256 (2007).
Nakamaye et al., "Direct sequencing of polymerase chain reaction amplified DNA fragments through the incorporation of deoxynucleoside α-thiotriphosphates," Nucleic Acids Research, 16(21), pp. 9947-9959 (1988).
Ngo et al., "Catalytic Hydrogenation of Cytotoxic Aldehydes Using Nicotinamide Adenine Dinucleotide (NADH) in Cell Growth Media," ACS Catal., 6, pp. 2637-2641 (2016).
"Potsdam Standard—BBF_RFC_91: Phosphorothioate-based BioBrick cloning Standard," 3 pages (2012); retrieved online from: <http://2012.igem.org/Team:Potsdam_Bioware/Project/Potsdam_Standard>.
Salis et al., "Automated design of synthetic ribosome binding sites to control protein expression," Nature Biotechnology, 27(10), pp. 946-950, 7 pages (2009).
Santos et al., "Rational, combinatorial, and genomic approaches for engineering L-tyrosine production in *Escherichia coli*," PNAS, 109(34), pp. 13538-13543 (2012).
Shao et al., "DNA assembler, an in vivo genetic method for rapid construction of biochemical pathways," Nucleic Acids Research, 37(2), e16, 10 pages (2009).
Shetty et al., "Engineering BioBrick vectors from BioBrick parts," Journal of Biological Engineering, 2(5), 12 pages (2008).
Smanski et al., "Functional optimization of gene clusters by combinatorial design and assembly," Nature Biotechnology, 32(12), pp. 1241-1248, 12 pages (2014).
Smolke, "Building outside of the box: IGEM and the BioBricks Foundation," Nature Biotechnology, 27(12), pp. 1099-1102 (2009).
Storch et al., "BASIC: A New Biopart Assembly Standard for Idempotent Cloning Provides Accurate, Single-Tier DNA Assembly for Synthetic Biology," ACS Synth. Biol., 4, pp. 781-787 (2015).
Tsuge et al., "Method of preparing an equimolar DNA mixture for one-step DNA assembly of over 50 fragments," Scientific Reports, 5(10655), 11 pages (2015).
Tsuge et al., "One step assembly of multiple DNA fragments with a designed order and orientation in *Bacillus subtilis* plasmid," Nucleic Acids Research, 31(21), e133, 8 pages (2003).
Yim et al., "Metabolic engineering of *Escherichia coli* for direct production of 1,4-butanediol," Nature Chemical Biology, 7, pp. 445-452 (2011).
Zhou et al., "Engineering Microbes to Synthesize Plant Isoprenoids," Methods in Enzymology, 575, pp. 225-245 (2016).
Zhou et al., "MiYA, an efficient machine-learning workflow in conjunction with the YeastFab assembly strategy for combinatorial optimization of heterologous metabolic pathways in *Saccharomyces cerevisiae*," Metabolic Engineering, 47, pp. 294-302 (2018).
Zou et al., "Combinatorial Engineering of 1-Deoxy-D-Xylulose 5-Phosphate Pathway Using Cross-Lapping In Vitro Assembly (CLIVA) Method," PLOS One, 8(11), e79557, 12 pages (2013).

* cited by examiner

SEQUENCE LISTING

```
<160> NUMBER OF SEQ ID NOS: 470

<210> SEQ ID NO 1
<211> LENGTH: 41
<212> TYPE: DNA
<213> ORGANISM: Artificial Sequence
<220> FEATURE:
<223> OTHER INFORMATION: G-gRNA-nupG forward oligo
<220> FEATURE:
<221> NAME/KEY: misc_binding
<222> LOCATION: (1)..(2)
<223> OTHER INFORMATION: phosphorothioate bond

<400> SEQUENCE: 1
gtacgagtta atcaatatca cagttttaga gctagaaata g                41

<210> SEQ ID NO 2
<211> LENGTH: 21
<212> TYPE: DNA
<213> ORGANISM: Artificial Sequence
<220> FEATURE:
<223> OTHER INFORMATION: gRNA-T reverse oligo
<220> FEATURE:
<221> NAME/KEY: misc_binding
<222> LOCATION: (1)..(2)
<223> OTHER INFORMATION: phosphorothioate bond
```

```
<400> SEQUENCE: 2
atctagagaa ttcaaaaaaa g                                                 21

<210> SEQ ID NO 3
<211> LENGTH: 41
<212> TYPE: DNA
<213> ORGANISM: Artificial Sequence
<220> FEATURE:
<223> OTHER INFORMATION: G-gRNA-aslA forward oligo
<220> FEATURE:
<221> NAME/KEY: misc_binding
<222> LOCATION: (1)..(2)
<223> OTHER INFORMATION: phosphorothioate bond

<400> SEQUENCE: 3
gtgcagaact tgagaaaaaa acgttttaga gctagaaata g                           41

<210> SEQ ID NO 4
<211> LENGTH: 41
<212> TYPE: DNA
<213> ORGANISM: Artificial Sequence
<220> FEATURE:
<223> OTHER INFORMATION: G-gRNA-melB forward oligo
<220> FEATURE:
<221> NAME/KEY: misc_binding
<222> LOCATION: (1)..(2)
<223> OTHER INFORMATION: phosphorothioate bond

<400> SEQUENCE: 4
gtctaccatt tgttaattat gtgttttaga gctagaaata g                           41

<210> SEQ ID NO 5
<211> LENGTH: 41
<212> TYPE: DNA
<213> ORGANISM: Artificial Sequence
<220> FEATURE:
<223> OTHER INFORMATION: G-gRNA-rcsB forward oligo
<220> FEATURE:
<221> NAME/KEY: misc_binding
<222> LOCATION: (1)..(2)
<223> OTHER INFORMATION: phosphorothioate bond

<400> SEQUENCE: 5
gtaatcactt gagcaaattg aggttttaga gctagaaata g                           41

<210> SEQ ID NO 6
<211> LENGTH: 41
<212> TYPE: DNA
<213> ORGANISM: Artificial Sequence
<220> FEATURE:
<223> OTHER INFORMATION: G-gRNA-tyrR forward oligo
<220> FEATURE:
<221> NAME/KEY: misc_binding
<222> LOCATION: (1)..(2)
<223> OTHER INFORMATION: phosphorothioate bond

<400> SEQUENCE: 6
gtttaatacc gagcgttcaa aagttttaga gctagaaata g                           41

<210> SEQ ID NO 7
<211> LENGTH: 41
<212> TYPE: DNA
<213> ORGANISM: Artificial Sequence
<220> FEATURE:
<223> OTHER INFORMATION: G-gRNA-pheA forward oligo
<220> FEATURE:
<221> NAME/KEY: misc_binding
<222> LOCATION: (1)..(2)
<223> OTHER INFORMATION: phosphorothioate bond
```

<400> SEQUENCE: 7
gttttgagca attcattgaa aggttttaga gctagaaata g        41

<210> SEQ ID NO 8
<211> LENGTH: 41
<212> TYPE: DNA
<213> ORGANISM: Artificial Sequence
<220> FEATURE:
<223> OTHER INFORMATION: G-gRNA-ptsI forward oligo
<220> FEATURE:
<221> NAME/KEY: misc_binding
<222> LOCATION: (1)..(2)
<223> OTHER INFORMATION: phosphorothioate bond

<400> SEQUENCE: 8
gtgaagttga tttctttagt atgttttaga gctagaaata g        41

<210> SEQ ID NO 9
<211> LENGTH: 19
<212> TYPE: DNA
<213> ORGANISM: Artificial Sequence
<220> FEATURE:
<223> OTHER INFORMATION: G-nupG-HF0.5 forward oligo
<220> FEATURE:
<221> NAME/KEY: misc_binding
<222> LOCATION: (1)..(2)
<223> OTHER INFORMATION: phosphorothioate bond

<400> SEQUENCE: 9
gttgatcctg ccagcaata        19

<210> SEQ ID NO 10
<211> LENGTH: 19
<212> TYPE: DNA
<213> ORGANISM: Artificial Sequence
<220> FEATURE:
<223> OTHER INFORMATION: nupG-HF0.5-T reverse oligo
<220> FEATURE:
<221> NAME/KEY: misc_binding
<222> LOCATION: (1)..(2)
<223> OTHER INFORMATION: phosphorothioate bond

<400> SEQUENCE: 10
acatcgtgat gcggatgag        19

<210> SEQ ID NO 11
<211> LENGTH: 21
<212> TYPE: DNA
<213> ORGANISM: Artificial Sequence
<220> FEATURE:
<223> OTHER INFORMATION: G-nupG-HF1.0 forward oligo
<220> FEATURE:
<221> NAME/KEY: misc_binding
<222> LOCATION: (1)..(2)
<223> OTHER INFORMATION: phosphorothioate bond

<400> SEQUENCE: 11
gaccatcgcc gggacagaac c        21

<210> SEQ ID NO 12
<211> LENGTH: 21
<212> TYPE: DNA
<213> ORGANISM: Artificial Sequence
<220> FEATURE:
<223> OTHER INFORMATION: G-nupG-HF1.5 forward oligo
<220> FEATURE:
<221> NAME/KEY: misc_binding
<222> LOCATION: (1)..(2)

```
<223> OTHER INFORMATION: phosphorothioate bond

<400> SEQUENCE: 12
gtgcaacgtg aagcagaagg t                                              21

<210> SEQ ID NO 13
<211> LENGTH: 19
<212> TYPE: DNA
<213> ORGANISM: Artificial Sequence
<220> FEATURE:
<223> OTHER INFORMATION: G-aslA-HF0.5 forward oligo
<220> FEATURE:
<221> NAME/KEY: misc_binding
<222> LOCATION: (1)..(2)
<223> OTHER INFORMATION: phosphorothioate bond

<400> SEQUENCE: 13
gcaccgtaaa cggctctgc                                                 19

<210> SEQ ID NO 14
<211> LENGTH: 20
<212> TYPE: DNA
<213> ORGANISM: Artificial Sequence
<220> FEATURE:
<223> OTHER INFORMATION: aslA-HF0.5-T reverse oligo
<220> FEATURE:
<221> NAME/KEY: misc_binding
<222> LOCATION: (1)..(2)
<223> OTHER INFORMATION: phosphorothioate bond

<400> SEQUENCE: 14
agtttcatgt catcaaaatg                                                20

<210> SEQ ID NO 15
<211> LENGTH: 19
<212> TYPE: DNA
<213> ORGANISM: Artificial Sequence
<220> FEATURE:
<223> OTHER INFORMATION: G-aslA-HF1.0 forward oligo
<220> FEATURE:
<221> NAME/KEY: misc_binding
<222> LOCATION: (1)..(2)
<223> OTHER INFORMATION: phosphorothioate bond

<400> SEQUENCE: 15
gccagtacga cgatcgcct                                                 19

<210> SEQ ID NO 16
<211> LENGTH: 21
<212> TYPE: DNA
<213> ORGANISM: Artificial Sequence
<220> FEATURE:
<223> OTHER INFORMATION: G-melB-HF1.0 forward oligo
<220> FEATURE:
<221> NAME/KEY: misc_binding
<222> LOCATION: (1)..(2)
<223> OTHER INFORMATION: phosphorothioate bond

<400> SEQUENCE: 16
gcccaatggc gatgaatacc t                                              21

<210> SEQ ID NO 17
<211> LENGTH: 21
<212> TYPE: DNA
<213> ORGANISM: Artificial Sequence
<220> FEATURE:
<223> OTHER INFORMATION: melB-HF1.0-T reverse oligo
<220> FEATURE:
<221> NAME/KEY: misc_binding
```

-continued

```
<222> LOCATION: (1)..(2)
<223> OTHER INFORMATION: phosphorothioate bond

<400> SEQUENCE: 17
agctgttacc aacgcccgcc t                                              21

<210> SEQ ID NO 18
<211> LENGTH: 21
<212> TYPE: DNA
<213> ORGANISM: Artificial Sequence
<220> FEATURE:
<223> OTHER INFORMATION: G-rcsB-HF1.0 forward oligo
<220> FEATURE:
<221> NAME/KEY: misc_binding
<222> LOCATION: (1)..(2)
<223> OTHER INFORMATION: phosphorothioate bond

<400> SEQUENCE: 18
ggttagcgaa catgcttgcg g                                              21

<210> SEQ ID NO 19
<211> LENGTH: 21
<212> TYPE: DNA
<213> ORGANISM: Artificial Sequence
<220> FEATURE:
<223> OTHER INFORMATION: rcsB-HF1.0-T reverse oligo
<220> FEATURE:
<221> NAME/KEY: misc_binding
<222> LOCATION: (1)..(2)
<223> OTHER INFORMATION: phosphorothioate bond

<400> SEQUENCE: 19
attgctacag caagctcttg a                                              21

<210> SEQ ID NO 20
<211> LENGTH: 19
<212> TYPE: DNA
<213> ORGANISM: Artificial Sequence
<220> FEATURE:
<223> OTHER INFORMATION: G-tyrR-HF0.5 forward oligo
<220> FEATURE:
<221> NAME/KEY: misc_binding
<222> LOCATION: (1)..(2)
<223> OTHER INFORMATION: phosphorothioate bond

<400> SEQUENCE: 20
gcagcccgct ggcgttggt                                                 19

<210> SEQ ID NO 21
<211> LENGTH: 21
<212> TYPE: DNA
<213> ORGANISM: Artificial Sequence
<220> FEATURE:
<223> OTHER INFORMATION: tyrR-HF0.5-T reverse oligo
<220> FEATURE:
<221> NAME/KEY: misc_binding
<222> LOCATION: (1)..(2)
<223> OTHER INFORMATION: phosphorothioate bond

<400> SEQUENCE: 21
agtcagcacc cgatattgca t                                              21

<210> SEQ ID NO 22
<211> LENGTH: 20
<212> TYPE: DNA
<213> ORGANISM: Artificial Sequence
<220> FEATURE:
<223> OTHER INFORMATION: G-pheA-HF0.5 forward oligo
<220> FEATURE:
```

```
<221> NAME/KEY: misc_binding
<222> LOCATION: (1)..(2)
<223> OTHER INFORMATION: phosphorothioate bond

<400> SEQUENCE: 22
gcatgtcgca gaccgtctcg                                                     20

<210> SEQ ID NO 23
<211> LENGTH: 20
<212> TYPE: DNA
<213> ORGANISM: Artificial Sequence
<220> FEATURE:
<223> OTHER INFORMATION: pheA-HF0.5-T reverse oligo
<220> FEATURE:
<221> NAME/KEY: misc_binding
<222> LOCATION: (1)..(2)
<223> OTHER INFORMATION: phosphorothioate bond

<400> SEQUENCE: 23
acgaaacgcc tcccattcag                                                     20

<210> SEQ ID NO 24
<211> LENGTH: 20
<212> TYPE: DNA
<213> ORGANISM: Artificial Sequence
<220> FEATURE:
<223> OTHER INFORMATION: G-ptsI-HF0.7 forward oligo
<220> FEATURE:
<221> NAME/KEY: misc_binding
<222> LOCATION: (1)..(2)
<223> OTHER INFORMATION: phosphorothioate bond

<400> SEQUENCE: 24
ggcccgcata aaattcaggg                                                     20

<210> SEQ ID NO 25
<211> LENGTH: 21
<212> TYPE: DNA
<213> ORGANISM: Artificial Sequence
<220> FEATURE:
<223> OTHER INFORMATION: ptsI-HF0.7-T reverse oligo
<220> FEATURE:
<221> NAME/KEY: misc_binding
<222> LOCATION: (1)..(2)
<223> OTHER INFORMATION: phosphorothioate bond

<400> SEQUENCE: 25
aggaactaaa gtctagcctg g                                                   21

<210> SEQ ID NO 26
<211> LENGTH: 19
<212> TYPE: DNA
<213> ORGANISM: Artificial Sequence
<220> FEATURE:
<223> OTHER INFORMATION: G-nupG-HT0.5 forward oligo
<220> FEATURE:
<221> NAME/KEY: misc_binding
<222> LOCATION: (1)..(2)
<223> OTHER INFORMATION: phosphorothioate bond

<400> SEQUENCE: 26
gttacgcaaa gaaaaacgg                                                      19

<210> SEQ ID NO 27
<211> LENGTH: 19
<212> TYPE: DNA
<213> ORGANISM: Artificial Sequence
<220> FEATURE:
<223> OTHER INFORMATION: nupG-HT0.5-T reverse oligo
```

```
<220> FEATURE:
<221> NAME/KEY: misc_binding
<222> LOCATION: (1)..(2)
<223> OTHER INFORMATION: phosphorothioate bond

<400> SEQUENCE: 27
agccgctggt tgaggtgtt                                                19

<210> SEQ ID NO 28
<211> LENGTH: 21
<212> TYPE: DNA
<213> ORGANISM: Artificial Sequence
<220> FEATURE:
<223> OTHER INFORMATION: nupG-HT1.0-T reverse oligo
<220> FEATURE:
<221> NAME/KEY: misc_binding
<222> LOCATION: (1)..(2)
<223> OTHER INFORMATION: phosphorothioate bond

<400> SEQUENCE: 28
aacgccttta tgctccatgc t                                             21

<210> SEQ ID NO 29
<211> LENGTH: 21
<212> TYPE: DNA
<213> ORGANISM: Artificial Sequence
<220> FEATURE:
<223> OTHER INFORMATION: nupG-HT1.5-T reverse oligo
<220> FEATURE:
<221> NAME/KEY: misc_binding
<222> LOCATION: (1)..(2)
<223> OTHER INFORMATION: phosphorothioate bond

<400> SEQUENCE: 29
agcgacgccg gtctatctgg a                                             21

<210> SEQ ID NO 30
<211> LENGTH: 19
<212> TYPE: DNA
<213> ORGANISM: Artificial Sequence
<220> FEATURE:
<223> OTHER INFORMATION: G-aslA-HT0.5 forward oligo
<220> FEATURE:
<221> NAME/KEY: misc_binding
<222> LOCATION: (1)..(2)
<223> OTHER INFORMATION: phosphorothioate bond

<400> SEQUENCE: 30
ggccggcgct atcgctgag                                                19

<210> SEQ ID NO 31
<211> LENGTH: 19
<212> TYPE: DNA
<213> ORGANISM: Artificial Sequence
<220> FEATURE:
<223> OTHER INFORMATION: aslA-HT0.5-T reverse oligo
<220> FEATURE:
<221> NAME/KEY: misc_binding
<222> LOCATION: (1)..(2)
<223> OTHER INFORMATION: phosphorothioate bond

<400> SEQUENCE: 31
acactatgtt tatccgcaa                                                19

<210> SEQ ID NO 32
<211> LENGTH: 19
<212> TYPE: DNA
<213> ORGANISM: Artificial Sequence
<220> FEATURE:
```

<223> OTHER INFORMATION: aslA-HT1.0-T reverse oligo
<220> FEATURE:
<221> NAME/KEY: misc_binding
<222> LOCATION: (1)..(2)
<223> OTHER INFORMATION: phosphorothioate bond

<400> SEQUENCE: 32
agcccgcctg agatccaca                                        19

<210> SEQ ID NO 33
<211> LENGTH: 21
<212> TYPE: DNA
<213> ORGANISM: Artificial Sequence
<220> FEATURE:
<223> OTHER INFORMATION: G-melB-HT1.0 forward oligo
<220> FEATURE:
<221> NAME/KEY: misc_binding
<222> LOCATION: (1)..(2)
<223> OTHER INFORMATION: phosphorothioate bond

<400> SEQUENCE: 33
ggtgcagtga gtgatgtgaa a                                     21

<210> SEQ ID NO 34
<211> LENGTH: 21
<212> TYPE: DNA
<213> ORGANISM: Artificial Sequence
<220> FEATURE:
<223> OTHER INFORMATION: melB-HT1.0-T reverse oligo
<220> FEATURE:
<221> NAME/KEY: misc_binding
<222> LOCATION: (1)..(2)
<223> OTHER INFORMATION: phosphorothioate bond

<400> SEQUENCE: 34
agggtatgga agctatctgg a                                     21

<210> SEQ ID NO 35
<211> LENGTH: 21
<212> TYPE: DNA
<213> ORGANISM: Artificial Sequence
<220> FEATURE:
<223> OTHER INFORMATION: G-rcsB-HT1.0 forward oligo
<220> FEATURE:
<221> NAME/KEY: misc_binding
<222> LOCATION: (1)..(2)
<223> OTHER INFORMATION: phosphorothioate bond

<400> SEQUENCE: 35
gtcacctgta ggccagataa g                                     21

<210> SEQ ID NO 36
<211> LENGTH: 21
<212> TYPE: DNA
<213> ORGANISM: Artificial Sequence
<220> FEATURE:
<223> OTHER INFORMATION: rcsB-HT1.0-T reverse oligo
<220> FEATURE:
<221> NAME/KEY: misc_binding
<222> LOCATION: (1)..(2)
<223> OTHER INFORMATION: phosphorothioate bond

<400> SEQUENCE: 36
aattcagaac cgggaatggg c                                     21

<210> SEQ ID NO 37
<211> LENGTH: 19
<212> TYPE: DNA
<213> ORGANISM: Artificial Sequence

```
<220> FEATURE:
<223> OTHER INFORMATION: G-tyrR-HT0.5 forward oligo
<220> FEATURE:
<221> NAME/KEY: misc_binding
<222> LOCATION: (1)..(2)
<223> OTHER INFORMATION: phosphorothioate bond

<400> SEQUENCE: 37
ggcgcgaata tgcctgatg                                           19

<210> SEQ ID NO 38
<211> LENGTH: 19
<212> TYPE: DNA
<213> ORGANISM: Artificial Sequence
<220> FEATURE:
<223> OTHER INFORMATION: tyrR-HT0.5-T reverse oligo
<220> FEATURE:
<221> NAME/KEY: misc_binding
<222> LOCATION: (1)..(2)
<223> OTHER INFORMATION: phosphorothioate bond

<400> SEQUENCE: 38
acatcccgca ggcgggtag                                           19

<210> SEQ ID NO 39
<211> LENGTH: 21
<212> TYPE: DNA
<213> ORGANISM: Artificial Sequence
<220> FEATURE:
<223> OTHER INFORMATION: G-pheA-HT0.5 forward oligo
<220> FEATURE:
<221> NAME/KEY: misc_binding
<222> LOCATION: (1)..(2)
<223> OTHER INFORMATION: phosphorothioate bond

<400> SEQUENCE: 39
gttactggcg attgtcattc g                                        21

<210> SEQ ID NO 40
<211> LENGTH: 20
<212> TYPE: DNA
<213> ORGANISM: Artificial Sequence
<220> FEATURE:
<223> OTHER INFORMATION: pheA-HT0.5-T reverse oligo
<220> FEATURE:
<221> NAME/KEY: misc_binding
<222> LOCATION: (1)..(2)
<223> OTHER INFORMATION: phosphorothioate bond

<400> SEQUENCE: 40
aaaatgggcc attacaggcc                                          20

<210> SEQ ID NO 41
<211> LENGTH: 20
<212> TYPE: DNA
<213> ORGANISM: Artificial Sequence
<220> FEATURE:
<223> OTHER INFORMATION: G-ptsI-HT0.7 forward oligo
<220> FEATURE:
<221> NAME/KEY: misc_binding
<222> LOCATION: (1)..(2)
<223> OTHER INFORMATION: phosphorothioate bond

<400> SEQUENCE: 41
gagcgcatca cttccagtac                                          20

<210> SEQ ID NO 42
<211> LENGTH: 21
<212> TYPE: DNA
```

```
<213> ORGANISM: Artificial Sequence
<220> FEATURE:
<223> OTHER INFORMATION: ptsI-HT0.7-T reverse oligo
<220> FEATURE:
<221> NAME/KEY: misc_binding
<222> LOCATION: (1)..(2)
<223> OTHER INFORMATION: phosphorothioate bond

<400> SEQUENCE: 42
ataacgataa gagtagggca c                                              21

<210> SEQ ID NO 43
<211> LENGTH: 18
<212> TYPE: DNA
<213> ORGANISM: Artificial Sequence
<220> FEATURE:
<223> OTHER INFORMATION: G-spectR forward oligo
<220> FEATURE:
<221> NAME/KEY: misc_binding
<222> LOCATION: (1)..(2)
<223> OTHER INFORMATION: phosphorothioate bond

<400> SEQUENCE: 43
gtcgacctgc agaagctt                                                  18

<210> SEQ ID NO 44
<211> LENGTH: 18
<212> TYPE: DNA
<213> ORGANISM: Artificial Sequence
<220> FEATURE:
<223> OTHER INFORMATION: spectR-T reverse oligo
<220> FEATURE:
<221> NAME/KEY: misc_binding
<222> LOCATION: (1)..(2)
<223> OTHER INFORMATION: phosphorothioate bond

<400> SEQUENCE: 44
acgttaaggg attttggt                                                  18

<210> SEQ ID NO 45
<211> LENGTH: 18
<212> TYPE: DNA
<213> ORGANISM: Artificial Sequence
<220> FEATURE:
<223> OTHER INFORMATION: G-ampR forward oligo
<220> FEATURE:
<221> NAME/KEY: misc_binding
<222> LOCATION: (1)..(2)
<223> OTHER INFORMATION: phosphorothioate bond

<400> SEQUENCE: 45
gtttctacaa actcttt                                                   18

<210> SEQ ID NO 46
<211> LENGTH: 21
<212> TYPE: DNA
<213> ORGANISM: Artificial Sequence
<220> FEATURE:
<223> OTHER INFORMATION: G-repA/p5 forward oligo
<220> FEATURE:
<221> NAME/KEY: misc_binding
<222> LOCATION: (1)..(2)
<223> OTHER INFORMATION: phosphorothioate bond

<400> SEQUENCE: 46
gccgttttca tctgtgcata t                                              21

<210> SEQ ID NO 47
<211> LENGTH: 21
```

```
<212> TYPE: DNA
<213> ORGANISM: Artificial Sequence
<220> FEATURE:
<223> OTHER INFORMATION: repA/p5-T reverse oligo
<220> FEATURE:
<221> NAME/KEY: misc_binding
<222> LOCATION: (1)..(2)
<223> OTHER INFORMATION: phosphorothioate bond

<400> SEQUENCE: 47
atccttttgt aatactgcgg a                                          21

<210> SEQ ID NO 48
<211> LENGTH: 19
<212> TYPE: DNA
<213> ORGANISM: Artificial Sequence
<220> FEATURE:
<223> OTHER INFORMATION: G-p15A forward oligo
<220> FEATURE:
<221> NAME/KEY: misc_binding
<222> LOCATION: (1)..(2)
<223> OTHER INFORMATION: phosphorothioate bond

<400> SEQUENCE: 48
gttgttcagc tactgacgg                                             19

<210> SEQ ID NO 49
<211> LENGTH: 18
<212> TYPE: DNA
<213> ORGANISM: Artificial Sequence
<220> FEATURE:
<223> OTHER INFORMATION: p15A-T reverse oligo
<220> FEATURE:
<221> NAME/KEY: misc_binding
<222> LOCATION: (1)..(2)
<223> OTHER INFORMATION: phosphorothioate bond

<400> SEQUENCE: 49
agacatcacc gatgggga                                              18

<210> SEQ ID NO 50
<211> LENGTH: 18
<212> TYPE: DNA
<213> ORGANISM: Artificial Sequence
<220> FEATURE:
<223> OTHER INFORMATION: G-pMB1 forward oligo
<220> FEATURE:
<221> NAME/KEY: misc_binding
<222> LOCATION: (1)..(2)
<223> OTHER INFORMATION: phosphorothioate bond

<400> SEQUENCE: 50
gagttttcgt tccactga                                              18

<210> SEQ ID NO 51
<211> LENGTH: 18
<212> TYPE: DNA
<213> ORGANISM: Artificial Sequence
<220> FEATURE:
<223> OTHER INFORMATION: pMB1-T reverse oligo
<220> FEATURE:
<221> NAME/KEY: misc_binding
<222> LOCATION: (1)..(2)
<223> OTHER INFORMATION: phosphorothioate bond

<400> SEQUENCE: 51
aggatccagc atatgcgg                                              18

<210> SEQ ID NO 52
```

```
<211> LENGTH: 19
<212> TYPE: DNA
<213> ORGANISM: Artificial Sequence
<220> FEATURE:
<223> OTHER INFORMATION: G-pUC forward oligo
<220> FEATURE:
<221> NAME/KEY: misc_binding
<222> LOCATION: (1)..(2)
<223> OTHER INFORMATION: phosphorothioate bond

<400> SEQUENCE: 52
ggctcactca aaggcggta                                              19

<210> SEQ ID NO 53
<211> LENGTH: 19
<212> TYPE: DNA
<213> ORGANISM: Artificial Sequence
<220> FEATURE:
<223> OTHER INFORMATION: pUC-T reverse oligo
<220> FEATURE:
<221> NAME/KEY: misc_binding
<222> LOCATION: (1)..(2)
<223> OTHER INFORMATION: phosphorothioate bond

<400> SEQUENCE: 53
aattaccgcc tttgagtga                                              19

<210> SEQ ID NO 54
<211> LENGTH: 20
<212> TYPE: DNA
<213> ORGANISM: Artificial Sequence
<220> FEATURE:
<223> OTHER INFORMATION: G-pLac forward oligo
<220> FEATURE:
<221> NAME/KEY: misc_binding
<222> LOCATION: (1)..(2)
<223> OTHER INFORMATION: phosphorothioate bond

<400> SEQUENCE: 54
gcaacgcaat taatgtgagt                                             20

<210> SEQ ID NO 55
<211> LENGTH: 20
<212> TYPE: DNA
<213> ORGANISM: Artificial Sequence
<220> FEATURE:
<223> OTHER INFORMATION: pLac-T reverse oligo
<220> FEATURE:
<221> NAME/KEY: misc_binding
<222> LOCATION: (1)..(2)
<223> OTHER INFORMATION: phosphorothioate bond

<400> SEQUENCE: 55
attgttatcc gctcacaatt                                             20

<210> SEQ ID NO 56
<211> LENGTH: 21
<212> TYPE: DNA
<213> ORGANISM: Artificial Sequence
<220> FEATURE:
<223> OTHER INFORMATION: G-lacIT7 forward oligo
<220> FEATURE:
<221> NAME/KEY: misc_binding
<222> LOCATION: (1)..(2)
<223> OTHER INFORMATION: phosphorothioate bond

<400> SEQUENCE: 56
ggaaactacc cataatacaa g                                           21
```

```
<210> SEQ ID NO 57
<211> LENGTH: 40
<212> TYPE: DNA
<213> ORGANISM: Artificial Sequence
<220> FEATURE:
<223> OTHER INFORMATION: LacIT7-T reverse oligo
<220> FEATURE:
<221> NAME/KEY: misc_binding
<222> LOCATION: (1)..(2)
<223> OTHER INFORMATION: phosphorothioate bond

<400> SEQUENCE: 57 agagggaat tgttatccgc tcacaattcc cctatagtga                40

<210> SEQ ID NO 58
<211> LENGTH: 18
<212> TYPE: DNA
<213> ORGANISM: Artificial Sequence
<220> FEATURE:
<223> OTHER INFORMATION: G-t7t forward oligo
<220> FEATURE:
<221> NAME/KEY: misc_binding
<222> LOCATION: (1)..(2)
<223> OTHER INFORMATION: phosphorothioate bond

<400> SEQUENCE: 58
gggctgctaa caaagccc                                       18

<210> SEQ ID NO 59
<211> LENGTH: 19
<212> TYPE: DNA
<213> ORGANISM: Artificial Sequence
<220> FEATURE:
<223> OTHER INFORMATION: t7t-T reverse oligo
<220> FEATURE:
<221> NAME/KEY: misc_binding
<222> LOCATION: (1)..(2)
<223> OTHER INFORMATION: phosphorothioate bond

<400> SEQUENCE: 59
aggcaccgtc accctggat                                      19

<210> SEQ ID NO 60
<211> LENGTH: 19
<212> TYPE: DNA
<213> ORGANISM: Artificial Sequence
<220> FEATURE:
<223> OTHER INFORMATION: lacI-T reverse oligo
<220> FEATURE:
<221> NAME/KEY: misc_binding
<222> LOCATION: (1)..(2)
<223> OTHER INFORMATION: phosphorothioate bond

<400> SEQUENCE: 60
atcccggaca ccatcgaat                                      19

<210> SEQ ID NO 61
<211> LENGTH: 21
<212> TYPE: DNA
<213> ORGANISM: Artificial Sequence
<220> FEATURE:
<223> OTHER INFORMATION: G-dxs forward oligo
<220> FEATURE:
<221> NAME/KEY: misc_binding
<222> LOCATION: (1)..(2)
<223> OTHER INFORMATION: phosphorothioate bond

<400> SEQUENCE: 61
gagttttgat attgccaaat a                                   21
```

```
<210> SEQ ID NO 62
<211> LENGTH: 17
<212> TYPE: DNA
<213> ORGANISM: Artificial Sequence
<220> FEATURE:
<223> OTHER INFORMATION: dxs-T reverse oligo
<220> FEATURE:
<221> NAME/KEY: misc_binding
<222> LOCATION: (1)..(2)
<223> OTHER INFORMATION: phosphorothioate bond

<400> SEQUENCE: 62
atgccagcca ggccttg                                                  17

<210> SEQ ID NO 63
<211> LENGTH: 21
<212> TYPE: DNA
<213> ORGANISM: Artificial Sequence
<220> FEATURE:
<223> OTHER INFORMATION: G-idi forward oligo
<220> FEATURE:
<221> NAME/KEY: misc_binding
<222> LOCATION: (1)..(2)
<223> OTHER INFORMATION: phosphorothioate bond

<400> SEQUENCE: 63
gcaaacggaa cacgtcattt t                                             21

<210> SEQ ID NO 64
<211> LENGTH: 21
<212> TYPE: DNA
<213> ORGANISM: Artificial Sequence
<220> FEATURE:
<223> OTHER INFORMATION: idi-T reverse oligo
<220> FEATURE:
<221> NAME/KEY: misc_binding
<222> LOCATION: (1)..(2)
<223> OTHER INFORMATION: phosphorothioate bond

<400> SEQUENCE: 64
atttaagctg ggtaaatgca g                                             21

<210> SEQ ID NO 65
<211> LENGTH: 18
<212> TYPE: DNA
<213> ORGANISM: Artificial Sequence
<220> FEATURE:
<223> OTHER INFORMATION: G-ispA forward oligo
<220> FEATURE:
<221> NAME/KEY: misc_binding
<222> LOCATION: (1)..(2)
<223> OTHER INFORMATION: phosphorothioate bond

<400> SEQUENCE: 65
ggactttccg cagcaact                                                 18

<210> SEQ ID NO 66
<211> LENGTH: 21
<212> TYPE: DNA
<213> ORGANISM: Artificial Sequence
<220> FEATURE:
<223> OTHER INFORMATION: ispA-T reverse oligo
<220> FEATURE:
<221> NAME/KEY: misc_binding
<222> LOCATION: (1)..(2)
<223> OTHER INFORMATION: phosphorothioate bond

<400> SEQUENCE: 66
atttattacg ctggatgatg t                                             21
```

```
<210> SEQ ID NO 67
<211> LENGTH: 18
<212> TYPE: DNA
<213> ORGANISM: Artificial Sequence
<220> FEATURE:
<223> OTHER INFORMATION: G-ValC forward oligo
<220> FEATURE:
<221> NAME/KEY: misc_binding
<222> LOCATION: (1)..(2)
<223> OTHER INFORMATION: phosphorothioate bond

<400> SEQUENCE: 67
ggccgagatg ttcaacgg                                              18

<210> SEQ ID NO 68
<211> LENGTH: 17
<212> TYPE: DNA
<213> ORGANISM: Artificial Sequence
<220> FEATURE:
<223> OTHER INFORMATION: ValC-T reverse oligo
<220> FEATURE:
<221> NAME/KEY: misc_binding
<222> LOCATION: (1)..(2)
<223> OTHER INFORMATION: phosphorothioate bond

<400> SEQUENCE: 68
aggggatgat gggctcg                                               17

<210> SEQ ID NO 69
<211> LENGTH: 21
<212> TYPE: DNA
<213> ORGANISM: Artificial Sequence
<220> FEATURE:
<223> OTHER INFORMATION: G-tyrR mutant forward oligo
<220> FEATURE:
<221> NAME/KEY: misc_binding
<222> LOCATION: (1)..(2)
<223> OTHER INFORMATION: phosphorothioate bond

<400> SEQUENCE: 69
ggttgctgaa ttgaccgcat t                                          21

<210> SEQ ID NO 70
<211> LENGTH: 19
<212> TYPE: DNA
<213> ORGANISM: Artificial Sequence
<220> FEATURE:
<223> OTHER INFORMATION: tyrR mutant-T reverse oligo
<220> FEATURE:
<221> NAME/KEY: misc_binding
<222> LOCATION: (1)..(2)
<223> OTHER INFORMATION: phosphorothioate bond

<400> SEQUENCE: 70
actggcgatt gtcattcgc                                             19

<210> SEQ ID NO 71
<211> LENGTH: 21
<212> TYPE: DNA
<213> ORGANISM: Artificial Sequence
<220> FEATURE:
<223> OTHER INFORMATION: G-aroG mutant forward oligo
<220> FEATURE:
<221> NAME/KEY: misc_binding
<222> LOCATION: (1)..(2)
<223> OTHER INFORMATION: phosphorothioate bond

<400> SEQUENCE: 71
```
gaattatcag aacgacgatt t                                        21

<210> SEQ ID NO 72
<211> LENGTH: 18
<212> TYPE: DNA
<213> ORGANISM: Artificial Sequence
<220> FEATURE:
<223> OTHER INFORMATION: aroG mutant-T reverse oligo
<220> FEATURE:
<221> NAME/KEY: misc_binding
<222> LOCATION: (1)..(2)
<223> OTHER INFORMATION: phosphorothioate bond

<400> SEQUENCE: 72
acccgcgacg cgctttta                                            18

<210> SEQ ID NO 73
<211> LENGTH: 43
<212> TYPE: DNA
<213> ORGANISM: Artificial Sequence
<220> FEATURE:
<223> OTHER INFORMATION: RBS1 UDS barcode

<400> SEQUENCE: 73
tagaaataat tttgtttaac tttaagaagg agatatacat atg                43

<210> SEQ ID NO 74
<211> LENGTH: 35
<212> TYPE: DNA
<213> ORGANISM: Artificial Sequence
<220> FEATURE:
<223> OTHER INFORMATION: RBS2stop UDS barcode

<400> SEQUENCE: 74
taaccgttca tttatcacaa aaggattgtt cgatg                         35

<210> SEQ ID NO 75
<211> LENGTH: 24
<212> TYPE: DNA
<213> ORGANISM: Artificial Sequence
<220> FEATURE:
<223> OTHER INFORMATION: RBS3stop UDS barcode

<400> SEQUENCE: 75
tgattcacac aggaaacagc tatg                                     24

<210> SEQ ID NO 76
<211> LENGTH: 38
<212> TYPE: DNA
<213> ORGANISM: Artificial Sequence
<220> FEATURE:
<223> OTHER INFORMATION: RBS4stop UDS barcode

<400> SEQUENCE: 76
taaattaatt gttcttttt caggtgaagg ttcccatg                       38

<210> SEQ ID NO 77
<211> LENGTH: 34
<212> TYPE: DNA
<213> ORGANISM: Artificial Sequence
<220> FEATURE:
<223> OTHER INFORMATION: pJ23119 UDS barcode

<400> SEQUENCE: 77
ttgacagcta gctcagtcct aggtataata ctag                          34

```
<210> SEQ ID NO 78
<211> LENGTH: 21
<212> TYPE: DNA
<213> ORGANISM: Artificial Sequence
<220> FEATURE:
<223> OTHER INFORMATION: N21 UDS barcode

<400> SEQUENCE: 78
ttccctcgac tcacacttgg g                                      21

<210> SEQ ID NO 79
<211> LENGTH: 21
<212> TYPE: DNA
<213> ORGANISM: Artificial Sequence
<220> FEATURE:
<223> OTHER INFORMATION: N22 UDS barcode

<400> SEQUENCE: 79
ttcacacaac atagccacgg g                                      21

<210> SEQ ID NO 80
<211> LENGTH: 21
<212> TYPE: DNA
<213> ORGANISM: Artificial Sequence
<220> FEATURE:
<223> OTHER INFORMATION: N23 UDS barcode

<400> SEQUENCE: 80
ttcaaacaga aaggccatgg g                                      21

<210> SEQ ID NO 81
<211> LENGTH: 21
<212> TYPE: DNA
<213> ORGANISM: Artificial Sequence
<220> FEATURE:
<223> OTHER INFORMATION: N24 UDS barcode

<400> SEQUENCE: 81
ttcctcatgg attctacggg g                                      21

<210> SEQ ID NO 82
<211> LENGTH: 21
<212> TYPE: DNA
<213> ORGANISM: Artificial Sequence
<220> FEATURE:
<223> OTHER INFORMATION: N31 UDS barcode

<400> SEQUENCE: 82
tgatgggctg aagggtttaa g                                      21

<210> SEQ ID NO 83
<211> LENGTH: 21
<212> TYPE: DNA
<213> ORGANISM: Artificial Sequence
<220> FEATURE:
<223> OTHER INFORMATION: N32 UDS barcode

<400> SEQUENCE: 83
tgtcccatca cagcttacaa g                                      21

<210> SEQ ID NO 84
<211> LENGTH: 21
<212> TYPE: DNA
<213> ORGANISM: Artificial Sequence
<220> FEATURE:
<223> OTHER INFORMATION: LK3 UDS barcode
```

<400> SEQUENCE: 84
tcaggctcgt cttcttcagg g                                        21

<210> SEQ ID NO 85
<211> LENGTH: 38
<212> TYPE: DNA
<213> ORGANISM: Artificial Sequence
<220> FEATURE:
<223> OTHER INFORMATION: T-N21'_pT2 forward oligo
<220> FEATURE:
<221> NAME/KEY: misc_binding
<222> LOCATION: (1)..(2)
<223> OTHER INFORMATION: phosphorothioate bond

<400> SEQUENCE: 85
ttccctcgac tcacactttc gagttcatgt gcagctcc                      38

<210> SEQ ID NO 86
<211> LENGTH: 38
<212> TYPE: DNA
<213> ORGANISM: Artificial Sequence
<220> FEATURE:
<223> OTHER INFORMATION: pT2_N21''-G reverse oligo
<220> FEATURE:
<221> NAME/KEY: misc_binding
<222> LOCATION: (1)..(2)
<223> OTHER INFORMATION: phosphorothioate bond

<400> SEQUENCE: 86
cccaagtgtg agtcgaggtc agctcactca aaggcggt                      38

<210> SEQ ID NO 87
<211> LENGTH: 38
<212> TYPE: DNA
<213> ORGANISM: Artificial Sequence
<220> FEATURE:
<223> OTHER INFORMATION: T-N22'_pT2 forward oligo
<220> FEATURE:
<221> NAME/KEY: misc_binding
<222> LOCATION: (1)..(2)
<223> OTHER INFORMATION: phosphorothioate bond

<400> SEQUENCE: 87
ttcacacaac atagccactc gagttcatgt gcagctcc                      38

<210> SEQ ID NO 88
<211> LENGTH: 38
<212> TYPE: DNA
<213> ORGANISM: Artificial Sequence
<220> FEATURE:
<223> OTHER INFORMATION: pT2_N22''-G reverse oligo
<220> FEATURE:
<221> NAME/KEY: misc_binding
<222> LOCATION: (1)..(2)
<223> OTHER INFORMATION: phosphorothioate bond

<400> SEQUENCE: 88
cccgtggcta tgttgtgttc agctcactca aaggcggt                      38

<210> SEQ ID NO 89
<211> LENGTH: 38
<212> TYPE: DNA
<213> ORGANISM: Artificial Sequence
<220> FEATURE:
<223> OTHER INFORMATION: T-N23'_pT2 forward oligo
<220> FEATURE:
<221> NAME/KEY: misc_binding
<222> LOCATION: (1)..(2)
<223> OTHER INFORMATION: phosphorothioate bond

```
<400> SEQUENCE: 89
ttcaaacaga aaggccattc gagttcatgt gcagctcc                               38

<210> SEQ ID NO 90
<211> LENGTH: 39
<212> TYPE: DNA
<213> ORGANISM: Artificial Sequence
<220> FEATURE:
<223> OTHER INFORMATION: pT2_N23''-G reverse oligo
<220> FEATURE:
<221> NAME/KEY: misc_binding
<222> LOCATION: (1)..(2)
<223> OTHER INFORMATION: phosphorothioate bond

<400> SEQUENCE: 90
cccatggcct ttctgtttgt cagctcactc aaaggcggt                              39

<210> SEQ ID NO 91
<211> LENGTH: 38
<212> TYPE: DNA
<213> ORGANISM: Artificial Sequence
<220> FEATURE:
<223> OTHER INFORMATION: T-N24'_pT2 forward oligo
<220> FEATURE:
<221> NAME/KEY: misc_binding
<222> LOCATION: (1)..(2)
<223> OTHER INFORMATION: phosphorothioate bond

<400> SEQUENCE: 91
ttcctcatgg attctacgtc gagttcatgt gcagctcc                               38

<210> SEQ ID NO 92
<211> LENGTH: 38
<212> TYPE: DNA
<213> ORGANISM: Artificial Sequence
<220> FEATURE:
<223> OTHER INFORMATION: pT2_N24''-G reverse oligo
<220> FEATURE:
<221> NAME/KEY: misc_binding
<222> LOCATION: (1)..(2)
<223> OTHER INFORMATION: phosphorothioate bond

<400> SEQUENCE: 92
ccccgtagaa tccatgagtc agctcactca aaggcggt                               38

<210> SEQ ID NO 93
<211> LENGTH: 43
<212> TYPE: DNA
<213> ORGANISM: Artificial Sequence
<220> FEATURE:
<223> OTHER INFORMATION: T-pJ23119'_pT2 forward oligo
<220> FEATURE:
<221> NAME/KEY: misc_binding
<222> LOCATION: (1)..(2)
<223> OTHER INFORMATION: phosphorothioate bond

<400> SEQUENCE: 93
ttgacagcta gctcagtcct aggtcgagtt catgtgcagc tcc                         43

<210> SEQ ID NO 94
<211> LENGTH: 46
<212> TYPE: DNA
<213> ORGANISM: Artificial Sequence
<220> FEATURE:
<223> OTHER INFORMATION: pT2_pJ23119''-G reverse oligo
<220> FEATURE:
<221> NAME/KEY: misc_binding
<222> LOCATION: (1)..(2)
```

<223> OTHER INFORMATION: phosphorothioate bond

<400> SEQUENCE: 94
ctagtattat acctaggact gagctatcag ctcactcaaa ggcggt    46

<210> SEQ ID NO 95
<211> LENGTH: 17
<212> TYPE: DNA
<213> ORGANISM: Artificial Sequence
<220> FEATURE:
<223> OTHER INFORMATION: N21s-Bff forward oligo

<400> SEQUENCE: 95
cctcgactca cacttgg    17

<210> SEQ ID NO 96
<211> LENGTH: 16
<212> TYPE: DNA
<213> ORGANISM: Artificial Sequence
<220> FEATURE:
<223> OTHER INFORMATION: N21s-Bfr reverse oligo
<220> FEATURE:
<221> NAME/KEY: misc_feature
<222> LOCATION: (1)..(1)
<223> OTHER INFORMATION: 5'-end phosphorylation

<400> SEQUENCE: 96
caagtgtgag tcgagg    16

<210> SEQ ID NO 97
<211> LENGTH: 17
<212> TYPE: DNA
<213> ORGANISM: Artificial Sequence
<220> FEATURE:
<223> OTHER INFORMATION: N22s-Bff forward oligo

<400> SEQUENCE: 97
acacaacata gccacgg    17

<210> SEQ ID NO 98
<211> LENGTH: 16
<212> TYPE: DNA
<213> ORGANISM: Artificial Sequence
<220> FEATURE:
<223> OTHER INFORMATION: N22s-Bfr reverse oligo
<220> FEATURE:
<221> NAME/KEY: misc_feature
<222> LOCATION: (1)..(1)
<223> OTHER INFORMATION: 5'-end phosphorylation

<400> SEQUENCE: 98
cgtggctatg ttgtgt    16

<210> SEQ ID NO 99
<211> LENGTH: 18
<212> TYPE: DNA
<213> ORGANISM: Artificial Sequence
<220> FEATURE:
<223> OTHER INFORMATION: N23s-Bff forward oligo

<400> SEQUENCE: 99
caaacagaaa ggccatgg    18

<210> SEQ ID NO 100
<211> LENGTH: 17
<212> TYPE: DNA
<213> ORGANISM: Artificial Sequence

```
<220> FEATURE:
<223> OTHER INFORMATION: N23s-Bfr reverse oligo
<220> FEATURE:
<221> NAME/KEY: misc_feature
<222> LOCATION: (1)..(1)
<223> OTHER INFORMATION: 5'-end phosphorylation

<400> SEQUENCE: 100
catggccttt ctgtttg                                                      17

<210> SEQ ID NO 101
<211> LENGTH: 17
<212> TYPE: DNA
<213> ORGANISM: Artificial Sequence
<220> FEATURE:
<223> OTHER INFORMATION: N24s-Bff forward oligo

<400> SEQUENCE: 101
ctcatggatt ctacggg                                                      17

<210> SEQ ID NO 102
<211> LENGTH: 16
<212> TYPE: DNA
<213> ORGANISM: Artificial Sequence
<220> FEATURE:
<223> OTHER INFORMATION: N24s-Bfr reverse oligo
<220> FEATURE:
<221> NAME/KEY: misc_feature
<222> LOCATION: (1)..(1)
<223> OTHER INFORMATION: 5'-end phosphorylation

<400> SEQUENCE: 102
ccgtagaatc catgag                                                       16

<210> SEQ ID NO 103
<211> LENGTH: 26
<212> TYPE: DNA
<213> ORGANISM: Artificial Sequence
<220> FEATURE:
<223> OTHER INFORMATION: pJ23119s-Bff forward oligo

<400> SEQUENCE: 103
tagctcagtc ctaggtataa tactag                                            26

<210> SEQ ID NO 104
<211> LENGTH: 25
<212> TYPE: DNA
<213> ORGANISM: Artificial Sequence
<220> FEATURE:
<223> OTHER INFORMATION: pJ23119s-Bfr reverse oligo
<220> FEATURE:
<221> NAME/KEY: misc_feature
<222> LOCATION: (1)..(1)
<223> OTHER INFORMATION: 5'-end phosphorylation

<400> SEQUENCE: 104
tagtattata cctaggactg agcta                                             25

<210> SEQ ID NO 105
<211> LENGTH: 16
<212> TYPE: DNA
<213> ORGANISM: Artificial Sequence
<220> FEATURE:
<223> OTHER INFORMATION: N21s-Brf forward oligo
<220> FEATURE:
<221> NAME/KEY: misc_feature
<222> LOCATION: (1)..(1)
<223> OTHER INFORMATION: 5'-end phosphorylation
```

```
<400> SEQUENCE: 105
ccctcgactc acactt                                                        16

<210> SEQ ID NO 106
<211> LENGTH: 17
<212> TYPE: DNA
<213> ORGANISM: Artificial Sequence
<220> FEATURE:
<223> OTHER INFORMATION: N21s-Brr reverse oligo

<400> SEQUENCE: 106
aagtgtgagt cgaggga                                                       17

<210> SEQ ID NO 107
<211> LENGTH: 16
<212> TYPE: DNA
<213> ORGANISM: Artificial Sequence
<220> FEATURE:
<223> OTHER INFORMATION: N22s-Brf forward oligo
<220> FEATURE:
<221> NAME/KEY: misc_feature
<222> LOCATION: (1)..(1)
<223> OTHER INFORMATION: 5'-end phosphorylation

<400> SEQUENCE: 107
cacacaacat agccac                                                        16

<210> SEQ ID NO 108
<211> LENGTH: 17
<212> TYPE: DNA
<213> ORGANISM: Artificial Sequence
<220> FEATURE:
<223> OTHER INFORMATION: N22s-Brr reverse oligo

<400> SEQUENCE: 108
gtggctatgt tgtgtga                                                       17

<210> SEQ ID NO 109
<211> LENGTH: 16
<212> TYPE: DNA
<213> ORGANISM: Artificial Sequence
<220> FEATURE:
<223> OTHER INFORMATION: N23s-Brf forward oligo
<220> FEATURE:
<221> NAME/KEY: misc_feature
<222> LOCATION: (1)..(1)
<223> OTHER INFORMATION: 5'-end phosphorylation

<400> SEQUENCE: 109
caaacagaaa ggccat                                                        16

<210> SEQ ID NO 110
<211> LENGTH: 17
<212> TYPE: DNA
<213> ORGANISM: Artificial Sequence
<220> FEATURE:
<223> OTHER INFORMATION: N23s-Brr reverse oligo

<400> SEQUENCE: 110
atggcctttc tgtttga                                                       17

<210> SEQ ID NO 111
<211> LENGTH: 16
<212> TYPE: DNA
<213> ORGANISM: Artificial Sequence
<220> FEATURE:
<223> OTHER INFORMATION: N24s-Brf forward oligo
```

```
<220> FEATURE:
<221> NAME/KEY: misc_feature
<222> LOCATION: (1)..(1)
<223> OTHER INFORMATION: 5'-end phosphorylation

<400> SEQUENCE: 111
cctcatggat tctacg                                                      16

<210> SEQ ID NO 112
<211> LENGTH: 17
<212> TYPE: DNA
<213> ORGANISM: Artificial Sequence
<220> FEATURE:
<223> OTHER INFORMATION: N24s-Brr reverse oligo

<400> SEQUENCE: 112
cgtagaatcc atgagga                                                     17

<210> SEQ ID NO 113
<211> LENGTH: 22
<212> TYPE: DNA
<213> ORGANISM: Artificial Sequence
<220> FEATURE:
<223> OTHER INFORMATION: pJ23119s-Brf forward oligo
<220> FEATURE:
<221> NAME/KEY: misc_feature
<222> LOCATION: (1)..(1)
<223> OTHER INFORMATION: 5'-end phosphorylation

<400> SEQUENCE: 113
tgacagctag ctcagtccta gg                                               22

<210> SEQ ID NO 114
<211> LENGTH: 23
<212> TYPE: DNA
<213> ORGANISM: Artificial Sequence
<220> FEATURE:
<223> OTHER INFORMATION: pJ23119s-Brr reverse oligo

<400> SEQUENCE: 114
cctaggactg agctagctgt caa                                              23

<210> SEQ ID NO 115
<211> LENGTH: 69
<212> TYPE: DNA
<213> ORGANISM: Artificial Sequence
<220> FEATURE:
<223> OTHER INFORMATION: RBS1-Bf-SL forward oligo

<400> SEQUENCE: 115
atatgtatat ctccttctta aagttaaaca atatgttttg tttaacttta agaaggagat      60
atacatatg                                                              69

<210> SEQ ID NO 116
<211> LENGTH: 65
<212> TYPE: DNA
<213> ORGANISM: Artificial Sequence
<220> FEATURE:
<223> OTHER INFORMATION: RBS1-Br-SL reverse oligo

<400> SEQUENCE: 116
agaaataatt tgtttaact ttaagaaggt ctactccttc ttaaagtaaa acaaaattat       60
ttcta                                                                  65

<210> SEQ ID NO 117
```

<211> LENGTH: 63
<212> TYPE: DNA
<213> ORGANISM: Artificial Sequence
<220> FEATURE:
<223> OTHER INFORMATION: RBS2stop-Bf-SL forward oligo

<400> SEQUENCE: 117
atcgaacaat cctttttgtga taaatgaatc ggttttcatt tatcacaaaa ggattgttcg    60
atg                                                                 63

<210> SEQ ID NO 118
<211> LENGTH: 55
<212> TYPE: DNA
<213> ORGANISM: Artificial Sequence
<220> FEATURE:
<223> OTHER INFORMATION: RBS2stop-Br-SL reverse oligo

<400> SEQUENCE: 118
aaccgttcat ttatcacaaa aggatatcac tccttttgtg ataaatgaac ggtta         55

<210> SEQ ID NO 119
<211> LENGTH: 41
<212> TYPE: DNA
<213> ORGANISM: Artificial Sequence
<220> FEATURE:
<223> OTHER INFORMATION: RBS3stop-Bf-SL forward oligo

<400> SEQUENCE: 119
atagctgttt cctgtgtgcc tggacacagg aaacagctat g                       41

<210> SEQ ID NO 120
<211> LENGTH: 47
<212> TYPE: DNA
<213> ORGANISM: Artificial Sequence
<220> FEATURE:
<223> OTHER INFORMATION: RBS3stop-Br-SL reverse oligo

<400> SEQUENCE: 120
gattcacaca ggaaacagct tcttcgagct gtttcctgtg tgaatca                 47

<210> SEQ ID NO 121
<211> LENGTH: 41
<212> TYPE: DNA
<213> ORGANISM: Artificial Sequence
<220> FEATURE:
<223> OTHER INFORMATION: RBS4stop-Bf-SL forward oligo

<400> SEQUENCE: 121
atgggaacct tcacctgaag ttacaggtga aggttcccat g                       41

<210> SEQ ID NO 122
<211> LENGTH: 75
<212> TYPE: DNA
<213> ORGANISM: Artificial Sequence
<220> FEATURE:
<223> OTHER INFORMATION: RBS4stop-Br-SL reverse oligo

<400> SEQUENCE: 122
aaattaattg ttctttttc aggtgaaggt tccctcacat gggaaccttc acctgaaaaa    60
agaacaatta attta                                                    75

<210> SEQ ID NO 123
<211> LENGTH: 57
<212> TYPE: DNA
<213> ORGANISM: Artificial Sequence

```
<220> FEATURE:
<223> OTHER INFORMATION: pJ23119-Bf-SL forward oligo

<400> SEQUENCE: 123
tagtattata cctaggactg agctaagagg gtagctcagt cctaggtata atactag      57

<210> SEQ ID NO 124
<211> LENGTH: 51
<212> TYPE: DNA
<213> ORGANISM: Artificial Sequence
<220> FEATURE:
<223> OTHER INFORMATION: pJ23119-Br-SL reverse oligo

<400> SEQUENCE: 124
tgacagctag ctcagtccta gggcacagcc taggactgag ctagctgtca a            51

<210> SEQ ID NO 125
<211> LENGTH: 41
<212> TYPE: DNA
<213> ORGANISM: Artificial Sequence
<220> FEATURE:
<223> OTHER INFORMATION: N21-Bf-SL forward oligo

<400> SEQUENCE: 125
ccaagtgtga gtcgaggaag ggccctcgac tcacacttgg g                       41

<210> SEQ ID NO 126
<211> LENGTH: 41
<212> TYPE: DNA
<213> ORGANISM: Artificial Sequence
<220> FEATURE:
<223> OTHER INFORMATION: N21-Br-SL reverse oligo

<400> SEQUENCE: 126
tccctcgact cacacttgcg agaaagtgtg agtcgaggga a                       41

<210> SEQ ID NO 127
<211> LENGTH: 41
<212> TYPE: DNA
<213> ORGANISM: Artificial Sequence
<220> FEATURE:
<223> OTHER INFORMATION: N22-Bf-SL forward oligo

<400> SEQUENCE: 127
ccgtggctat gttgtgtcgt attacacaac atagccacgg g                       41

<210> SEQ ID NO 128
<211> LENGTH: 41
<212> TYPE: DNA
<213> ORGANISM: Artificial Sequence
<220> FEATURE:
<223> OTHER INFORMATION: N22-Br-SL reverse oligo

<400> SEQUENCE: 128
tcacacaaca tagccacttg ctggtggcta tgttgtgtga a                       41

<210> SEQ ID NO 129
<211> LENGTH: 43
<212> TYPE: DNA
<213> ORGANISM: Artificial Sequence
<220> FEATURE:
<223> OTHER INFORMATION: N23-Bf-SL forward oligo

<400> SEQUENCE: 129
ccatggcctt tctgtttgac catacaaaca gaaaggccat ggg                     43
```

<210> SEQ ID NO 130
<211> LENGTH: 41
<212> TYPE: DNA
<213> ORGANISM: Artificial Sequence
<220> FEATURE:
<223> OTHER INFORMATION: N23-Br-SL reverse oligo

<400> SEQUENCE: 130
tcaaacagaa aggccatcat tcaatggcct ttctgtttga a         41

<210> SEQ ID NO 131
<211> LENGTH: 41
<212> TYPE: DNA
<213> ORGANISM: Artificial Sequence
<220> FEATURE:
<223> OTHER INFORMATION: N24-Bf-SL forward oligo

<400> SEQUENCE: 131
cccgtagaat ccatgagaac cgctcatgg attctacggg g          41

<210> SEQ ID NO 132
<211> LENGTH: 41
<212> TYPE: DNA
<213> ORGANISM: Artificial Sequence
<220> FEATURE:
<223> OTHER INFORMATION: N24-Br-SL reverse oligo

<400> SEQUENCE: 132
tcctcatgga ttctacgact atgcgtagaa tccatgagga a         41

<210> SEQ ID NO 133
<211> LENGTH: 41
<212> TYPE: DNA
<213> ORGANISM: artificial
<220> FEATURE:
<223> OTHER INFORMATION: N31-Bf-SL forward oligo

<400> SEQUENCE: 133 ttaaacccett cagcccacac acatgggctg aagggtttaa g        41

<210> SEQ ID NO 134
<211> LENGTH: 41
<212> TYPE: DNA
<213> ORGANISM: Artificial Sequence
<220> FEATURE:
<223> OTHER INFORMATION: N31-Br-SL reverse oligo

<400> SEQUENCE: 134
gatgggctga agggtttcac acaaaaccct tcagcccatc a         41

<210> SEQ ID NO 135
<211> LENGTH: 41
<212> TYPE: DNA
<213> ORGANISM: artificial
<220> FEATURE:
<223> OTHER INFORMATION: N32-Bf-SL forward oligo

<400> SEQUENCE: 135
ttgtaagctg tgatggggcc tggcccatca cagcttacaa g         41

<210> SEQ ID NO 136
<211> LENGTH: 41
<212> TYPE: DNA
<213> ORGANISM: Artificial Sequence
<220> FEATURE:
<223> OTHER INFORMATION: N32-Br-SL reverse oligo

```
<400> SEQUENCE: 136
gtcccatcac agcttacgct tcggtaagct gtgatgggac a                          41

<210> SEQ ID NO 137
<211> LENGTH: 41
<212> TYPE: DNA
<213> ORGANISM: Artificial Sequence
<220> FEATURE:
<223> OTHER INFORMATION: LK3-Bf-SL forward oligo

<400> SEQUENCE: 137
cctgaagaag acgagcccac acaggctcgt cttcttcagg g                          41

<210> SEQ ID NO 138
<211> LENGTH: 41
<212> TYPE: DNA
<213> ORGANISM: Artificial Sequence
<220> FEATURE:
<223> OTHER INFORMATION: LK3-Br-SL reverse oligo

<400> SEQUENCE: 138
caggctcgtc ttcttcacac acatgaagaa gacgagcctg a                          41

<210> SEQ ID NO 139
<211> LENGTH: 32
<212> TYPE: DNA
<213> ORGANISM: Artificial Sequence
<220> FEATURE:
<223> OTHER INFORMATION: RBS1-Bff UDS forward universal oligo
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (21)..(22)
<223> OTHER INFORMATION: phosphorothioate bond

<400> SEQUENCE: 139
ttgtttaact ttaagaagga gatatacata tg                                    32

<210> SEQ ID NO 140
<211> LENGTH: 29
<212> TYPE: DNA
<213> ORGANISM: Artificial Sequence
<220> FEATURE:
<223> OTHER INFORMATION: RBS2stop-Bff UDS forward universal oligo
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (19)..(20)
<223> OTHER INFORMATION: phosphorothioate bond

<400> SEQUENCE: 140
ttcatttatc acaaaaggat tgttcgatg                                        29

<210> SEQ ID NO 141
<211> LENGTH: 18
<212> TYPE: DNA
<213> ORGANISM: Artificial Sequence
<220> FEATURE:
<223> OTHER INFORMATION: RBS3-Bff UDS forward universal oligo
<220> FEATURE:
<221> NAME/KEY: misc_binding
<222> LOCATION: (7)..(8)
```

<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 141
acacaggaaa cagctatg                                                    18

<210> SEQ ID NO 142
<211> LENGTH: 18
<212> TYPE: DNA
<213> ORGANISM: Artificial Sequence
<220> FEATURE:
<223> OTHER INFORMATION: RBS4-Bff UDS forward universal oligo
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 142
caggtgaagg ttcccatg                                                    18

<210> SEQ ID NO 143
<211> LENGTH: 26
<212> TYPE: DNA
<213> ORGANISM: Artificial Sequence
<220> FEATURE:
<223> OTHER INFORMATION: pJ23119-Bff UDS forward universal oligo
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 143
tagctcagtc ctaggtataa tactag                                           26

<210> SEQ ID NO 144
<211> LENGTH: 18
<212> TYPE: DNA
<213> ORGANISM: Artificial Sequence
<220> FEATURE:
<223> OTHER INFORMATION: N21-Bff UDS forward universal oligo
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 144
cctcgactca cacttggg                                                    18

<210> SEQ ID NO 145
<211> LENGTH: 18
<212> TYPE: DNA
<213> ORGANISM: Artificial Sequence
<220> FEATURE:
<223> OTHER INFORMATION: N22-Bff UDS forward universal oligo
<220> FEATURE:
<221> NAME/KEY: misc_binding

```
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 145
acacaacata gccacggg                                                 18

<210> SEQ ID NO 146
<211> LENGTH: 19
<212> TYPE: DNA
<213> ORGANISM: Artificial Sequence
<220> FEATURE:
<223> OTHER INFORMATION: N23-Bff UDS forward universal oligo
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (16)..(17)
<223> OTHER INFORMATION: phosphorothioate bond

<400> SEQUENCE: 146
caaacagaaa ggccatggg                                                19

<210> SEQ ID NO 147
<211> LENGTH: 18
<212> TYPE: DNA
<213> ORGANISM: Artificial Sequence
<220> FEATURE:
<223> OTHER INFORMATION: N24-Bff UDS forward universal oligo
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 147
ctcatggatt ctacgggg                                                 18

<210> SEQ ID NO 148
<211> LENGTH: 18
<212> TYPE: DNA
<213> ORGANISM: Artificial Sequence
<220> FEATURE:
<223> OTHER INFORMATION: N31-Bff UDS forward universal oligo
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 148
tgggctgaag ggtttaag                                                 18

<210> SEQ ID NO 149
<211> LENGTH: 18
<212> TYPE: DNA
<213> ORGANISM: Artificial Sequence
<220> FEATURE:
<223> OTHER INFORMATION: N32-Bff UDS forward universal oligo
<220> FEATURE:
```

```
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 149
cccatcacag cttacaag                                                 18

<210> SEQ ID NO 150
<211> LENGTH: 18
<212> TYPE: DNA
<213> ORGANISM: Artificial Sequence
<220> FEATURE:
<223> OTHER INFORMATION: LK3-Bff UDS forward universal oligo
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 150
ggctcgtctt cttcaggg                                                 18

<210> SEQ ID NO 151
<211> LENGTH: 30
<212> TYPE: DNA
<213> ORGANISM: Artificial Sequence
<220> FEATURE:
<223> OTHER INFORMATION: RBS1-Brr UDS reverse universal oligo
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (19)..(20)
<223> OTHER INFORMATION: phosphorothioate bond

<400> SEQUENCE: 151
ccttcttaaa gttaaacaaa attatttcta                                    30

<210> SEQ ID NO 152
<211> LENGTH: 25
<212> TYPE: DNA
<213> ORGANISM: Artificial Sequence
<220> FEATURE:
<223> OTHER INFORMATION: RBS2stop-Brr UDS reverse universal oligo
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (19)..(20)
<223> OTHER INFORMATION: phosphorothioate bond

<400> SEQUENCE: 152
tccttttgtg ataaatgaac ggtta                                         25

<210> SEQ ID NO 153
<211> LENGTH: 21
<212> TYPE: DNA
<213> ORGANISM: artificial
<220> FEATURE:
<223> OTHER INFORMATION: RBS3stop-Brr UDS reverse universal oligo
```

```
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 153
agctgtttcc tgtgtgaatc a                                         21

<210> SEQ ID NO 154
<211> LENGTH: 35
<212> TYPE: DNA
<213> ORGANISM: Artificial Sequence
<220> FEATURE:
<223> OTHER INFORMATION: RBS4stop-Brr UDS reverse universal oligo
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 154
gggaaccttc acctgaaaaa agaacaatta attta                          35

<210> SEQ ID NO 155
<211> LENGTH: 23
<212> TYPE: DNA
<213> ORGANISM: Artificial Sequence
<220> FEATURE:
<223> OTHER INFORMATION: pJ23119-Brr UDS reverse universal oligo
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 155
cctaggactg agctagctgt caa                                       23

<210> SEQ ID NO 156
<211> LENGTH: 18
<212> TYPE: DNA
<213> ORGANISM: Artificial Sequence
<220> FEATURE:
<223> OTHER INFORMATION: N21-Brr UDS reverse universal oligo
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 156
aagtgtgagt cgagggaa                                             18

<210> SEQ ID NO 157
<211> LENGTH: 18
<212> TYPE: DNA
<213> ORGANISM: Artificial Sequence
<220> FEATURE:
```

-continued

```
<223> OTHER INFORMATION: N22-Brr UDS reverse universal oligo
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 157
gtggctatgt tgtgtgaa                                                 18

<210> SEQ ID NO 158
<211> LENGTH: 18
<212> TYPE: DNA
<213> ORGANISM: Artificial Sequence
<220> FEATURE:
<223> OTHER INFORMATION: N23-Brr UDS reverse universal oligo
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (16)..(17)
<223> OTHER INFORMATION: phosphorothioate bond

<400> SEQUENCE: 158
atggcctttc tgtttgaa                                                 18

<210> SEQ ID NO 159
<211> LENGTH: 18
<212> TYPE: DNA
<213> ORGANISM: Artificial Sequence
<220> FEATURE:
<223> OTHER INFORMATION: N24-Brr UDS reverse universal oligo
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 159
cgtagaatcc atgaggaa                                                 18

<210> SEQ ID NO 160
<211> LENGTH: 18
<212> TYPE: DNA
<213> ORGANISM: Artificial Sequence
<220> FEATURE:
<223> OTHER INFORMATION: N31-Brr UDS reverse universal oligo
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 160
aaacccttca gcccatca                                                 18

<210> SEQ ID NO 161
<211> LENGTH: 19
<212> TYPE: DNA
<213> ORGANISM: Artificial Sequence
```

```
<220> FEATURE:
<223> OTHER INFORMATION: N32-Brr UDS reverse universal oligo
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 161
gtaagctgtg atgggaaca                                                    19

<210> SEQ ID NO 162
<211> LENGTH: 18
<212> TYPE: DNA
<213> ORGANISM: Artificial Sequence
<220> FEATURE:
<223> OTHER INFORMATION: LK3-Brr UDS reverse universal oligo
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 162
tgaagaagac gagcctga                                                     18

<210> SEQ ID NO 163
<211> LENGTH: 171
<212> TYPE: DNA
<213> ORGANISM: Artificial Sequence
<220> FEATURE:
<223> OTHER INFORMATION: (pJ23119)gRNA-nupG(N23) barcoded fragment

<400> SEQUENCE: 163
ttgacagcta gctcagtcct aggtataata ctagtacgag ttaatcaata tcacagtttt        60
agagctagaa atagcaagtt aaaataaggc tagtccgtta tcaacttgaa aaagtggcac      120
cgagtcggtg cttttttga attctctaga ttcaaacaga aaggccatgg g                171

<210> SEQ ID NO 164
<211> LENGTH: 171
<212> TYPE: DNA
<213> ORGANISM: Artificial Sequence
<220> FEATURE:
<223> OTHER INFORMATION: (pJ23119)gRNA-aslA(N23) barcoded fragment

<400> SEQUENCE: 164
ttgacagcta gctcagtcct aggtataata ctagttccag atcttccata tatttgtttt        60
agagctagaa atagcaagtt aaaataaggc tagtccgtta tcaacttgaa aaagtggcac      120
cgagtcggtg cttttttga attctctaga ttcaaacaga aaggccatgg g                171

<210> SEQ ID NO 165
<211> LENGTH: 171
<212> TYPE: DNA
<213> ORGANISM: Artificial Sequence
<220> FEATURE:
<223> OTHER INFORMATION: (pJ23119)gRNA-melB(N23) barcoded fragment

<400> SEQUENCE: 165
ttgacagcta gctcagtcct aggtataata ctagtctacc atttgttaat tatgtgtttt        60
```
agagctagaa atagcaagtt aaaataaggc tagtccgtta tcaacttgaa aaagtggcac    120
cgagtcggtg cttttttga attctctaga ttcaaacaga aaggccatgg g              171

<210> SEQ ID NO 166
<211> LENGTH: 171
<212> TYPE: DNA
<213> ORGANISM: Artificial Sequence
<220> FEATURE:
<223> OTHER INFORMATION: (pJ23119)gRNA-rcsB(N23) barcoded fragment

<400> SEQUENCE: 166
ttgacagcta gctcagtcct aggtataata ctagtaatca cttgagcaaa ttgaggtttt    60
agagctagaa atagcaagtt aaaataaggc tagtccgtta tcaacttgaa aaagtggcac    120
cgagtcggtg cttttttga attctctaga ttcaaacaga aaggccatgg g              171

<210> SEQ ID NO 167
<211> LENGTH: 171
<212> TYPE: DNA
<213> ORGANISM: Artificial Sequence
<220> FEATURE:
<223> OTHER INFORMATION: (pJ23119)gRNA-tyrR(N23) barcoded fragment

<400> SEQUENCE: 167
ttgacagcta gctcagtcct aggtataata ctagtttaat accgagcgtt caaaagtttt    60
agagctagaa atagcaagtt aaaataaggc tagtccgtta tcaacttgaa aaagtggcac    120
cgagtcggtg cttttttga attctctaga ttcaaacaga aaggccatgg g              171

<210> SEQ ID NO 168
<211> LENGTH: 171
<212> TYPE: DNA
<213> ORGANISM: Artificial Sequence
<220> FEATURE:
<223> OTHER INFORMATION: (pJ23119)gRNA-pheA(N23) barcoded fragment

<400> SEQUENCE: 168
ttgacagcta gctcagtcct aggtataata ctagttttga gcaattcatt gaaaggtttt    60
agagctagaa atagcaagtt aaaataaggc tagtccgtta tcaacttgaa aaagtggcac    120
cgagtcggtg cttttttga attctctaga ttcaaacaga aaggccatgg g              171

<210> SEQ ID NO 169
<211> LENGTH: 171
<212> TYPE: DNA
<213> ORGANISM: Artificial Sequence
<220> FEATURE:
<223> OTHER INFORMATION: (pJ23119)gRNA-ptsI(N23) barcoded fragment

<400> SEQUENCE: 169
ttgacagcta gctcagtcct aggtataata ctagtgaagt tgatttcttt agtatgtttt    60
agagctagaa atagcaagtt aaaataaggc tagtccgtta tcaacttgaa aaagtggcac    120
cgagtcggtg cttttttga attctctaga ttcaaacaga aaggccatgg g              171

<210> SEQ ID NO 170
<211> LENGTH: 529
<212> TYPE: DNA
<213> ORGANISM: Artificial Sequence
<220> FEATURE:
<223> OTHER INFORMATION: (N23)nupG-HF0.5(N24) barcoded fragment

<400> SEQUENCE: 170
ttcaaacaga aaggccatgg gttgatcctg ccagcaatat tgataccggc accgcgtatc    60

```
tggcgatgct gaacaatgtt tatctcggcg gaattgataa cccaacatcg cggcgttatg      120
ccgtcatcac cgcctataac ggcggcgcag gcagcgtgct gcgagtcttt tcgaatgata      180
agattcaggc tgccaatatt attaacacca tgacgccggg cgatgtttat cagacgctga      240
cgacccgcca tccctctgcg gaatctcgcc gttatcttta taaagtgaat accgcgcaaa      300
aatcctaccg ccgccgataa ttccattaac cgccctgac gatgctcagg ggcaaaaatg       360
ttatccacat cacaatttcg ttttgcaaat tgggaatgtt tgcaattatt tgccacaggt      420
aacaaaaaac cagtccgcga agttgataga atcccatcat ctcgcacggt caaatgtgct      480
ttttcaaaca ctcatccgca tcacgatgtt cctcatggat tctacgggg                 529

<210> SEQ ID NO 171
<211> LENGTH: 1046
<212> TYPE: DNA
<213> ORGANISM: Artificial Sequence
<220> FEATURE:
<223> OTHER INFORMATION: (N23)nupG-HF1.0(N24) barcoded fragment

<400> SEQUENCE: 171
ttcaaacaga aaggccatgg gaccatcgcc gggacagaac ctgccgcgca tttgcgccgg       60
gcaattatca aaacgttatt gatgggtgac gatccgagtt cggtcgatct ctattccgac     120
gttgatgata ttacgatttc gaaagaacct ttcctttacg gtcaggtggt ggacaacacc     180
gggcagccga ttcgctggga aggtcgcgca agcaacttcg cggattatct gctgaaaaac     240
cgtctgaaga gccgcagcaa cgggctgcgt atcatctaca gcgtcaccat taacatggtg     300
ccgaaccacc ttgataaacg tgcgcacaaa tatctcggca tggtccgcca ggcgtcacgg     360
aaatatggcg ttgatgagtc gctgattctg gcaattatgc agaccgaatc ttcctttaac     420
ccgtatgcgg tcagccgttc cgatgcgctg ggattaatgc aggtggtaca acatactgcc     480
gggaaagatg tgttccgctc gcaggggaaa tccggcacgc cgagccgcag tttcttgttt     540
gatcctgcca gcaatattga taccggcacc gcgtatctgg cgatgctgaa caatgtttat     600
ctcggcggaa ttgataaccc aacatcgcgc cgttatgccg tcatcaccgc ctataacggc     660
ggcgcaggca gcgtgctgcg agtcttttcg aatgataaga ttcaggctgc caatattatt     720
aacaccatga cgccgggcga tgtttatcag acgctgacga cccgccatcc ctctgcggaa     780
tctcgccgtt atctttataa agtgaatacc gcgcaaaaat cctaccgccg ccgataattc     840
cattaaccgc ccctgacgat gctcaggggc aaaaatgtta tccacatcac aatttcgttt     900
tgcaaattgg gaatgtttgc aattatttgc acaggtaaca aaaaaccag tccgcgaagt      960 tgatagaatc ccatcatctc gcacggtcaa atgtgctttt tcaaacactc atccgcatca    1020
cgatgttcct catggattct acgggg                                         1046

<210> SEQ ID NO 172
<211> LENGTH: 1622
<212> TYPE: DNA
<213> ORGANISM: Artificial Sequence
<220> FEATURE:
<223> OTHER INFORMATION: (N23)nupG-HF1.5(N24) barcoded fragment

<400> SEQUENCE: 172
ttcaaacaga aaggccatgg gtgcaacgtg aagcagaagg tcaggatttt cagctgtacc       60
ccggcgagct gggaaaacgc atctataacg agatctccaa agaagcctgg gcgcagtggc     120
agcacaagca aaccatgctg attaatgaaa agaaactcaa catgatgaat gccgagcacc     180
```

```
gcaagctgct tgagcaggag atggtcaact tcctgttcga gggtaaagag gtgcatatcg    240
agggctatac gccggaagat aaaaaataaa aacagtgccg gagcacgcct ccggcaactt    300
gcataaaaac aaacacaaca cgcacccgga atgatgaaaa aatatctcgc gctggctttg    360
attgcgccgt tgctcatctc ctgttcgacg accaaaaaag gcgataccta taacgaagcc    420
tgggtcaaag ataccaacgg ttttgatatt ctgatggggc aatttgccca caatattgag    480
aacatctggg gcttcaaaga ggtggtgatc gctggtccta aggactacgt gaaatacacc    540
gatcaatatc agacccgcag ccacatcaac ttcgatgacg gtacgattac tatcgaaacc    600
atcgccggga cagaacctgc cgcgcatttg cgccgggcaa ttatcaaaac gttattgatg    660
ggtgacgatc cgagttcggt cgatctctat tccgacgttg atgatattac gatttcgaaa    720
gaacctttcc tttacggtca ggtggtggac aacaccgggc agccgattcg ctgggaaggt    780
cgcgcaagca acttcgcgga ttatctgctg aaaaaccgtc tgaagagccg cagcaacggg    840
ctgcgtatca tctacagcgt caccattaac atggtgccga accaccttga taaacgtgcg    900
cacaaatatc tcggcatggt ccgccaggcg tcacggaaat atggcgttga tgagtcgctg    960
attctggcaa ttatgcagac cgaatcttcc tttaacccgt atgcggtcag ccgttccgat   1020
gcgctgggat taatgcaggt ggtacaacat actgccggga agatgtgtt ccgctcgcag   1080 gggaaatccg gcacgccgag ccgcagtttc ttgtttgatc ctgccagcaa tattgatacc   1140
ggcaccgcgt atctggcgat gctgaacaat gtttatctcg gcggaattga tacccaaca    1200 tcgcggcgtt atgccgtcat caccgcctat aacggcggcg caggcagcgt gctgcgagtc   1260 tttttcgaatg ataagattca ggctgccaat attattaaca ccatgacgcc gggcgatgtt   1320
tatcagacgc tgacgacccg ccatccctct gcggaatctc gccgttatct ttataaagtg   1380
aataccgcgc aaaaatccta ccgccgccga taattccatt aaccgcccct gacgatgctc   1440
aggggcaaaa atgttatcca catcacaatt tcgtttttgca aattgggaat gttttgcaatt   1500 atttgccaca ggtaacaaaa aaccagtccg cgaagttgat agaatcccat catctcgcac   1560
ggtcaaatgt gcttttttcaa acactcatcc gcatcacgat gttcctcatg gattctacgg   1620
gg                                                                  1622
```

<210> SEQ ID NO 173
<211> LENGTH: 529
<212> TYPE: DNA
<213> ORGANISM: Artificial Sequence
<220> FEATURE:
<223> OTHER INFORMATION: (N23)aslA-HF0.5(N24) barcoded fragment

<400> SEQUENCE: 173

```
ttcaaacaga aaggccatgg gcaccgtaaa cggctctgcg tcattccgga gtttatgagg     60
cactaaggcg aacataagag atggaatgag catctactcg tttattatgc cacagagaat    120
cgggaaataa catcccttaa cacttgttat gagataattc tgtaatcctc tttgcttcct    180
gagtaataac ttcctgagtg aatatttaac ctgagcttga tcctacacat acttattatg    240
aatgataaaa ttcattcaat taataacaca tatattaatt gccgttaaaa ctaaaaacag    300
catcaataat caacgcgata taataaacct gccttacata tcaactgcgc cagaggtagg    360
attgaaaacg ctctcctgat tttccaattc attttctgga taaataaata atttattttt    420
gtcactatta tttatgtaat catcctgtca gggagaggga tctcaattat caatgcttaa    480
ttacgtcatc attttgatga catgaaactt cctcatggat tctacgggg                529
```

<210> SEQ ID NO 174
<211> LENGTH: 1029
<212> TYPE: DNA
<213> ORGANISM: Artificial Sequence
<220> FEATURE:
<223> OTHER INFORMATION: (N23)aslA-HF1.0(N24) barcoded fragment

<400> SEQUENCE: 174

```
ttcaaacaga aaggccatgg gccagtacga cgatcgccta ctgctgccga ttcctcgact      60
gaaaacaaac aatccggaac agctggaaaa agtgctgcgc cagcaaatca aaaacgtcgg     120
cgatcgcccg ctgttgtgga gcacactggg ccagtcactg atgaagcacg agaatggca     180
ggaagcatcg ctcgccttcc gcgcagcgct gaaacaacgt ccggacgcct acgattacgc     240
atggcttgcc gacgcgctgg acagactgca caagccggaa gaagctgcag ctatgcgtcg     300
cgacggtttg atgttaacgt tgcagaataa cccgccacag tagttccttc tcacccggag     360
gcaagcacct ccggggcctt cctgatacat aaaaaaacgc ctgctcttat tacggagcag     420
gcgttaaaac aggtctgtat gacaacaagt gggtgcttca ctcaacgttg tgtccatggt     480
gtctgatgag gcataagcga catctgtcag tggacgataa gcaccgtaaa cggctctgcg     540
tcattccgga gttatgagg cactaaggcg aacataagag atggaatgag catctactcg     600
tttattatgc cacagagaat cgggaaataa catcccttaa cacttgttat gagataattc     660
tgtaatcctc tttgcttcct gagtaataac ttcctgagtg aatatttaac ctgagcttga     720
tcctacacat acttattatg aatgataaaa ttcattcaat taataacaca tatattaatt     780
gccgttaaaa ctaaaaacag catcaataat caacgcgata taaaaacct gccttacata     840
tcaactgcgc cagaggtagg attgaaaacg ctctcctgat tttccaattc attttctgga     900
taaataaata atttatttt gtcactatta tttatgtaat catcctgtca gggagaggga     960
tctcaattat caatgcttaa ttacgtcatc attttgatga catgaaactt cctcatggat    1020
tctacgggg                                                           1029
```

<210> SEQ ID NO 175
<211> LENGTH: 1035
<212> TYPE: DNA
<213> ORGANISM: Artificial Sequence
<220> FEATURE:
<223> OTHER INFORMATION: (N23)melB-HF1.0(N24) barcoded fragment

<400> SEQUENCE: 175

```
ttcaaacaga aaggccatgg gcccaatggc gatgaatacc tgggcgatgt atgcccgcta      60
tccgcatatc aaacaggtcg ggctgtgcca ttcggtgcag ggaacggcgg aagagttggc     120
gcgtgacctc aatatcgacc cagctacgct gcgttaccgt tgcgcaggta tcaaccatat     180
ggcgttttac ctggagctgg agcgcaaaac cgccgacggc agttatgtga atctctaccc     240
ggaactgctg gcggcttatg aagcagggca ggcaccgaag ccgaatattc atggcaatac     300
tcgctgccag aatattgtgc gctacgaaat gttcaaaaag ctgggctatt cgtcacgga     360
atcgtcagaa cattttgctg agtacacacc gtggtttatt aagccaggtc gtgaggattt     420
gattgagcgt tataaagtac cgctggatga gtacccgaaa cgctgcgtcg agcagctggc     480
gaactggcat aaagagctgg aggagtataa aaaagcctcc cggattgata ttaaaccgtc     540
acgggaatat gccagcacaa tcatgaacgc tatctggact ggcgagccga gtgtgattta     600
cggcaacgtc cgtaacgatg gtttgattga taacctgcca caaggatgtt gcgtggaagt     660
agcctgtctg gttgatgcta atggcattca gccgaccaaa gtcggtacgc taccttcgca     720
```

| | |
|---|---|
| tctggccgcc ctgatgcaaa ccaacatcaa cgtacagacg ctgctgaccg aagctattct | 780 |
| tacggaaaat cgcgaccgtg tttaccacgc cgcgatgatg gacccgcata ctgccgccgt | 840 |
| gctgggcatt gacgaaatat atgctcttgt tgacgacctg attgccgccc acggcgactg | 900 |
| gctgccaggc tggttgcacc gttaaaacgc gactaaacgc tactgcgccg ggggatttat | 960 |
| tccggcgcac acctctgacg ataccaataa cagaaggcgg gcgttggtaa cagcttcctc | 1020 |
| atggattcta cgggg | 1035 |

<210> SEQ ID NO 176
<211> LENGTH: 1189
<212> TYPE: DNA
<213> ORGANISM: Artificial Sequence
<220> FEATURE:
<223> OTHER INFORMATION: (N23)rcsB-HF1.0(N24) barcoded fragment

<400> SEQUENCE: 176

| | |
|---|---|
| ttcaaacaga aaggccatgg ggttagcgaa catgcttgcg gatgatagct ggaaaagtga | 60 |
| gacggtgctg ttctccgtgc aggatttaat tgatgaagtt gtgccttcag tgttgcctgc | 120 |
| catcaagcgt aaaggtctgc aactgctgat taacaatcat ctgaaagcac acgtatgcg | 180 |
| ccgcggcgat cgcgatgcct tacgacgtat tttgctgcta ctgatgcaat atgccgtgac | 240 |
| ctcaacgcaa ttgggaaaaa tcacccttga ggttgatcag gatgagtcct ccgaagaccg | 300 |
| cctgacgttc cgcattctgg acacgggaga aggcgtaagt attcatgaaa tggataattt | 360 |
| gcacttcccg tttatcaacc agacccaaaa cgatcgctat ggcaaggcgg acccgctggc | 420 |
| attctggctg agcgatcaac tggcacgtaa actgggcggt catttaaaca tcaaaacgcg | 480 |
| ggatgggctt ggtacacgct actctgtgca tatcaaaatg ctcgcagctg acccggaagt | 540 |
| tgaagaggaa gaagagcgtt tactggatga tgtctgcgta atggtggatg ttacttcggc | 600 |
| agaaattcgg aatattgtca ctcgccagtt agaaaattgg ggtgcaacct gtatcacacc | 660 |
| cgatgaaaga ttaattagtc aagattatga tatcttttta acggataatc cgtctaatct | 720 |
| tactgcctct ggcttgcttt taagcgatga tgagtctggc gtacgggaaa ttgggcctgg | 780 |
| tcaattgtgc gtcaacttca atatgagcaa cgctatgcag gaagcggtct tacaattaat | 840 |
| tgaagtgcaa ctggcgcagg aagaggtgac agaatcgcct ctgggcggag atgaaaatgc | 900 |
| gcaactccat gccagcggct attatgcgct ctttgtagac acagtaccgg atgatgttaa | 960 |
| gaggctgtat actgaagcag caaccagtga ctttgctgcg ttagcccaaa cggctcatcg | 1020 |
| tcttaaaggc gtatttgcca tgctaaatct ggtacccggc aagcagttat gtgaaacgct | 1080 |
| ggaacatctg attcgtgaga aggatgttcc aggaatagaa aaatacatca gcgacattga | 1140 |
| cagttatgtc aagagcttgc tgtagcaatt cctcatggat tctacgggg | 1189 |

<210> SEQ ID NO 177
<211> LENGTH: 443
<212> TYPE: DNA
<213> ORGANISM: Artificial Sequence
<220> FEATURE:
<223> OTHER INFORMATION: (N23)tyrR-HF0.5(N24) barcoded fragment

<400> SEQUENCE: 177

| | |
|---|---|
| cagcccgctg gcgttggtcg atatggcgtt tatcgcctgg cgcaatctgc gtttaattaa | 60 |
| tcgcatcgcc acgctgtatg gcattgaact ggggtattac agccgtttgc gtctgtttaa | 120 |
| gctggtattg ctgaatatcg cttttgccgg agccagcgaa ctggtgcgcg aagtggggat | 180 |
| ggactggatg tcgcaagatc tcgctgctcg tttgtctacc cgcgcagctc aggggattgg | 240 |

```
tgcaggactt ctgacggcac gactcgggat taaagctatg gagctttgcc gcccgctgcc    300
gtggattgac gatgacaaac ctcgcctcgg ggatttccgt cgtcagctta tcggtcaggt    360
gaaagaaacg ctgcaaaaag gcaaaacgcc cagcgaaaaa taatgcaata tcgggtgctg    420
acttcctcat ggattctacg ggg                                            443
```

```
<210> SEQ ID NO 178
<211> LENGTH: 496
<212> TYPE: DNA
<213> ORGANISM: Artificial Sequence
<220> FEATURE:
<223> OTHER INFORMATION: N23)pheA-HF0.5(N24) barcoded fragment

<400> SEQUENCE: 178
ttcaaacaga aaggccatgg gcatgtcgca gaccgtctcg ccaaactgga aaaatggcaa     60
acacatctga ttaatccaca tatcattctg tccaaagagc cacaagggtt tgttgctgac    120
gccacaatca atacacctaa cggcgttctg gttgccagtg gtaaacatga agatatgtac    180
accgcaatta acgaattgat caacaagctg gaacggcagc tcaataaact gcagcacaaa    240
ggcgaagcac gtcgtgccgc aacatcggtg aaagacgcca acttcgtcga agaagttgaa    300
gaagagtagt cctttatatt gagtgtatcg ccaacgcgcc ttcgggcgcg ttttttgttg    360
acagcgtgaa aacagtacgg gtactgtact aaagtcactt aaggaaacaa acatgaaaca    420
cataccgttt ttcttcgcat tctttttttac cttcccctga atgggaggcg tttcgttcct    480
catggattct acgggg                                                   496
```

```
<210> SEQ ID NO 179
<211> LENGTH: 496
<212> TYPE: DNA
<213> ORGANISM: Artificial Sequence
<220> FEATURE:
<223> OTHER INFORMATION: (N23)ptsI-HF0.7(N24) barcoded fragment

<400> SEQUENCE: 179
ttcaaacaga aaggccatgg gcatgtcgca gaccgtctcg ccaaactgga aaaatggcaa     60
acacatctga ttaatccaca tatcattctg tccaaagagc cacaagggtt tgttgctgac    120
gccacaatca atacacctaa cggcgttctg gttgccagtg gtaaacatga agatatgtac    180
accgcaatta acgaattgat caacaagctg gaacggcagc tcaataaact gcagcacaaa    240
ggcgaagcac gtcgtgccgc aacatcggtg aaagacgcca acttcgtcga agaagttgaa    300
gaagagtagt cctttatatt gagtgtatcg ccaacgcgcc ttcgggcgcg ttttttgttg    360
acagcgtgaa aacagtacgg gtactgtact aaagtcactt aaggaaacaa acatgaaaca    420
cataccgttt ttcttcgcat tctttttttac cttcccctga atgggaggcg tttcgttcct    480
catggattct acgggg                                                   496
```

```
<210> SEQ ID NO 180
<211> LENGTH: 542
<212> TYPE: DNA
<213> ORGANISM: Artificial Sequence
<220> FEATURE:
<223> OTHER INFORMATION: (N24)nupG-HT0.5(N21) barcoded fragment

<400> SEQUENCE: 180
ttcctcatgg attctacggg gttacgcaaa gaaaaacggg tcgccagaag gtgacccgtt     60 tttttttattc ttacttcaac acataaccgt acaaccgttt cacgccatcc gcatcggttt    120
```

```
cgctataaac accttgcagc tccggcgaaa atcccggcaa caaattcacc ccttcttcca    180
gtgcaaggaa ataacgttga accgccccac cccagacttc cccgggtacc acgcaaagca    240
cgccaggtgg ataaggcaac gccccttctg ccgcaattcg cccttcggca tcacgaatcc    300
gcaccaactc cacgtcaccg cgaatataag cgctatgcgc atcctggggg ttcatcacca    360
ctgacgggaa actctgctgg cggaacatcg cttttttgtag gtctttgacg tcgaaactga   420
catacagatc gtgcatctcc tgacacaact ggcgcagggt gtagtcgcga tagcgcaccg    480
gatacttgtt ataaacgctc ggcaacacct caaccagcgg cttccctcga ctcacacttg    540
gg                                                                  542

<210> SEQ ID NO 181
<211> LENGTH: 1092
<212> TYPE: DNA
<213> ORGANISM: Artificial Sequence
<220> FEATURE:
<223> OTHER INFORMATION: (N24)nupG-HT1.0(N21) barcoded fragment

<400> SEQUENCE: 181
ttcctcatgg attctacggg gttacgcaaa gaaaaacggg tcgccagaag gtgacccgtt    60 tttttttattc ttacttcaac acataaccgt acaaccgttt cacgccatcc gcatcggttt   120
cgctataaac accttgcagc tccggcgaaa atcccggcaa caaattcacc ccttcttcca    180
gtgcaaggaa ataacgttga accgccccac cccagacttc cccgggtacc acgcaaagca    240
cgccaggtgg ataaggcaac gccccttctg ccgcaattcg cccttcggca tcacgaatcc    300
gcaccaactc cacgtcaccg cgaatataag cgctatgcgc atcctggggg ttcatcacca    360
ctgacgggaa actctgctgg cggaacatcg cttttttgtag gtctttgacg tcgaaactga   420
catacagatc gtgcatctcc tgacacaact ggcgcagggt gtagtcgcga tagcgcaccg    480
gatacttgtt ataaacgctc ggcaacacct caaccagcgg cgagtcatcc tcaatatgct    540
gttcaaattg cgccagcatc gccaccagtt gtgccagctt ctcgtggctt tccgccggag    600
ttaataaaaa cagaatggag ttgagatcgc acttctccgg cacaatgccg ttctcacgca    660
gatagtgcgc cagaatcgtc gccggaacgc caaagtcgct atattcgccg gtttcggcat    720
cgatacctgg tgtagtgagt aacagcttgc acggatcaac aaaatactga tccgcggcat    780
atccttcaaa gccgtgccac ttcgcccccg gctcaaaact gaaaaaacgg cggtcgctgg    840
ctaacactga tgtcggataa tcctgccaca atttgccatc aacaacgggc gggataaacg    900
ggcggaacag cttacagcgc gcaagaatag ccttgcgcgc ttcaatccct atctcaacac    960
actcagccca cagccgacgc ccactctccc cttcatgaat tttggcgtta acatccagtg    1020
cagcaaacag cggatagaaa gggctggtag aagcatggag cataaaggcg tttccctcga    1080
ctcacacttg gg                                                       1092

<210> SEQ ID NO 182
<211> LENGTH: 1543
<212> TYPE: DNA
<213> ORGANISM: Artificial Sequence
<220> FEATURE:
<223> OTHER INFORMATION: (N24)nupG-HT1.5(N21) barcoded fragment

<400> SEQUENCE: 182
ttcctcatgg attctacggg gttacgcaaa gaaaaacggg tcgccagaag gtgacccgtt    60 tttttttattc ttacttcaac acataaccgt acaaccgttt cacgccatcc gcatcggttt   120
cgctataaac accttgcagc tccggcgaaa atcccggcaa caaattcacc ccttcttcca    180
```

```
gtgcaaggaa ataacgttga accgccccac cccagacttc cccgggtacc acgcaaagca      240
cgccaggtgg ataaggcaac gccccttctg ccgcaattcg cccttcggca tcacgaatcc      300
gcaccaactc cacgtcaccg cgaatataag cgctatgcgc atcctggggg ttcatcacca      360
ctgacgggaa actctgctgg cggaacatcg cttttgtag gtctttgacg tcgaaactga       420
catacagatc gtgcatctcc tgacacaact ggcgcagggt gtagtcgcga tagcgcaccg      480
gatacttgtt ataaacgctc ggcaacacct caaccagcgg cgagtcatcc tcaatatgct      540
gttcaaattg cgccagcatc gccaccagtt gtgccagctt ctcgtggctt tccgccggag      600
ttaataaaaa cagaatggag ttgagatcgc acttctccgg cacaatgccg ttctcacgca      660
gatagtgcgc cagaatcgtc gccggaacgc caaagtcgct atattcgccg gtttcggcat      720
cgatacctgg tgtagtgagt aacagcttgc acggatcaac aaaatactga tccgcggcat      780
atccttcaaa gccgtgccac ttcgcccccg gctcaaaact gaaaaaacgg cggtcgctgg      840
ctaacactga tgtcggataa tcctgccaca atttgccatc aacaacgggc gggataaacg      900
ggcggaacag cttacagcgc gcaagaatag ccttgcgcgc ttcaatccct atctcaacac      960
actcagccca cagccgacgc ccactctccc cttcatgaat tttggcgtta acatccagtg     1020
cagcaaacag cggatagaaa gggctggtag aagcatggag cataaaggcg ttattcaacc     1080
gcttatgcgg gcaaaaacgc gcctgtccgc ggatatggtt atctttttta tggatctgcg     1140
acgtctgtga gaatcccgcc tgctgtttgt gcaccgactg agtcacaaag atccccggat     1200
cgttttcgtt aagttctaac agcagcggcg agctatccgc catcatcggg ataaattgtt     1260
cataaccgac ccacgcggaa tcaaacagaa tgtaatcaca cagatgccca acggtatcga     1320
tcacctgacg ggcgttatag acagtgccgt cataggttcc cagctgaata atcgccaggc     1380
gatacgggcg cggcaggtcg gctttttctg gcgcaacgtc gcgaatttgc tggcgcagat     1440
actcttcatt aaaacagtgc gcatcaatac cgccaatgaa accaaacggg ttgcgtgaag     1500
cttccagata gaccggcgtc gcttccctcg actcacactt ggg                       1543
```

<210> SEQ ID NO 183
<211> LENGTH: 542
<212> TYPE: DNA
<213> ORGANISM: Artificial Sequence
<220> FEATURE:
<223> OTHER INFORMATION: (N24)aslA-HT0.5(N21) barcoded fragment

<400> SEQUENCE: 183

```
ttcctcatgg attctacggg ggccggcgct atcgctgaga tctgcctttg ccggatgcga       60
tgctgacgca tcttatccag cctacagaac gctgcaattt attgaatttg cacgatcatg      120
taggccggat aaggcgttta cgccgcatcc ggcaatcaac cgcaggcggc cgccgatttc      180
tacttactca ccaccagcaa atgcgcatgc ataatgtcgc tggccgggcg accgtgcgcc      240
agcaaatcag ccattgcttt aagatatggc ggtagatggc ggaaataacg ctgatacccg      300
gcacacaaat aattcagtcc cggtttgccg ctggcatcga gcatgaagcg gtgtttcggg      360
cagcctcccc agcacgcttt taacacgtta caactgcgac actgcgcggt taactgctta      420
aatttatctt caccaaacgc ctgctgttgc ggggaatcga tcatttctgc aattgtttgc      480
tggtgcatat tccccagccg atattgcgga taaacatagt gttccctcga ctcacacttg      540
gg                                                                     542
```

<210> SEQ ID NO 184

```
<211> LENGTH: 1042
<212> TYPE: DNA
<213> ORGANISM: Artificial Sequence
<220> FEATURE:
<223> OTHER INFORMATION: (N24)aslA-HT1.0(N21) barcoded fragment

<400> SEQUENCE: 184
ttcctcatgg attctacggg gcggtaaact cgctgctgtg cgtatggatg agttcaagta      60
tcacgtcctg attcagcaac cttacgctta tacccagagc ggatatcagg gtggattcac    120
cggcacagta atgcaaacgg cgggatcgtc ggtgtttaac ctctacaccg atccgcagga    180
aagcgactcc atcggcgtgc gccatattcc gatgggtgta ccgctacaga ccgaaatgca    240
cgcgtatatg gagatcctga aaaaatatcc accacgcgcg cagattaaat ctgactaagc    300
cggcgctatc gctgagatct gcctttgccg gatgcgatgc tgacgcatct tatccagcct    360
acagaacgct gcaatttatt gaatttgcac gatcatgtag gccggataag gcgtttacgc    420
cgcatccggc aatcaaccgc aggcggccgc cgatttctac ttactcacca ccagcaaatg    480
cgcatgcata atgtcgctgg ccgggcgacc gtgcgccagc aaatcagcca ttgctttaag    540
atatggcggt agatggcgga ataacgctg atacccggca cacaaataat tcagtcccgg    600
tttgccgctg gcatcgagca tgaagcggtg tttcgggcag cctccccagc acgcttttaa    660
cacgttacaa ctgcgacact gcgccggtaa ctgcttaaat ttatcttcac caaacgcctg    720
ctgttgcggg gaatcgatca tttctgcaat tgtttgctgg tgcatattcc ccagccgata    780
ttgcggataa acatagtgat cacaggcgta acgtcgccg ttgtgctcaa caatcaccga    840
gcgcccacag gttggctgat gatggcaaac cgcacccggc gcaccgacaa aattggcaaa    900
cgcccattcg atattcatca cgaaaatctt gccgacgtcg cgtttgatcc agtggtcgaa    960
tatcgccacc agaaactcac cgaactcctc ggggcgcacc gaccattccg ttagctcacc   1020
cttccctcga ctcacacttg gg                                             1042

<210> SEQ ID NO 185
<211> LENGTH: 1543
<212> TYPE: DNA
<213> ORGANISM: Artificial Sequence
<220> FEATURE:
<223> OTHER INFORMATION: (N24)melB-HT1.0(N21) barcoded fragment

<400> SEQUENCE: 185
ttcctcatgg attctacggg gttacgcaaa gaaaaacggg tcgccagaag gtgacccgtt     60
ttttttattc ttacttcaac acataaccgt acaaccgttt cacgccatcc gcatcggttt    120
cgctataaac accttgcagc tccggcgaaa atcccggcaa caaattcacc ccttcttcca    180
gtgcaaggaa ataacgttga accgccccac cccagacttc cccgggtacc acgcaaagca    240
cgccaggtgg ataaggcaac gcccttctg ccgcaattcg cccttcggca tcacgaatcc    300
gcaccaactc cacgtcaccg cgaatataag cgctatgcgc atcctggggg ttcatcacca    360
ctgacgggaa actctgctgg cggaacatcg ctttttgtag gtctttgacg tcgaaactga    420
catacagatc gtgcatctcc tgacacaact ggcgcagggt gtagtcgcga tagcgcaccg    480
gatacttgtt ataaacgctc ggcaacacct caaccagcgg cgagtcatcc tcaatatgct    540
gttcaaattg cgccagcatc gccaccagtt gtgccagctt ctcgtggctt tccgccggag    600
ttaataaaaa cagaatggag ttgagatcgc acttctccgg cacaatgccg ttctcacgca    660
gatagtgcgc cagaatcgtc gccggaacgc caaagtcgct atattcgccg gtttcggcat    720
cgatacctgg tgtagtgagt aacagcttgc acggatcaac aaaatactga tccgcggcat    780
```

```
atccttcaaa gccgtgccac ttcgcccccg gctcaaaact gaaaaaacgg cggtcgctgg    840
ctaacactga tgtcggataa tcctgccaca atttgccatc aacaacgggc gggataaacg    900
ggcggaacag cttacagcgc gcaagaatag ccttgcgcgc ttcaatccct atctcaacac    960
actcagccca cagccgacgc ccactctccc cttcatgaat tttggcgtta acatccagtg   1020
cagcaaacag cggatagaaa gggctggtag aagcatggag cataaaggcg ttattcaacc   1080
gcttatgcgg gcaaaaacgc gcctgtccgc ggatatggtt atcttttta tggatctgcg    1140 acgtctgtga aatcccgcc tgctgtttgt gcaccgactg agtcacaaag atccccggat    1200
cgttttcgtt aagttctaac agcagcggcg agctatccgc catcatcggg ataaattgtt   1260
cataaccgac ccacgcggaa tcaaacagaa tgtaatcaca cagatgccca acggtatcga   1320
tcacctgacg ggcgttatag acagtgccgt cataggttcc cagctgaata atcgccaggc   1380
gatacgggcg cggcaggtcg gcttttctg gcgcaacgtc gcgaatttgc tggcgcagat    1440
actcttcatt aaaacagtgc gcatcaatac cgccaatgaa accaaacggg ttgcgtgaag   1500
cttccagata gaccggcgtc gcttccctcg actcacactt ggg                      1543
```

<210> SEQ ID NO 186
<211> LENGTH: 542
<212> TYPE: DNA
<213> ORGANISM: Artificial Sequence
<220> FEATURE:
<223> OTHER INFORMATION: (N24)rcsB-HT1.0(N21) barcoded fragment

<400> SEQUENCE: 186

```
ttcctcatgg attctacggg ggccggcgct atcgctgaga tctgcctttg ccggatgcga     60
tgctgacgca tcttatccag cctacagaac gctgcaattt attgaatttg cacgatcatg    120
taggccggat aaggcgttta cgccgcatcc ggcaatcaac cgcaggcggc cgccgatttc    180
tacttactca ccaccagcaa atgcgcatgc ataatgtcgc tggccgggcg accgtgcgcc    240
agcaaatcag ccattgcttt aagatatggc ggtagatggc ggaaataacg ctgatacccg    300
gcacacaaat aattcagtcc cggttttgccg ctggcatcga gcatgaagcg gtgtttcggg   360
cagcctcccc agcacgcttt taacacgtta caactgcgac actgcgccgg taactgctta    420
aatttatctt caccaaacgc ctgctgttgc ggggaatcga tcatttctgc aattgtttgc    480
tggtgcatat tccccagccg atattgcgga taaacatagt gttccctcga ctcacacttg    540
gg                                                                   542
```

<210> SEQ ID NO 187
<211> LENGTH: 549
<212> TYPE: DNA
<213> ORGANISM: Artificial Sequence
<220> FEATURE:
<223> OTHER INFORMATION: (N24)tyrR-HT0.5(N21) barcoded fragment

<400> SEQUENCE: 187

```
ttcctcatgg attctacggg gttatgcttt cagtacagcc agagctgctt cgtaatccgg     60
ctcggtggtg atttcatcca ccagctggct gaaaatcaca ttgtcatttt cgtcaataac    120
cacaacggca cgcgctgcca gacctttcag tgggccatca gcaattgcca caccgtaagc    180
ttgcagaaat tcagcgttac ggaaagtgga gagggtgata acgttgttca gaccttctgc    240
gccgcagaaa cgagactggg cgaacggcag atcggcagag atacacagca caacggtgtt    300
gtcgatctca gttgccagtt ggttaaactt acgtactgat gcggcgcaaa caccggtatc    360
```

```
aatactcggg aaaatgttca gcactttgcg tttacccgca aactgaccga gggtgacgtc    420
agacagatct tttgccacga gagtaaaagt ctgcgctttg ctacccgcct gcgggatgga    480
attggcgact gtaaccgggt tgccctggaa atgaacggtt tgtgacattt ccctcgactc    540
acacttggg                                                            549

<210> SEQ ID NO 188
<211> LENGTH: 631
<212> TYPE: DNA
<213> ORGANISM: Artificial Sequence
<220> FEATURE:
<223> OTHER INFORMATION: (N24)pheA-HT0.5(N21) barcoded fragment

<400> SEQUENCE: 188
ttcctcatgg attctacggg gttactggcg attgtcattc gcctgacgca ataacacgcg     60
gctttcactc tgaaaacgct gtgcgtaatc gccgaaccag tgctccacct tgcggaaact    120
gtcaataaac gcctgcttat cgccctgctc cagcaactca atcgcctcgc cgaaacgctt    180
atagtaacgt ttgattaacg ccagattacg ctctgacgac ataatgatgt cggcataaag    240
ctgcggatcc tgagcaaaca gtcgcccgac catcgccagc tcaaggcggt aaatcggcga    300
agagagcgcc agaagttgct caagctgaac attttcttct gccaggtgca gcccgtaagc    360
aaaagtagca agtggcgca gtgcctgaat aaacgccata ttctgatcgt gctcgacggc    420
gctaatacga tgcagccgag cgccccgac ctgaatttgc tccagaaacc attggtatgc    480
ttccggttta cgtccatcac accagaccac aacttgcttt gccaggctac cgctgtccgg    540
accgaacatc gggtgtagcc ccagcaccgg accatcatgc gccaccagca tggcctgtaa    600
tggcccattt ttccctcgac tcacacttgg g                                   631

<210> SEQ ID NO 189
<211> LENGTH: 818
<212> TYPE: DNA
<213> ORGANISM: Artificial Sequence
<220> FEATURE:
<223> OTHER INFORMATION: (N24)ptsI-HT0.7(N21) barcoded fragment

<400> SEQUENCE: 189
ttcctcatgg attctacggg gagcgcatca cttccagtac gcgcaacccc gctcggtgca     60
ctgcatcggt taacgccttc cctttcagca agccactgat gagctgagca caaaacaggt    120
cgccagtccc tttcaggtcg gttttttaccc gtgaatggga aatgacattc acgctgtcgg   180
cagtgaccac cacaacctgc atctcctgat tttcttcatt accggaggcg ctggtaacca    240
ccacccattt taatgtgtct gaaagcagac tttttgcggc agcaatggca ctgtcgagat    300
cgcggcaatt tttaccggtc aggatttcca actcaaagat attgggggta attccctgcg    360
ccagcggcag taaatattgt cgatacgctt cgggaaggtc aggtttgaca taaattccgc    420
tatcaatatc gccaatcacc ggatcgacca tgatcaatag gtcaggatgg tctttgcgta    480
gcgcagtcag ccactcggca aggattttga tttgcgatgc cgttcccata tagcccgtgg    540
ttacagcacg aagttggcgc agcgcatcac gctcctgaag cgcacgcaaa tagccgctaa    600
accattcgtc cggaatcgca ccaccgtaga aagtgtcata atgcggcgta ttgctcagca    660
ataccgtcgg cacggcaaag acattcaggc cgttctgttt gatagcaggc acggcaatgc    720
tgttgcccac gctgccgtaa accacctgcg actgcacggc gacgatatcc gcctgcagtg    780
ccctactctt atcgttattc cctcgactca cacttggg                            818
```

<210> SEQ ID NO 190
<211> LENGTH: 1119
<212> TYPE: DNA
<213> ORGANISM: Artificial Sequence
<220> FEATURE:
<223> OTHER INFORMATION: (N21)aadA(N22) barcoded fragment

<400> SEQUENCE: 190

```
ttccctcgac tcacacttgg gtcgacctgc agaagcttag atctattacc ctgttatccc      60
tactcgagtt catgtgcagc tccatcagca aaagggatg ataagtttat caccaccgac      120
tatttgcaac agtgccgttg atcgtgctat gatcgactga tgtcatcagc ggtggagtgc      180
aatgtcatga gggaagcggt gatcgccgaa gtatcgactc aactatcaga ggtagttggc      240
gtcatcgagc gccatctcga accgacgttg ctggccgtac atttgtacgg ctccgcagtg      300
gatggcggcc tgaagccaca cagtgatatt gatttgctgg ttacggtgac cgtaaggctt      360
gatgaaacaa cgcggcgagc tttgatcaac gaccttttgg aaacttcggc ttcccctgga      420
gagagcgaga ttctccgcgc tgtagaagtc accattgttg tgcacgacga catcattccg      480
tggcgttatc cagctaagcg cgaactgcaa tttggagaat ggcagcgcaa tgacattctt      540
gcaggtatct tcgagccagc cacgatcgac attgatctgg ctatcttgct gacaaaagca      600
agagaacata gcgttgcctt ggtaggtcca gcggcggagg aactctttga tccggttcct      660
gaacaggatc tatttgaggc gctaaatgaa accttaacgc tatggaactc gccgcccgac      720
tgggctggcg atgagcgaaa tgtagtgctt acgttgtccc gcatttggta cagcgcagta      780
accggcaaaa tcgcgccgaa ggatgtcgct gccgactggg caatggagcg cctgccggcc      840
cagtatcagc ccgtcatact tgaagctaga caggcttatc ttggacaaga agaagatcgc      900
ttggcctcgc gcgcagatca gttggaagaa tttgtccact acgtgaaagg cgagatcacc      960
aaggtagtcg gcaaataaga tgccgctcgc cagtcgattg gctgagctca tgaagttcct     1020
attccgaagt tccgcgaacg cgtaaaggat ctaggtgaag atccttttg ataatctcat     1080 gaccaaaatc ccttaacgtt cacacaacat agccacggg                             1119
```

<210> SEQ ID NO 191
<211> LENGTH: 1125
<212> TYPE: DNA
<213> ORGANISM: Artificial Sequence
<220> FEATURE:
<223> OTHER INFORMATION: (N21)bla(N22) barcoded fragment

<400> SEQUENCE: 191

```
ttccctcgac tcacacttgg gtttctacaa actcttttgt ttatttttct aaatacattc      60
aaatatgtat ccgctcatga gacaataacc ctgataaatg cttcaataat attgaaaaag      120
gaagagtatg agtattcaac atttccgtgt cgcccttatt ccctttttg cggcattttg      180 ccttcctgtt tttgctcacc cagaaacgct ggtgaaagta aaagatgctg aagatcagtt      240
gggtgcacga gtgggttaca tcgaactgga tctcaacagc ggtaagatcc ttgagagttt      300
tcgccccgaa gaacgttttc caatgatgag cacttttaaa gttctgctat gtggcgcggt      360
attatcccgt gttgacgccg ggcaagagca actcggtcgc cgcatacact attctcagaa      420
tgacttggtt gagtactcac cagtcacaga aaagcatctt acggatggca tgacagtaag      480
agaattatgc agtgctgcca taaccatgag tgataacact gcggccaact tacttctgac      540
aacgatcgga ggaccgaagg agctaaccgc ttttttgcac aacatggggg atcatgtaac      600
tcgccttgat cgttgggaac cggagctgaa tgaagccata ccaaacgacg agcgtgacac      660
```

```
cacgatgcct gtagcaatgg caacaacgtt gcgcaaacta ttaactggcg aactacttac    720
tctagcttcc cggcaacaat taatagactg gatggaggcg gataaagttg caggaccact    780
tctgcgctcg gcccttccgg ctggctggtt tattgctgat aaatctggag ccggtgagcg    840
tgggtctcgc ggtatcattg cagcactggg gccagatggt aagccctccc gtatcgtagt    900
tatctacacg acggggagtc aggcaactat ggatgaacga aatagacaga tcgctgagat    960
aggtgcctca ctgattaagc attggtaact gtcagaccaa gtttactcat atatacttta   1020
gattgattta aaacttcatt tttaatttaa aaggatctag gtgaagatcc ttttttgataa   1080 tctcatgacc aaaatccctt aacgttcaca acatagcc acggg                     1125
```

<210> SEQ ID NO 192
<211> LENGTH: 1414
<212> TYPE: DNA
<213> ORGANISM: Artificial Sequence
<220> FEATURE:
<223> OTHER INFORMATION: (N22)p5(N23) barcoded fragment

<400> SEQUENCE: 192

```
ttcacacaac atagccacgg gccgttttca tctgtgcata tggacagttt tcccttttgat     60 atgtaacggt gaacagttgt tctacttttg tttgttagtc ttgatgcttc actgatagat    120
acaagagcca taagaacctc agatccttcc gtatttagcc agtatgttct ctagtgtggt    180
tcgttgtttt tgcgtgagcc atgagaacga accattgaga tcatacttac tttgcatgtc    240
actcaaaaat tttgcctcaa aactggtgag ctgaattttt gcagttaaag catcgtgtag    300
tgtttttctt agtccgttat gtaggtagga atctgatgta atggttgttg gtattttgtc    360
accattcatt tttatctggt tgttctcaag ttcggttacg agatccattt gtctatctag    420
ttcaacttgg aaaatcaacg tatcagtcgg gcggcctcgc ttatcaacca ccaatttcat    480
attgctgtaa gtgtttaaat ctttacttat tggtttcaaa acccattggt taagccttt    540 aaactcatgg tagttatttt caagcattaa catgaactta aattcatcaa ggctaatctc    600
tatatttgcc ttgtgagttt tcttttgtgt tagttcttt aataaccact cataaatcct    660
catagagtat ttgttttcaa aagacttaac atgttccaga ttatattta tgaattttt     720 taactggaaa agataaggca atatctcttc actaaaaact aattctaatt tttcgcttga    780
gaacttggca tagtttgtcc actggaaaat ctcaaagcct ttaaccaaag gattcctgat    840
ttccacagtt ctcgtcatca gctctctggt tgctttagct aatacaccat aagcattttc    900
cctactgatg ttcatcatct gagcgtattg gttataagtg aacgataccg tccgttcttt    960
ccttgtaggg ttttcaatcg tggggttgag tagtgccaca cagcataaaa ttagcttggt   1020
ttcatgctcc gttaagtcat agcgactaat cgctagttca tttgctttga aaacaactaa   1080
ttcagacata catctcaatt ggtctaggtg attttaatca ctataccaat tgagatgggc   1140
tagtcaatga taattactag tccttttcct ttgagttgtg ggtatctgta aattctgcta   1200
gacctttgct ggaaaacttg taaattctgc tagaccctct gtaaattccg ctagaccttt   1260
gtgtgttttt tttgtttata ttcaagtggt tataatttat agaataaaga aagaataaaa   1320
aaagataaaa agaatagatc ccagcccgt gtataactca ctactttagt cagttccgca   1380
gtattacaaa aggattcaaa cagaaaggcc atgg                                1414
```

<210> SEQ ID NO 193
<211> LENGTH: 1130
<212> TYPE: DNA
<213> ORGANISM: Artificial Sequence

```
<220> FEATURE:
<223> OTHER INFORMATION: (N22)p15(N23) barcoded fragment

<400> SEQUENCE: 193
ttcacacaac atagccacgg gtgttcagct actgacgggg tggtgcgtaa cggcaaaagc      60
accgccggac atcagcgcta gcggagtgta tactggctta ctatgttggc actgatgagg     120
gtgtcagtga agtgcttcat gtggcaggag aaaaaaggct gcaccggtgc gtcagcagaa     180
tatgtgatac aggatatatt ccgcttcctc gctcactgac tcgctacgct cggtcgttcg     240
actgcggcga gcggaaatgg cttacgaacg gggcggagat tcctggaag atgccaggaa      300 gatacttaac agggaagtga gagggccgcg gcaaagccgt ttttccatag gctccgcccc     360
cctgacaagc atcacgaaat ctgacgctca aatcagtggt ggcgaaaccc gacaggacta     420
taaagatacc aggcgtttcc ccctggcggc tccctcgtgc gctctcctgt tcctgccttt     480
cggtttaccg gtgtcattcc gctgttatgg ccgcgtttgt ctcattccac gcctgacact     540
cagttccggg taggcagttc gctccaagct ggactgtatg cacgaacccc ccgttcagtc     600
cgaccgctgc gccttatccg gtaactatcg tcttgagtcc aacccggaaa gacatgcaaa     660
agcaccactg gcagcagcca ctggtaattg atttagagga gttagtcttg aagtcatgcg     720
ccggttaagg ctaaactgaa aggacaagtt ttggtgactg cgctcctcca gccagttac      780 ctcggttcaa agagttggta gctcagagaa ccttcgaaaa accgcctgc aaggcggttt      840 tttcgttttc agagcaagag attacgcgca gaccaaaacg atctcaagaa gatcatctta     900
ttaatcagat aaaatatttc tagatttcag tgcaatttat ctcttcaaat gtagcacctg     960
aagtcagccc catacgatat aagttgtaat tctcatgttt gacagcttat cacccagtcc    1020
tgctcgcttc gctacttggc catacccacg ccgaaacaag cgctcatgag cccgaagtgg    1080
cgagcccgat cttccccatc ggtgatgtct caaacagaa aggccatggg                1130

<210> SEQ ID NO 194
<211> LENGTH: 943
<212> TYPE: DNA
<213> ORGANISM: Artificial Sequence
<220> FEATURE:
<223> OTHER INFORMATION: (N22)pMB1(N23) barcoded fragment

<400> SEQUENCE: 194
ttcacacaac atagccacgg gagttttcgt tccactgagc gtcagacccc gtagaaaaga      60
tcaaaggatc ttcttgagat cctttttttc tgcgcgtaat ctgctgcttg caaacaaaaa     120
aaccaccgct accagcggtg gtttgtttgc cggatcaaga gctaccaact cttttttccga    180 aggtaactgg cttcagcaga gcgcagatac caaatactgt ccttctagtg tagccgtagt     240
taggccacca cttcaagaac tctgtagcac cgcctacata cctcgctctg ctaatcctgt     300
taccagtggc tgctgccagt ggcgataagt cgtgtcttac cgggttggac tcaagacgat     360
agttaccgga taaggcgcag cggtcgggct gaacggggg ttcgtgcaca cagcccagct      420
tggagcgaac gacctacacc gaactgagat acctacagcg tgagctatga gaaagcgcca     480
cgcttcccga agggagaaag gcggacaggt atccggtaag cggcagggtc ggaacaggag     540
agcgcacgag ggagcttcca gggggaaacg cctggtatct ttatagtcct gtcgggtttc     600
gccacctctg acttgagcgt cgatttttgt gatgctcgtc agggggggcgg agcctatgga     660 aaaacgccag caacgcggcc ttttttacggt tcctggcctt ttgctggcct tttgctcaca     720
tgttctttcc tgcgttatcc cctgattctg tggataaccg tattaccgcc tttgagtgag     780
```

```
ctgataccgc tcgccgcagc cgaacgaccg agcgcagcga gtcagtgagc gaggaagcgg    840
aagagcgcct gatgcggtat tttctcctta cgcatctgtg cggtatttca caccgcatat    900
gctggatcct tgacagctag ctcagtccta ggtataatac tag                      943
```

<210> SEQ ID NO 195
<211> LENGTH: 857
<212> TYPE: DNA
<213> ORGANISM: Artificial Sequence
<220> FEATURE:
<223> OTHER INFORMATION: (N22)pMB1 mutant(N23) barcoded fragment

<400> SEQUENCE: 195

```
ttcacacaac atagccacgg ggctcactca aaggcggtaa tacggttatc cacagaatca     60
ggggataacg caggaaagaa catgtgagca aaaggccagc aaaaggccag gaaccgtaaa    120
aaggccgcgt tgctggcgtt tttccatagg ctccgccccc ctgacgagca tcacaaaaat    180
cgacgctcaa gtcagaggtg gcgaaacccg acaggactat aaagatacca ggcgtttccc    240
cctggaagct ccctcgtgcg ctctcctgtt ccgaccctgc cgcttaccgg atacctgtcc    300
gcctttctcc cttcgggaag cgtggcgctt tctcatagct cacgctgtag gtatctcagt    360
tcggtgtagg tcgttcgctc caagctgggc tgtgtgcacg aaccccccgt tcagcccgac    420
cgctgcgcct tatccggtaa ctatcgtctt gagtccaacc cggtaagaca cgacttatcg    480
ccactggcag cagccactgg taacaggatt agcagagcga ggtatgtagg cggtgctaca    540
gagttcttga agtggtggcc taactacggc tacactagaa gaacagtatt tggtatctgc    600
gctctgctga agccagttac cttcggaaaa agagttggta gctcttgatc cggcaaacaa    660
accaccgctg gtagcggtgg tttttttgtt tgcaagcagc agattacgcg cagaaaaaaa    720
ggatctcaag aagatccttt gatcttttct acggggtctg acgctcagtg gaacgaaaac    780
tcacgttaag ggattttggt catgagatta tcaaaaagga tcttcaccta gatcctttca    840
aacagaaagg ccatggg                                                   857
```

<210> SEQ ID NO 196
<211> LENGTH: 164
<212> TYPE: DNA
<213> ORGANISM: Artificial Sequence
<220> FEATURE:
<223> OTHER INFORMATION: (N23)pLac(RBS1) barcoded fragment

<400> SEQUENCE: 196

```
ttcaaacaga aaggccatgg gcaacgcaat taatgtgagt tagctcactc attaggcacc     60
ccaggcttta cactttatgc ttccggctcg tatgttgtgt ggaattgtga gcggataaca    120
atagaaataa ttttgtttaa ctttaagaag gagatataca tatg                     164
```

<210> SEQ ID NO 197
<211> LENGTH: 1780
<212> TYPE: DNA
<213> ORGANISM: Artificial Sequence
<220> FEATURE:
<223> OTHER INFORMATION: N23)LacIT7(RBS1) barcoded fragment

<400> SEQUENCE: 197

```
tcaaacagaa aggccatggg gaaactaccc ataatacaag aaaagcccgt cacgggcttc     60
tcagggcgtt ttatggcggg tctgctatgt ggtgctatct gacttttgc tgttcagcag    120 ttcctgccct ctgattttcc agtctgacca cttcggatta tccgtgaca ggtcattcag    180 actggctaat gcacccagta aggcagcggt atcatcaaca ggcttacccg tcttactgtc    240
```

```
gggaattcgc gttggccgat tcattaatgc agctggcacg acaggtttcc tctagatttc      300
agtgcaattt atctcttcaa atgtagcacc tgaagtcagc ccatacgat ataagttgta       360 attctcatgt tagtcatgcc ccgcgccac cggaaggagc tgactgggtt gaaggctctc       420
aagggcatcg gtcgagatcc cggtgcctaa tgagtgagct aacttacatt aattgcgttg      480
cgctcactgc ccgctttcca gtcgggaaac ctgtcgtgcc agctgcatta atgaatcggc      540
caacgcgcgg ggagaggcgg tttgcgtatt ggcgccagg gtggttttc ttttcaccag        600 tgagacgggc aacagctgat tgcccttcac cgcctggccc tgagagagtt gcagcaagcg      660
gtccacgctg gtttgcccca gcaggcgaaa atcctgtttg atggtggtta acggcgggat      720
ataacatgag ctgtcttcgg tatcgtcgta tcccactacc gagatgtccg caccaacgcg      780
cagcccggac tcggtaatgg cgcgcattgc gcccagcgcc atctgatcgt tggcaaccag      840
catcgcagtg gaacgatgc cctcattcag catttgcatg gtttgttgaa aaccggacat       900
ggcactccag tcgccttccc gttccgctat cggctgaatt tgattgcgag tgagatattt      960
atgccagcca gccagacgca gacgcgccga cagaacttt aatgggcccg ctaacagcgc       1020
gatttgctgg tgacccaatg cgaccagatg ctccacgccc agtcgcgtac cgtcttcatg      1080
ggagaaaata atactgttga tgggtgtctg gtcagagaca tcaagaaata acgccggaac      1140
attagtgcag gcagcttcca cagcaatggc atcctggtca tccagcggat agttaatgat      1200
cagcccactg acgcgttgcg cgagaagatt gtgcaccgcc gctttacagg cttcgacgcc      1260
gcttcgttct accatcgaca ccaccacgct ggcacccagt tgatcggcgc gagatttaat      1320
cgccgcgaca atttgcgacg gcgcgtgcag ggccagactg gaggtggcaa cgccaatcag      1380
caacgactgt ttgcccgcca gttgttgtgc cacgcggttg ggaatgtaat tcagctccgc      1440
catcgccgct tccactttt cccgcgtttt cgcagaaacg tggctggcct ggttcaccac       1500
gcgggaaacg gtctgataag agacaccggc atactctgcg acatcgtata acgttactgg      1560
tttcacattc accaccctga attgactctc ttccgggcgc tatcatgcca taccgcgaaa      1620
ggttttgcgc cattcgatgg tgtccggat ctcgacgctc tcccttatgc gactcctgca       1680
ttaggaaatt aatacgactc actataggg aattgtgagc ggataacaat tcccctctag       1740
aaataatttt gtttaacttt aagaaggaga tatacatatg                             1780
```

<210> SEQ ID NO 198
<211> LENGTH: 242
<212> TYPE: DNA
<213> ORGANISM: Artificial Sequence
<220> FEATURE:
<223> OTHER INFORMATION: (N31)t7t(N21) barcoded fragment

<400> SEQUENCE: 198

```
tgatgggctg aagggtttaa gggctgctaa caaagcccga aggaagctg agttggctgc        60 tgccaccgct gagcaataac tagcataacc ccttgggggcc tctaaacggg tcttgagggg      120 tttttttgctg aaaggaggaa ctatatccgg atatcccgca agaggcccgg cagtaccggc     180
ataaccaagc ctatgcctac agcatccagg gtgacggtgc cttccctcga ctcacacttg      240
gg                                                                      242
```

<210> SEQ ID NO 199
<211> LENGTH: 242
<212> TYPE: DNA
<213> ORGANISM: Artificial Sequence
<220> FEATURE:

<223> OTHER INFORMATION: (N31)t7t(LK3) barcoded fragment

<400> SEQUENCE: 199

```
tgatgggctg aagggtttaa gggctgctaa caaagcccga aaggaagctg agttggctgc     60
tgccaccgct gagcaataac tagcataacc ccttggggcc tctaaacggg tcttgagggg    120
tttttttgctg aaaggaggaa ctatatccgg atatcccgca agaggcccgg cagtaccggc   180
ataaccaagc ctatgcctac agcatccagg gtgacggtgc ctcaggctcg tcttcttcag    240
gg                                                                    242
```

<210> SEQ ID NO 200
<211> LENGTH: 1671
<212> TYPE: DNA
<213> ORGANISM: Artificial Sequence
<220> FEATURE:
<223> OTHER INFORMATION: (LK3)LacI(N21) barcoded fragment

<400> SEQUENCE: 200

```
tcaggctcgt cttcttcagg ggaaactacc cataatacaa gaaaagcccg tcacgggctt     60
ctcagggcgt tttatggcgg gtctgctatg tggtgctatc tgacttttg ctgttcagca    120
gttcctgccc tctgattttc cagtctgacc acttcggatt atcccgtgac aggtcattca   180
gactggctaa tgcacccagt aaggcagcgg tatcatcaac aggcttaccc gtcttactgt   240
cgggaattcg cgttggccga ttcattaatg cagctggcac gacaggtttc ctctagattt   300
cagtgcaatt tatctcttca aatgtagcac ctgaagtcag ccccatacga tataagttgt   360
aattctcatg ttagtcatgc cccgcgccca ccggaaggag ctgactgggt tgaaggctct   420
caagggcatc ggtcgagatc ccggtgccta atgagtgagc taacttacat taattgcgtt   480
gcgctcactg cccgctttcc agtcgggaaa cctgtcgtgc cagctgcatt aatgaatcgg   540
ccaacgcgcg gggagaggcg gtttgcgtat tgggcgccag ggtggttttt cttttcacca   600
gtgagacggg caacagctga ttgcccttca ccgcctggcc ctgagagagt tgcagcaagc   660
ggtccacgct ggtttgcccc agcaggcgaa aatcctgttt gatggtggtt aacggcggga   720
tataacatga gctgtcttcg gtatcgtcgt atcccactac cgagatgtcc gcaccaacgc   780
gcagcccgga ctcggtaatg gcgcgcattg cgcccagcgc catctgatcg ttggcaacca   840
gcatcgcagt gggaacgatg ccctcattca gcatttgcat ggtttgttga aaaccggaca   900
tggcactcca gtcgccttcc cgttccgcta tcggctgaat ttgattgcga gtgagatatt   960
tatgccagcc agccagacgc agacgcgccg agacagaact taatgggccc gctaacagcg  1020
cgatttgctg gtgacccaat gcgaccagat gctccacgcc cagtcgcgta ccgtcttcat  1080
gggagaaaat aatactgttg atgggtgtct ggtcagagac atcaagaaat aacgccggaa  1140
cattagtgca ggcagcttcc acagcaatgg catcctggtc atccagcgga tagttaatga  1200
tcagcccact gacgcgttgc gcgagaagat tgtgcaccgc cgctttacag gcttcgacgc  1260
cgcttcgttc taccatcgac accaccacgc tggcacccag ttgatcggcg cgagatttaa  1320
tcgccgcgac aatttgcgac ggcgcgtgca gggccagact ggaggtggca acgccaatca  1380
gcaacgactg tttgcccgcc agttgttgtg ccacgcggtt gggaatgtaa ttcagctccg  1440
ccatcgccgc ttccactttt tcccgcgttt tcgcagaaac gtggctggcc tggttcacca  1500
cgcgggaaac ggtctgataa gagacaccgg catactctgc gacatcgtat aacgttactg  1560
gtttcacatt caccaccctg aattgactct cttccgggcg ctatcatgcc ataccgcgaa  1620
aggttttgcg ccattcgatg gtgtccggga ttccctcgac tcacacttgg g            1671
```

<210> SEQ ID NO 201
<211> LENGTH: 1935
<212> TYPE: DNA
<213> ORGANISM: Artificial Sequence
<220> FEATURE:
<223> OTHER INFORMATION: (RBS1)dxs(RBS2stop) barcoded fragment

<400> SEQUENCE: 201

```
tagaaataat tttgtttaac tttaagaagg agatatacat atgagttttg atattgccaa      60
atacccgacc ctggcactgg tcgactccac ccaggagtta cgactgttgc cgaaagagag     120
tttaccgaaa ctctgcgacg aactgcgccg ctatttactc gacagcgtga gccgttccag     180
cgggcacttc gcctccgggc tgggcacggt cgaactgacc gtggcgctgc actatgtcta     240
caacaccccg tttgaccaat tgatttggga tgtggggcat caggcttatc cgcataaaat     300
tttgaccgga cgccgcgaca aaatcggcac catccgtcag aaaggcggtc tgcacccgtt     360
cccgtggcgc ggcgaaagcg aatatgacgt attaagcgtc gggcattcat caacctccat     420
cagtgccgga attggtattg cggttgctgc cgaaaaagaa ggcaaaaatc gccgcaccgt     480
ctgtgtcatt ggcgatggcg cgattaccgc aggcatggcg tttgaagcga tgaatcacgc     540
gggcgatatc cgtcctgata tgctggtgat tctcaacgac aatgaaatgt cgatttccga     600
aaatgtcggc gcgctcaaca accatctggc acagctgctt tccggtaagc tttactcttc     660
actgcgcgaa ggcgggaaaa agttttctc tggcgtgccg ccaattaaag agctgctcaa     720
acgcaccgaa gaacatatta aaggcatggt agtgcctggc acgttgtttg aagagctggg     780
ctttaactac atcggcccgg tggacggtca cgatgtgctg gggcttatca ccacgctaaa     840
gaacatgcgc gacctgaaag cccgcagtt cctgcatatc atgaccaaaa aaggtcgtgg     900
ttatgaaccg gcagaaaaag acccgatcac tttccacgcc gtgcctaaat tgatccctc      960
cagcggttgt tgccgaaaaa gtagcggcgg tttgccgagc tattcaaaaa tctttggcga    1020
ctggttgtgc gaaacggcag cgaaagacaa caagctgatg gcgattactc cggcgatgcg    1080
tgaaggttcc ggcatggtcg agttttcacg taaattcccg gatcgctact cgacgtggc     1140
aattgccgag caacacgcgg tgacctttgc tgcgggtctg gcgattggtg ggtacaaacc    1200
cattgtcgcg atttactcca cttttcctgca acgcgcctat gatcaggtgc tgcatgacgt    1260
ggcgattcaa aagcttccgg tcctgttcgc catcgaccgc gcgggcattg ttggtgctga    1320
cggtcaaacc catcagggtg cttttgatct ctcttacctg cgctgcatac cggaaatggt    1380
cattatgacc ccgagcgatg aaaacgaatg tcgccagatg ctctataccg ctatcacta    1440
taacgatggc ccgtcagcgg tgcgctaccc gcgtggcaac gcggtcggcg tggaactgac    1500
gccgctggaa aaactaccaa ttggcaaagg cattgtgaag cgtcgtggcg agaaactggc    1560
gatccttaac tttggtacgc tgatgccaga agcggcgaaa gtcgccgaat cgctgaacgc    1620
cacgctggtc gatatgcgtt ttgtgaaacc gcttgatgaa gcgttaattc tggaaatggc    1680
cgccagccat gaagcgctgg tcaccgtaga agaaaacgcc attatgggcg gcgcaggcag    1740
cggcgtgaac gaagtgctga tggcccatcg taaccagta cccgtgctga acattggcct    1800
gccggacttc tttattccgc aaggaactca ggaagaaatg cgcgccgaac tcggcctcga    1860
tgccgctggt atggaagcca aaatcaaggc ctggctggca taaccgttca tttatcacaa    1920
aaggattgtt cgatg                                                    1935
```

<210> SEQ ID NO 202

```
<211> LENGTH: 602
<212> TYPE: DNA
<213> ORGANISM: Artificial Sequence
<220> FEATURE:
<223> OTHER INFORMATION: (RBS2stop)idi(RBS3stop) barcoded fragment

<400> SEQUENCE: 202
taaccgttca tttatcacaa aaggattgtt cgatgcaaac ggaacacgtc attttattga    60
atgcacaggg agttcccacg ggtacgctgg aaaagtatgc cgcacacacg gcagacaccc   120
gcttacatct cgcgttctcc agttggctgt ttaatgccaa aggacaatta ttagttaccc   180
gccgcgcact gagcaaaaaa gcatggcctg gcgtgtggac taactcggtt tgtgggcacc   240
cacaactggg agaaagcaac gaagacgcag tgatccgccg ttgccgttat gagcttggcg   300
tggaaattac gcctcctgaa tctatctatc ctgactttcg ctaccgcgcc accgatccga   360
gtggcattgt ggaaaatgaa gtgtgtccgg tatttgccgc acgcaccact agtgcgttac   420
agatcaatga tgatgaagtg atggattatc aatggtgtga tttagcagat gtattacacg   480
gtattgatgc cacgccgtgg gcgttcagtc cgtggatggt gatgcaggcg acaaatcgcg   540
aagccagaaa acgattatct gcatttaccc agcttaaatg attcacacag gaaacagcta   600
tg                                                                  602

<210> SEQ ID NO 203
<211> LENGTH: 1826
<212> TYPE: DNA
<213> ORGANISM: Artificial Sequence
<220> FEATURE:
<223> OTHER INFORMATION: (RBS3stop)valC(RBS4stop) barcoded fragment

<400> SEQUENCE: 203
tgattcacac aggaaacagc tatggccgag atgttcaacg gcaactcttc taacgacgga    60
tcttcttgca tgcccgtgaa ggacgccctg cgacgaaccg gcaaccacca ccccaacctg   120
tggaccgacg acttcatcca gtctctgaac tctccctact ctgactcttc ttaccacaag   180
caccgagaga tcctgatcga cgagatccga gacatgttct ctaacggcga gggcgacgag   240
ttcggcgtgc tcgagaacat ctggttcgtg gacgtggtgc agcgactggg catcgaccga   300
cacttccagg aggagatcaa gaccgccctg gactacatct acaagttctg gaaccacgac   360
tctatcttcg cgacctgaa catggtggcc ctgggcttcc gaatcctgcg actgaaccga   420
tacgtggcct cttctgacgt gttcaagaag ttcaagggcg aggagggcca gttctctggc   480
ttcgagtcct ctgaccagga cgctaagctc gaaatgatgc tgaacctgta caaggcctct   540
gagctggact tccccgacga ggacatcctg aaggaggccc gagccttcgc ctctatgtac   600
ctgaagcacg tgatcaagga gtacggcgac atccaggagt ctaagaaccc cctgctgatg   660
gagatcgagt acaccttcaa gtaccctgg cgatgccgac tgccccgact cgaggcctgg   720
aacttcatcc acatcatgcg acagcaggac tgcaacatct ctctggccaa caacctctac   780
aagatcccca gatctacat gaagaagatc ctcgagctgg ccatcctgga cttcaacatc   840
ctgcagtctc agcaccagca cgagatgaag ctgatctcta cctggtggaa gaactcttct   900
gctatccagc tggacttctt ccgacaccga cacatcgagt cttacttttg gtgggcctcg   960
cccctgttcg agcccgagtt ctctacctgc cgaatcaact gcaccaagct gtctaccaag  1020
atgttcctgc tggacgacat ctacgacacc tacggcaccg tcgaggagct gaagcccttc  1080
accaccaccc tgacccgatg ggacgtgtct accgtggaca accaccccga ctacatgaag  1140
atcgccttca cttctcttta cgagatctac aaggagatcg cctctgaggc cgagcgaaag  1200
```

| | | |
|---|---|---|
| cacggcccct tcgtgtacaa gtacctgcag tcttgctgga agtcttacat cgaggcctac | 1260 | |
| atgcaggagg ccgagtggat cgcctctaac cacatccccg gcttcgacga gtacctgatg | 1320 | |
| aacggcgtga agtcctctgg catgcgaatc ctgatgatcc acgccctgat cctgatggac | 1380 | |
| accccctgt ctgacgagat tctcgagcag ctggacatcc cctcgtctaa gtctcaggcc | 1440 | |
| ctgctgtctc tgatcacccg actggtggac gacgtgaagg acttcgagga cgagcaggcc | 1500 | |
| cacggcgaga tggcctcttc tatcgagtgc tacatgaagg acaaccacgg ctctacccga | 1560 | |
| gaggacgccc tgaactacct gaagatccga atcgagtctt gcgtgcagga gctgaacaag | 1620 | |
| gagctgctcg agccctctaa catgcacgga tctttccgaa acctgtacct gaacgtggga | 1680 | |
| atgcgagtga ttttcttcat gctgaacgac ggcgacctgt tcacccactc taaccgaaag | 1740 | |
| gagatccagg acgccatcac caagttcttc gtcgagccca tcatcccta aattaattgt | 1800 | |
| tcttttttca ggtgaaggtt cccatg | 1826 | |

<210> SEQ ID NO 204
<211> LENGTH: 953
<212> TYPE: DNA
<213> ORGANISM: Artificial Sequence
<220> FEATURE:
<223> OTHER INFORMATION: (RBS4stop)ispA(N31) barcoded fragment

<400> SEQUENCE: 204

| | | |
|---|---|---|
| taaattaatt gttctttttt caggtgaagg ttcccatgga ctttccgcag caactcgaag | 60 | |
| cctgcgttaa gcaggccaac caggcgctga gccgttttat cgcccccactg ccctttcaga | 120 | |
| acactcccgt ggtcgaaacc atgcagtatg gcgcattatt aggtggtaag cgcctgcgac | 180 | |
| ctttcctggt ttatgccacc ggtcatatgt tcggcgttag cacaaacacg ctggacgcac | 240 | |
| ccgctgccgc cgttgagtgt atccacgctt actcattaat tcatgatgat ttaccggcaa | 300 | |
| tggatgatga cgatctgcgt cgcggtttgc caacctgcca tgtgaagttt ggcgaagcaa | 360 | |
| acgcgattct cgctggcgac gctttacaaa cgctggcgtt ctcgatttta agcgatgccg | 420 | |
| atatgccgga agtgtcggac cgcgacagaa tttcgatgat ttctgaactg gcagagccca | 480 | |
| gtggtattgc cggaatgtgc ggtggtcagg cattagattt agacgcggaa ggcaaacacg | 540 | |
| tacctctgga cgcgcttgag cgtattcatc gtcataaaac cggcgcattg attcgcgccg | 600 | |
| ccgttcgcct tggtgcatta agcgccgag ataaggacg tcgtgctctg ccggtactcg | 660 | |
| acaagtatgc agagagcatc ggccttgcct tccaggttca ggatgacatc ctggatgtgg | 720 | |
| tgggagatac tgcaacgttg gaaaacgcc agggtgccga ccagcaactt ggtaaaagta | 780 | |
| cctaccctgc acttctgggt cttgagcaag cccggaagaa agcccgggat ctgatcgacg | 840 | |
| atgcccgtca gtcgctgaaa caactggctg aacagtcact cgatacctcg gcactggaag | 900 | |
| cgctagcgga ctacatcatc cagcgtaata atgatgggc tgaagggttt aag | 953 | |

<210> SEQ ID NO 205
<211> LENGTH: 621
<212> TYPE: DNA
<213> ORGANISM: Artificial Sequence
<220> FEATURE:
<223> OTHER INFORMATION: (RBS1)idi(RBS2stop) barcoded fragment

<400> SEQUENCE: 205

| | | |
|---|---|---|
| tagaaataat tttgtttaac tttaagaagg agatatacat atgcaaacgg aacacgtcat | 60 | |
| tttattgaat gcacagggag ttcccacggg tacgctggaa aagtatgccg cacacacggc | 120 | |

| | |
|---|---|
| agacacccgc ttacatctcg cgttctccag ttggctgttt aatgccaaag gacaattatt | 180 |
| agttacccgc cgcgcactga gcaaaaaagc atggcctggc gtgtggacta actcggtttg | 240 |
| tgggcaccca caactgggag aaagcaacga agacgcagtg atccgccgtt gccgttatga | 300 |
| gcttggcgtg gaaattacgc ctcctgaatc tatctatcct gactttcgct accgcgccac | 360 |
| cgatccgagt ggcattgtgg aaaatgaagt gtgtccggta tttgccgcac gcaccactag | 420 |
| tgcgttacag atcaatgatg atgaagtgat ggattatcaa tggtgtgatt tagcagatgt | 480 |
| attacacggt attgatgcca cgccgtgggc gttcagtccg tggatggtga tgcaggcgac | 540 |
| aaatcgcgaa gccagaaaac gattatctgc atttacccag cttaaataac cgttcattta | 600 |
| tcacaaaagg attgttcgat g | 621 |

<210> SEQ ID NO 206
<211> LENGTH: 1916
<212> TYPE: DNA
<213> ORGANISM: Artificial Sequence
<220> FEATURE:
<223> OTHER INFORMATION: (RBS2stop)dxs(RBS3stop) barcoded fragment

<400> SEQUENCE: 206

| | |
|---|---|
| taaccgttca tttatcacaa aaggattgtt cgatgagttt tgatattgcc aaatacccga | 60 |
| ccctggcact ggtcgactcc acccaggagt tacgactgtt gccgaaagag agtttaccga | 120 |
| aactctgcga cgaactgcgc cgctatttac tcgacagcgt gagccgttcc agcgggcact | 180 |
| tcgcctccgg gctgggcacg gtcgaactga ccgtggcgct gcactatgtc tacaacaccc | 240 |
| cgtttgacca attgatttgg gatgtggggc atcaggctta ccgcataaaa attttgaccg | 300 |
| gacgccgcga caaaatcggc accatccgtc agaaaggcgg tctgcacccg ttcccgtggc | 360 |
| gcggcgaaag cgaatatgac gtattaagcg tcgggcattc atcaacctcc atcagtgccg | 420 |
| gaattggtat tgcggttgct gccgaaaaag aaggcaaaaa tcgccgcacc gtctgtgtca | 480 |
| ttggcgatgg cgcgattacc gcaggcatgg cgtttgaagc gatgaatcac gcgggcgata | 540 |
| tccgtcctga tatgctggtg attctcaacg acaatgaaat gtcgatttcc gaaaatgtcg | 600 |
| gcgcgctcaa caaccatctg gcacagctgc tttccggtaa gctttactct tcactgcgcg | 660 |
| aaggcgggaa aaaagttttc tctggcgtgc cgccaattaa agagctgctc aaacgcaccg | 720 |
| aagaacatat taaaggcatg gtagtgcctg gcacgttgtt tgaagagctg ggctttaact | 780 |
| acatcggccc ggtggacggt cacgatgtgc tggggcttat caccacgcta aagaacatgc | 840 |
| gcgacctgaa aggcccgcag ttcctgcata tcatgaccaa aaaaggtcgt ggttatgaac | 900 |
| cggcagaaaa agaccccgatc actttccacg ccgtgcctaa atttgatccc tccagcggtt | 960 |
| gtttgccgaa aagtagcggc ggtttgccga gctattcaaa aatctttggc gactggttgt | 1020 |
| gcgaaacggc agcgaaagac aacaagctga tggcgattac tccggcgatg cgtgaaggtt | 1080 |
| ccggcatggt cgagttttca cgtaaaattc cggatcgcta cttcgacgtg gcaattgccg | 1140 |
| agcaacacgc ggtgacccttt gctgcgggtc tggcgattgg tgggtacaaa cccattgtcg | 1200 |
| cgatttactc cactttcctg caacgcgcct atgatcaggt gctgcatgac gtggcgattc | 1260 |
| aaaagcttcc ggtcctgttc gccatcgacc gcgcgggcat tgttggtgct gacggtcaaa | 1320 |
| cccatcaggg tgcttttgat ctctcttacc tgcgctgcat accggaaatg gtcattatga | 1380 |
| ccccgagcga tgaaaacgaa tgtcgccaga tgctctatac cggctatcac tataacgatg | 1440 |
| gcccgtcagc ggtgcgctac ccgcgtgcaa acgcggtcgg cgtggaactg acgccgctgg | 1500 |
| aaaaactacc aattggcaaa ggcattgtga agcgtcgtgg cgagaaactg gcgatcctta | 1560 |

```
actttggtac gctgatgcca gaagcggcga aagtcgccga atcgctgaac gccacgctgg     1620
tcgatatgcg ttttgtgaaa ccgcttgatg aagcgttaat tctggaaatg gccgccagcc     1680
atgaagcgct ggtcaccgta gaagaaaacg ccattatggg cggcgcaggc agcggcgtga     1740
acgaagtgct gatggcccat cgtaaaccag tacccgtgct gaacattggc ctgccggact     1800
tctttattcc gcaaggaact caggaagaaa tgcgcgccga actcggcctc gatgccgctg     1860
gtatggaagc caaaatcaag gcctggctgg catgattcac acaggaaaca gctatg        1916
```

<210> SEQ ID NO 207
<211> LENGTH: 1919
<212> TYPE: DNA
<213> ORGANISM: Artificial Sequence
<220> FEATURE:
<223> OTHER INFORMATION: (RBS3stop)dxs(RBS4stop) barcoded fragment

<400> SEQUENCE: 207

```
tgattcacac aggaaacagc tatgagtttt gatattgcca ataccccgac cctggcactg       60
gtcgactcca cccaggagtt acgactgttg ccgaaagaga gtttaccgaa actctgcgac      120
gaactgcgcc gctatttact cgacagcgtg agccgttcca gcgggcactt cgcctccggg      180
ctgggcacgg tcgaactgac cgtggcgctg cactatgtct acaacacccc gtttgaccaa      240
ttgatttggg atgtggggca tcaggcttat ccgcataaaa ttttgaccgg acgccgcgac      300
aaaatcggca ccatccgtca gaaggcggt ctgcacccgt tcccgtggcg cggcgaaagc      360
gaatatgacg tattaagcgt cgggcattca tcaacctcca tcagtgccgg aattggtatt      420
gcggttgctg ccgaaaaaga aggcaaaaat cgccgcaccg tctgtgtcat tggcgatggc      480
gcgattaccg caggcatggc gtttgaagcg atgaatcacg cgggcgatat ccgtcctgat      540
atgctggtga ttctcaacga caatgaaatg tcgatttccg aaaatgtcgg cgcgctcaac      600
aaccatctgg cacagctgct ttccggtaag ctttactctt cactgcgcga aggcgggaaa      660
aaagttttct ctggcgtgcc gccaattaaa gagctgctca aacgcaccga gaacatatt      720 aaaggcatgg tagtgcctgg cacgttgttt gaagagctgg gctttaacta catcggcccg      780
gtggacggtc acgatgtgct ggggcttatc accacgctaa agaacatgcg cgacctgaaa      840 ggccgcagt tcctgcatat catgaccaaa aaaggtcgtg ttatgaacc ggcagaaaaa      900 gacccgatca ctttccacgc cgtgcctaaa tttgatccct ccagcggttg tttgccgaaa      960
agtagcggcg gtttgccgag ctattcaaaa atctttggcg actggttgtg cgaaacggca     1020
gcgaaagaca acaagctgat ggcgattact ccggcgatgc gtgaaggttc cggcatggtc     1080
gagttttcac gtaaattccc ggatcgctac ttcgacgtgg caattgccga gcaacacgcg     1140 gtgaccttg ctgcgggtct ggcgattggt gggtacaaac ccattgtcgc gatttactcc     1200
actttcctgc aacgcgccta tgatcaggtg ctgcatgacg tggcgattca aaagcttccg     1260
gtcctgttcg ccatcgaccg cgcgggcatt gttggtgctg acggtcaaac ccatcagggt     1320
gcttttgatc tctcttacct gcgctgcata ccggaaatgg tcattatgac cccgagcgat     1380
gaaaacgaat gtcgccagat gctctatacc ggctatcact ataacgatgg cccgtcagcg     1440
gtgcgctacc cgcgtggcaa cgcggtcggc gtggaactga cgccgctgga aaaactacca     1500
attggcaaag gcattgtgaa gcgtcgtggc gagaaactgg cgatccttaa ctttggtacg     1560
ctgatgccag aagcggcgaa agtcgccgaa tcgctgaacg ccacgctggt cgatatgcgt     1620
tttgtgaaac cgcttgatga agcgttaatt ctggaaatgg ccgccagcca tgaagcgctg     1680
```

```
gtcaccgtag aagaaaacgc cattatgggc ggcgcaggca gcggcgtgaa cgaagtgctg    1740
atggcccatc gtaaaccagt acccgtgctg aacattggcc tgccggactt ctttattccg    1800
caaggaactc aggaagaaat gcgcgccgaa ctcggcctcg atgccgctgg tatggaagcc    1860
aaaatcaagg cctggctggc ataaattaat tgttcttttt tcaggtgaag gttcccatg     1919
```

<210> SEQ ID NO 208
<211> LENGTH: 1916
<212> TYPE: DNA
<213> ORGANISM: Artificial Sequence
<220> FEATURE:
<223> OTHER INFORMATION: (RBS4stop)dxs(N31) barcoded fragment

<400> SEQUENCE: 208

```
taaattaatt gttcttttt caggtgaagg ttcccatgag ttttgatatt gccaaatacc      60
cgaccctggc actggtcgac tccacccagg agttacgact gttgccgaaa gagagtttac    120
cgaaactctg cgacgaactg cgccgctatt tactcgacag cgtgagccgt tccagcgggc    180
acttcgcctc cgggctgggc acggtcgaac tgaccgtggc gctgcactat gtctacaaca    240
ccccgtttga ccaattgatt tgggatgtgg ggcatcaggc ttatccgcat aaaattttga    300
ccggacgccg cgacaaaatc ggcaccatcc gtcagaaagg cggtctgcac ccgttcccgt    360
ggcgcggcga aagcgaatat gacgtattaa gcgtcgggca ttcatcaacc tccatcagtg    420
ccggaattgg tattgcggtt gctgccgaaa agaaggcaa aaatcgccgc accgtctgtg    480
tcattggcga tggcgcgatt accgcaggca tggcgtttga agcgatgaat cacgcgggcg    540
atatccgtcc tgatatgctg gtgattctca acgacaatga aatgtcgatt ccgaaaatg     600 tcggcgcgct caacaaccat ctggcacagc tgctttccgg taagctttac tcttcactgc    660
gcgaaggcgg gaaaaagtt ttctctggcg tgccgccaat taaagagctg ctcaaacgca    720
ccgaagaaca tattaaaggc atggtagtgc ctggcacgtt gtttgaagag ctgggcttta    780
actacatcgg cccggtggac ggtcacgatg tgctggggct tatcaccacg ctaaagaaca    840
tgcgcgacct gaaaggcccg cagttcctgc atatcatgac caaaaaaggt cgtggttatg    900
aaccggcaga aaaagacccg atcacttttcc acgccgtgcc taaatttgat ccctccagcg    960
gttgtttgcc gaaaagtagc ggcggtttgc cgagctattc aaaaatcttt ggcgactggt   1020
tgtgcgaaac ggcagcgaaa gacaacaagc tgatggcgat tactccggcg atgcgtgaag   1080
gttccggcat ggtcgagttt tcacgtaaat tcccggatcg ctacttcgac gtggcaattg   1140
ccgagcaaca cgcggtgacc tttgctgcgg tgtctggcga tggtgggtac aaacccattg   1200
tcgcgattta ctccactttc ctgcaacgcg cctatgatca ggtgctgcat gacgtggcga   1260
ttcaaaagct tccggtcctg ttcgccatcg accgcgcggg cattgttggt gctgacggtc   1320
aaacccatca gggtgctttt gatctctctt acctgcgctg cataccggaa atggtcatta   1380
tgaccccgag cgatgaaaac gaatgtcgcc agatgctcta taccggctat cactataacg   1440
atggcccgtc agcggtgcgc tacccgcgtg caacgcggt cggcgtggaa ctgacgccgc   1500
tggaaaaact accaattggc aaaggcattg tgaagcgtcg tggcgagaaa ctggcgatcc   1560
ttaactttgg tacgctgatg ccagaagcgg cgaaagtcgc cgaatcgctg aacgccacgc   1620
tggtcgatat gcgttttgtg aaaccgcttg atgaagcgtt aattctggaa atggccgcca   1680
gccatgaagc gctggtcacc gtagaagaaa acgccattat gggcggcgca ggcagcggcg   1740
tgaacgaagt gctgatggcc catcgtaaac cagtacccgt gctgaacatt ggcctgccgg   1800 acttcttat tccgcaagga actcaggaag aaatgcgcgc cgaactcggc ctcgatgccg   1860
```

<210> SEQ ID NO 209
<211> LENGTH: 1842
<212> TYPE: DNA
<213> ORGANISM: Artificial Sequence
<220> FEATURE:
<223> OTHER INFORMATION: (RBS1)valC(RBS2stop) barcoded fragment

<400> SEQUENCE: 209

```
tagaaataat tttgtttaac tttaagaagg agatatacat atggccgaga tgttcaacgg      60
caactcttct aacgacggat cttcttgcat gcccgtgaag gacgccctgc gacgaaccgg     120
caaccaccac cccaacctgt ggaccgacga cttcatccag tctctgaact ctccctactc     180
tgactcttct taccacaagc accgagagat cctgatcgac gagatccgag acatgttctc     240
taacggcgag ggcgacgagt tcggcgtgct cgagaacatc tggttcgtgg acgtggtgca     300
gcgactgggc atcgaccgac acttccagga ggagatcaag accgccctgg actacatcta     360
caagttctgg aaccacgact ctatcttcgg cgacctgaac atggtggccc tgggcttccg     420
aatcctgcga ctgaaccgat acgtggcctc ttctgacgtg ttcaagaagt tcaagggcga     480
ggagggccag ttctctggct tcgagtcctc tgaccaggac gctaagctcg aaatgatgct     540
gaacctgtac aaggcctctg agctggactt ccccgacgag gacatcctga aggaggcccg     600
agccttcgcc tctatgtacc tgaagcacgt gatcaaggag tacggcgaca tccaggagtc     660
taagaacccc ctgctgatgg agatcgagta caccttcaag taccccctggc gatgccgact     720
gccccgactc gaggcctgga acttcatcca catcatgcga cagcaggact gcaacatctc     780
tctggccaac aacctctaca agatccccaa gatctcatg aagaagatcc tcgagctggc     840
catcctggac ttcaacatcc tgcagtctca gcaccagcac gagatgaagc tgatctctac     900
ctggtggaag aactcttctg ctatccagct ggacttcttc cgacaccgac acatcgagtc     960
ttacttttgg tgggcctcgc ccctgttcga gcccgagttc tctacctgcc gaatcaactg    1020
caccaagctg tctaccaaga tgttcctgct ggacgacatc tacgacacct acggcaccgt    1080
cgaggagctg aagcccttca ccaccaccct gacccgatgg gacgtgtcta ccgtggacaa    1140
ccacccccgac tacatgaaga tcgccttcaa cttctcttac gagatctaca aggagatcgc    1200
ctctgaggcc gagcgaaagc acggcccctt cgtgtacaag tacctgcagt cttgctggaa    1260
gtcttacatc gaggcctaca tgcaggaggc cgagtggatc gcctctaacc acatccccgg    1320
cttcgacgag tacctgatga acggcgtgaa gtcctctggc atgcgaatcc tgatgatcca    1380
cgccctgatc ctgatggaca ccccccctgtc tgacgagatt ctcgagcagc tggacatccc    1440
ctcgtctaag tctcaggccc tgctgtctct gatcacccga ctggtggacg acgtgaagga    1500
cttcgaggac gagcaggccc acggcgagat ggcctcttct atcgagtgct acatgaagga    1560
caaccacggc tctacccgag aggacgccct gaactacctg aagatccgaa tcgagtcttg    1620
cgtgcaggag ctgaacaagg agctgctcga gccctctaac atgcacggat ctttccgaaa    1680
cctgtacctg aacgtgggaa tgcgagtgat tttcttcatg ctgaacgacg gcgacctgtt    1740
cacccactct aaccgaaagg agatccagga cgccatcacc aagttcttcg tcgagcccat    1800
catccctaa ccgttcattt atcacaaaag gattgttcga tg                      1842
```

<210> SEQ ID NO 210
<211> LENGTH: 1823
<212> TYPE: DNA

<213> ORGANISM: Artificial Sequence
<220> FEATURE:
<223> OTHER INFORMATION: (RBS2stop)valC(RBS3stop) barcoded fragment

<400> SEQUENCE: 210

```
taaccgttca tttatcacaa aaggattgtt cgatggccga gatgttcaac ggcaactctt      60
ctaacgacgg atcttcttgc atgcccgtga aggacgccct gcgacgaacc ggcaaccacc     120
accccaacct gtggaccgac gacttcatcc agtctctgaa ctctccctac tctgactctt     180
cttaccacaa gcaccgagag atcctgatcg acgagatccg agacatgttc tctaacggcg     240
agggcgacga gttcggcgtg ctcgagaaca tctggttcgt ggacgtggtg cagcgactgg     300
gcatcgaccg acacttccag gaggagatca agaccgccct ggactacatc tacaagttct     360
ggaaccacga ctctatcttc ggcgacctga acatggtggc cctgggcttc cgaatcctgc     420
gactgaaccg atacgtggcc tcttctgacg tgttcaagaa gttcaagggc gaggagggcc     480
agttctctgg cttcgagtcc tctgaccagg acgctaagct cgaaatgatg ctgaacctgt     540
acaaggcctc tgagctggac ttccccgacg aggacatcct gaaggaggcc cgagccttcg     600
cctctatgta cctgaagcac gtgatcaagg agtacggcga catccaggag tctaagaacc     660
ccctgctgat ggagatcgag tacaccttca gtaccccctg gcgatgccga ctgccccgac     720
tcgaggcctg gaacttcatc cacatcatgc gacagcagga ctgcaacatc tctctggcca     780
acaacctcta caagatcccc aagatctaca tgaagaagat cctcgagctg ccatcctgg      840
acttcaacat cctgcagtct cagcaccagc acgagatgaa gctgatctct acctggtgga     900
agaactcttc tgctatccag ctggacttct tccgacaccg acacatcgag tcttactttt     960
ggtgggcctc gcccctgttc gagcccgagt ctctacctg ccgaatcaac tgcaccaagc     1020
tgtctaccaa gatgttcctg ctggacgaca tctacgacac ctacggcacc gtcgaggagc     1080
tgaagccctt caccaccacc ctgacccgat gggacgtgtc taccgtggac aaccacccg     1140
actacatgaa gatcgccttc aacttctctt acgagatcta caggagatc gcctctgagg     1200
ccgagcgaaa gcacggcccc ttcgtgtaca gtacctgca gtcttgctgg aagtcttaca     1260
tcgaggccta catgcaggag gccgagtgga tcgcctctaa ccacatcccc ggcttcgacg     1320
agtacctgat gaacggcgtg aagtcctctg gcatgcgaat cctgatgatc cacgccctga     1380
tcctgatgga caccccctg tctgacgaga ttctcgagca gctggacatc ccctcgtcta     1440
agtctcaggc cctgctgtct ctgatcaccc gactggtgga cgacgtgaag gacttcgagg     1500
acgagcaggc ccacggcgag atggcctctt ctatcgagtg ctacatgaag gacaaccacg     1560
gctctacccg agaggacgcc ctgaactacc tgaagatccg aatcgagtct tgcgtgcagg     1620
agctgaacaa ggagctgctc gagccctcta acatgcacgg atctttccga aacctgtacc     1680
tgaacgtggg aatgcgagtg attttcttca tgctgaacga cggcgacctg ttcacccact     1740
ctaaccgaaa ggagatccag gacgccatca ccaagttctt cgtcgagccc atcatccct      1800
gattcacaca ggaaacagct atg                                             1823
```

<210> SEQ ID NO 211
<211> LENGTH: 605
<212> TYPE: DNA
<213> ORGANISM: Artificial Sequence
<220> FEATURE:
<223> OTHER INFORMATION: (RBS3stop)idi(RBS4stop) barcoded fragment

<400> SEQUENCE: 211

```
tgattcacac aggaaacagc tatgcaaacg gaacacgtca ttttattgaa tgcacaggga      60
```

```
gttcccacgg gtacgctgga aaagtatgcc gcacacacgg cagacacccg cttacatctc    120
gcgttctcca gttggctgtt taatgccaaa ggacaattat tagttacccg ccgcgcactg    180
agcaaaaaag catggcctgg cgtgtggact aactcggttt gtgggcaccc acaactggga    240
gaaagcaacg aagacgcagt gatccgccgt tgccgttatg agcttggcgt ggaaattacg    300
cctcctgaat ctatctatcc tgactttcgc taccgcgcca ccgatccgag tggcattgtg    360
gaaaatgaag tgtgtccggt atttgccgca cgcaccacta gtgcgttaca gatcaatgat    420
gatgaagtga tggattatca atggtgtgat ttagcagatg tattacacgg tattgatgcc    480
acgccgtggg cgttcagtcc gtggatggtg atgcaggcga caaatcgcga agccagaaaa    540
cgattatctg catttaccca gcttaaataa attaattgtt cttttttcag gtgaaggttc    600
ccatg                                                                605

<210> SEQ ID NO 212
<211> LENGTH: 602
<212> TYPE: DNA
<213> ORGANISM: Artificial Sequence
<220> FEATURE:
<223> OTHER INFORMATION: (RBS4stop)idi(N31) barcoded fragment

<400> SEQUENCE: 212
taaattaatt gttcttttt caggtgaagg ttcccatgca aacggaacac gtcattttat     60
tgaatgcaca gggagttccc acgggtacgc tggaaaagta tgccgcacac acggcagaca    120
cccgcttaca tctcgcgttc tccagttggc tgtttaatgc caaggacaa ttattagtta    180 cccgccgcgc actgagcaaa aaagcatggc ctggcgtgtg gactaactcg gtttgtgggc    240
acccacaact gggagaaagc aacgaagacg cagtgatccg ccgttgccgt tatgagcttg    300
gcgtggaaat tacgcctcct gaatctatct atcctgactt tcgctaccgc gccaccgatc    360
cgagtggcat tgtggaaaat gaagtgtgtc cggtatttgc cgcacgcacc actagtgcgt    420
tacagatcaa tgatgatgaa gtgatggatt atcaatggtg tgatttagca gatgtattac    480
acggtattga tgccacgccg tgggcgttca gtccgtggat ggtgatgcag gcgacaaatc    540
gcgaagccag aaaacgatta tctgcattta cccagcttaa atgatgggct gaagggttta    600
ag                                                                   602

<210> SEQ ID NO 213
<211> LENGTH: 972
<212> TYPE: DNA
<213> ORGANISM: Artificial Sequence
<220> FEATURE:
<223> OTHER INFORMATION: (RBS1)ispA(RBS2stop) barcoded fragment

<400> SEQUENCE: 213
tagaaataat tttgttaac tttaagaagg agatatacat atggactttc cgcagcaact     60
cgaagcctgc gttaagcagg ccaaccaggc gctgagccgt tttatcgccc cactgccctt    120
tcagaacact cccgtggtcg aaaccatgca gtatggcgca ttattaggtg gtaagcgcct    180
gcgacctttc ctggtttatg ccaccggtca tatgttcggc gttagcacaa acacgctgga    240
cgcacccgct gccgccgttg agtgtatcca cgcttactca ttaattcatg atgatttacc    300
ggcaatggat gatgacgatc tgcgtcgcgg tttgccaacc tgccatgtga gtttggcga    360 agcaaacgcg attctcgctg gcgacgcttt acaaacgctg gcgttctcga ttttaagcga    420
tgccgatatg ccggaagtgt cggaccgcga cagaatttcg atgatttctg aactggcgag    480
```

| | |
|---|---|
| cgccagtggt attgccggaa tgtgcggtgg tcaggcatta gatttagacg cggaaggcaa | 540 |
| acacgtacct ctggacgcgc ttgagcgtat tcatcgtcat aaaaccggcg cattgattcg | 600 |
| cgccgccgtt cgccttggtg cattaagcgc cggagataaa ggacgtcgtg ctctgccggt | 660 |
| actcgacaag tatgcagaga gcatcggcct tgccttccag gttcaggatg acatcctgga | 720 |
| tgtggtggga gatactgcaa cgttgggaaa acgccagggt gccgaccagc aacttggtaa | 780 |
| aagtacctac cctgcacttc tgggtcttga gcaagcccgg aagaaagccc gggatctgat | 840 |
| cgacgatgcc cgtcagtcgc tgaaacaact ggctgaacag tcactcgata cctcggcact | 900 |
| ggaagcgcta gcggactaca tcatccagcg taataaataa ccgttcattt atcacaaaag | 960 |
| gattgttcga tg | 972 |

<210> SEQ ID NO 214
<211> LENGTH: 953
<212> TYPE: DNA
<213> ORGANISM: Artificial Sequence
<220> FEATURE:
<223> OTHER INFORMATION: (RBS2stop)ispA(RBS3stop) barcoded fragment

<400> SEQUENCE: 214

| | |
|---|---|
| taaccgttca tttatcacaa aaggattgtt cgatggactt tccgcagcaa ctcgaagcct | 60 |
| gcgttaagca ggccaaccag gcgctgagcc gttttatcgc cccactgccc tttcagaaca | 120 |
| ctcccgtggt cgaaaccatg cagtatggcg cattattagg tggtaagcgc ctgcgacctt | 180 |
| tcctggttta tgccaccggt catatgttcg gcgttagcac aaacacgctg gacgcacccg | 240 |
| ctgccgccgt tgagtgtatc cacgcttact cattaattca tgatgattta ccggcaatgg | 300 |
| atgatgacga tctgcgtcgc ggtttgccaa cctgccatgt gaagtttggc gaagcaaacg | 360 |
| cgattctcgc tggcgacgct ttacaaacgc tggcgttctc gattttaagc gatgccgata | 420 |
| tgccggaagt gtcggaccgc gacagaattt cgatgatttc tgaactggcg agcgccagtg | 480 |
| gtattgccgg aatgtgcggt ggtcaggcat tagatttaga cgcggaaggc aaacacgtac | 540 |
| ctctggacgc gcttgagcgt attcatcgtc ataaaaccgg cgcattgatt cgcgccgccg | 600 |
| ttcgccttgg tgcattaagc gccggagata aggacgtcg tgctctgccg gtactcgaca | 660 |
| agtatgcaga gagcatcggc cttgccttcc aggttcagga tgacatcctg gatgtggtgg | 720 |
| gagatactgc aacgttggga aaacgccagg gtgccgacca gcaacttggt aaaagtacct | 780 |
| accctgcact tctgggtctt gagcaagccc ggaagaaagc ccgggatctg atcgacgatg | 840 |
| cccgtcagtc gctgaaacaa ctggctgaac agtcactcga tacctcggca ctggaagcgc | 900 |
| tagcggacta catcatccag cgtaataaat gattcacaca ggaaacagct atg | 953 |

<210> SEQ ID NO 215
<211> LENGTH: 956
<212> TYPE: DNA
<213> ORGANISM: Artificial Sequence
<220> FEATURE:
<223> OTHER INFORMATION: (RBS3stop)ispA(RBS4stop) barcoded fragment

<400> SEQUENCE: 215

| | |
|---|---|
| tgattcacac aggaaacagc tatggacttt ccgcagcaac tcgaagcctg cgttaagcag | 60 |
| gccaaccagg cgctgagccg ttttatcgcc ccactgccct ttcagaacac tcccgtggtc | 120 |
| gaaaccatgc agtatggcgc attattaggt ggtaagcgcc tgcgaccttt cctggtttat | 180 |
| gccaccggtc atatgttcgg cgttagcaca aacacgctgg acgcacccgc tgccgccgtt | 240 |
| gagtgtatcc acgcttactc attaattcat gatgatttac cggcaatgga tgatgacgat | 300 |

```
ctgcgtcgcg gtttgccaac ctgccatgtg aagtttggcg aagcaaacgc gattctcgct    360
ggcgacgctt tacaaacgct ggcgttctcg attttaagcg atgccgatat gccggaagtg    420
tcggaccgcg acagaatttc gatgatttct gaactggcga gcgccagtgg tattgccgga    480
atgtgcggtg gtcaggcatt agatttagac gcggaaggca aacacgtacc tctggacgcg    540
cttgagcgta ttcatcgtca taaaaccggc gcattgattc gcgccgccgt tcgccttggt    600
gcattaagcg ccggagataa aggacgtcgt gctctgccgg tactcgacaa gtatgcagag    660
agcatcggcc ttgccttcca ggttcaggat gacatcctgg atgtggtggg agatactgca    720
acgttgggaa aacgccaggg tgccgaccag caacttggta aaagtaccta ccctgcactt    780
ctgggtcttg agcaagcccg gaagaaagcc cgggatctga tcgacgatgc ccgtcagtcg    840
ctgaaacaac tggctgaaca gtcactcgat acctcggcac tggaagcgct agcggactac    900
atcatccagc gtaataaata aattaattgt tcttttttca ggtgaaggtt cccatg         956
```

<210> SEQ ID NO 216
<211> LENGTH: 1823
<212> TYPE: DNA
<213> ORGANISM: Artificial Sequence
<220> FEATURE:
<223> OTHER INFORMATION: (RBS4stop)valC(N31) barcoded fragment

<400> SEQUENCE: 216

```
taaattaatt gttcttttt caggtgaagg ttcccatggc cgagatgttc aacggcaact     60
cttctaacga cggatcttct tgcatgcccg tgaaggacgc cctgcgacga accggcaacc    120
accaccccaa cctgtggacc gacgacttca tccagtctct gaactctccc tactctgact    180
cttcttacca caagcaccga gagatcctga tcgacgagat ccgagacatg ttctctaacg    240
gcgagggcga cgagttcggc gtgctcgaga acatctggtt cgtggacgtg gtgcagcgac    300
tgggcatcga ccgacacttc caggaggaga tcaagaccgc cctggactac atctacaagt    360
tctggaacca cgactctatc ttcggcgacc tgaacatggt ggccctgggc ttccgaatcc    420
tgcgactgaa ccgatacgtg gcctcttctg acgtgttcaa gaagttcaag ggcgaggagg    480
gccagttctc tggcttcgag tcctctgacc aggacgctaa gctcgaaatg atgctgaacc    540
tgtacaaggc ctctgagctg gacttccccg acgaggacat cctgaaggag gcccgagcct    600
tcgcctctat gtacctgaag cacgtgatca aggagtacgg cgacatccag gagtctaaga    660
accccctgct gatggagatc gagtacacct tcaagtaccc ctggcgatgc cgactgcccc    720
gactcgaggc ctgaacttc atccacatca tgcgacagca ggactgcaac atctctctgg    780
ccaacaacct ctacaagatc cccaagatct acatgaagaa gatcctcgag ctggccatcc    840
tggacttcaa catcctgcag tctcagcacc agcacgagat gaagctgatc tctacctggt    900
ggaagaactc ttctgctatc cagctggact tcttccgaca ccgacacatc gagtcttact    960
tttggtgggc ctcgcccctg ttcgagcccg agttctctac ctgccgaatc aactgcacca   1020
agctgtctac caagatgttc ctgctggacg acatctacga cacctacggc accgtcgagg   1080
agctgaagcc cttcaccacc accctgaccg atgggacgt gtctaccgtg gacaaccacc   1140
ccgactacat gaagatcgcc ttcaacttct cttacgagat ctacaaggag atcgcctctg   1200
aggccgagcg aaagcacggc cccttcgtgt acaagtacct gcagtcttgc tggaagtctt   1260
acatcgaggc ctacatgcag gaggccgagt ggatcgcctc taaccacatc cccggcttcg   1320
acgagtacct gatgaacggc gtgaagtcct ctggcatgcg aatcctgatg atccacgccc   1380
```

```
tgatcctgat ggacacccccc ctgtctgacg agattctcga gcagctggac atcccctcgt    1440
ctaagtctca ggccctgctg tctctgatca cccgactggt ggacgacgtg aaggacttcg    1500
aggacgagca ggcccacggc gagatggcct cttctatcga gtgctacatg aaggacaacc    1560
acggctctac ccgagaggac gccctgaact acctgaagat ccgaatcgag tcttgcgtgc    1620
aggagctgaa caaggagctg ctcgagccct caacatgca cggatctttc cgaaacctgt    1680
acctgaacgt gggaatgcga gtgatttttct tcatgctgaa cgacggcgac ctgttcaccc    1740
actctaaccg aaaggagatc caggacgcca tcaccaagtt cttcgtcgag cccatcatcc    1800
cctgatgggc tgaagggttt aag                                             1823

<210> SEQ ID NO 217
<211> LENGTH: 1128
<212> TYPE: DNA
<213> ORGANISM: Artificial Sequence
<220> FEATURE:
<223> OTHER INFORMATION: (RBS1)aroG mutant(RBS4stop) barcoded fragment

<400> SEQUENCE: 217
tagaaataat tttgtttaac tttaagaagg agatatacat atgaattatc agaacgacga      60
tttacgcatc aaagaaatca agagttact tcctcctgtc gcattgctgg aaaaattccc     120
cgctactgaa atgccgcga atacggttgc ccatgcccga aaagcgatcc ataagatcct     180
gaaaggtaat gatgatcgcc tgttggttgt gattggccca tgctcaattc atgatcctgt     240
cgcggcaaaa gagtatgcca ctcgcttgct ggcgctgcgt gaagagctga agatgagct     300 ggaaatcgta atgcgcgtct atttgaaaa gccgcgtacc acggtgggct ggaaagggct     360
gattaacgat ccgcatatgg ataatagctt ccagatcaac gacggtctgc gtatagcccg     420
taaattgctg cttgatatta cgacagcgg tctgccagcg gcaggtgagt ttctcaatat     480
gatcacccca caatatctcg ctgacctgat gagctggggc gcaattggcg cacgtaccac     540
cgaatcgcag gtgcaccgcg aactggcatc agggctttct tgtccggtcg gcttcaaaaa     600
tggcaccgac ggtacgatta agtggctat cgatgccatt aatgccgccg gtgcgccgca     660
ctgcttcctg tccgtaacga atgggggca ttcggcgatt gtgaatacca gcggtaacgg     720
cgattgccat atcattctgc gcggcggtaa agagcctaac tacagcgcga agcacgttgc     780
tgaagtgaaa gaagggctga acaaagcagg cctgccagca caggtgatga tcgatttcag     840
ccatgctaac tcgtccaaac aattcaaaaa gcagatggat gtttgtgctg acgtttgcca     900
gcagattgcc ggtggcgaaa aggccattat tggcgtgatg gtggaaagcc atctggtgga     960
aggcaatcag agcctcgaga gcggggagcc gctggcctac ggtaagagca tcaccgatgc    1020
ctgcatcggc tgggaagata ccgatgctct gttacgtcaa ctggcgaatg cagtaaaagc    1080
gcgtcgcggg taaattaatt gttctttttt caggtgaagg ttcccatg                  1128

<210> SEQ ID NO 218
<211> LENGTH: 1197
<212> TYPE: DNA
<213> ORGANISM: Artificial Sequence
<220> FEATURE:
<223> OTHER INFORMATION: (RBS1)tyrA mutant(RBS4stop) barcoded fragment

<400> SEQUENCE: 218
tagaaataat tttgtttaac tttaagaagg agatatacat atggttgctg aattgaccgc      60
attacgcgat caaattgatg aagtcgataa agcgctgctg aatttattag cgaagcgtct    120
ggaactggtt gctgaagtgg gcgaggtgaa aagccgcttt ggactgccta tttatgttcc    180
```

```
ggagcgcgag gcatctattt tggcctcgcg tcgtgcagag gcggaagctc tgggtgtacc        240
gccagatctg attgaggatg ttttgcgtcg ggtgatgcgt gaatcttact ccagtgaaaa        300
cgacaaagga tttaaaacac tttgtccgtc actgcgtccg gtggttatcg tcggcggtgg        360
cggtcagatg ggacgcctgt tcgagaagat gctgaccctc tcgggttatc aggtgcggat        420
tctggagcaa catgactggg atcgagcggc tgatattgtt gccgatgccg gaatggtgat        480
tgttagtgtg ccaatccacg ttactgagca agttattggc aaattaccgc ctttaccgaa        540
agattgtatt ctggtcgatc tggcatcagt gaaaaatggg ccattacagg ccatgctggt        600
ggcgcatgat ggtccggtgc tggggctaca cccgatgttc ggtccggaca gcggtagcct        660
ggcaaagcaa gttgtggtct ggtgtgatgg acgtaaaccg gaagcatacc aatggtttct        720
ggagcaaatt caggtctggg gcgctcggct gcatcgtatt agcgccgtcg agcacgatca        780
gaatatggcg tttattcagg cactgcgcca ctttgctact tttgcttacg ggctgcacct        840
ggcagaagaa aatgttcagc ttgagcaact tctggcgctc tcttcgccga tttaccgcct        900
tgagctggcg atggtcgggc gactgtttgc tcaggatccg cagctttatg ccgacatcat        960
tatgtcgtca gagcgtaatc tggcgttaat caaacgttac tataagcgtt tcggcgaggc       1020
gattgagttg ctggagcagg gcgataagca ggcgtttatt gacagtttcc gcaaggtgga       1080
gcactggttc ggcgattacg tacagcgttt tcagagtgaa agccgcgtgt tattgcgtca       1140
ggcgaatgac aatcgccagt aaattaattg ttcttttttc aggtgaaggt tcccatg         1197
```

<210> SEQ ID NO 219
<211> LENGTH: 1175
<212> TYPE: DNA
<213> ORGANISM: Artificial Sequence
<220> FEATURE:
<223> OTHER INFORMATION: (RBS4stop)tyrA mutant(N31) barcoded fragment

<400> SEQUENCE: 219

```
taaattaatt gttcttttt caggtgaagg ttcccatggt tgctgaattg accgcattac         60
gcgatcaaat tgatgaagtc gataaagcgc tgctgaattt attagcgaag cgtctggaac        120
tggttgctga agtgggcgag gtgaaaagcc gctttggact gcctatttat gttccggagc        180
gcgaggcatc tattttggcc tcgcgtcgtg cagaggcgga agctctgggt gtaccgccag        240
atctgattga ggatgttttg cgtcgggtga tgcgtgaatc ttactccagt gaaaacgaca        300
aaggatttaa aacactttgt ccgtcactgc gtccggtggt tatcgtcggc ggtggcggtc        360
agatgggacg cctgttcgag aagatgctga ccctctcggg ttatcaggtg cggattctgg        420
agcaacatga ctgggatcga gcggctgata ttgttgccga tgccggaatg gtgattgtta        480
gtgtgccaat ccacgttact gagcaagtta ttggcaaatt accgccttta ccgaaagatt        540
gtattctggt cgatctggca tcagtgaaaa atgggccatt acaggccatg ctggtggcgc        600
atgatggtcc ggtgctgggg ctacacccga tgttcggtcc ggacagcggt agcctggcaa        660
agcaagttgt ggtctggtgt gatggacgta aaccggaagc ataccaatgg tttctggagc        720
aaattcaggt ctggggcgct cggctgcatc gtattagcgc cgtcgagcac gatcagaata        780
tggcgtttat tcaggcactg cgccactttg ctacttttgc ttacgggctg cacctggcag        840
aagaaaatgt tcagcttgag caacttctgg cgctctcttc gccgatttac cgccttgagc        900
tggcgatggt cgggcgactg tttgctcagg atccgcagct ttatgccgac atcattatgt        960
cgtcagagcg taatctggcg ttaatcaaac gttactataa gcgtttcggc gaggcgattg       1020
```

```
agttgctgga gcagggcgat aagcaggcgt ttattgacag tttccgcaag gtggagcact   1080
ggttcggcga ttacgtacag cgttttcaga gtgaaagccg cgtgttattg cgtcaggcga   1140
atgacaatcg ccagtgatgg gctgaagggt ttaag                              1175

<210> SEQ ID NO 220
<211> LENGTH: 1106
<212> TYPE: DNA
<213> ORGANISM: Artificial Sequence
<220> FEATURE:
<223> OTHER INFORMATION: (RBS4stop)aroG mutant(N31) barcoded fragment

<400> SEQUENCE: 220
taaattaatt gttctttttt caggtgaagg ttcccatgaa ttatcagaac gacgatttac    60
gcatcaaaga aatcaaagag ttacttcctc ctgtcgcatt gctggaaaaa ttccccgcta   120
ctgaaaatgc cgcgaatacg gttgcccatg cccgaaaagc gatccataag atcctgaaag   180
gtaatgatga tcgcctgttg gttgtgattg gcccatgctc aattcatgat cctgtcgcgg   240
caaaagagta tgccactcgc ttgctggcgc tgcgtgaaga gctgaaagat gagctggaaa   300
tcgtaatgcg cgtctatttt gaaaagccgc gtaccacggt gggctggaaa gggctgatta   360
acgatccgca tatggataat agcttccaga tcaacgacgg tctgcgtata gcccgtaaat   420
tgctgcttga tattaacgac agcggtctgc cagcggcagg tgagtttctc aatatgatca   480
ccccacaata tctcgctgac ctgatgagct ggggcgcaat tggcgcacgt accaccgaat   540
cgcaggtgca ccgcgaactg gcatcagggc tttcttgtcc ggtcggcttc aaaaatggca   600
ccgacggtac gattaaagtg gctatcgatg ccattaatgc cgccggtgcg ccgcactgct   660
tcctgtccgt aacgaaatgg gggcattcgg cgattgtgaa taccagcggt aacggcgatt   720
gccatatcat tctgcgcggc ggtaaagagc taactacag cgcgaagcac gttgctgaag    780
tgaaagaagg gctgaacaaa gcaggcctgc cagcacaggt gatgatcgat ttcagccatg   840
ctaactcgtc caaacaattc aaaaagcaga tggatgtttg tgctgacgtt tgccagcaga   900
ttgccggtgg cgaaaaggcc attattggcg tgatggtgga aagccatctg gtggaaggca   960
atcagagcct cgagagcggg gagccgctgg cctacggtaa gagcatcacc gatgcctgca   1020
tcggctggga agataccgat gctctgttac gtcaactggc gaatgcagta aaagcgcgtc   1080
gcgggtgatg ggctgaaggg tttaag                                       1106

<210> SEQ ID NO 221
<211> LENGTH: 20
<212> TYPE: DNA
<213> ORGANISM: Artificial Sequence
<220> FEATURE:
<223> OTHER INFORMATION: aslA screening 4 forward oligo

<400> SEQUENCE: 221
tggaacaaca ggcatggatt                                                20

<210> SEQ ID NO 222
<211> LENGTH: 19
<212> TYPE: DNA
<213> ORGANISM: Artificial Sequence
<220> FEATURE:
<223> OTHER INFORMATION: aslA screening 4 reverse oligo

<400> SEQUENCE: 222
acaggcgaaa tatggtgct                                                 19
```

-continued

```
<210> SEQ ID NO 223
<211> LENGTH: 20
<212> TYPE: DNA
<213> ORGANISM: Artificial Sequence
<220> FEATURE:
<223> OTHER INFORMATION: nupG screening 2 forward oligo

<400> SEQUENCE: 223
ggaaatatgg cgttgatgag                                              20

<210> SEQ ID NO 224
<211> LENGTH: 20
<212> TYPE: DNA
<213> ORGANISM: Artificial Sequence
<220> FEATURE:
<223> OTHER INFORMATION: nupG screening 2 reverse oligo

<400> SEQUENCE: 224
aggattatcc gacatcagtg                                              20

<210> SEQ ID NO 225
<211> LENGTH: 20
<212> TYPE: DNA
<213> ORGANISM: Artificial Sequence
<220> FEATURE:
<223> OTHER INFORMATION: pheA screening forward oligo

<400> SEQUENCE: 225
tcatcaaata tggctcgctt                                              20

<210> SEQ ID NO 226
<211> LENGTH: 20
<212> TYPE: DNA
<213> ORGANISM: Artificial Sequence
<220> FEATURE:
<223> OTHER INFORMATION: pheA screening reverse oligo

<400> SEQUENCE: 226
tcgagcggct gatattgttg                                              20

<210> SEQ ID NO 227
<211> LENGTH: 20
<212> TYPE: DNA
<213> ORGANISM: Artificial Sequence
<220> FEATURE:
<223> OTHER INFORMATION: tyrR screening forward oligo

<400> SEQUENCE: 227
aacgctggta tgcctcaatc                                              20

<210> SEQ ID NO 228
<211> LENGTH: 20
<212> TYPE: DNA
<213> ORGANISM: Artificial Sequence
<220> FEATURE:
<223> OTHER INFORMATION: tyrR screening reverse oligo

<400> SEQUENCE: 228
aggcttcctc gaatacctta                                              20

<210> SEQ ID NO 229
<211> LENGTH: 20
<212> TYPE: DNA
<213> ORGANISM: Artificial Sequence
<220> FEATURE:
<223> OTHER INFORMATION: nupG screening 4 forward oligo
```

<400> SEQUENCE: 229
tattgtgcct atgtggcttc                                           20

<210> SEQ ID NO 230
<211> LENGTH: 21
<212> TYPE: DNA
<213> ORGANISM: Artificial Sequence
<220> FEATURE:
<223> OTHER INFORMATION: nupG screening 4 reverse oligo

<400> SEQUENCE: 230
cgaataaagt ggtgacgaat g                                         21

<210> SEQ ID NO 231
<211> LENGTH: 21
<212> TYPE: DNA
<213> ORGANISM: Artificial Sequence
<220> FEATURE:
<223> OTHER INFORMATION: melB screening 2 forward oligo

<400> SEQUENCE: 231
gtaagcggca tggtctggaa c                                         21

<210> SEQ ID NO 232
<211> LENGTH: 20
<212> TYPE: DNA
<213> ORGANISM: Artificial Sequence
<220> FEATURE:
<223> OTHER INFORMATION: melB screening 2 reverse oligo

<400> SEQUENCE: 232
gcaggccgta tggactccta                                           20

<210> SEQ ID NO 233
<211> LENGTH: 19
<212> TYPE: DNA
<213> ORGANISM: Artificial Sequence
<220> FEATURE:
<223> OTHER INFORMATION: rcsB screening 3 forward oligo

<400> SEQUENCE: 233
aactggcgaa tcaggcaga                                            19

<210> SEQ ID NO 234
<211> LENGTH: 20
<212> TYPE: DNA
<213> ORGANISM: Artificial Sequence
<220> FEATURE:
<223> OTHER INFORMATION: rcsB screening 3 reverse oligo

<400> SEQUENCE: 234
gcgattatct ctctatccgt                                           20

<210> SEQ ID NO 235
<211> LENGTH: 20
<212> TYPE: DNA
<213> ORGANISM: Artificial Sequence
<220> FEATURE:
<223> OTHER INFORMATION: ptsH/I_crr screening forward oligo

<400> SEQUENCE: 235
agaccgatct tatctctgtc                                           20

<210> SEQ ID NO 236
<211> LENGTH: 20

```
<212> TYPE: DNA
<213> ORGANISM: Artificial Sequence
<220> FEATURE:
<223> OTHER INFORMATION: ptsH/I_crr screening reverse oligo

<400> SEQUENCE: 236
tagtgtaatg accagacaaa                                            20

<210> SEQ ID NO 237
<211> LENGTH: 40
<212> TYPE: DNA
<213> ORGANISM: Artificial Sequence
<220> FEATURE:
<223> OTHER INFORMATION: G-gRNA-xylB forward foligo
<220> FEATURE:
<221> NAME/KEY: misc_binding
<222> LOCATION: (1)..(2)
<223> OTHER INFORMATION: phosphorothioate bond

<400> SEQUENCE: 237
gtataatact tgtcgatttt gattttagag ctagaaatag                      40

<210> SEQ ID NO 238
<211> LENGTH: 40
<212> TYPE: DNA
<213> ORGANISM: Artificial Sequence
<220> FEATURE:
<223> OTHER INFORMATION: G-gRNA-manZ forward foligo
<220> FEATURE:
<221> NAME/KEY: misc_binding
<222> LOCATION: (1)..(2)
<223> OTHER INFORMATION: phosphorothioate bond

<400> SEQUENCE: 238
gttttaacga tatcgatacc tttttagag ctagaaatag                       40

<210> SEQ ID NO 239
<211> LENGTH: 40
<212> TYPE: DNA
<213> ORGANISM: Artificial Sequence
<220> FEATURE:
<223> OTHER INFORMATION: G-gRNA-glk forward foligo
<220> FEATURE:
<221> NAME/KEY: misc_binding
<222> LOCATION: (1)..(2)
<223> OTHER INFORMATION: phosphorothioate bond

<400> SEQUENCE: 239
gtaatcgtta ataatttcca gattttagag ctagaaatag                      40

<210> SEQ ID NO 240
<211> LENGTH: 21
<212> TYPE: DNA
<213> ORGANISM: Artificial Sequence
<220> FEATURE:
<223> OTHER INFORMATION: G-manZ-HF0.5 forward foligo
<220> FEATURE:
<221> NAME/KEY: misc_binding
<222> LOCATION: (1)..(2)
<223> OTHER INFORMATION: phosphorothioate bond

<400> SEQUENCE: 240
gcgggccagg tactgaccat c                                          21

<210> SEQ ID NO 241
<211> LENGTH: 21
<212> TYPE: DNA
<213> ORGANISM: Artificial Sequence
<220> FEATURE:
```

<223> OTHER INFORMATION: manZ-HF0.5-T reverse foligo
<220> FEATURE:
<221> NAME/KEY: misc_binding
<222> LOCATION: (1)..(2)
<223> OTHER INFORMATION: phosphorothioate bond

<400> SEQUENCE: 241
atagtccagt tcgttatcga g                                          21

<210> SEQ ID NO 242
<211> LENGTH: 21
<212> TYPE: DNA
<213> ORGANISM: Artificial Sequence
<220> FEATURE:
<223> OTHER INFORMATION: G-glk-HF0.5 forward foligo
<220> FEATURE:
<221> NAME/KEY: misc_binding
<222> LOCATION: (1)..(2)
<223> OTHER INFORMATION: phosphorothioate bond

<400> SEQUENCE: 242
gcgcagaggg cggaaccggt g                                          21

<210> SEQ ID NO 243
<211> LENGTH: 21
<212> TYPE: DNA
<213> ORGANISM: Artificial Sequence
<220> FEATURE:
<223> OTHER INFORMATION: glk-HF0.5-T reverse foligo
<220> FEATURE:
<221> NAME/KEY: misc_binding
<222> LOCATION: (1)..(2)
<223> OTHER INFORMATION: phosphorothioate bond

<400> SEQUENCE: 243
acgctaaagt caaaataatt c                                          21

<210> SEQ ID NO 244
<211> LENGTH: 19
<212> TYPE: DNA
<213> ORGANISM: Artificial Sequence
<220> FEATURE:
<223> OTHER INFORMATION: G-xylB-HF0.5 forward foligo
<220> FEATURE:
<221> NAME/KEY: misc_binding
<222> LOCATION: (1)..(2)
<223> OTHER INFORMATION: phosphorothioate bond

<400> SEQUENCE: 244
gcgtggcgat gcgcaactg                                             19

<210> SEQ ID NO 245
<211> LENGTH: 21
<212> TYPE: DNA
<213> ORGANISM: Artificial Sequence
<220> FEATURE:
<223> OTHER INFORMATION: xylB-HF0.5-T reverse foligo
<220> FEATURE:
<221> NAME/KEY: misc_binding
<222> LOCATION: (1)..(2)
<223> OTHER INFORMATION: phosphorothioate bond

<400> SEQUENCE: 245
aagatctatc ccgatataca t                                          21

<210> SEQ ID NO 246
<211> LENGTH: 21
<212> TYPE: DNA
<213> ORGANISM: Artificial Sequence

```
<220> FEATURE:
<223> OTHER INFORMATION: G-manZ-HT0.5 forward foligo
<220> FEATURE:
<221> NAME/KEY: misc_binding
<222> LOCATION: (1)..(2)
<223> OTHER INFORMATION: phosphorothioate bond

<400> SEQUENCE: 246
ggactgttgt acactaccgg g                                              21

<210> SEQ ID NO 247
<211> LENGTH: 21
<212> TYPE: DNA
<213> ORGANISM: Artificial Sequence
<220> FEATURE:
<223> OTHER INFORMATION: manZ-HT0.5-T reverse foligo
<220> FEATURE:
<221> NAME/KEY: misc_binding
<222> LOCATION: (1)..(2)
<223> OTHER INFORMATION: phosphorothioate bond

<400> SEQUENCE: 247
aacgagaagc ttataaattt t                                              21

<210> SEQ ID NO 248
<211> LENGTH: 21
<212> TYPE: DNA
<213> ORGANISM: Artificial Sequence
<220> FEATURE:
<223> OTHER INFORMATION: G-glk-HT0.5 forward foligo
<220> FEATURE:
<221> NAME/KEY: misc_binding
<222> LOCATION: (1)..(2)
<223> OTHER INFORMATION: phosphorothioate bond

<400> SEQUENCE: 248
gatccttcct tttatatcgg g                                              21

<210> SEQ ID NO 249
<211> LENGTH: 21
<212> TYPE: DNA
<213> ORGANISM: Artificial Sequence
<220> FEATURE:
<223> OTHER INFORMATION: glk-HT0.7-T reverse foligo
<220> FEATURE:
<221> NAME/KEY: misc_binding
<222> LOCATION: (1)..(2)
<223> OTHER INFORMATION: phosphorothioate bond

<400> SEQUENCE: 249
agcccgcagc gttttttaatt g                                             21

<210> SEQ ID NO 250
<211> LENGTH: 19
<212> TYPE: DNA
<213> ORGANISM: Artificial Sequence
<220> FEATURE:
<223> OTHER INFORMATION: G-xylB-HT0.5 forward foligo
<220> FEATURE:
<221> NAME/KEY: misc_binding
<222> LOCATION: (1)..(2)
<223> OTHER INFORMATION: phosphorothioate bond

<400> SEQUENCE: 250
gacgttatcc cctgcctga                                                 19

<210> SEQ ID NO 251
<211> LENGTH: 19
<212> TYPE: DNA
```

```
<213> ORGANISM: Artificial Sequence
<220> FEATURE:
<223> OTHER INFORMATION: xylB-HT0.5-T reverse foligo
<220> FEATURE:
<221> NAME/KEY: misc_binding
<222> LOCATION: (1)..(2)
<223> OTHER INFORMATION: phosphorothioate bond

<400> SEQUENCE: 251
acgaaacaaa cgcatttga                                              19

<210> SEQ ID NO 252
<211> LENGTH: 22
<212> TYPE: DNA
<213> ORGANISM: Artificial Sequence
<220> FEATURE:
<223> OTHER INFORMATION: G-pthrC3 forward foligo
<220> FEATURE:
<221> NAME/KEY: misc_binding
<222> LOCATION: (1)..(2)
<223> OTHER INFORMATION: phosphorothioate bond

<400> SEQUENCE: 252
gagcttttca ttctgactgc aa                                          22

<210> SEQ ID NO 253
<211> LENGTH: 21
<212> TYPE: DNA
<213> ORGANISM: Artificial Sequence
<220> FEATURE:
<223> OTHER INFORMATION: pthrC3-T reverse foligo
<220> FEATURE:
<221> NAME/KEY: misc_binding
<222> LOCATION: (1)..(2)
<223> OTHER INFORMATION: phosphorothioate bond

<400> SEQUENCE: 253
aggttgttac ctcgttacct t                                           21

<210> SEQ ID NO 254
<211> LENGTH: 21
<212> TYPE: DNA
<213> ORGANISM: Artificial Sequence
<220> FEATURE:
<223> OTHER INFORMATION: G-tal forward foligo
<220> FEATURE:
<221> NAME/KEY: misc_binding
<222> LOCATION: (1)..(2)
<223> OTHER INFORMATION: phosphorothioate bond

<400> SEQUENCE: 254
gacccaggtt gttgaacgtc a                                           21

<210> SEQ ID NO 255
<211> LENGTH: 25
<212> TYPE: DNA
<213> ORGANISM: Artificial Sequence
<220> FEATURE:
<223> OTHER INFORMATION: tal-T reverse foligo
<220> FEATURE:
<221> NAME/KEY: misc_binding
<222> LOCATION: (1)..(2)
<223> OTHER INFORMATION: phosphorothioate bond

<400> SEQUENCE: 255
agccaaaatc tttaccatct gcttc                                       25

<210> SEQ ID NO 256
<211> LENGTH: 21
```

-continued

```
<212> TYPE: DNA
<213> ORGANISM: Artificial Sequence
<220> FEATURE:
<223> OTHER INFORMATION: G-eGFP forward foligo
<220> FEATURE:
<221> NAME/KEY: misc_binding
<222> LOCATION: (1)..(2)
<223> OTHER INFORMATION: phosphorothioate bond

<400> SEQUENCE: 256
gagcaagggc gaggagctgt t                                     21

<210> SEQ ID NO 257
<211> LENGTH: 21
<212> TYPE: DNA
<213> ORGANISM: Artificial Sequence
<220> FEATURE:
<223> OTHER INFORMATION: eGFP-T reverse foligo
<220> FEATURE:
<221> NAME/KEY: misc_binding
<222> LOCATION: (1)..(2)
<223> OTHER INFORMATION: phosphorothioate bond

<400> SEQUENCE: 257
acttgtacag ctcgtccatg c                                     21

<210> SEQ ID NO 258
<211> LENGTH: 19
<212> TYPE: DNA
<213> ORGANISM: Artificial Sequence
<220> FEATURE:
<223> OTHER INFORMATION: G-ppsA forward foligo
<220> FEATURE:
<221> NAME/KEY: misc_binding
<222> LOCATION: (1)..(2)
<223> OTHER INFORMATION: phosphorothioate bond

<400> SEQUENCE: 258
gtccaacaat ggctcgtca                                        19

<210> SEQ ID NO 259
<211> LENGTH: 23
<212> TYPE: DNA
<213> ORGANISM: Artificial Sequence
<220> FEATURE:
<223> OTHER INFORMATION: ppsA-T reverse foligo
<220> FEATURE:
<221> NAME/KEY: misc_binding
<222> LOCATION: (1)..(2)
<223> OTHER INFORMATION: phosphorothioate bond

<400> SEQUENCE: 259
attatttctt cagttcagcc agg                                   23

<210> SEQ ID NO 260
<211> LENGTH: 20
<212> TYPE: DNA
<213> ORGANISM: Artificial Sequence
<220> FEATURE:
<223> OTHER INFORMATION: G-tktA forward foligo
<220> FEATURE:
<221> NAME/KEY: misc_binding
<222> LOCATION: (1)..(2)
<223> OTHER INFORMATION: phosphorothioate bond

<400> SEQUENCE: 260
gtcctcacgt aaagagcttg                                       20

<210> SEQ ID NO 261
```

```
<211> LENGTH: 20
<212> TYPE: DNA
<213> ORGANISM: Artificial Sequence
<220> FEATURE:
<223> OTHER INFORMATION: tktA-T reverse foligo
<220> FEATURE:
<221> NAME/KEY: misc_binding
<222> LOCATION: (1)..(2)
<223> OTHER INFORMATION: phosphorothioate bond

<400> SEQUENCE: 261
acagcagttc ttttgctttc                                         20

<210> SEQ ID NO 262
<211> LENGTH: 23
<212> TYPE: DNA
<213> ORGANISM: Artificial Sequence
<220> FEATURE:
<223> OTHER INFORMATION: G-aroE forward foligo
<220> FEATURE:
<221> NAME/KEY: misc_binding
<222> LOCATION: (1)..(2)
<223> OTHER INFORMATION: phosphorothioate bond

<400> SEQUENCE: 262
ggaaacctat gctgtttttg gta                                     23

<210> SEQ ID NO 263
<211> LENGTH: 20
<212> TYPE: DNA
<213> ORGANISM: Artificial Sequence
<220> FEATURE:
<223> OTHER INFORMATION: aroE-T reverse foligo
<220> FEATURE:
<221> NAME/KEY: misc_binding
<222> LOCATION: (1)..(2)
<223> OTHER INFORMATION: phosphorothioate bond

<400> SEQUENCE: 263
acgcggacaa ttcctcctgc                                         20

<210> SEQ ID NO 264
<211> LENGTH: 61
<212> TYPE: DNA
<213> ORGANISM: Artificial Sequence
<220> FEATURE:
<223> OTHER INFORMATION: CelN20-Noligo forward noligo

<400> SEQUENCE: 264
gagggtaata cacgcgaaga caactttaag cacttattgg gtaacgacaa cgttaagcgc   60
t                                                             61

<210> SEQ ID NO 265
<211> LENGTH: 61
<212> TYPE: DNA
<213> ORGANISM: Artificial Sequence
<220> FEATURE:
<223> OTHER INFORMATION: CelN20-Noligo reverse noligo

<400> SEQUENCE: 265
gcgcttaacg ttgtcgttac ccaataagtg cttaaagttg tcttcgcgtg tattaccctc   60
c                                                             61

<210> SEQ ID NO 266
<211> LENGTH: 33
<212> TYPE: DNA
<213> ORGANISM: Artificial Sequence
```

```
<220> FEATURE:
<223> OTHER INFORMATION: AS-Noligo forward noligo

<400> SEQUENCE: 266
agtcgacctg caggtatgtt aatatggact act                         33

<210> SEQ ID NO 267
<211> LENGTH: 33
<212> TYPE: DNA
<213> ORGANISM: Artificial Sequence
<220> FEATURE:
<223> OTHER INFORMATION: AS-Noligo reverse noligo

<400> SEQUENCE: 267
gtagtccata ttaacatacc tgcaggtcga ctc                         33

<210> SEQ ID NO 268
<211> LENGTH: 15
<212> TYPE: DNA
<213> ORGANISM: Artificial Sequence
<220> FEATURE:
<223> OTHER INFORMATION: N21 sticky end barcode

<400> SEQUENCE: 268
cctcgactca cactt                                             15

<210> SEQ ID NO 269
<211> LENGTH: 19
<212> TYPE: DNA
<213> ORGANISM: Artificial Sequence
<220> FEATURE:
<223> OTHER INFORMATION: N21 complete sequence barcode

<400> SEQUENCE: 269
tccctcgact cacacttgg                                         19

<210> SEQ ID NO 270
<211> LENGTH: 15
<212> TYPE: DNA
<213> ORGANISM: Artificial Sequence
<220> FEATURE:
<223> OTHER INFORMATION: N22 sticky end barcode

<400> SEQUENCE: 270
acacaacata gccac                                             15

<210> SEQ ID NO 271
<211> LENGTH: 19
<212> TYPE: DNA
<213> ORGANISM: Artificial Sequence
<220> FEATURE:
<223> OTHER INFORMATION: N22 complete sequence barcode

<400> SEQUENCE: 271
tcacacaaca tagccacgg                                         19

<210> SEQ ID NO 272
<211> LENGTH: 16
<212> TYPE: DNA
<213> ORGANISM: Artificial Sequence
<220> FEATURE:
<223> OTHER INFORMATION: N23 sticky end barcode

<400> SEQUENCE: 272
caaacagaaa ggccat                                            16
```

<210> SEQ ID NO 273
<211> LENGTH: 19
<212> TYPE: DNA
<213> ORGANISM: Artificial Sequence
<220> FEATURE:
<223> OTHER INFORMATION: N23 complete sequence barcode

<400> SEQUENCE: 273
tcaaacagaa aggccatgg                                              19

<210> SEQ ID NO 274
<211> LENGTH: 15
<212> TYPE: DNA
<213> ORGANISM: Artificial Sequence
<220> FEATURE:
<223> OTHER INFORMATION: N24 sticky end barcode

<400> SEQUENCE: 274
ctcatggatt ctacg                                                  15

<210> SEQ ID NO 275
<211> LENGTH: 19
<212> TYPE: DNA
<213> ORGANISM: Artificial Sequence
<220> FEATURE:
<223> OTHER INFORMATION: N24 complete sequence barcode

<400> SEQUENCE: 275
tcctcatgga ttctacggg                                              19

<210> SEQ ID NO 276
<211> LENGTH: 15
<212> TYPE: DNA
<213> ORGANISM: Artificial Sequence
<220> FEATURE:
<223> OTHER INFORMATION: 3UTR1 sticky end barcode

<400> SEQUENCE: 276
tgggctgaag ggttt                                                  15

<210> SEQ ID NO 277
<211> LENGTH: 19
<212> TYPE: DNA
<213> ORGANISM: Artificial Sequence
<220> FEATURE:
<223> OTHER INFORMATION: 3UTR1 complete sequence barcode

<400> SEQUENCE: 277
gatgggctga agggtttaa                                              19

<210> SEQ ID NO 278
<211> LENGTH: 15
<212> TYPE: DNA
<213> ORGANISM: Artificial Sequence
<220> FEATURE:
<223> OTHER INFORMATION: N32 sticky end barcode

<400> SEQUENCE: 278
cccatcacag cttac                                                  15

<210> SEQ ID NO 279
<211> LENGTH: 19
<212> TYPE: DNA
<213> ORGANISM: Artificial Sequence
<220> FEATURE:
<223> OTHER INFORMATION: N32 complete sequence barcode

```
<400> SEQUENCE: 279
gtcccatcac agcttacaa                                                19

<210> SEQ ID NO 280
<211> LENGTH: 15
<212> TYPE: DNA
<213> ORGANISM: Artificial Sequence
<220> FEATURE:
<223> OTHER INFORMATION: N36 sticky end barcode

<400> SEQUENCE: 280
taagggcgaa tgtac                                                    15

<210> SEQ ID NO 281
<211> LENGTH: 19
<212> TYPE: DNA
<213> ORGANISM: Artificial Sequence
<220> FEATURE:
<223> OTHER INFORMATION: N36 complete sequence barcode

<400> SEQUENCE: 281
actaagggcg aatgtacag                                                19

<210> SEQ ID NO 282
<211> LENGTH: 15
<212> TYPE: DNA
<213> ORGANISM: Artificial Sequence
<220> FEATURE:
<223> OTHER INFORMATION: N37 sticky end barcode

<400> SEQUENCE: 282
ctttgggtca tgtgc                                                    15

<210> SEQ ID NO 283
<211> LENGTH: 19
<212> TYPE: DNA
<213> ORGANISM: Artificial Sequence
<220> FEATURE:
<223> OTHER INFORMATION: N37  complete sequence barcode

<400> SEQUENCE: 283
aactttgggt catgtgctg                                                19

<210> SEQ ID NO 284
<211> LENGTH: 15
<212> TYPE: DNA
<213> ORGANISM: Artificial Sequence
<220> FEATURE:
<223> OTHER INFORMATION: N38 sticky end barcode

<400> SEQUENCE: 284
actaaaccac agcct                                                    15

<210> SEQ ID NO 285
<211> LENGTH: 19
<212> TYPE: DNA
<213> ORGANISM: Artificial Sequence
<220> FEATURE:
<223> OTHER INFORMATION: N38 complete sequence barcode

<400> SEQUENCE: 285
tcactaaacc acagcctac                                                19

<210> SEQ ID NO 286
```

```
<211> LENGTH: 15
<212> TYPE: DNA
<213> ORGANISM: Artificial Sequence
<220> FEATURE:
<223> OTHER INFORMATION: N39 sticky end barcode

<400> SEQUENCE: 286
gtgggacatc tgttt                                                    15

<210> SEQ ID NO 287
<211> LENGTH: 19
<212> TYPE: DNA
<213> ORGANISM: Artificial Sequence
<220> FEATURE:
<223> OTHER INFORMATION: N39 complete sequence barcode

<400> SEQUENCE: 287
acgtgggaca tctgtttcg                                                19

<210> SEQ ID NO 288
<211> LENGTH: 15
<212> TYPE: DNA
<213> ORGANISM: Artificial Sequence
<220> FEATURE:
<223> OTHER INFORMATION: N40 sticky end barcode

<400> SEQUENCE: 288
gcggaacccc tattt                                                    15

<210> SEQ ID NO 289
<211> LENGTH: 19
<212> TYPE: DNA
<213> ORGANISM: Artificial Sequence
<220> FEATURE:
<223> OTHER INFORMATION: N40 complete sequence barcode

<400> SEQUENCE: 289
gtgcgcggaa ccctattt                                                 19

<210> SEQ ID NO 290
<211> LENGTH: 15
<212> TYPE: DNA
<213> ORGANISM: Artificial Sequence
<220> FEATURE:
<223> OTHER INFORMATION: pJ23119 sticky end barcode

<400> SEQUENCE: 290
tagctcagtc ctagg                                                    15

<210> SEQ ID NO 291
<211> LENGTH: 10
<212> TYPE: DNA
<213> ORGANISM: Artificial Sequence
<220> FEATURE:
<223> OTHER INFORMATION: pJ23119 right barcode

<400> SEQUENCE: 291
tataatacta                                                          10

<210> SEQ ID NO 292
<211> LENGTH: 32
<212> TYPE: DNA
<213> ORGANISM: Artificial Sequence
<220> FEATURE:
<223> OTHER INFORMATION: pJ23119 complete sequence barcode

<400> SEQUENCE: 292
```
tgacagctag ctcagtccta ggtataatac ta          32

<210> SEQ ID NO 293
<211> LENGTH: 19
<212> TYPE: DNA
<213> ORGANISM: Artificial Sequence
<220> FEATURE:
<223> OTHER INFORMATION: SRBS2 sticky end barcode

<400> SEQUENCE: 293
ttcatttatc acaaaagga                         19

<210> SEQ ID NO 294
<211> LENGTH: 33
<212> TYPE: DNA
<213> ORGANISM: Artificial Sequence
<220> FEATURE:
<223> OTHER INFORMATION: SRBS2 complete sequence barcode

<400> SEQUENCE: 294
aaccgttcat ttatcacaaa aggattgttc gat          33

<210> SEQ ID NO 295
<211> LENGTH: 15
<212> TYPE: DNA
<213> ORGANISM: Artificial Sequence
<220> FEATURE:
<223> OTHER INFORMATION: SRBS3 sticky end barcode

<400> SEQUENCE: 295
acacaggaaa cagct                             15

<210> SEQ ID NO 296
<211> LENGTH: 22
<212> TYPE: DNA
<213> ORGANISM: Artificial Sequence
<220> FEATURE:
<223> OTHER INFORMATION: SRBS3 complete sequence barcode

<400> SEQUENCE: 296
gattcacaca ggaaacagct at                     22

<210> SEQ ID NO 297
<211> LENGTH: 19
<212> TYPE: DNA
<213> ORGANISM: Artificial Sequence
<220> FEATURE:
<223> OTHER INFORMATION: SRBS4 left barcode

<400> SEQUENCE: 297
aaattaattg ttctttttt                         19

<210> SEQ ID NO 298
<211> LENGTH: 15
<212> TYPE: DNA
<213> ORGANISM: Artificial Sequence
<220> FEATURE:
<223> OTHER INFORMATION: SRBS4 sticky end barcode

<400> SEQUENCE: 298
caggtgaagg ttccc                             15

<210> SEQ ID NO 299
<211> LENGTH: 36
<212> TYPE: DNA

```
<213> ORGANISM: Artificial Sequence
<220> FEATURE:
<223> OTHER INFORMATION: SRBS4 complete sequence barcode

<400> SEQUENCE: 299
aaattaattg ttcttttttc aggtgaaggt tcccat                              36

<210> SEQ ID NO 300
<211> LENGTH: 15
<212> TYPE: DNA
<213> ORGANISM: Artificial Sequence
<220> FEATURE:
<223> OTHER INFORMATION: SRBS5 left barcode

<400> SEQUENCE: 300
gactccatac ccgtt                                                     15

<210> SEQ ID NO 301
<211> LENGTH: 15
<212> TYPE: DNA
<213> ORGANISM: Artificial Sequence
<220> FEATURE:
<223> OTHER INFORMATION: SRBS5 sticky end barcode

<400> SEQUENCE: 301
ttttgggcta acagg                                                     15

<210> SEQ ID NO 302
<211> LENGTH: 16
<212> TYPE: DNA
<213> ORGANISM: Artificial Sequence
<220> FEATURE:
<223> OTHER INFORMATION: SRBS5 right barcode

<400> SEQUENCE: 302
aggaggaatt aaccat                                                    16

<210> SEQ ID NO 303
<211> LENGTH: 46
<212> TYPE: DNA
<213> ORGANISM: Artificial Sequence
<220> FEATURE:
<223> OTHER INFORMATION: SRBS5 complete sequence barcode

<400> SEQUENCE: 303
gactccatac ccgttttttg ggctaacagg aggaggaatt aaccat                   46

<210> SEQ ID NO 304
<211> LENGTH: 30
<212> TYPE: DNA
<213> ORGANISM: Artificial Sequence
<220> FEATURE:
<223> OTHER INFORMATION: T2A left barcode

<400> SEQUENCE: 304
caggaagcgg agagggcaga ggaagtctgc                                     30

<210> SEQ ID NO 305
<211> LENGTH: 15
<212> TYPE: DNA
<213> ORGANISM: Artificial Sequence
<220> FEATURE:
<223> OTHER INFORMATION: T2A sticky end barcode

<400> SEQUENCE: 305
taacatgcgg tgacg                                                     15
```

<210> SEQ ID NO 306
<211> LENGTH: 22
<212> TYPE: DNA
<213> ORGANISM: Artificial Sequence
<220> FEATURE:
<223> OTHER INFORMATION: T2A right barcode

<400> SEQUENCE: 306
tcgaggagaa tcctggtcct gg                                            22

<210> SEQ ID NO 307
<211> LENGTH: 67
<212> TYPE: DNA
<213> ORGANISM: Artificial Sequence
<220> FEATURE:
<223> OTHER INFORMATION: T2A complete sequence barcode

<400> SEQUENCE: 307
caggaagcgg agagggcaga ggaagtctgc taacatgcgg tgacgtcgag gagaatcctg   60
gtcctgg                                                             67

<210> SEQ ID NO 308
<211> LENGTH: 30
<212> TYPE: DNA
<213> ORGANISM: Artificial Sequence
<220> FEATURE:
<223> OTHER INFORMATION: F2A left barcode

<400> SEQUENCE: 308
caggaagcgg agtgaaacag actttgaatt                                    30

<210> SEQ ID NO 309
<211> LENGTH: 15
<212> TYPE: DNA
<213> ORGANISM: Artificial Sequence
<220> FEATURE:
<223> OTHER INFORMATION: F2A sticky end barcode

<400> SEQUENCE: 309
tcgaccttct caagt                                                    15

<210> SEQ ID NO 310
<211> LENGTH: 31
<212> TYPE: DNA
<213> ORGANISM: Artificial Sequence
<220> FEATURE:
<223> OTHER INFORMATION: F2A right barcode

<400> SEQUENCE: 310
tggcgggaga cgtggagtcc aaccctggtc c                                  31

<210> SEQ ID NO 311
<211> LENGTH: 76
<212> TYPE: DNA
<213> ORGANISM: Artificial Sequence
<220> FEATURE:
<223> OTHER INFORMATION: F2A complete sequence barcode

<400> SEQUENCE: 311
caggaagcgg agtgaaacag actttgaatt tcgaccttct caagttggcg ggagacgtgg   60
agtccaaccc tggtcc                                                   76

<210> SEQ ID NO 312

```
<211> LENGTH: 15
<212> TYPE: DNA
<213> ORGANISM: Artificial Sequence
<220> FEATURE:
<223> OTHER INFORMATION: LK3 sticky end barcode

<400> SEQUENCE: 312
ggctcgtctt cttca                                                    15

<210> SEQ ID NO 313
<211> LENGTH: 19
<212> TYPE: DNA
<213> ORGANISM: Artificial Sequence
<220> FEATURE:
<223> OTHER INFORMATION: LK3 complete sequence barcode

<400> SEQUENCE: 313
caggctcgtc ttcttcagg                                                19

<210> SEQ ID NO 314
<211> LENGTH: 15
<212> TYPE: DNA
<213> ORGANISM: Artificial Sequence
<220> FEATURE:
<223> OTHER INFORMATION: LK5 sticky end barcode

<400> SEQUENCE: 314
tcatcgtcag gcacc                                                    15

<210> SEQ ID NO 315
<211> LENGTH: 19
<212> TYPE: DNA
<213> ORGANISM: Artificial Sequence
<220> FEATURE:
<223> OTHER INFORMATION: LK5 complete sequence barcode

<400> SEQUENCE: 315
cctcatcgtc aggcacctc                                                19

<210> SEQ ID NO 316
<211> LENGTH: 16
<212> TYPE: DNA
<213> ORGANISM: Artificial Sequence
<220> FEATURE:
<223> OTHER INFORMATION: LK6 sticky end barcode

<400> SEQUENCE: 316
gacaacctgt atttcc                                                   16

<210> SEQ ID NO 317
<211> LENGTH: 25
<212> TYPE: DNA
<213> ORGANISM: Artificial Sequence
<220> FEATURE:
<223> OTHER INFORMATION: LK6 complete sequence barcode

<400> SEQUENCE: 317
ataaggacaa cctgtatttc caggg                                         25

<210> SEQ ID NO 318
<211> LENGTH: 15
<212> TYPE: DNA
<213> ORGANISM: Artificial Sequence
<220> FEATURE:
<223> OTHER INFORMATION: LK7 sticky end barcode

<400> SEQUENCE: 318
```

-continued agcaggagca cacat                                              15

<210> SEQ ID NO 319
<211> LENGTH: 19
<212> TYPE: DNA
<213> ORGANISM: Artificial Sequence
<220> FEATURE:
<223> OTHER INFORMATION: LK7 complete sequence barcode

<400> SEQUENCE: 319
cagcagcagg agcacacat                                          19

<210> SEQ ID NO 320
<211> LENGTH: 16
<212> TYPE: DNA
<213> ORGANISM: Artificial Sequence
<220> FEATURE:
<223> OTHER INFORMATION: Shistag sticky end barcode

<400> SEQUENCE: 320
catcatcatc accatc                                             16

<210> SEQ ID NO 321
<211> LENGTH: 23
<212> TYPE: DNA
<213> ORGANISM: Artificial Sequence
<220> FEATURE:
<223> OTHER INFORMATION: Shistag complete sequence barcode

<400> SEQUENCE: 321
ctcatcatca tcaccatcac tga                                     23

<210> SEQ ID NO 322
<211> LENGTH: 17
<212> TYPE: DNA
<213> ORGANISM: Artificial Sequence
<220> FEATURE:
<223> OTHER INFORMATION: 5UTR sticky end barcode

<400> SEQUENCE: 322
gcaatctaat ctaagtt                                            17

<210> SEQ ID NO 323
<211> LENGTH: 12
<212> TYPE: DNA
<213> ORGANISM: Artificial Sequence
<220> FEATURE:
<223> OTHER INFORMATION: 5UTR right barcode

<400> SEQUENCE: 323
ttctagaaaa at                                                 12

<210> SEQ ID NO 324
<211> LENGTH: 30
<212> TYPE: DNA
<213> ORGANISM: Artificial Sequence
<220> FEATURE:
<223> OTHER INFORMATION: 5UTR complete sequence barcode

<400> SEQUENCE: 324
agcaatctaa tctaagtttt ctagaaaaat                              30

<210> SEQ ID NO 325
<211> LENGTH: 16
<212> TYPE: DNA

```
<213> ORGANISM: Artificial Sequence
<220> FEATURE:
<223> OTHER INFORMATION: 5UTR2 sticky end barcode

<400> SEQUENCE: 325
tcgacggatt ctagta                                                      16

<210> SEQ ID NO 326
<211> LENGTH: 23
<212> TYPE: DNA
<213> ORGANISM: Artificial Sequence
<220> FEATURE:
<223> OTHER INFORMATION: 5UTR2 complete sequence barcode

<400> SEQUENCE: 326
tcgacggatt ctagtaaaat cat                                              23

<210> SEQ ID NO 327
<211> LENGTH: 17
<212> TYPE: DNA
<213> ORGANISM: Artificial Sequence
<220> FEATURE:
<223> OTHER INFORMATION: 5UTR3 sticky end barcode

<400> SEQUENCE: 327
caactatcaa aacacaa                                                     17

<210> SEQ ID NO 328
<211> LENGTH: 25
<212> TYPE: DNA
<213> ORGANISM: Artificial Sequence
<220> FEATURE:
<223> OTHER INFORMATION: 5UTR3 complete sequence barcode

<400> SEQUENCE: 328
tgaacaacta tcaaaacaca atgat                                            25

<210> SEQ ID NO 329
<211> LENGTH: 17
<212> TYPE: DNA
<213> ORGANISM: Artificial Sequence
<220> FEATURE:
<223> OTHER INFORMATION: 5UTR4 sticky end barcode

<400> SEQUENCE: 329
gcaatctaat ctaagtt                                                     17

<210> SEQ ID NO 330
<211> LENGTH: 19
<212> TYPE: DNA
<213> ORGANISM: Artificial Sequence
<220> FEATURE:
<223> OTHER INFORMATION: 5UTR4 right barcode

<400> SEQUENCE: 330
ttaattacaa atctagaat                                                   19

<210> SEQ ID NO 331
<211> LENGTH: 37
<212> TYPE: DNA
<213> ORGANISM: Artificial Sequence
<220> FEATURE:
<223> OTHER INFORMATION: 5UTR4 complete sequence barcode

<400> SEQUENCE: 331
agcaatctaa tctaagtttt aattacaaat ctagaat                               37
```

<210> SEQ ID NO 332
<211> LENGTH: 17
<212> TYPE: DNA
<213> ORGANISM: Artificial Sequence
<220> FEATURE:
<223> OTHER INFORMATION: 5UTR5 sticky end barcode

<400> SEQUENCE: 332
gcaatctaat ctaagtt                                                  17

<210> SEQ ID NO 333
<211> LENGTH: 13
<212> TYPE: DNA
<213> ORGANISM: Artificial Sequence
<220> FEATURE:
<223> OTHER INFORMATION: 5UTR5 right barcode

<400> SEQUENCE: 333
ttaattacaa aat                                                      13

<210> SEQ ID NO 334
<211> LENGTH: 31
<212> TYPE: DNA
<213> ORGANISM: Artificial Sequence
<220> FEATURE:
<223> OTHER INFORMATION: 5UTR5 complete sequence barcode

<400> SEQUENCE: 334
agcaatctaa tctaagtttt aattacaaaa t                                  31

<210> SEQ ID NO 335
<211> LENGTH: 17
<212> TYPE: DNA
<213> ORGANISM: Artificial Sequence
<220> FEATURE:
<223> OTHER INFORMATION: 5UTR6 sticky end barcode

<400> SEQUENCE: 335
gcaatctaat ctaagtt                                                  17

<210> SEQ ID NO 336
<211> LENGTH: 26
<212> TYPE: DNA
<213> ORGANISM: Artificial Sequence
<220> FEATURE:
<223> OTHER INFORMATION: 5UTR6 complete sequence barcode

<400> SEQUENCE: 336
agcaatctaa tctaagttta ccccat                                        26

<210> SEQ ID NO 337
<211> LENGTH: 17
<212> TYPE: DNA
<213> ORGANISM: Artificial Sequence
<220> FEATURE:
<223> OTHER INFORMATION: 5UTR7 sticky end barcode

<400> SEQUENCE: 337
gcaatctaat ctaagtt                                                  17

<210> SEQ ID NO 338
<211> LENGTH: 24
<212> TYPE: DNA
<213> ORGANISM: Artificial Sequence
<220> FEATURE:

<223> OTHER INFORMATION: 5UTR7 complete sequence barcode

<400> SEQUENCE: 338
agcaatctaa tctaagttta aaat                                          24

<210> SEQ ID NO 339
<211> LENGTH: 17
<212> TYPE: DNA
<213> ORGANISM: Artificial Sequence
<220> FEATURE:
<223> OTHER INFORMATION: 3UTR2 sticky end barcode

<400> SEQUENCE: 339
catcatcatc accatca                                                  17

<210> SEQ ID NO 340
<211> LENGTH: 25
<212> TYPE: DNA
<213> ORGANISM: Artificial Sequence
<220> FEATURE:
<223> OTHER INFORMATION: 3UTR2 complete sequence barcode

<400> SEQUENCE: 340
aacatcatca tcaccatcac taaaa                                         25

<210> SEQ ID NO 341
<211> LENGTH: 18
<212> TYPE: DNA
<213> ORGANISM: Artificial Sequence
<220> FEATURE:
<223> OTHER INFORMATION: 3UTR3 sticky end barcode

<400> SEQUENCE: 341
tgatttctga agaagatt                                                 18

<210> SEQ ID NO 342
<211> LENGTH: 35
<212> TYPE: DNA
<213> ORGANISM: Artificial Sequence
<220> FEATURE:
<223> OTHER INFORMATION: 3UTR3 complete sequence barcode

<400> SEQUENCE: 342
ctcaaaaatt gatttctgaa gaagatttgt aatga                              35

<210> SEQ ID NO 343
<211> LENGTH: 15
<212> TYPE: DNA
<213> ORGANISM: Artificial Sequence
<220> FEATURE:
<223> OTHER INFORMATION: 3UTR4 sticky end barcode

<400> SEQUENCE: 343
catcatcacc atcac                                                    15

<210> SEQ ID NO 344
<211> LENGTH: 15
<212> TYPE: DNA
<213> ORGANISM: Artificial Sequence
<220> FEATURE:
<223> OTHER INFORMATION: 3UTR4 right barcode

<400> SEQUENCE: 344
catcatcatt aatga                                                    15

-continued

```
<210> SEQ ID NO 345
<211> LENGTH: 38
<212> TYPE: DNA
<213> ORGANISM: Artificial Sequence
<220> FEATURE:
<223> OTHER INFORMATION: 3UTR4 complete sequence barcode

<400> SEQUENCE: 345
ctctcgagca tcatcaccat caccatcatc attaatga                              38

<210> SEQ ID NO 346
<211> LENGTH: 16
<212> TYPE: DNA
<213> ORGANISM: Artificial Sequence
<220> FEATURE:
<223> OTHER INFORMATION: 3UTR5 sticky end barcode

<400> SEQUENCE: 346
gcaatcgcat cacatt                                                      16

<210> SEQ ID NO 347
<211> LENGTH: 26
<212> TYPE: DNA
<213> ORGANISM: Artificial Sequence
<220> FEATURE:
<223> OTHER INFORMATION: 3UTR5 complete sequence barcode

<400> SEQUENCE: 347
gacgggcaat cgcatcacat tcaaga                                           26

<210> SEQ ID NO 348
<211> LENGTH: 16
<212> TYPE: DNA
<213> ORGANISM: Artificial Sequence
<220> FEATURE:
<223> OTHER INFORMATION: 3UTR6 sticky end barcode

<400> SEQUENCE: 348
ttatgtcacg cttaca                                                      16

<210> SEQ ID NO 349
<211> LENGTH: 26
<212> TYPE: DNA
<213> ORGANISM: Artificial Sequence
<220> FEATURE:
<223> OTHER INFORMATION: 3UTR6 complete sequence barcode

<400> SEQUENCE: 349
attagttatg tcacgcttac attcac                                           26

<210> SEQ ID NO 350
<211> LENGTH: 16
<212> TYPE: DNA
<213> ORGANISM: Artificial Sequence
<220> FEATURE:
<223> OTHER INFORMATION: 3UTR7 sticky end barcode

<400> SEQUENCE: 350
catcatcatc atcacc                                                      16

<210> SEQ ID NO 351
<211> LENGTH: 21
<212> TYPE: DNA
<213> ORGANISM: Artificial Sequence
<220> FEATURE:
<223> OTHER INFORMATION: 3UTR7 complete sequence barcode
```

```
<400> SEQUENCE: 351
ctcatcatca tcatcaccat g                                              21

<210> SEQ ID NO 352
<211> LENGTH: 17
<212> TYPE: DNA
<213> ORGANISM: Artificial Sequence
<220> FEATURE:
<223> OTHER INFORMATION: ICeuI sticky end barcode

<400> SEQUENCE: 352
ataacggtcc taaggta                                                   17

<210> SEQ ID NO 353
<211> LENGTH: 26
<212> TYPE: DNA
<213> ORGANISM: Artificial Sequence
<220> FEATURE:
<223> OTHER INFORMATION: ICeuI complete sequence barcode

<400> SEQUENCE: 353
aactataacg gtcctaaggt agcgaa                                         26

<210> SEQ ID NO 354
<211> LENGTH: 18
<212> TYPE: DNA
<213> ORGANISM: Artificial Sequence
<220> FEATURE:
<223> OTHER INFORMATION: SEC17_L sticky end barcode

<400> SEQUENCE: 354
atgtagtagg gaaatata                                                  18

<210> SEQ ID NO 355
<211> LENGTH: 23
<212> TYPE: DNA
<213> ORGANISM: Artificial Sequence
<220> FEATURE:
<223> OTHER INFORMATION: SEC17_L  complete sequence barcode

<400> SEQUENCE: 355
atgtagtagg gaaatatatc aaa                                            23

<210> SEQ ID NO 356
<211> LENGTH: 16
<212> TYPE: DNA
<213> ORGANISM: Artificial Sequence
<220> FEATURE:
<223> OTHER INFORMATION: SEC17_R sticky end barcode

<400> SEQUENCE: 356
gatatttccc gttgtg                                                    16

<210> SEQ ID NO 357
<211> LENGTH: 21
<212> TYPE: DNA
<213> ORGANISM: Artificial Sequence
<220> FEATURE:
<223> OTHER INFORMATION: SEC17_R complete sequence barcode

<400> SEQUENCE: 357
tgatatttcc cgttgtgtta a                                              21

<210> SEQ ID NO 358
<211> LENGTH: 18
```

```
<212> TYPE: DNA
<213> ORGANISM: Artificial Sequence
<220> FEATURE:
<223> OTHER INFORMATION: EFB1_L sticky end barcode

<400> SEQUENCE: 358
atgttccgat ttagttta                                              18

<210> SEQ ID NO 359
<211> LENGTH: 25
<212> TYPE: DNA
<213> ORGANISM: Artificial Sequence
<220> FEATURE:
<223> OTHER INFORMATION: EFB1_L complete sequence barcode

<400> SEQUENCE: 359
atgttccgat ttagtttact ttata                                      25

<210> SEQ ID NO 360
<211> LENGTH: 18
<212> TYPE: DNA
<213> ORGANISM: Artificial Sequence
<220> FEATURE:
<223> OTHER INFORMATION: EFB1_R sticky end barcode

<400> SEQUENCE: 360
gttttgtttc tcctttta                                              18

<210> SEQ ID NO 361
<211> LENGTH: 23
<212> TYPE: DNA
<213> ORGANISM: Artificial Sequence
<220> FEATURE:
<223> OTHER INFORMATION: EFB1_R complete sequence barcode

<400> SEQUENCE: 361
gttttgtttc tccttttaaa ata                                        23

<210> SEQ ID NO 362
<211> LENGTH: 16
<212> TYPE: DNA
<213> ORGANISM: Artificial Sequence
<220> FEATURE:
<223> OTHER INFORMATION: N21 RG-f conventional oligo

<400> SEQUENCE: 362
cctcgactca cacttg                                                16

<210> SEQ ID NO 363
<211> LENGTH: 17
<212> TYPE: DNA
<213> ORGANISM: Artificial Sequence
<220> FEATURE:
<223> OTHER INFORMATION: N21 RG-r conventional oligo
<220> FEATURE:
<221> NAME/KEY: misc_feature
<222> LOCATION: (1)..(1)
<223> OTHER INFORMATION: 5'-end phosphorylation

<400> SEQUENCE: 363
ccaagtgtga gtcgagg                                               17

<210> SEQ ID NO 364
<211> LENGTH: 18
<212> TYPE: DNA
<213> ORGANISM: Artificial Sequence
<220> FEATURE:
```

<223> OTHER INFORMATION: N22 RG-f conventional oligo

<400> SEQUENCE: 364
acacaacata gccacggg                                                        18

<210> SEQ ID NO 365
<211> LENGTH: 17
<212> TYPE: DNA
<213> ORGANISM: Artificial Sequence
<220> FEATURE:
<223> OTHER INFORMATION: N22 Rg-r conventional oligo
<220> FEATURE:
<221> NAME/KEY: misc_feature
<222> LOCATION: (1)..(1)
<223> OTHER INFORMATION: 5'-end phosphorylation

<400> SEQUENCE: 365
ccgtggctat gttgtgt                                                         17

<210> SEQ ID NO 366
<211> LENGTH: 19
<212> TYPE: DNA
<213> ORGANISM: Artificial Sequence
<220> FEATURE:
<223> OTHER INFORMATION: N23 RG-f conventional oligo

<400> SEQUENCE: 366
caaacagaaa ggccatggg                                                       19

<210> SEQ ID NO 367
<211> LENGTH: 18
<212> TYPE: DNA
<213> ORGANISM: Artificial Sequence
<220> FEATURE:
<223> OTHER INFORMATION: N23 RG-r conventional oligo
<220> FEATURE:
<221> NAME/KEY: misc_feature
<222> LOCATION: (1)..(1)
<223> OTHER INFORMATION: 5'-end phosphorylation

<400> SEQUENCE: 367
ccatggcctt tctgtttg                                                        18

<210> SEQ ID NO 368
<211> LENGTH: 18
<212> TYPE: DNA
<213> ORGANISM: Artificial Sequence
<220> FEATURE:
<223> OTHER INFORMATION: N24 RG-f conventional oligo

<400> SEQUENCE: 368
ctcatggatt ctacgggg                                                        18

<210> SEQ ID NO 369
<211> LENGTH: 17
<212> TYPE: DNA
<213> ORGANISM: Artificial Sequence
<220> FEATURE:
<223> OTHER INFORMATION: N24 RG-r conventional oligo
<220> FEATURE:
<221> NAME/KEY: misc_feature
<222> LOCATION: (1)..(1)
<223> OTHER INFORMATION: 5'-end phosphorylation

<400> SEQUENCE: 369
cccgtagaat ccatgag                                                         17

```
<210> SEQ ID NO 370
<211> LENGTH: 26
<212> TYPE: DNA
<213> ORGANISM: Artificial Sequence
<220> FEATURE:
<223> OTHER INFORMATION: pJ23119 RG-f conventional oligo

<400> SEQUENCE: 370
tagctcagtc ctaggtataa tactag                                      26

<210> SEQ ID NO 371
<211> LENGTH: 25
<212> TYPE: DNA
<213> ORGANISM: Artificial Sequence
<220> FEATURE:
<223> OTHER INFORMATION: pJ23119 RG-r conventional oligo
<220> FEATURE:
<221> NAME/KEY: misc_feature
<222> LOCATION: (1)..(1)
<223> OTHER INFORMATION: 5'-end phosphorylation

<400> SEQUENCE: 371
tagtattata cctaggactg agcta                                       25

<210> SEQ ID NO 372
<211> LENGTH: 17
<212> TYPE: DNA
<213> ORGANISM: Artificial Sequence
<220> FEATURE:
<223> OTHER INFORMATION: N21 LG-f conventional oligo
<220> FEATURE:
<221> NAME/KEY: misc_feature
<222> LOCATION: (1)..(1)
<223> OTHER INFORMATION: 5'-end phosphorylation

<400> SEQUENCE: 372
tccctcgact cacactt                                                17

<210> SEQ ID NO 373
<211> LENGTH: 18
<212> TYPE: DNA
<213> ORGANISM: Artificial Sequence
<220> FEATURE:
<223> OTHER INFORMATION: N21 LG-r conventional oligo

<400> SEQUENCE: 373
aagtgtgagt cgagggaa                                               18

<210> SEQ ID NO 374
<211> LENGTH: 17
<212> TYPE: DNA
<213> ORGANISM: Artificial Sequence
<220> FEATURE:
<223> OTHER INFORMATION: N22 LG-f conventional oligo
<220> FEATURE:
<221> NAME/KEY: misc_feature
<222> LOCATION: (1)..(1)
<223> OTHER INFORMATION: 5'-end phosphorylation

<400> SEQUENCE: 374
tcacacaaca tagccac                                                17

<210> SEQ ID NO 375
<211> LENGTH: 18
<212> TYPE: DNA
<213> ORGANISM: Artificial Sequence
<220> FEATURE:
<223> OTHER INFORMATION: N22 LG-r conventional oligo
```

<400> SEQUENCE: 375
gtggctatgt tgtgtgaa                                                18

<210> SEQ ID NO 376
<211> LENGTH: 17
<212> TYPE: DNA
<213> ORGANISM: artificial
<220> FEATURE:
<223> OTHER INFORMATION: N23 LG-f
<220> FEATURE:
<221> NAME/KEY: misc_feature
<222> LOCATION: (1)..(1)
<223> OTHER INFORMATION: 5'-end phosphorylation

<400> SEQUENCE: 376
tcaaacagaa aggccat                                                 17

<210> SEQ ID NO 377
<211> LENGTH: 18
<212> TYPE: DNA
<213> ORGANISM: Artificial Sequence
<220> FEATURE:
<223> OTHER INFORMATION: N23 LG-r conventional oligo

<400> SEQUENCE: 377
atggcctttc tgtttgaa                                                18

<210> SEQ ID NO 378
<211> LENGTH: 17
<212> TYPE: DNA
<213> ORGANISM: Artificial Sequence
<220> FEATURE:
<223> OTHER INFORMATION: N24 LG-f conventional oligo
<220> FEATURE:
<221> NAME/KEY: misc_feature
<222> LOCATION: (1)..(1)
<223> OTHER INFORMATION: 5'-end phosphorylation

<400> SEQUENCE: 378
tcctcatgga ttctacg                                                 17

<210> SEQ ID NO 379
<211> LENGTH: 18
<212> TYPE: DNA
<213> ORGANISM: Artificial Sequence
<220> FEATURE:
<223> OTHER INFORMATION: N24 LG-r conventional oligo

<400> SEQUENCE: 379
cgtagaatcc atgaggaa                                                18

<210> SEQ ID NO 380
<211> LENGTH: 22
<212> TYPE: DNA
<213> ORGANISM: Artificial Sequence
<220> FEATURE:
<223> OTHER INFORMATION: pJ23119 LG-f conventional oligo
<220> FEATURE:
<221> NAME/KEY: misc_feature
<222> LOCATION: (1)..(1)
<223> OTHER INFORMATION: 5'-end phosphorylation

<400> SEQUENCE: 380
tgacagctag ctcagtccta gg                                           22

<210> SEQ ID NO 381
<211> LENGTH: 23

```
<212> TYPE: DNA
<213> ORGANISM: Artificial Sequence
<220> FEATURE:
<223> OTHER INFORMATION: pJ23119 LG-r conventional oligo

<400> SEQUENCE: 381
cctaggactg agctagctgt caa                                            23

<210> SEQ ID NO 382
<211> LENGTH: 69
<212> TYPE: DNA
<213> ORGANISM: Artificial Sequence
<220> FEATURE:
<223> OTHER INFORMATION: RBS1 RG-Boligo

<400> SEQUENCE: 382
atatgtatat ctccttctta agttaaaca atatgttttg tttaacttta agaaggagat    60
atacatatg                                                            69

<210> SEQ ID NO 383
<211> LENGTH: 65
<212> TYPE: DNA
<213> ORGANISM: Artificial Sequence
<220> FEATURE:
<223> OTHER INFORMATION: RBS1 LA-Boligo

<400> SEQUENCE: 383
agaaataatt ttgtttaact ttaagaaggt ctactccttc ttaaagttaa acaaaattat    60
ttcta                                                                65

<210> SEQ ID NO 384
<211> LENGTH: 63
<212> TYPE: DNA
<213> ORGANISM: Artificial Sequence
<220> FEATURE:
<223> OTHER INFORMATION: SRBS2 RG-Boligo

<400> SEQUENCE: 384
atcgaacaat cctttgtga taaatgaatc ggttttcatt tatcacaaaa ggattgttcg     60
atg                                                                  63

<210> SEQ ID NO 385
<211> LENGTH: 55
<212> TYPE: DNA
<213> ORGANISM: Artificial Sequence
<220> FEATURE:
<223> OTHER INFORMATION: SRBS2 LA-Boligo

<400> SEQUENCE: 385
aaccgttcat ttatcacaaa aggatatcac tcctttgtg ataaatgaac ggtta          55

<210> SEQ ID NO 386
<211> LENGTH: 41
<212> TYPE: DNA
<213> ORGANISM: Artificial Sequence
<220> FEATURE:
<223> OTHER INFORMATION: SRBS3 RG-Boligo

<400> SEQUENCE: 386
atagctgttt cctgtgtgcc tggacacagg aaacagctat g                        41

<210> SEQ ID NO 387
<211> LENGTH: 47
<212> TYPE: DNA
```

```
<213> ORGANISM: Artificial Sequence
<220> FEATURE:
<223> OTHER INFORMATION: SRBS3 LA-Boligo

<400> SEQUENCE: 387
gattcacaca ggaaacagct tcttcgagct gtttcctgtg tgaatca                          47

<210> SEQ ID NO 388
<211> LENGTH: 41
<212> TYPE: DNA
<213> ORGANISM: Artificial Sequence
<220> FEATURE:
<223> OTHER INFORMATION: SRBS4 RG-Boligo

<400> SEQUENCE: 388
atgggaacct tcacctgaag ttacaggtga aggttcccat g                                41

<210> SEQ ID NO 389
<211> LENGTH: 75
<212> TYPE: DNA
<213> ORGANISM: Artificial Sequence
<220> FEATURE:
<223> OTHER INFORMATION: SRBS4 LA-Boligo

<400> SEQUENCE: 389
aaattaattg ttcttttttc aggtgaaggt tccctcacat gggaaccttc acctgaaaaa            60
agaacaatta attta                                                            75

<210> SEQ ID NO 390
<211> LENGTH: 57
<212> TYPE: DNA
<213> ORGANISM: Artificial Sequence
<220> FEATURE:
<223> OTHER INFORMATION: pJ23119 RG-Boligo

<400> SEQUENCE: 390
tagtattata cctaggactg agctaagagg gtagctcagt cctaggtata atactag              57

<210> SEQ ID NO 391
<211> LENGTH: 51
<212> TYPE: DNA
<213> ORGANISM: Artificial Sequence
<220> FEATURE:
<223> OTHER INFORMATION: pJ23119 LA-Boligo

<400> SEQUENCE: 391
tgacagctag ctcagtccta gggcacagcc taggactgag ctagctgtca a                    51

<210> SEQ ID NO 392
<211> LENGTH: 41
<212> TYPE: DNA
<213> ORGANISM: Artificial Sequence
<220> FEATURE:
<223> OTHER INFORMATION: N21 RG-Boligo

<400> SEQUENCE: 392
ccaagtgtga gtcgaggaag ggccctcgac tcacacttgg g                                41

<210> SEQ ID NO 393
<211> LENGTH: 41
<212> TYPE: DNA
<213> ORGANISM: Artificial Sequence
<220> FEATURE:
<223> OTHER INFORMATION: N21 LA-Boligo

<400> SEQUENCE: 393
```
tccctcgact cacacttgcg agaaagtgtg agtcgaggga a        41

<210> SEQ ID NO 394
<211> LENGTH: 41
<212> TYPE: DNA
<213> ORGANISM: Artificial Sequence
<220> FEATURE:
<223> OTHER INFORMATION: N22 RG-Boligo

<400> SEQUENCE: 394
ccgtggctat gttgtgtcgt attacacaac atagccacgg g        41

<210> SEQ ID NO 395
<211> LENGTH: 41
<212> TYPE: DNA
<213> ORGANISM: Artificial Sequence
<220> FEATURE:
<223> OTHER INFORMATION: N22 LA-Boligo

<400> SEQUENCE: 395
tcacacaaca tagccacttg ctggtggcta tgttgtgtga a        41

<210> SEQ ID NO 396
<211> LENGTH: 43
<212> TYPE: DNA
<213> ORGANISM: Artificial Sequence
<220> FEATURE:
<223> OTHER INFORMATION: N23 RG-Boligo

<400> SEQUENCE: 396
ccatggcctt tctgtttgac catacaaaca gaaaggccat ggg        43

<210> SEQ ID NO 397
<211> LENGTH: 41
<212> TYPE: DNA
<213> ORGANISM: Artificial Sequence
<220> FEATURE:
<223> OTHER INFORMATION: N23 LA-Boligo

<400> SEQUENCE: 397
tcaaacagaa aggccatcat tcaatggcct ttctgtttga a        41

<210> SEQ ID NO 398
<211> LENGTH: 41
<212> TYPE: DNA
<213> ORGANISM: Artificial Sequence
<220> FEATURE:
<223> OTHER INFORMATION: N24 RG-Boligo

<400> SEQUENCE: 398
cccgtagaat ccatgagaac ccgctcatgg attctacggg g        41

<210> SEQ ID NO 399
<211> LENGTH: 41
<212> TYPE: DNA
<213> ORGANISM: Artificial Sequence
<220> FEATURE:
<223> OTHER INFORMATION: N24 LA-Boligo

<400> SEQUENCE: 399
tcctcatgga ttctacgact atgcgtagaa tccatgagga a        41

<210> SEQ ID NO 400
<211> LENGTH: 41
<212> TYPE: DNA

```
<213> ORGANISM: Artificial Sequence
<220> FEATURE:
<223> OTHER INFORMATION: 3UTR1 RG-Boligo

<400> SEQUENCE: 400
ttaaaccctt cagcccacac acatgggctg aagggtttaa g                 41

<210> SEQ ID NO 401
<211> LENGTH: 41
<212> TYPE: DNA
<213> ORGANISM: Artificial Sequence
<220> FEATURE:
<223> OTHER INFORMATION: 3UTR1 LA-Boligo

<400> SEQUENCE: 401
gatgggctga agggtttcac acaaaaccct tcagcccatc a                 41

<210> SEQ ID NO 402
<211> LENGTH: 41
<212> TYPE: DNA
<213> ORGANISM: Artificial Sequence
<220> FEATURE:
<223> OTHER INFORMATION: N32 RG-Boligo

<400> SEQUENCE: 402
ttgtaagctg tgatggggcc tggcccatca cagcttacaa g                 41

<210> SEQ ID NO 403
<211> LENGTH: 41
<212> TYPE: DNA
<213> ORGANISM: Artificial Sequence
<220> FEATURE:
<223> OTHER INFORMATION: N32 LA-Boligo

<400> SEQUENCE: 403
gtcccatcac agcttacgct tcggtaagct gtgatgggac a                 41

<210> SEQ ID NO 404
<211> LENGTH: 41
<212> TYPE: DNA
<213> ORGANISM: Artificial Sequence
<220> FEATURE:
<223> OTHER INFORMATION: LK3 RG-Boligo

<400> SEQUENCE: 404
cctgaagaag acgagcccac acaggctcgt cttcttcagg g                 41

<210> SEQ ID NO 405
<211> LENGTH: 41
<212> TYPE: DNA
<213> ORGANISM: Artificial Sequence
<220> FEATURE:
<223> OTHER INFORMATION: LK3 LA-Boligo

<400> SEQUENCE: 405
caggctcgtc ttcttcacac acatgaagaa gacgagcctg a                 41

<210> SEQ ID NO 406
<211> LENGTH: 65
<212> TYPE: DNA
<213> ORGANISM: Artificial Sequence
<220> FEATURE:
<223> OTHER INFORMATION: 5UTR RG-Boligo

<400> SEQUENCE: 406
atttttctag aaaacttaga ttagattgca agttagcaat ctaatctaag ttttctagaa    60
``` aaatg                                                              65

<210> SEQ ID NO 407
<211> LENGTH: 43
<212> TYPE: DNA
<213> ORGANISM: Artificial Sequence
<220> FEATURE:
<223> OTHER INFORMATION: 5UTR LA-Boligo

<400> SEQUENCE: 407
agcaatctaa tctaagttgc acataactta gattagattg cta                    43

<210> SEQ ID NO 408
<211> LENGTH: 53
<212> TYPE: DNA
<213> ORGANISM: Artificial Sequence
<220> FEATURE:
<223> OTHER INFORMATION: 3UTR2 RG-Boligo

<400> SEQUENCE: 408
ttttagtgat ggtgatgatg atgggcaatc atcatcatca ccatcactaa aag         53

<210> SEQ ID NO 409
<211> LENGTH: 45
<212> TYPE: DNA
<213> ORGANISM: Artificial Sequence
<220> FEATURE:
<223> OTHER INFORMATION: 3UTR2 LA-Boligo

<400> SEQUENCE: 409
aacatcatca tcaccatcaa tgtactgatg gtgatgatga tgtta                  45

<210> SEQ ID NO 410
<211> LENGTH: 41
<212> TYPE: DNA
<213> ORGANISM: Artificial Sequence
<220> FEATURE:
<223> OTHER INFORMATION: N36 RA-Boligo

<400> SEQUENCE: 410
ctgtacattc gcccttaagc ttgtaagggc gaatgtacag a                      41

<210> SEQ ID NO 411
<211> LENGTH: 41
<212> TYPE: DNA
<213> ORGANISM: Artificial Sequence
<220> FEATURE:
<223> OTHER INFORMATION: N36 LG-Boligo

<400> SEQUENCE: 411
actaagggcg aatgtacagc ttggtacatt cgcccttagt g                      41

<210> SEQ ID NO 412
<211> LENGTH: 51
<212> TYPE: DNA
<213> ORGANISM: Artificial Sequence
<220> FEATURE:
<223> OTHER INFORMATION: ICeuI RA-Boligo

<400> SEQUENCE: 412
ttcgctacct taggaccgtt atagcttgat aacggtccta aggtagcgaa a           51

<210> SEQ ID NO 413
<211> LENGTH: 49
<212> TYPE: DNA

```
<213> ORGANISM: Artificial Sequence
<220> FEATURE:
<223> OTHER INFORMATION: ICeuI LG-Boligo

<400> SEQUENCE: 413
aactataacg gtcctaaggt aagcttgtac cttaggaccg ttatagttg                49

<210> SEQ ID NO 414
<211> LENGTH: 41
<212> TYPE: DNA
<213> ORGANISM: Artificial Sequence
<220> FEATURE:
<223> OTHER INFORMATION: N22 RA-Boligo

<400> SEQUENCE: 414
ccgtggctat gttgtgtagc ttgacacaac atagccacgg a                       41

<210> SEQ ID NO 415
<211> LENGTH: 41
<212> TYPE: DNA
<213> ORGANISM: Artificial Sequence
<220> FEATURE:
<223> OTHER INFORMATION: N22 LG-Boligo

<400> SEQUENCE: 415
tcacacaaca tagccacagc ttggtggcta tgttgtgtga g                       41

<210> SEQ ID NO 416
<211> LENGTH: 53
<212> TYPE: DNA
<213> ORGANISM: Artificial Sequence
<220> FEATURE:
<223> OTHER INFORMATION: 3UTR2 RA-Boligo

<400> SEQUENCE: 416
ttttagtgat ggtgatgatg atgggcaatc atcatcatca ccatcactaa aaa          53

<210> SEQ ID NO 417
<211> LENGTH: 45
<212> TYPE: DNA
<213> ORGANISM: Artificial Sequence
<220> FEATURE:
<223> OTHER INFORMATION: 3UTR2 LG-Boligo

<400> SEQUENCE: 417
aacatcatca tcaccatcaa tgtactgatg gtgatgatga tgttg                   45

<210> SEQ ID NO 418
<211> LENGTH: 41
<212> TYPE: DNA
<213> ORGANISM: Artificial Sequence
<220> FEATURE:
<223> OTHER INFORMATION: N21 RA-Boligo

<400> SEQUENCE: 418
ccaagtgtga gtcgaggaag ggccctcgac tcacacttgg a                       41

<210> SEQ ID NO 419
<211> LENGTH: 41
<212> TYPE: DNA
<213> ORGANISM: Artificial Sequence
<220> FEATURE:
<223> OTHER INFORMATION: N21 LG-Boligo

<400> SEQUENCE: 419
tccctcgact cacacttgcg agaaagtgtg agtcgaggga g                       41
```

<210> SEQ ID NO 420
<211> LENGTH: 43
<212> TYPE: DNA
<213> ORGANISM: Artificial Sequence
<220> FEATURE:
<223> OTHER INFORMATION: N23 RA-Boligo

<400> SEQUENCE: 420
ccatggcctt tctgtttgac catacaaaca gaaaggccat gga        43

<210> SEQ ID NO 421
<211> LENGTH: 41
<212> TYPE: DNA
<213> ORGANISM: Artificial Sequence
<220> FEATURE:
<223> OTHER INFORMATION: N23 LG-Boligo

<400> SEQUENCE: 421
tcaaacagaa aggccatcat tcaatggcct ttctgtttga g          41

<210> SEQ ID NO 422
<211> LENGTH: 32
<212> TYPE: DNA
<213> ORGANISM: Artificial Sequence
<220> FEATURE:
<223> OTHER INFORMATION: RBS1-G-Assemble
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (19)..(20)
<223> OTHER INFORMATION: phosphorothioate bond

<400> SEQUENCE: 422
ttgtttaact ttaagaagga gatatacata tg                    32

<210> SEQ ID NO 423
<211> LENGTH: 30
<212> TYPE: DNA
<213> ORGANISM: Artificial Sequence
<220> FEATURE:
<223> OTHER INFORMATION: RBS1-T-Assemble
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (19)..(20)
<223> OTHER INFORMATION: phosphorothioate bond

<400> SEQUENCE: 423
ccttcttaaa gttaaacaaa attatttcta                       30

<210> SEQ ID NO 424
<211> LENGTH: 29
<212> TYPE: DNA
<213> ORGANISM: Artificial Sequence
<220> FEATURE:
<223> OTHER INFORMATION: SRBS2-G-Assemble
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (19)..(20)

<223> OTHER INFORMATION: phosphorothioate bond

<400> SEQUENCE: 424
ttcatttatc acaaaggat tgttcgatg                    29

<210> SEQ ID NO 425
<211> LENGTH: 25
<212> TYPE: DNA
<213> ORGANISM: Artificial Sequence
<220> FEATURE:
<223> OTHER INFORMATION: SRBS2-T-Assemble
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (19)..(20)
<223> OTHER INFORMATION: phosphorothioate bond

<400> SEQUENCE: 425
tccttttgtg ataaatgaac ggtta                       25

<210> SEQ ID NO 426
<211> LENGTH: 18
<212> TYPE: DNA
<213> ORGANISM: Artificial Sequence
<220> FEATURE:
<223> OTHER INFORMATION: SRBS3-G-Assemble
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 426
acacaggaaa cagctatg                               18

<210> SEQ ID NO 427
<211> LENGTH: 21
<212> TYPE: DNA
<213> ORGANISM: Artificial Sequence
<220> FEATURE:
<223> OTHER INFORMATION: SRBS3-T-Assemble
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 427
agctgtttcc tgtgtgaatc a                           21

<210> SEQ ID NO 428
<211> LENGTH: 18
<212> TYPE: DNA
<213> ORGANISM: Artificial Sequence
<220> FEATURE:
<223> OTHER INFORMATION: SRBS4-G-Assemble
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding

```
<222> LOCATION: (15)..(16)
<223> OTHER INFORMATION: phosphorothioate bond

<400> SEQUENCE: 428
caggtgaagg ttcccatg                                                    18

<210> SEQ ID NO 429
<211> LENGTH: 35
<212> TYPE: DNA
<213> ORGANISM: Artificial Sequence
<220> FEATURE:
<223> OTHER INFORMATION: SRBS4-T-Assemble
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 429
gggaaccttc acctgaaaaa agaacaatta attta                                 35

<210> SEQ ID NO 430
<211> LENGTH: 26
<212> TYPE: DNA
<213> ORGANISM: Artificial Sequence
<220> FEATURE:
<223> OTHER INFORMATION: pJ23119-G-Assemble
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 430
tagctcagtc ctaggtataa tactag                                           26

<210> SEQ ID NO 431
<211> LENGTH: 23
<212> TYPE: DNA
<213> ORGANISM: Artificial Sequence
<220> FEATURE:
<223> OTHER INFORMATION: pJ23119-T-Assemble
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 431
cctaggactg agctagctgt caa                                              23

<210> SEQ ID NO 432
<211> LENGTH: 18
<212> TYPE: DNA
<213> ORGANISM: Artificial Sequence
<220> FEATURE:
<223> OTHER INFORMATION: N21-G-Assemble
<220> FEATURE:
<221> NAME/KEY: misc_binding
<222> LOCATION: (7)..(8)
<223> OTHER INFORMATION: phosphorothioate bond
<220> FEATURE:
```

<221> NAME/KEY: misc_binding
<222> LOCATION: (15)..(16)
<223> OTHER INFORMATION: phosphorothioate bond

<400> SEQUENCE: 432
cctcgactca cacttggg                                                 18

<210> SEQ ID NO 433
<211> LENGTH: 18
<212> TYPE: DNA
<213> ORGANISM: Artificial Sequence
<220> FEATURE:
<223> OTHER INFORMATION: N21-T-Assemble
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 433
aagtgtgagt cgagggaa                                                 18

<210> SEQ ID NO 434
<211> LENGTH: 18
<212> TYPE: DNA
<213> ORGANISM: Artificial Sequence
<220> FEATURE:
<223> OTHER INFORMATION: N22-G-Assemble
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 434
acacaacata gccacggg                                                 18

<210> SEQ ID NO 435
<211> LENGTH: 18
<212> TYPE: DNA
<213> ORGANISM: Artificial Sequence
<220> FEATURE:
<223> OTHER INFORMATION: N22-T-Assemble
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 435
gtggctatgt tgtgtgaa                                                 18

<210> SEQ ID NO 436
<211> LENGTH: 19
<212> TYPE: DNA
<213> ORGANISM: Artificial Sequence
<220> FEATURE:
<223> OTHER INFORMATION: N23-G-Assemble
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (16)..(17)
<223> OTHER INFORMATION: phosphorothioate bond

<400> SEQUENCE: 436
caaacagaaa ggccatggg                                            19

<210> SEQ ID NO 437
<211> LENGTH: 18
<212> TYPE: DNA
<213> ORGANISM: Artificial Sequence
<220> FEATURE:
<223> OTHER INFORMATION: N23-T-Assemble
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (16)..(17)
<223> OTHER INFORMATION: phosphorothioate bond

<400> SEQUENCE: 437
atggcctttc tgtttgaa                                             18

<210> SEQ ID NO 438
<211> LENGTH: 19
<212> TYPE: DNA
<213> ORGANISM: Artificial Sequence
<220> FEATURE:
<223> OTHER INFORMATION: N24-G-Assemble
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 438
ctcatggatt ctacggggg                                            19

<210> SEQ ID NO 439
<211> LENGTH: 18
<212> TYPE: DNA
<213> ORGANISM: Artificial Sequence
<220> FEATURE:
<223> OTHER INFORMATION: N24-T-Assemble
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 439
cgtagaatcc atgaggaa                                             18

<210> SEQ ID NO 440
<211> LENGTH: 18
<212> TYPE: DNA
<213> ORGANISM: Artificial Sequence
<220> FEATURE:
<223> OTHER INFORMATION: 3UTR1-G-Assemble
<220> FEATURE:
<221> NAME/KEY: misc_binding
<222> LOCATION: (7)..(8)

<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 440
tgggctgaag ggtttaag                                                 18

<210> SEQ ID NO 441
<211> LENGTH: 18
<212> TYPE: DNA
<213> ORGANISM: Artificial Sequence
<220> FEATURE:
<223> OTHER INFORMATION: 3UTR1-T-Assemble
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 441
aaacccttca gcccatca                                                 18

<210> SEQ ID NO 442
<211> LENGTH: 18
<212> TYPE: DNA
<213> ORGANISM: Artificial Sequence
<220> FEATURE:
<223> OTHER INFORMATION: N32-G-Assemble
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 442
cccatcacag cttacaag                                                 18

<210> SEQ ID NO 443
<211> LENGTH: 18
<212> TYPE: DNA
<213> ORGANISM: Artificial Sequence
<220> FEATURE:
<223> OTHER INFORMATION: N32-T-Assemble
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 443
gtaagctgtg atgggaca                                                 18

<210> SEQ ID NO 444
<211> LENGTH: 18
<212> TYPE: DNA
<213> ORGANISM: Artificial Sequence
<220> FEATURE:
<223> OTHER INFORMATION: LK3-G-Assemble
<220> FEATURE:
<221> NAME/KEY: misc_binding

```
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 444
ggctcgtctt cttcaggg                                                 18

<210> SEQ ID NO 445
<211> LENGTH: 18
<212> TYPE: DNA
<213> ORGANISM: artificial
<220> FEATURE:
<223> OTHER INFORMATION: LK3-T-Assemble
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 445
tgaagaagac gagcctga                                                 18

<210> SEQ ID NO 446
<211> LENGTH: 30
<212> TYPE: DNA
<213> ORGANISM: Artificial Sequence
<220> FEATURE:
<223> OTHER INFORMATION: fiveUTR-G-Assemble
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (16)..(17)
<223> OTHER INFORMATION: phosphorothioate bond

<400> SEQUENCE: 446
gcaatctaat ctaagttttc tagaaaaatg                                    30

<210> SEQ ID NO 447
<211> LENGTH: 19
<212> TYPE: DNA
<213> ORGANISM: Artificial Sequence
<220> FEATURE:
<223> OTHER INFORMATION: fiveUTR-T-Assemble
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (16)..(17)
<223> OTHER INFORMATION: phosphorothioate bond

<400> SEQUENCE: 447
aacttagatt agattgcta                                                19

<210> SEQ ID NO 448
<211> LENGTH: 24
<212> TYPE: DNA
<213> ORGANISM: Artificial Sequence
<220> FEATURE:
<223> OTHER INFORMATION: 3UTR2-G-Assemble
<220> FEATURE:
```

```
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (17)..(18)
<223> OTHER INFORMATION: phosphorothioate bond

<400> SEQUENCE: 448
catcatcatc accatcacta aaag                                              24

<210> SEQ ID NO 449
<211> LENGTH: 20
<212> TYPE: DNA
<213> ORGANISM: Artificial Sequence
<220> FEATURE:
<223> OTHER INFORMATION: 3UTR2-T-Assemble
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (17)..(18)
<223> OTHER INFORMATION: phosphorothioate bond

<400> SEQUENCE: 449
tgatggtgat gatgatgtta                                                   20

<210> SEQ ID NO 450
<211> LENGTH: 18
<212> TYPE: DNA
<213> ORGANISM: Artificial Sequence
<220> FEATURE:
<223> OTHER INFORMATION: N36-A-Assemble
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 450
taagggcgaa tgtacaga                                                     18

<210> SEQ ID NO 451
<211> LENGTH: 18
<212> TYPE: DNA
<213> ORGANISM: Artificial Sequence
<220> FEATURE:
<223> OTHER INFORMATION: N36-C-Assemble
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 451
gtacattcgc ccttagtg                                                     18

<210> SEQ ID NO 452
<211> LENGTH: 23
<212> TYPE: DNA
<213> ORGANISM: Artificial Sequence
<220> FEATURE:
<223> OTHER INFORMATION: ICeuI-A-Assemble
```

```
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (17)..(18)
<223> OTHER INFORMATION: phosphorothioate bond

<400> SEQUENCE: 452
ataacggtcc taaggtagcg aaa                                         23

<210> SEQ ID NO 453
<211> LENGTH: 22
<212> TYPE: DNA
<213> ORGANISM: Artificial Sequence
<220> FEATURE:
<223> OTHER INFORMATION: ICeuI-C-Assemble
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (17)..(18)
<223> OTHER INFORMATION: phosphorothioate bond

<400> SEQUENCE: 453
taccttagga ccgttatagt tg                                          22

<210> SEQ ID NO 454
<211> LENGTH: 18
<212> TYPE: DNA
<213> ORGANISM: Artificial Sequence
<220> FEATURE:
<223> OTHER INFORMATION: N22-A-Assemble
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 454
acacaacata gccacgga                                               18

<210> SEQ ID NO 455
<211> LENGTH: 18
<212> TYPE: DNA
<213> ORGANISM: Artificial Sequence
<220> FEATURE:
<223> OTHER INFORMATION: N22-C-Assemble
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 455
gtggctatgt tgtgtgag                                               18

<210> SEQ ID NO 456
<211> LENGTH: 24
<212> TYPE: DNA
<213> ORGANISM: Artificial Sequence
<220> FEATURE:
```

```
<223> OTHER INFORMATION: 3UTR2-A-Assemble
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (17)..(18)
<223> OTHER INFORMATION: phosphorothioate bond

<400> SEQUENCE: 456
catcatcatc accatcacta aaaa                                          24

<210> SEQ ID NO 457
<211> LENGTH: 20
<212> TYPE: DNA
<213> ORGANISM: Artificial Sequence
<220> FEATURE:
<223> OTHER INFORMATION: 3UTR2-C-Assemble
<220> FEATURE:
<221> NAME/KEY: misc_binding
<222> LOCATION: (9)..(10)
<223> OTHER INFORMATION: phosphorothioate bond
<220> FEATURE:
<221> NAME/KEY: misc_binding
<222> LOCATION: (17)..(18)
<223> OTHER INFORMATION: phosphorothioate bond

<400> SEQUENCE: 457
tgatggtgat gatgatgttg                                               20

<210> SEQ ID NO 458
<211> LENGTH: 18
<212> TYPE: DNA
<213> ORGANISM: Artificial Sequence
<220> FEATURE:
<223> OTHER INFORMATION: N21-A-Assemble
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 458
cctcgactca cacttgga                                                 18

<210> SEQ ID NO 459
<211> LENGTH: 18
<212> TYPE: DNA
<213> ORGANISM: Artificial Sequence
<220> FEATURE:
<223> OTHER INFORMATION: N21-C-Assemble
<220> FEATURE:
<221> NAME/KEY: misc_binding
<222> LOCATION: (7)..(8)
<223> OTHER INFORMATION: phosphorothioate bond
<220> FEATURE:
<221> NAME/KEY: misc_binding
<222> LOCATION: (15)..(16)
<223> OTHER INFORMATION: phosphorothioate bond

<400> SEQUENCE: 459
aagtgtgagt cgagggag                                                 18

<210> SEQ ID NO 460
<211> LENGTH: 19
<212> TYPE: DNA
<213> ORGANISM: Artificial Sequence
```

```
<220> FEATURE:
<223> OTHER INFORMATION: N23-A-Assemble
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (16)..(17)
<223> OTHER INFORMATION: phosphorothioate bond

<400> SEQUENCE: 460
caaacagaaa ggccatgga                                                     19

<210> SEQ ID NO 461
<211> LENGTH: 18
<212> TYPE: DNA
<213> ORGANISM: Artificial Sequence
<220> FEATURE:
<223> OTHER INFORMATION: N23-C-Assemble
<220> FEATURE:
<221> NAME/KEY: misc_binding
<222> LOCATION: (8)..(9)
<223> OTHER INFORMATION: phosphorothioate bond
<220> FEATURE:
<221> NAME/KEY: misc_binding
<222> LOCATION: (16)..(17)
<223> OTHER INFORMATION: phosphorothioate bond

<400> SEQUENCE: 461
atggcctttc tgtttgag                                                      18

<210> SEQ ID NO 462
<211> LENGTH: 22
<212> TYPE: DNA
<213> ORGANISM: Artificial Sequence
<220> FEATURE:
<223> OTHER INFORMATION: xylB screening forward oligo

<400> SEQUENCE: 462
tcctgaaaca gtttggtctg ga                                                 22

<210> SEQ ID NO 463
<211> LENGTH: 20
<212> TYPE: DNA
<213> ORGANISM: Artificial Sequence
<220> FEATURE:
<223> OTHER INFORMATION: xylB screening reverse oligo

<400> SEQUENCE: 463
catggatagc tctcgttggt                                                    20

<210> SEQ ID NO 464
<211> LENGTH: 20
<212> TYPE: DNA
<213> ORGANISM: Artificial Sequence
<220> FEATURE:
<223> OTHER INFORMATION: R01-f (p5_library_f) forward oligo

<400> SEQUENCE: 464
tagaccctct gtaaattccg                                                    20

<210> SEQ ID NO 465
<211> LENGTH: 22
<212> TYPE: DNA
<213> ORGANISM: Artificial Sequence
<220> FEATURE:
<223> OTHER INFORMATION: ppsA-r (ppsA_library_r) reverse oligo
```

```
<400> SEQUENCE: 465
aagctgagta acatcgtcaa ta                                          22

<210> SEQ ID NO 466
<211> LENGTH: 21
<212> TYPE: DNA
<213> ORGANISM: Artificial Sequence
<220> FEATURE:
<223> OTHER INFORMATION: tal-f forward oligo

<400> SEQUENCE: 466
tgaactggca ggtatttgtc c                                           21

<210> SEQ ID NO 467
<211> LENGTH: 20
<212> TYPE: DNA
<213> ORGANISM: Artificial Sequence
<220> FEATURE:
<223> OTHER INFORMATION: AR1-r (AmpR_library_r) reverse oligo

<400> SEQUENCE: 467
taagggcgac acggaaatgt                                             20

<210> SEQ ID NO 468
<211> LENGTH: 20
<212> TYPE: DNA
<213> ORGANISM: Artificial Sequence
<220> FEATURE:
<223> OTHER INFORMATION: RO2-f (p15_library_f) forward oligo

<400> SEQUENCE: 468
caagagatta cgcgcagacc                                             20

<210> SEQ ID NO 469
<211> LENGTH: 22
<212> TYPE: DNA
<213> ORGANISM: Artificial Sequence
<220> FEATURE:
<223> OTHER INFORMATION: ppsA-r reverse oligo

<400> SEQUENCE: 469
aagctgagta acatcgtcaa ta                                          22

<210> SEQ ID NO 470
<211> LENGTH: 20
<212> TYPE: DNA
<213> ORGANISM: Artificial Sequence
<220> FEATURE:
<223> OTHER INFORMATION: AR2-r (SpecR_library_r) reverse oligo

<400> SEQUENCE: 470
agccgtacaa atgtacggcc                                             20
```

LIGATION AND/OR ASSEMBLY OF NUCLEIC ACID MOLECULES

CROSS-REFERENCES TO RELATED APPLICATIONS

This application is a U.S. National Phase Application of PCT International Application No. PCT/SG2018/050528, filed on Oct. 24, 2018, which is an International Application of and claims the benefit of priority to Singapore Patent Application No. 102017087640, filed on Oct. 25, 2017, the entire contents of which are herein incorporated by reference.

FIELD OF THE INVENTION

The present invention relates to the field of molecular biology, for example recombinant nucleic acid technology. In particular, the present invention relates to ligating, joining and/or assembly of nucleic acid molecules.

BACKGROUND OF THE INVENTION

Recombinant nucleic acid technology and/or genetic engineering is transforming how humans generate fuels[1], produce bulk chemicals[2], and treat diseases[3]. Most recombinant nucleic acid technology and/or genetic engineering works require construction of plasmid, a vector for carrying genetic information. Currently, tens of thousands of research laboratories across the globe are constructing plasmids every day in a highly inefficient way—researchers customize materials they need, pay commercial companies to synthesize them from scratch, wait for the materials to be delivered, and assemble the materials in their own laboratories. Some foundries have been built to solve this problem by using automation[4], but they have not addressed the central piece of the problem, that is use of customized Biological Parts[5] (BPs).

More than a decade ago, BioBricks Foundation was founded in the US to provide standardized BPs to the public. However, it has become less popular[5], because of the following flaws in it and corresponding DNA assembly method: (1) large scars (conserved, useless nucleotides) are left between BPs, which may affect biological function of BPs[6,7]; (2) only two BPs can be assembled in one round, resulting in long plasmid construction time; (3) certain restriction enzyme recognition sites must be avoided in sequence of BPs. Recently, a newer standard (BASIC) has been published[7], allowing multiple-fragment and multi-tier assembly, which however have only solved some of these problems and have not been widely adapted.

Existing methods such as Golden gate[15] and BASIC[7] do not satisfactorily address these problems.

It is therefore desirable to develop new improved recombinant nucleic acid and/or genetic engineering methodologies.

SUMMARY OF THE INVENTION

According to a first aspect, the present invention provides a method for ligating at least two nucleic acid molecules comprising:
(i) providing a first nucleic acid molecule comprising a first overhang of at least one nucleotide in length at a first end;
(ii) providing a second nucleic acid molecule capable of forming a stem-loop structure with an overhang of at least one nucleotide; wherein the overhang of the second nucleic acid molecule is substantially complementary to the first overhang of the first end of the first nucleic acid molecule; and
(iii) ligating the first nucleic acid molecule to the second nucleic acid molecule at the complementary overhangs to form a single nucleic acid molecule.

According to a second aspect, the present invention provides a method for ligating three nucleic acid molecules comprising:
(i) providing a first nucleic acid molecule comprising a first overhang of at least one nucleotide in length at a first end and a second overhang of at least one nucleotide of at least one nucleotide in length at its other (or second) end; wherein the first overhang and the second overhang have different sequences and/or are not complementary to each other;
(ii) providing a second nucleic acid molecule capable of forming a stem-loop structure with an overhang of at least one nucleotide; wherein the overhang of the second nucleic acid molecule is substantially complementary to the first overhang of the first end of the first nucleic acid molecule; and also providing a third nucleic acid molecule capable of forming a stem-loop structure with an overhang of at least one nucleotide; wherein the overhang of the third nucleic acid molecule is substantially complementary to the second overhang of the second end of the first nucleic acid molecule; and wherein the overhang of the second nucleic acid molecule and the overhang of the third nucleic acid molecule have different sequences and/or are not complementary to each other; and
(iii) ligating the first overhang at the first end of the first nucleic acid molecule to the overhang of the second nucleic acid molecule and also the second overhang of the second end of the first nucleic acid molecule to the overhang of the third nucleic acid molecule to form a single nucleic acid molecule.

The invention includes a nucleic acid molecule comprising of a defined sequence capable of forming a stem-loop structure with an overhang of one nucleotide.

The invention also includes a kit comprising a plurality of nucleic acid molecules; each with a defined sequence capable of forming a stem-loop structure with an overhang of at least one nucleotide. The kit may further comprise one or a plurality of oligonucleotide(s)

Figure 1:
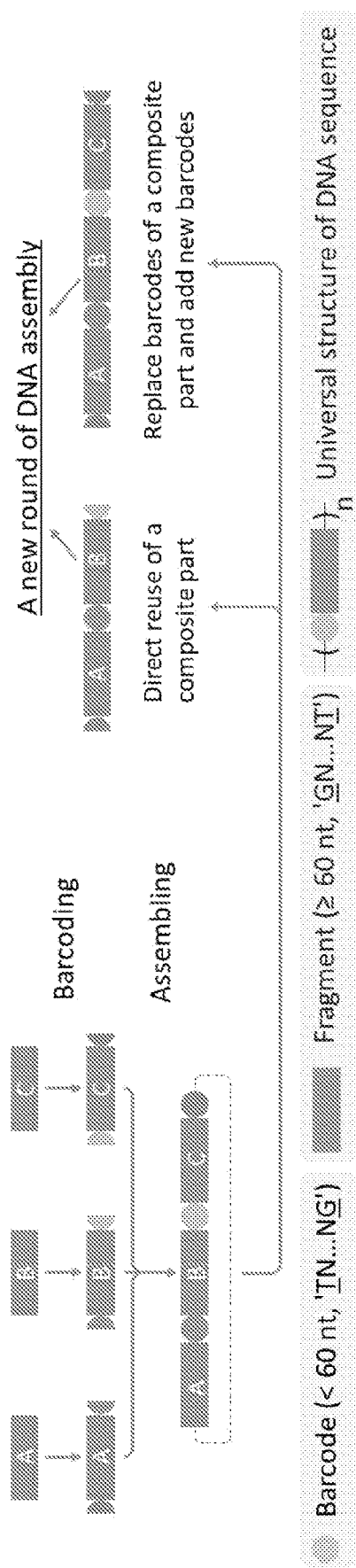
FIG. 1: Diagram of Universal DNA-Assembly Standard (UDS). Barcoding is adding specific barcode to each side of a fragment. We have developed technology that can perform barcoding without leaving any scar between barcode and fragment. Barcodes facilitate assembly of fragments. Composite parts are parts that are produced by assembly of simple ones, and can be easily reused in new rounds of DNA assembly according to UDS.

Comparison of three methods that barcode 1-mer sticky end-containing fragments: (c) Using entry vector: entry vector included two barcodes (shown as two semicircles) on its sides, and was prepared by using PCR. Similar to workflow in a, two 1-mer sticky ends were introduced to the entry vector, allowing it to be ligated to any fragment that contains compatible sticky ends. After the ligation, barcoded fragment was amplified by using two oligos targeting barcode regions (shown as two black arrows) for downstream DNA assembly. (d) Annealed oligos: each barcode with 1-mer sticky end was generated by annealing two complementary oligos, one of which was shorter than the other one by one nucleotide. The two barcodes (shown as semicircles) were ligated to a fragment that contained compatible sticky ends, and the ligation product was amplified by using two oligos (shown as two black arrows). (e) Stem-loop oligos: the two oligos used to create a barcode were made into one by them with a loop region, and the two barcodes (shown as semicircles) were ligated to a fragment that contained compatible sticky ends, and the ligation product was amplified by using two oligos (shown as two black arrows). The 3 methods were used to barcode 5 fragments, which can be used to create a CRISPR-Cas9 based knockout plasmid. 1: Antibiotic resistance marker (1.2 kb); 2: Replication origin (0.9 kb); 3: Guide RNA (0.2 kb); 4: Homologous arm 1 (0.5 kb); 5: Homologous arm 2 (0.5 kb). (f) The 5 fragments barcoded by using stem-loop oligos were successfully assembled into a plasmid through long sticky end mediated ligation. How to generate long SEs and assemble two BFs with long SEs are elaborated in FIG. 6. 8 randomly picked colonies were confirmed to be correct by colony PCR. Further sequencing and functionality tests were also positive (FIG. 7).

Figure 3:
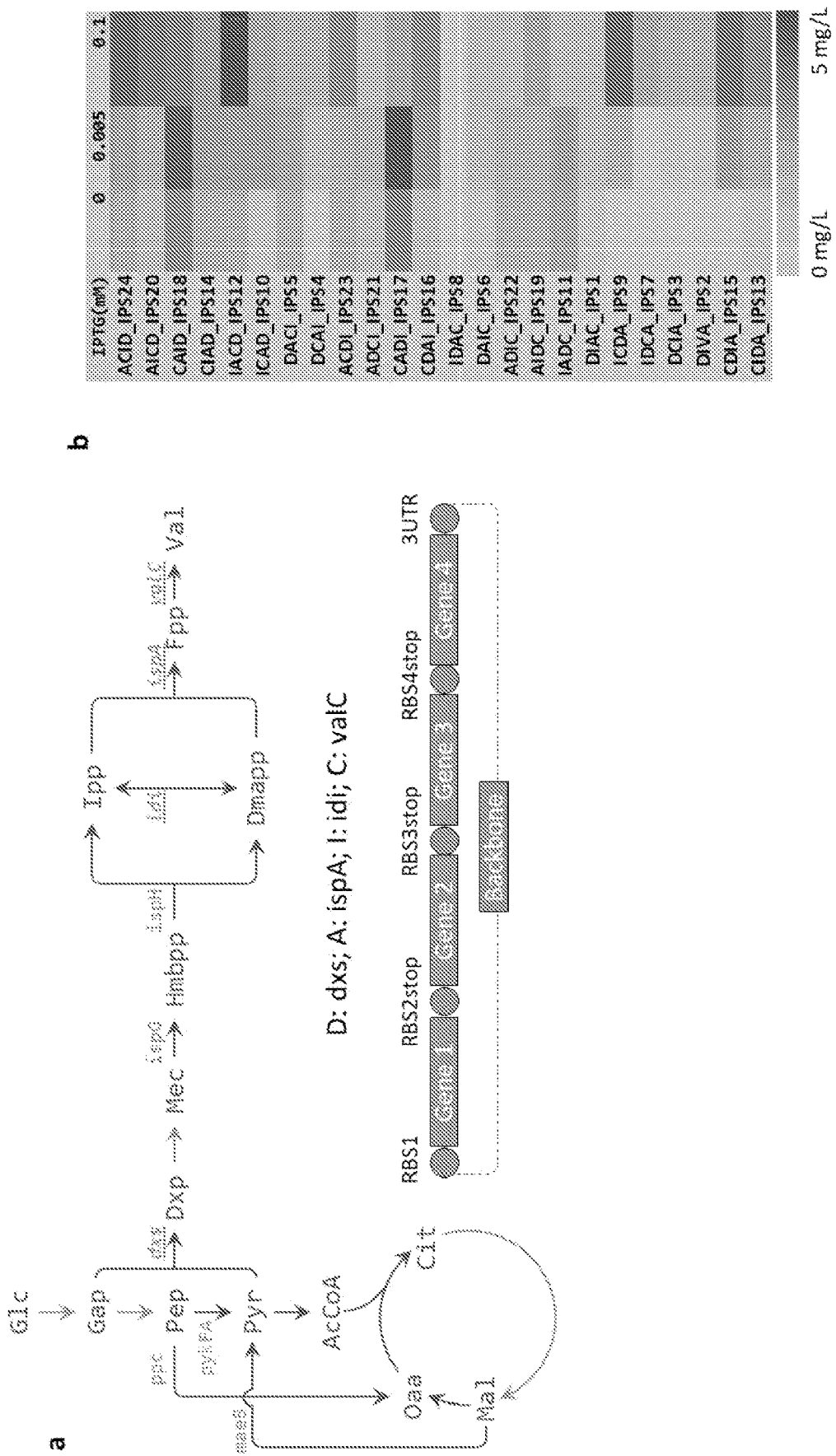

FIG. 3: Optimization of isoprenoid biosynthesis pathway to overproduce valencene in *E. coli*. (a) Central metabolism and valencene biosynthesis. Glc: glucose; Gap: glyceraldehyde 3-phosphate; Pep: phosphoenolpyruvate; Pyr: pyruvate; AcCoA: acetyl-CoA; Cit: citrate; Mal: malic acid; Oaa: oxaloacetate; Dxp: deoxy-xylulose 5-phosphate; Mec: methylerythritol cyclodiphosphate; Hmbpp: hydroxylmethylbutenyl diphosphate; Ipp: Isopentenyl diphosphate; Dmapp: dimethylallyl diphosphate; Fpp: farnesyl diphosphate; Dotted arrow indicates multi-step reaction; black arrow indicates single-step reaction. Underlined fonts in italic with indicate enzyme-encoding genes for the related reactions. Val: valencene. Four genes (dxs, ispA, idi and valC) in an operon will be shuffled in order, generating 24 (4!) variants, and then can be easily constructed by using 5 fragments (the 4 genes and 1 backbone plasmid) and 5 barcodes (RBS1, RBS2stop, RBS3stop, RBS4stop and 3UTR). (b) Screening 24 valencene-producing *E. coli* (MG1655_ΔrecA_ΔendA_DE3, IPS1-IPS24) strains, and the inducer of IPTG with varied concentration (0, 0.005 and 0.1 mM) were added for induction of gene expression for 72 hours.

Figure 4:
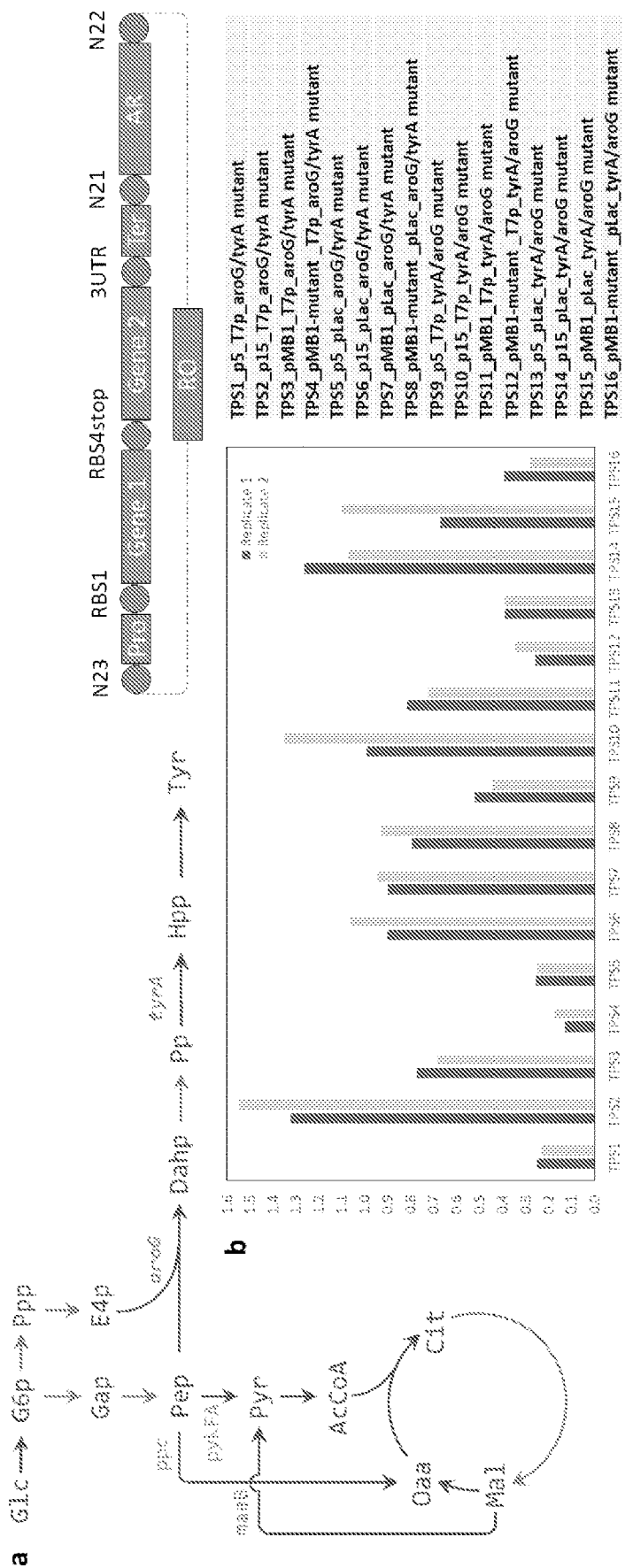

FIG. 4: Optimizing expression level of two genes (mutants of tyrA and aroG that were created to resist feedback inhibition imposed by tyrosine) for overproducing tyrosine in *E. coli*. (a) Central metabolism and tyrosine biosynthesis. Glc: glucose; G6p: Glucose 6-phosphate; Gap: glyceraldehyde 3-phosphate; Pep: phosphoenolpyruvate; Pyr: pyruvate; AcCoA: acetyl-CoA; Cit: citrate; Mal: malic acid; Oaa: oxaloacetate; Ppp: Pentose phosphate pathway; E4p: Erythrose 4-phosphate; Dahp: 3-Deoxy-D-arabinoheptulosonate 7-phosphate; Pp: prephenate; Hpp: 4-hydroxyphenylpyruvate; Tyr: tyrosine. Dotted arrow indicates multi-step reaction; black arrow indicates single-step reaction. Underlined fonts in italic with indicate enzyme-encoding genes for the related reactions. A small UDS library to express them at different levels, combining 2 promoters (T7 promoter with LacI expression cassette and Lac promoter), 2 genes (mutants of tyrA and aroG) orders and 4 replication origins (p5: low copy number; p15: medium copy number; pMB1: medium copy number; pMB1 mutant from pUC19: high copy number), spectinomycin antibiotic resistance and LacI expression cassette for 7 BFs assembly of plasmid with Lac promoter) and 7 barcodes (RBS1, RBS4stop, 3UTR, N21, N24, N22 and N23, leading to 16 (2×2×4) variants. AR: Antibiotic resistance; RO: Replicative Origin; Pro: promoter; Ter: terminator. (b) Screening of 16 tyrosine-producing *E. coli* (MG1655_ΔrecA_ΔendA_ΔpheA_ΔtyrR_DE3) strains with induction of 0.1 mM IPTG for 84 hours.

Figure 5:
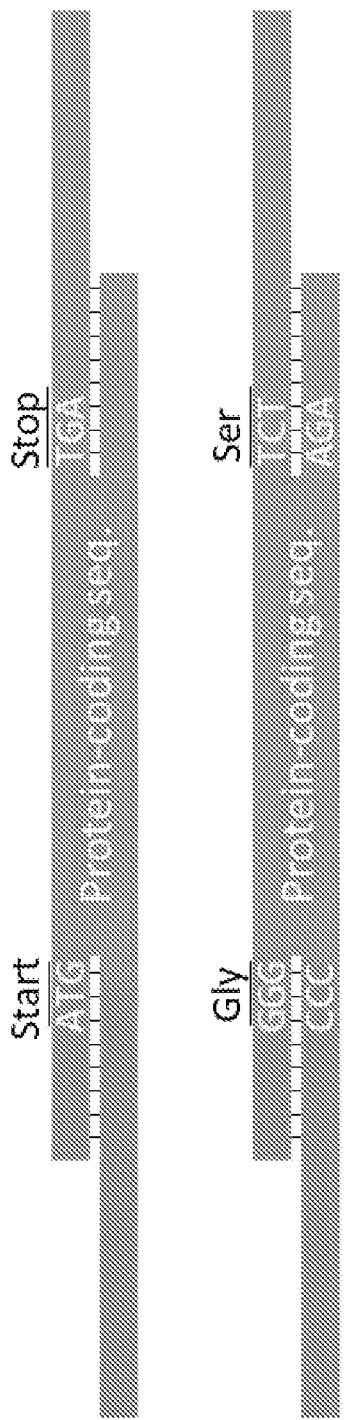

FIG. 5: Detailed illustration of adding barcodes to 1-mer SE based fragments without leaving scar in final construct.

Figure 6:
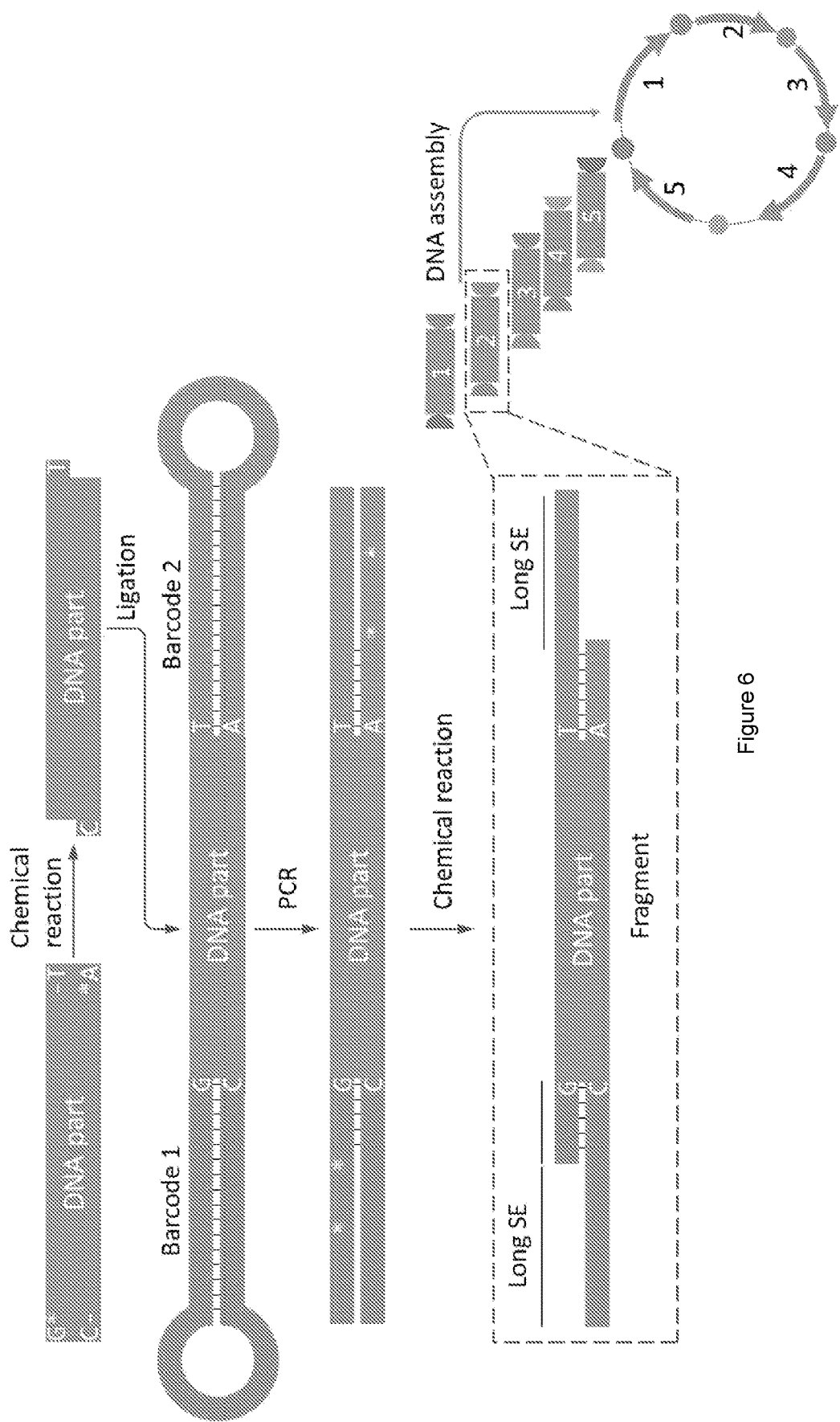
Figure 7:
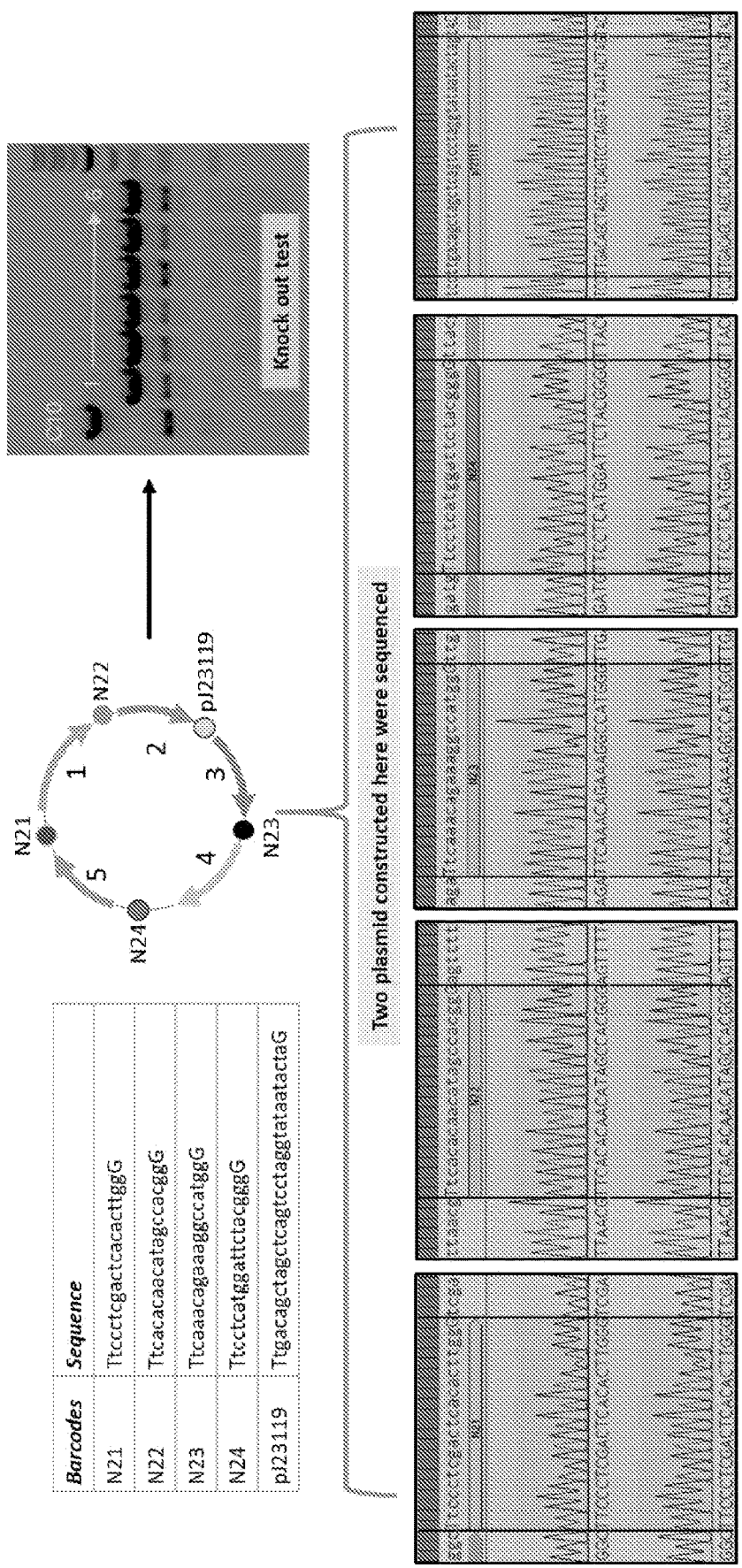

FIG. 6: Detailed illustration of fragment barcoding and creation of long sticky ends (15-20 bp). *: phosphorothioate bond; —: phosphodiester bond. DNA part 1 and part 2 with reverse complementary long SE can be annealed at 45° C. and nick will be repaired by a Taq ligase.

Figure 2:
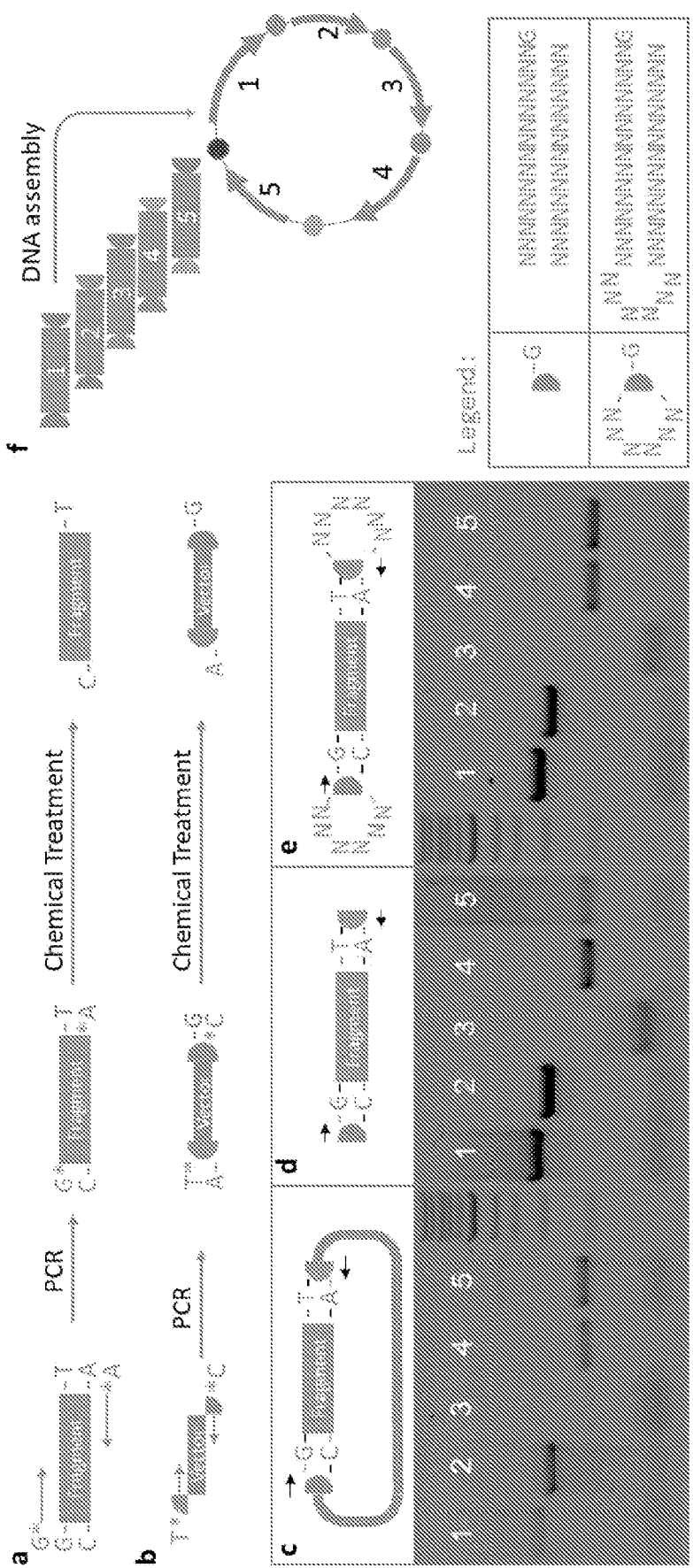
FIG. 2: 1 nucleotide barcoding method. (a) Workflow for creating 1-mer sticky end-containing fragments; *: phosphorothioate bond; —: phosphodiester bond. After chemicals treatment, 3' end overhang of 'C' and 'T' generated at the second end and at the first end, respectively. (b) Workflow for creating 1-mer sticky end-containing entry vector; *: phosphorothioate bond; —: phosphodiester bond. After chemicals treatment, 3' end overhang of 'A' and 'G' generated at the second end and at the first end, respectively.

FIG. 7: Sequencing and testing functionality of the plasmid constructed by assembling 5 fragments. The procedure was described in FIG. 2. The plasmid can knock out gene nupG in *E. coli* genome with aid of CRISPR-Cas9. Plasmids from 2 randomly selected colonies of 8 colonies were sequenced, and all junction regions (Barcodes) in were correct. The function of the plasmid was also verified by testing its efficiency of gene deletion, and colony PCR results indicated that nupG was deleted in all 6 colonies based on length of the bands and comparison with wild-type (C10: wild-type *E. coli*, MG1655_DE3; 1-6: colonies picked from the tested plate).

Figure 8:
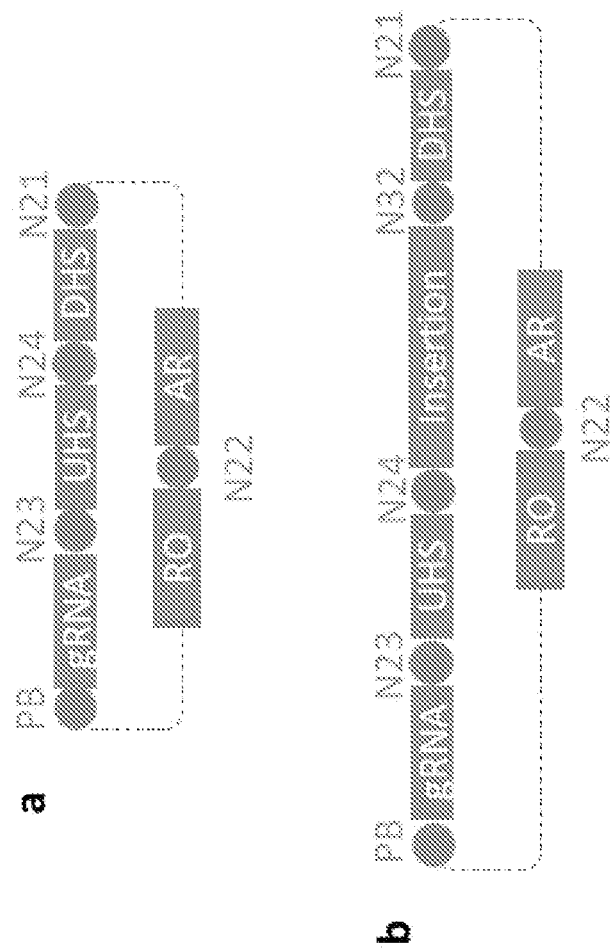

FIG. 8: (a) Details of the integration module, which can be used to gene deletion test. (b) The pre-constructed plasmid from above integration module can be obtained by PCR, then can be barcoded to assemble insertion to construction gene insertion test. DHS: downstream homologous sequence; UHS: upstream homologous sequence; gRNA: guide RNA; PB: promoter barcode (promoter as a barcode); P: promoter; N21-24: non-functional barcode.

Figure 9:
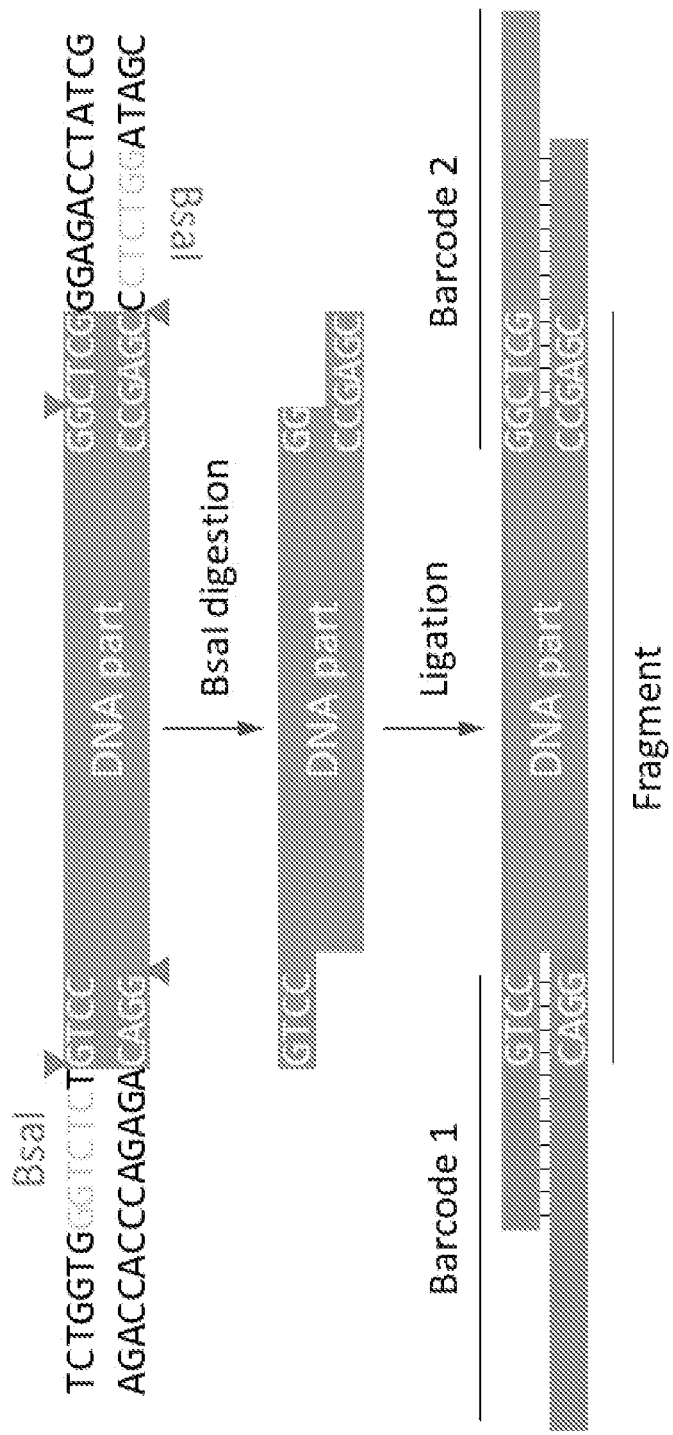

FIG. 9: Existing method leaves scars during barcoding because restriction enzyme was used. In this method, each barcode is created by annealing two oligos, and must be at least 33 mer long, otherwise the two oligos cannot form stable DNA duplex.

Figure 10:
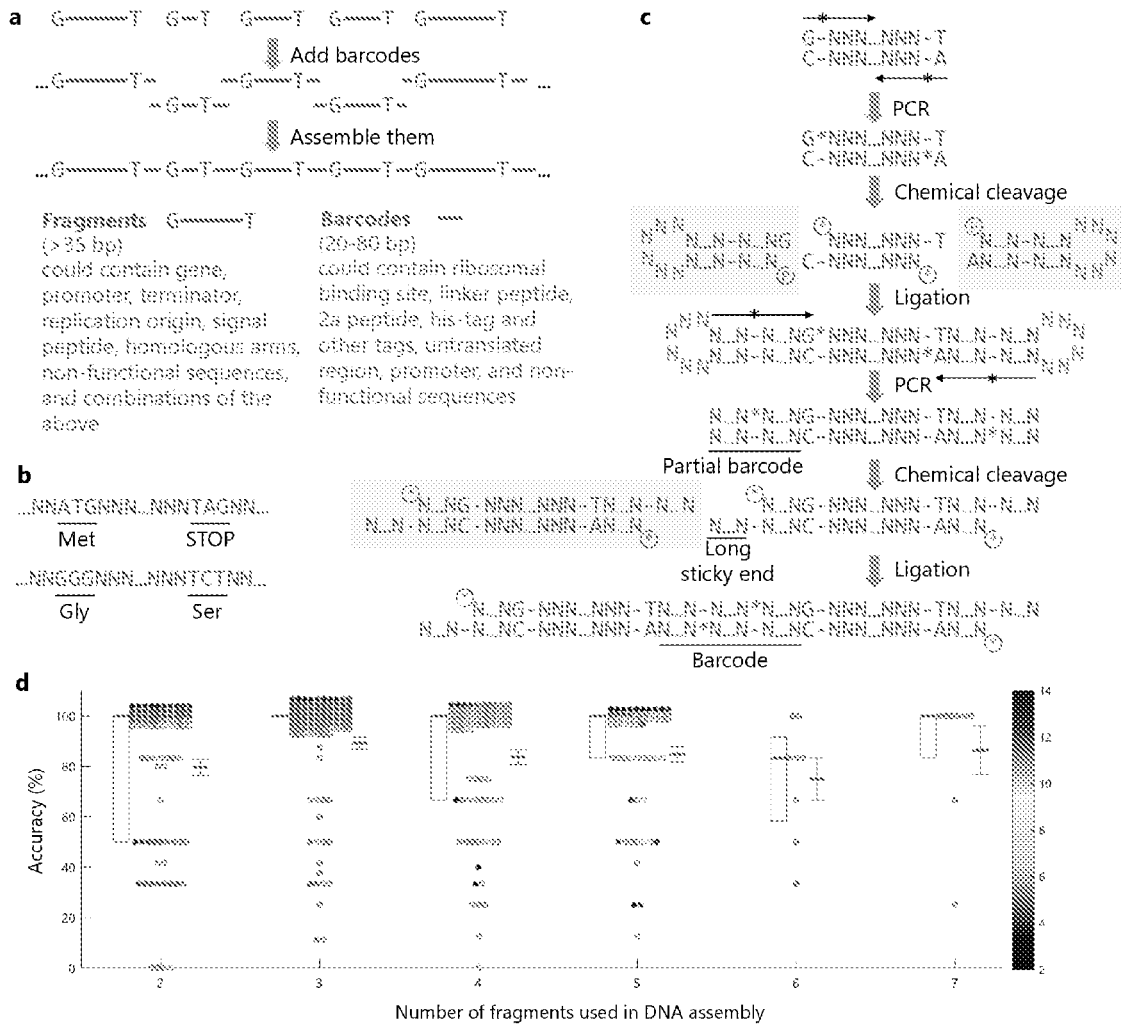

FIG. 10: GT assembly standard (GTas) for constructing plasmid from standard parts (fragments and barcodes). (a) The plasmid construction workflow and examples of fragments and barcodes; (b) Using minimal conserved sequence (one nt long, G and T) in fragment eliminated scar in most DNA assembly practices. Two scarless connections are shown here. (c) Mechanism of adding two partial barcodes to one fragment and of using two complementary partial barcodes to assemble two fragments. * indicates phosphorothioate (PS) bond; * in a circle indicates PS group; — indicates phosphodiester bond; P in a circle: phosphate group; . . . indicates omitted, unspecified nucleotides. Items in grey shade are new items introduced in the step. (d) Statistics of 370 plasmids (P1 to P370) we have constructed by using GTas. Accuracy was based on sequencing; as an example, 80% accuracy indicates 8 out of 10 colonies contained the correct plasmid based on Sanger sequencing of the plasmids. Each circle presents one plasmid construction. Face color of each circle indicates length of the plasmid (the color bar is provided, unit: kb). Each thick orange horizontal bar presents median of accuracies of a group (plasmids constructed from the same number of fragments were included in one group). Each orange box indicates $1^{st}$ and $3^{rd}$ quantiles of accuracies of a group. Each thick blue horizontal bar and the related error bar indicate mean and standard error of accuracies of a group respectively. For illustration purpose, circles with the same accuracy and fragment number are distributed around accurate values of accuracy and fragment number on the plot.

Figure 11:
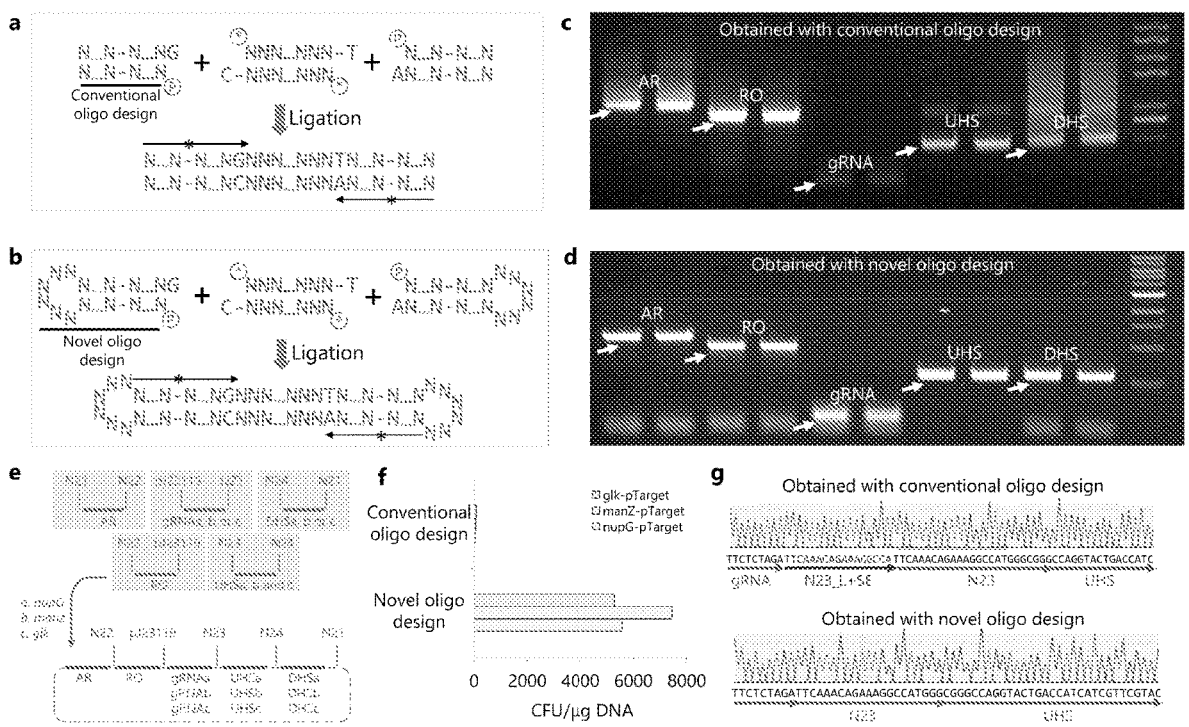

FIG. 11: Development of a scarless barcoding method. (a-b) Workflow of barcoding a fragment by using conventional (a) and novel (b) oligos. After the ligation, barcoded fragments were amplified by using two Assembling oligos (Aoligos, shown as long black arrow with *) that bind barcodes. (c-d) Analysis of PCR products from a-b by using gel electrophoresis. White arrows indicate the desired bands, and one sample was loaded into two lanes. The lane symbols are explained below. (e) The three plasmids used to compare the two barcoding methods. Each of the three plasmids can be used to delete a gene in E. coli (nupG, manZ or glk) by using CRISPR/Cas9 technology, and was constructed from five fragments: antibiotic resistance marker (AR), replication origin (RO), guide RNA (gRNA), upstream homologous sequence (UHS), and downstream homologous sequence (DHS). Five barcodes (indicated by green texts) were used in each plasmid construction. PCR test results of the nupG plasmid are shown in c-d (those of the other two plasmids are shown in FIG. 18a). (f) Colony forming unit (CFU/μg DNA) of three plasmids constructed using fragments that were barcoded by conventional and novel oligo design. (g) Representative sequencing results. Two plasmids in each plasmid construction were sequenced. All the plasmids constructed by using novel oligo design were sequenced to be correct (6/6). Half of the plasmids constructed by using conventional oligo design were found to have assembly errors (3/6). A pair of sequencing results from the manZ plasmid construction are shown here. The other sequencing data can be found in FIG. 18b. The red arrow and text indicate the insertion to the sequence.

Figure 12:
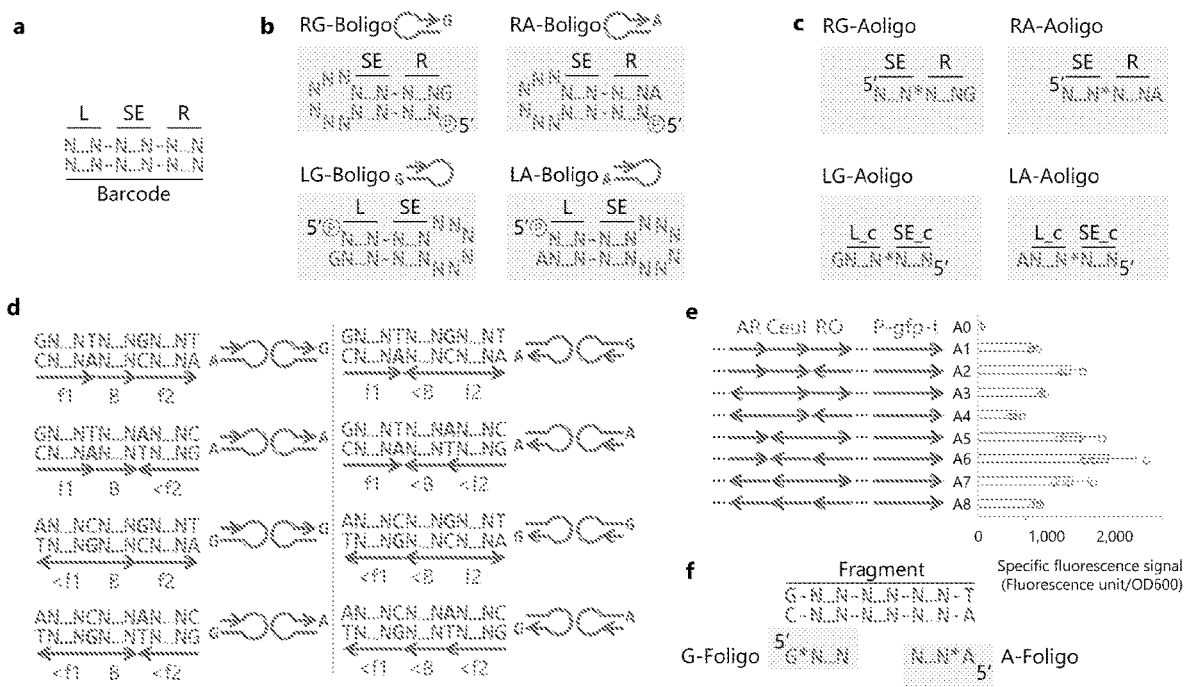

FIG. 12: Principles of designing and using the oligos. (a) Structure of barcodes. Any barcode is composed of L, SE and R. L and R can be empty. SE should be 15-20 nt depending on its melting temperature and should not contain any sequence that may result in self-ligation. (b) Barcoding oligos (Boligos). There are four Boligos to encode all the variants of a barcode. The six nucleotides (NNNNNN in grey) can be any sequence as long as the illustrated stem-loop structure can be formed. The arrow in Boligo indicates the strand on which the barcode half is encoded. The length of Boligo is no longer than 90 nt. (c) Each Boligo has a corresponding Aoligo (Assembling oligo). * indicates a PS bond; — indicates a phosphodiester bond. There is one more PS bond at the center of each SE (not shown for simplicity), which is used to improve DNA assembly efficiency. (d) Instructions for connecting two fragments (f1 and f2) through one barcode (B) in eight ways. Prefix "<" indicates that a part is flipped; The blue arrows below sequences indicate fragment's orientation, while green arrows indicate barcode's orientation. The pair of Boligos used in each way is shown at the right side of each sequence. The nucleotides (G and A) used in fragment-barcode ligation are shown in bold font. (e) Demonstration of the eight connection options in a simple example. AR: antibiotic resistance marker; Ceul: a barcode; RO: replication origin; P: promoter; gfp: a gene encoding green fluorescence protein; t: terminator. Each row indicates a plasmid (A1-A8). Arrow indicates orientation of fragment/barcode. Only relevant parts of each plasmid are illustrated. Each plasmid's performance (i.e. specific fluorescence signal) is shown in the chart. Empty circles indicate values of replicates. Each bar indicates the mean of triplicates at each condition. Error bars indicate standard error (n=3). One empty plasmid (A0) without gfp was used as a negative control. (d) Fragment oligos (Foligos) are used to amplify fragment by using PCR. Position of each PS bond is shown. Foligo should have sufficient melting temperature to allow good binding during PCR and the principle is the same to regular PCR oligo design.

Figure 13:
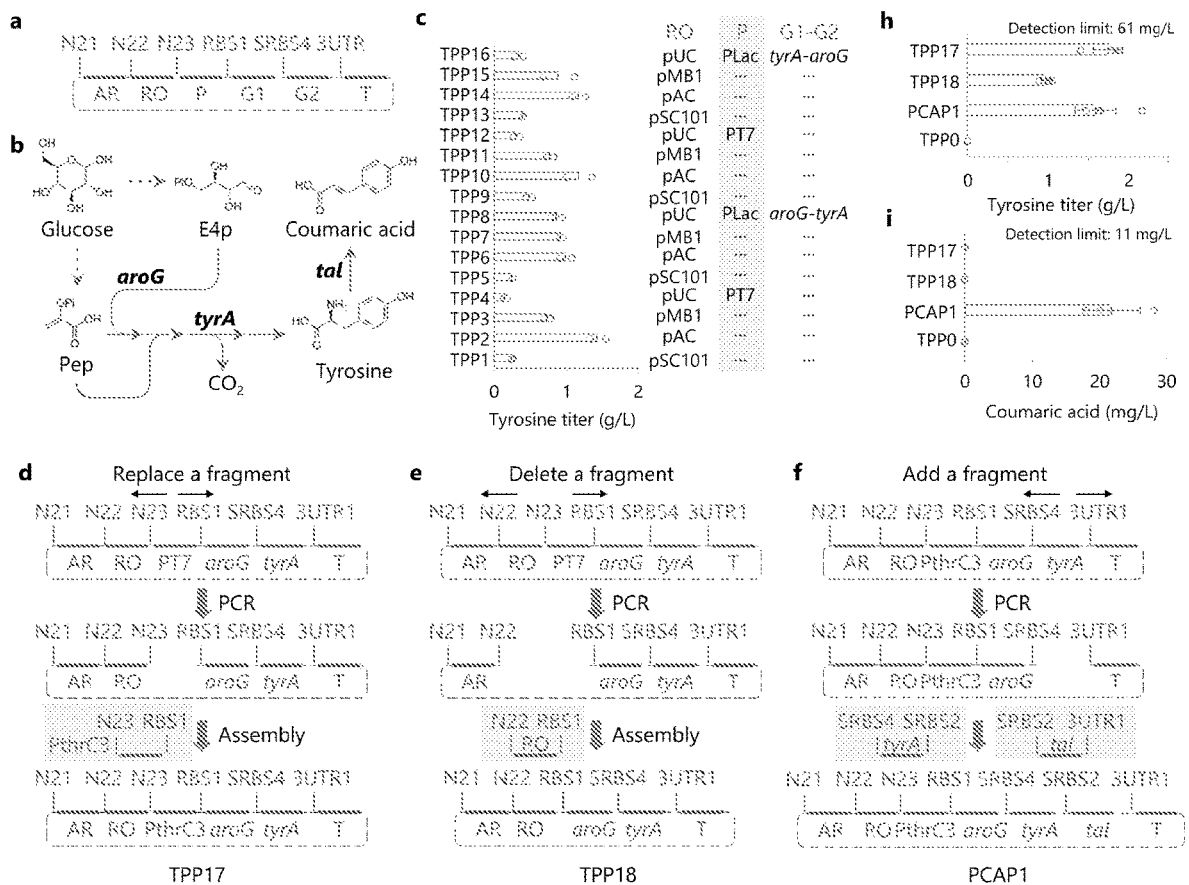

FIG. 13: Construct and edit plasmids by using standard parts under GTas. (a) Structure of the 16 plasmids for improving tyrosine production in E. coli. Blue thick horizontal bars represent fragments; RO: replication origin (pSC101, pAC, pMB1, or pUC); P: promoter (PT7 or PLac); G1, G2: two genes in an operon (tyrA-aroG or aroG-tyrA); t: terminator; AR: antibiotic resistance marker. Green texts indicate barcodes; N21, N22, N23: non-functional connectors; RBS1: ribosome binding site; SRBS4: stop codon and ribosome binding site; 3UTR: stop codon and untranslated region. (b) The biosynthetic pathway of tyrosine and coumaric acid from glucose. Pep: Phosphoenolpyruvate; E4p: Erythrose 4-phosphate; aroG: a gene encoding mutated E. coli 3-deoxy-7-phosphoheptulonate synthase; tyrA: a gene encoding mutated E. coli fused chorismate mutase/prephenate dehydrogenase; tal: a gene encoding tyrosine ammonialyase from Saccharothrix espanaensis. (c) Composition of the 16 plasmids and their corresponding tyrosine titer. TPP1-16: Tyrosine-Producing Plasmid 1-16, created by combination of RO, P and G1-G2 as indicated. Empty circles indicate values of replicates. Each bar indicates the mean of duplicates at each condition. (d-f) Editing a plasmid by replacing, deleting, or adding a component by using standard oligos. Orange texts indicates the component changed and added. Thin black arrows indicate primers used in PCR. (h-i) Characterization of strains carrying the three plasmids obtained from d-f in terms of tyrosine (h) and coumaric acid (i) production. Empty circles indicate values of replicates. Each bar indicates the mean of at least three replicates at each condition. Error bars indicate standard error (n>=3).

Figure 14:
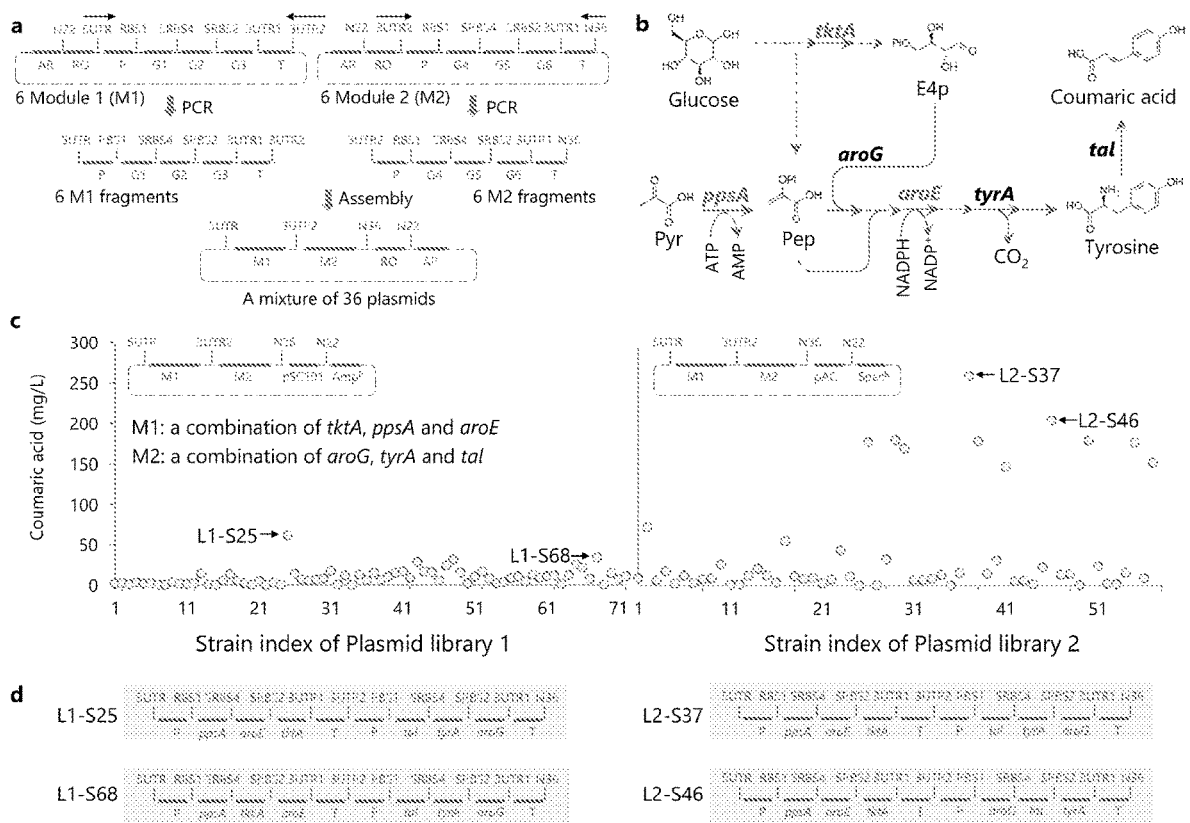

FIG. 14: Construct plasmid library for combinatorial optimization of microbial strains by using standard parts. (a) Construction of two combinatorial plasmid libraries to enhance coumaric acid production of E. coli. Six genes involved in shikimate production (ppsA, tktA and aroE) and coumaric acid production (aroG, tyrA and tal) were divided into two modules. Each module has six variants resulting from shuffling three genes. To prepare one library, six Module 1 (M1) plasmids and six Module 2 (M2) plasmids were made. Both M1 and M2 plasmids used the same promoter (pthrC3) and terminator (T7 terminator). Then, six M1 fragments and six M2 fragments were amplified from M1 and M2 plasmids by using two sets of Aoligos as indicated in black arrows (PCR results are presented in FIG. 23a). The amplified M1 and M2 fragments were mixed equimolarly, and assembled with a plasmid backbone (pSC101 or pAC). In library 1, pSC101 was used. In library 2, pAC was used. More details of the library construction and the quality control data are described in FIG. 23b. (b) Extended biosynthetic pathway of coumaric acid from glucose. ppsA: a gene encoding of E. coli phosphoenolpyruvate synthetase; tktA: a gene encoding of E. coli transketolase; aroE: a gene encoding of E. coli shikimate dehydrogenase. (c) Screening the two plasmid libraries. The mixture of plasmids was used to transform an E. coli strain (MG1655_ΔrecA_ΔendA_ΔpheA_ΔtyrR_DE3). For each library, seventy-two colonies (two times library size) were screened with coumaric acid titer as evaluation metric. Note that only a fraction of colonies from library 2 can be successfully cultured in liquid medium (57/72). Each circle indicates coumaric acid titer of a strain. (d) Top 2 strains from c were characterized by sequencing the corresponding plasmids (data not shown). The arrangement of the genetic parts of the corresponding plasmids is presented.

Figure 15:
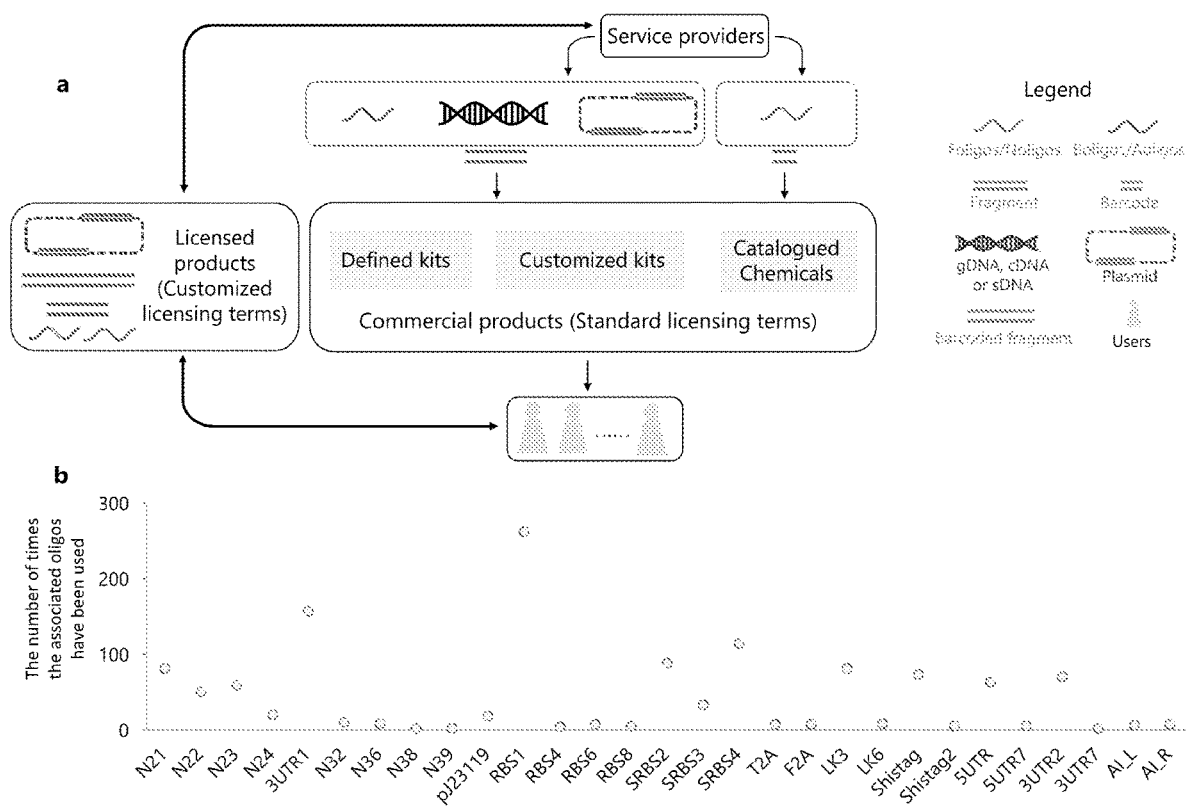

FIG. 15: The vision to transform plasmid construction practices in the global biotechnology community through using GTas parts. (a) A proposed network for users to share and/or acquire GTas parts. A user may receive or contribute GTas parts as licensed materials (through Materials Transfer Agreement [MTA]) or purchase GTas parts from commercial sources. The licensed materials may be transferred through a service provider (such as Addgene) to speed up execution of MTA, and can be licensed to another type of service providers that sell commercial products (commercial sources). The parts related to creating fragments are in the blue box, and those related to creating barcodes are in the green box. A legend to explain each symbol is provided. gDNA: genomic DNA; cDNA: complementary DNA; sDNA: synthetic DNA. (b) Usage frequency of Boligos and Aoligos in construction of the 370 plasmids. Each circle indicates the usage frequency related to a barcode (the raw data of times of barcode that has been reused in construction of 370 plasmids is not shown).

Figure 16:
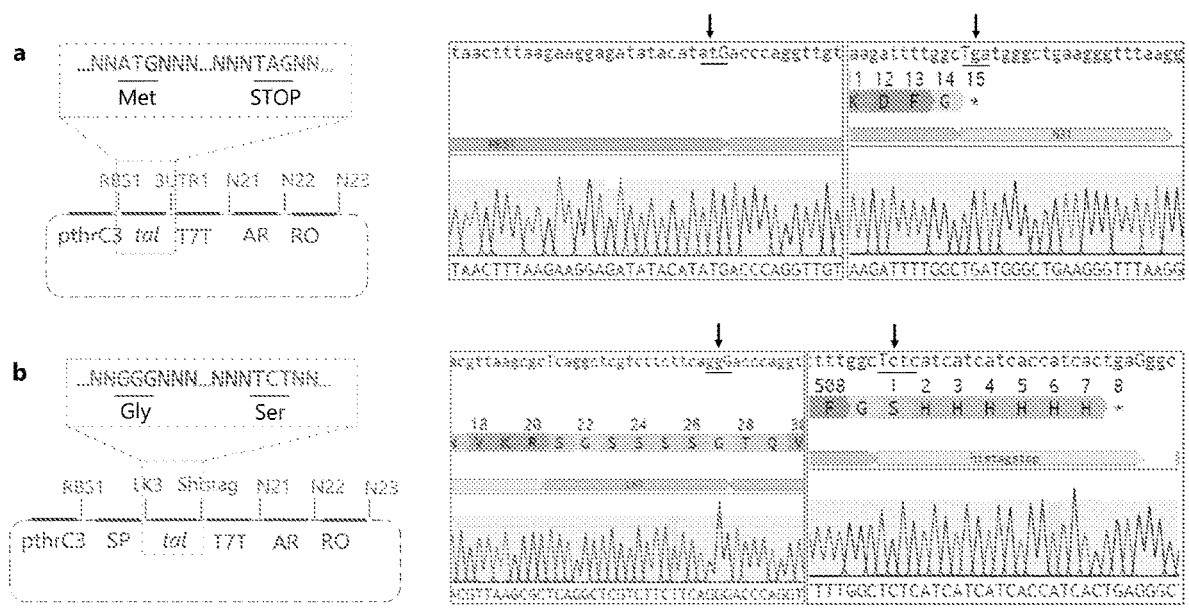

FIG. 16: GT standard enables placing the same gene into a standalone expression cassette or into a fusion protein without leaving a scar. (a) tal (a gene encoding tyrosine ammonia-lyase) was expressed by a standalone expression cassette containing a thrC3 promoter (an auto-inducible promoter[35]) and T7 terminator (T7T). Met: Start codon encoding a methionine; STOP: Stop codon. Sequencing results confirmed that the desired sequences have been successfully incorporated into the plasmid at the junction regions. Alignment between sequenced data and template are as shown in the boxes on the right. The black arrows indicate the start (ATG) and stop (TGA) codons, which were correctly incorporated into the open reading frame of the gene. RBS1: ribosome binding site; Shistag: stop codon and sequence encoding a six histidine-tag (histag). N21, N22, N23: non-function barcode; AR: Antibiotic resistance marker; RO: Replication origin; (b) tal was fused with a Signal Peptide[42] (SP) via a linker which consists of Glycerine (G) and Serine (S), inherently forming a fusion protein with a histag attached to its C-terminus. Sequencing results confirmed that the presence of two pre-designed sequences that encode the connecting amino acid residues within the constructed plasmid (indicated by the black arrows).

Figure 17:
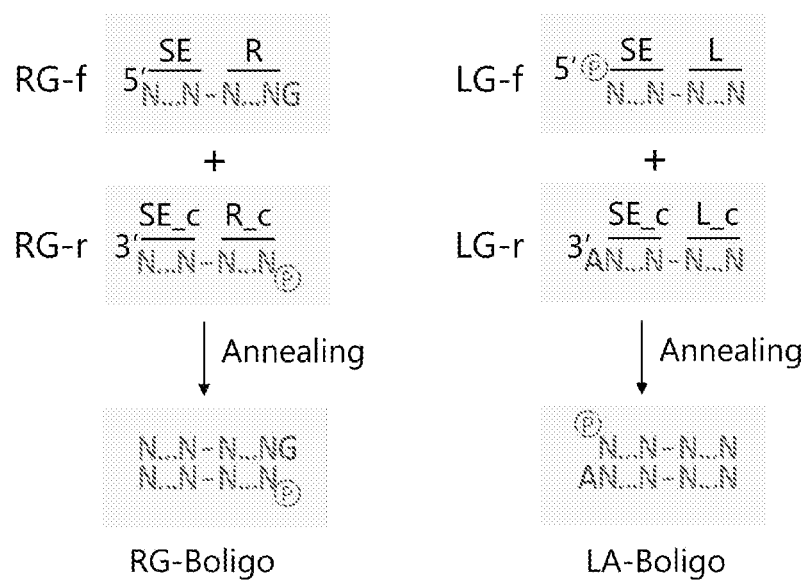

FIG. 17: To prepare conventional oligos (FIG. 11a), two Boligos (RG-Boligo and LA-Boligo) for one barcodes halve were annealed by using two complementary single strand oligos (RG-f/RG-r and LG-f/LG-r), one of which was shorter than the other one by one nucleotide. All oligos used to create conventional oligo are listed in Table 16.

Figure 18:
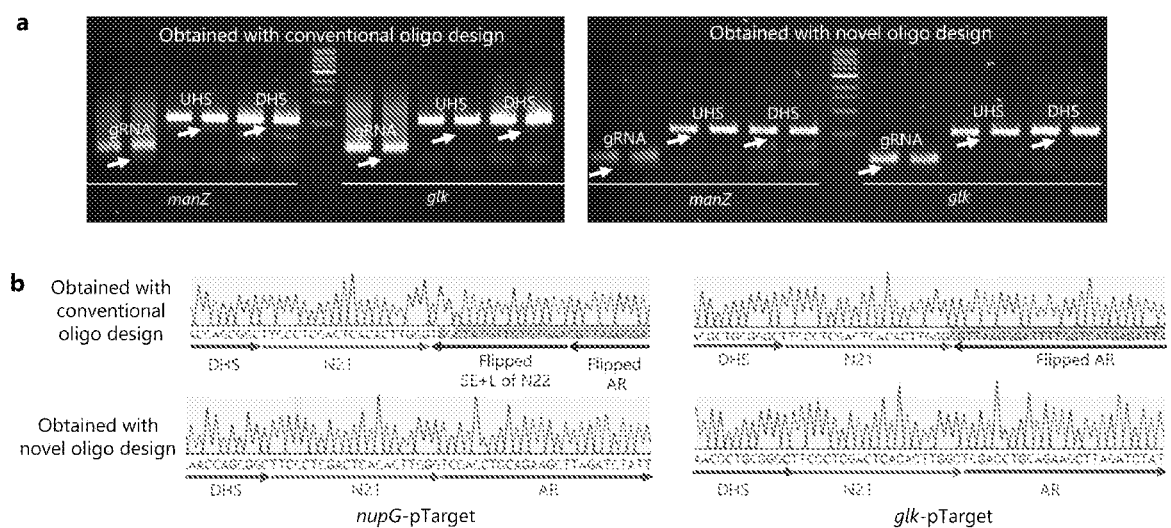

FIG. 18: (a) To construct the other two plasmids of manZ-pTarget and glk-pTarget as described in FIG. 11e, the barcoded fragments were amplified through ligation PCR. The ligation products used as templates in ligation PCR were prepared by using conventional oligo design and novel oligo design. The same three sets of Aoligo that have been described in FIGS. 11a and 11b were used accordingly. The desired bands are indicated by using white arrows, and one sample was loaded into two lanes. Smears were observed when conventional oligo design was used. Antibiotic resistance marker (AR), guide RNA (gRNA), upstream homologous sequence (UHS), and downstream homologous sequence (DHS). (b) Sequencing suggested that the plasmids (nupG-pTarget and g/k-pTarget) that were constructed by using conventional oligos design had the undesired insertion (flipped partial barcode of N22) and flipped fragment (AR was flipped). The red arrow and text indicate the problematic sequences. Sequencing results of the plasmids constructed with novel oligo design were shown to be correct.

Figure 19:
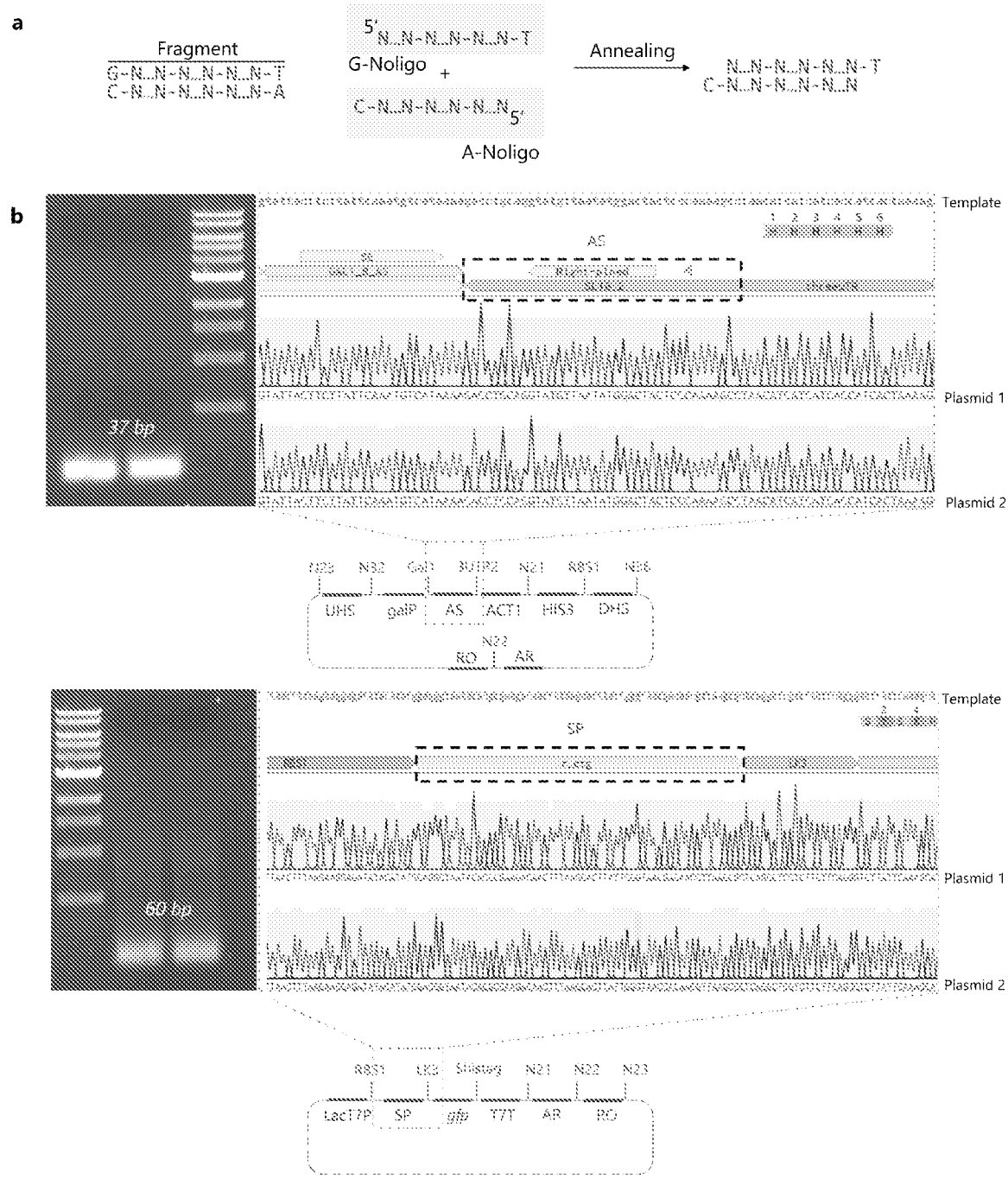

FIG. 19: Creating activated fragment by using Noligos. (a) The oligo to create the sense strand is termed as G-Noligo (the sense strand starts with G from its 5' end). G-Noligo is the same to the sense strand (5' to 3') sequence except it does not contain the first nucleotide (G). The oligo to create the anti-sense strand is termed as A-Noligo (the antisense strand starts with 'A' from its 5' end). A-Noligo is the same the antisense strand (5' to 3') sequence except it does not contain the first nucleotide (A). (b) Two short fragments can be efficiently amplified after barcoding, and ligated with two plasmid backbones accordingly. For each plasmid, sequencing confirmed that two plasmids extracted from two positive colonies had the accurate sequences at the junction region. AS (SL18-2): antisense RNA used to alter protein expression; SP (r_ctg): signal peptide used to create secretion expression system in *E. coli* as shown in FIG. 16b. UHS: Upstream homologous sequence; galP: galactose promoter from *S. cerevisiae*; ACT1: terminator from *S. cerevisiae*; HIS3: selection marker from S. cerevisiael; DHS: Downstream homologous sequence; RO: *E. coli* replication origin; AR: *E. coli* antibiotic resistance marker; LacIT7p: LacI repressor expression cassette with T7 promoter; gfp: a gene encoding green fluorescence protein; T7T: T7 terminator.

Figure 20:
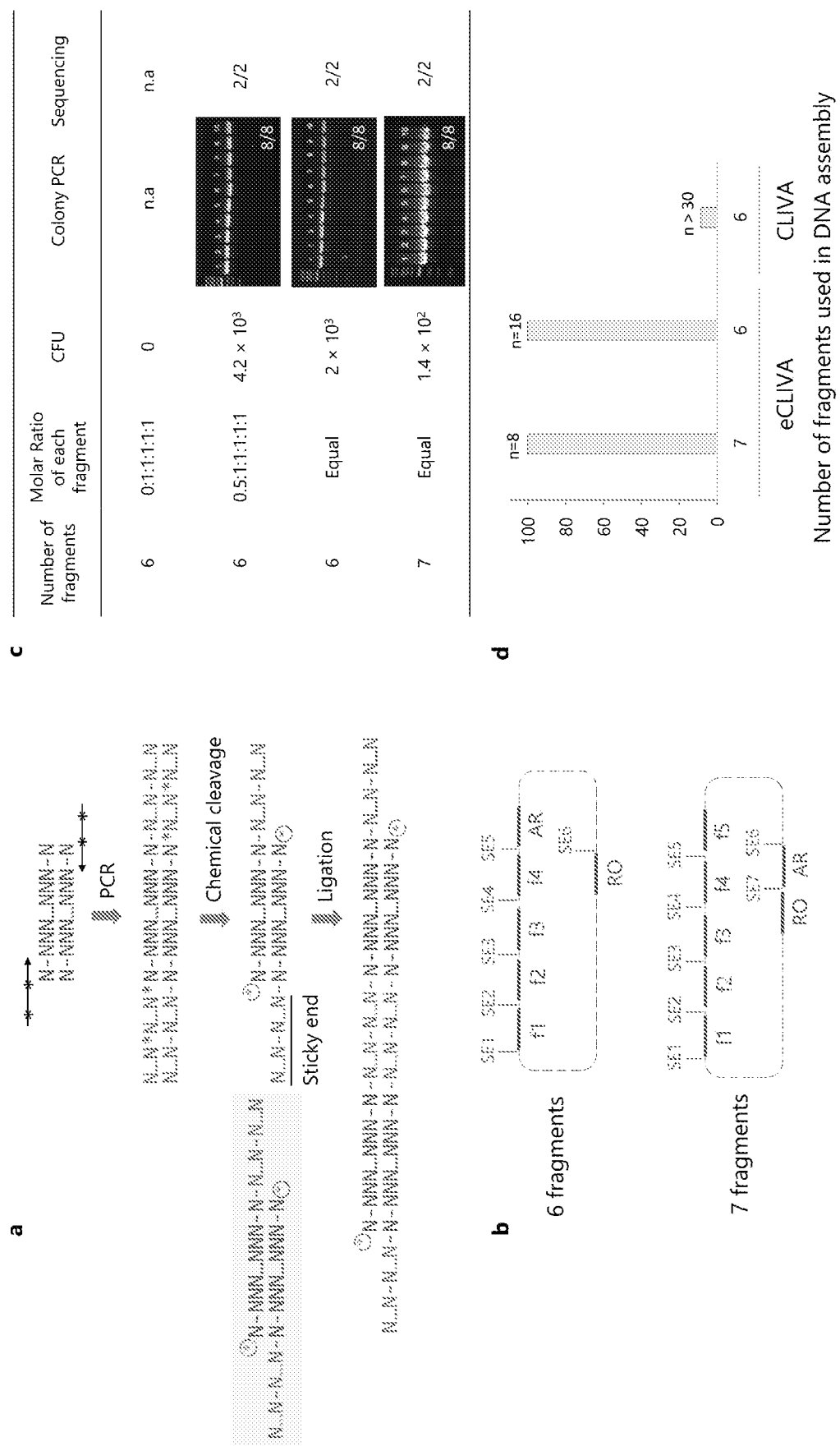

FIG. 20: Improvement of accuracy of CLIVA method by adding a thermophilic ligase in assembly step. (a) One fragment was amplified by using long oligos, which is consisted of binding region of template and with sticky-end (SE) creating region containing two phosphorothioate bonds (*). A 15 bp SE would be generated on both end of one fragment after chemical treatment, which can be annealed with another fragment with the respective complementary 15 bp SE. (b) We amplified the six and seven fragments by using above mentioned oligos, and assembled them into two testing plasmids. (c) Assembly efficiency and accuracy of six fragments with adjusted molar ratio. Assembly efficiency and accuracy of seven fragments, colony forming unit (CFU), and the results of colony PCR and sequencing are shown accordingly. (d) The assembly accuracy of six fragments by using this enhanced CLIVA (eCLIVA) method was significantly improved against the original CLIVA[24] method. However, it is should be noted that the plasmid size involved in the original CLIVA (22 kbp) was much larger than the one used in eCLIVA (4.2 kbp).

Figure 21:
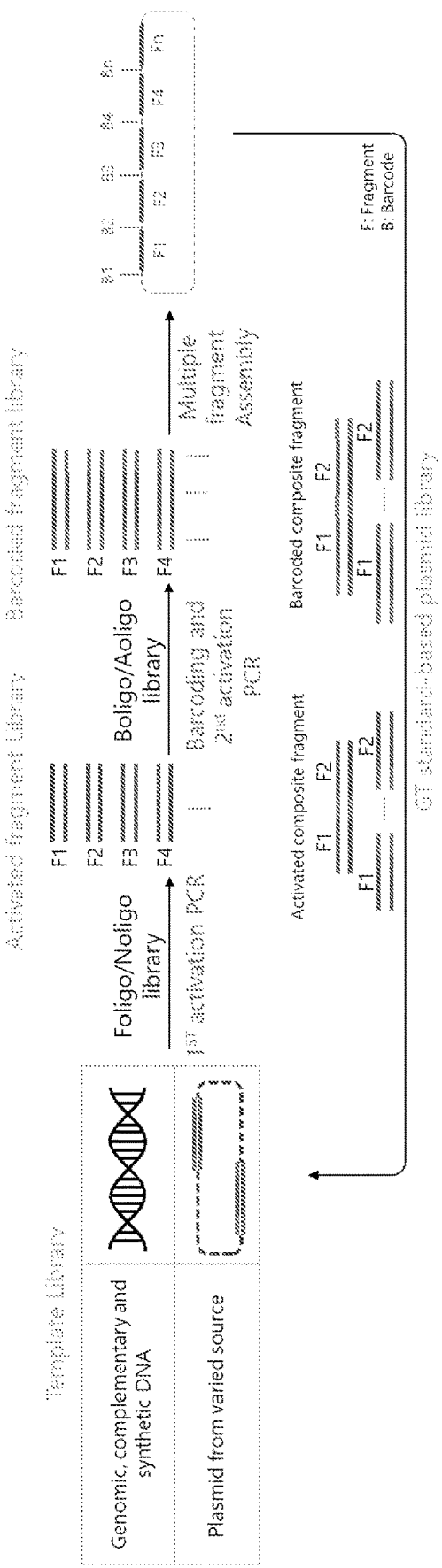

FIG. 21: GTas-based library building workflow. This library contains templates, oligos and plasmids. For preparation of activated fragments, Foligo or Noligo can be used, and the 1$^{st}$ activation PCR would be required if Foligo is used. For preparation of barcoded fragments, Boligo would be required for barcoding, followed by the 2$^{nd}$ activation PCR done with the respective Aoligos. The barcoded fragments acquired will be assembled into plasmids. All plasmids constructed under GTas can be deposited into template library for amplifying activated composite fragment through the 1$^{st}$ activation PCR. This can be barcoded by a new set of Boligos, and be activated through the 2$^{nd}$ round of PCR as barcoded composite fragment. With this iterative process, both flexibility of combination of activated fragments as well as utilization of activated fragments can be maximized, this results in an ever-expanding GT standard-based library with more versatile genetic parts.

Figure 22:
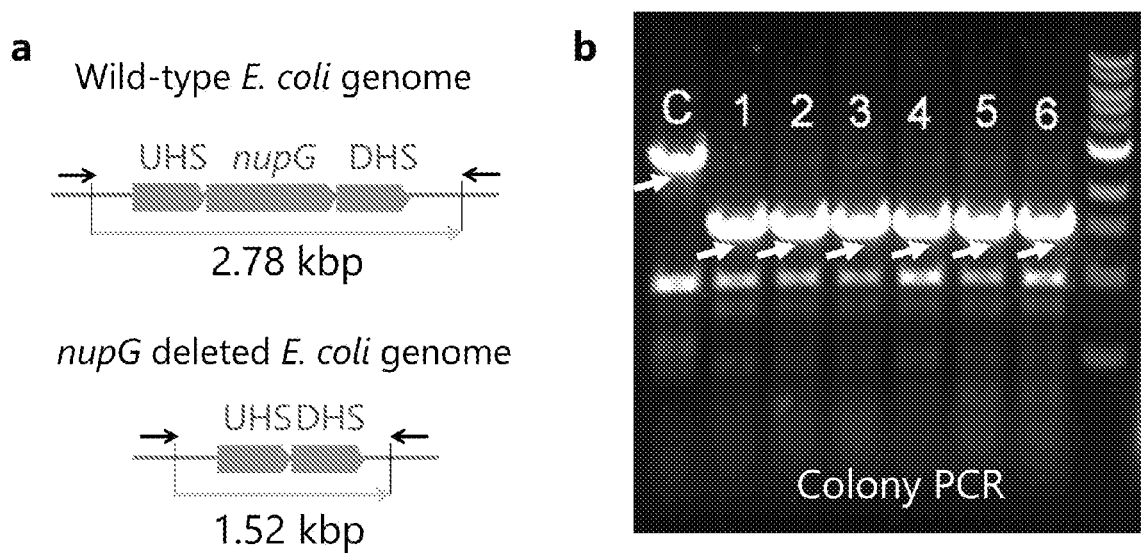

FIG. 22: Functionality test of nupG-pTarget constructed by using novel oligo design (FIG. 11e). (a) The schematic diagram of the wild-type and the deleted E. coli nupG locus. Black arrows indicate the oligos used to colony PCR verification. (b) Colony PCR demonstrated that six randomly picked colonies had the desired deletion, and the negative control (C) was provided by using wild-type E. coli cell as colony PCR template. White arrows indicate the desired bands. The oligos used for colony PCR test are listed in Table 19.

Figure 23:
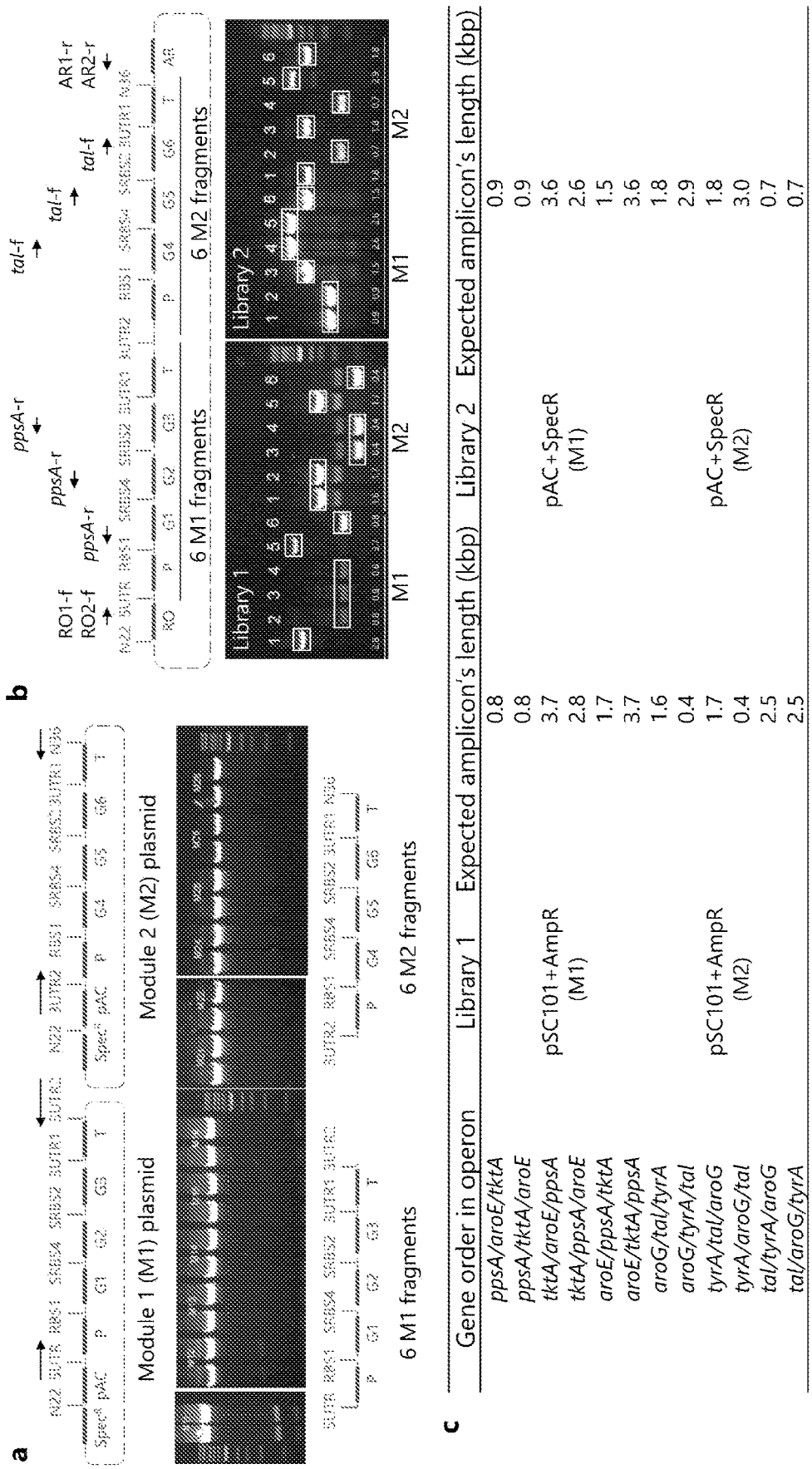

FIG. 23: Workflow for construction of the combinatorial plasmid libares. (a) Construction of 12 plasmids having M1 or M2. The use of M1 and M2 plasmids as PCR templates was executed, with positive results indicating that both M1 and M2 variates were amplified successfully by the use of two sets of Aoligos (indicated with black arrows). (b) Six M1 fragments and six M2 fragments were combinatorially assembled with one plasmid backbone (barcoded) in one reaction to create a mixture of 36 plasmids as a plasmid library. We used two plasmid backbones (pSC101+AmpR and pAC+SpecR) and created two plasmid libraries (Library 1 and Library 2). To confirm the existence of two modules in the plasmid from library 1, two sets of colony PCR, with the use of six colonies selected in random as template, were performed. The first colony PCR was done to detect the existence of the M1 by using oligos of RO1-f targeting on RO region and ppsA-r targeting on ppsA region, and it would generate varied length of amplicons due to the fact that ppsA was possibly arranged to the three locations. In parallel, the second colony PCR was done specifically to detect the existence of the M2 by using oligos of AR1-f targeting on AR region and tal-r targeting on tal region. Similarly, the quality of library 2 was verified by using the same strategy. The amplification results proved that each plasmid library had the plasmids containing varied combination of M1 and M2 variants. The desired amplicon from each module of plasmid from two libraries are highlighted by white rectangular box. (c) The expected amplicon's length is listed accordingly for each module of plasmid from library 1 and 2.

Figure 24:
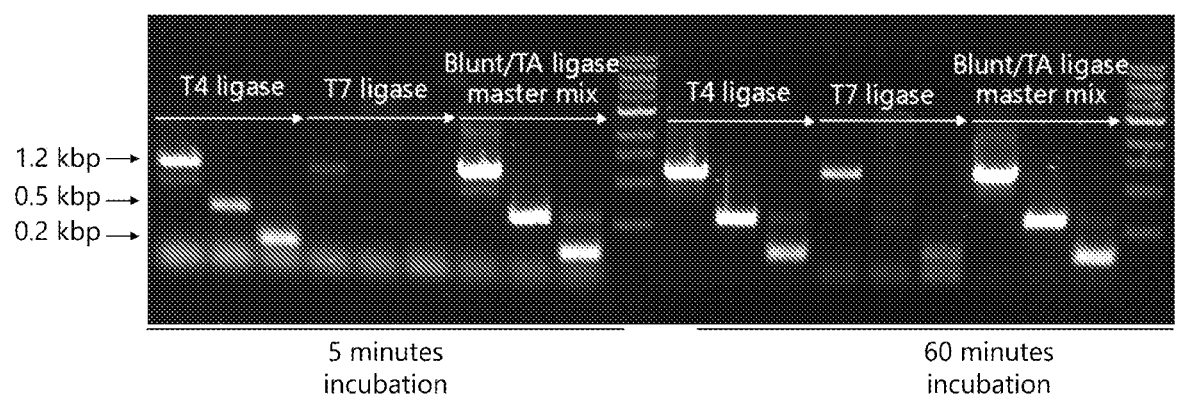

FIG. 24: Optimization of barcoding reaction by using three ligation kits. Three microliters of three fragments with various length were ligated with 0.3 µL of RG-Boligo (5UTR) and 0.3 µL of LA-Boligo (3UTR2). This ligation of Boligos with the activated fragments was performed by using three types of ligation kits (T4 ligase, T7 ligase and Blunt/TA ligase master mix). Three sets of ligation mixtures were incubated at 25° C. for 5 or 60 min. One microliter of each ligation product was used as template in PCR by using oligos of RG-Aoligo (5UTR) and LA-Aoligo (3UTR2). We found that, after 5 min incubation, Blunt/TA ligase master mix evidently outperformed the other ligation kits in term of the efficiency of barcoding three fragments. T4 ligase-mediated barcoding achieved similar results, as compared to Blunt/TA ligase master mix after 60 min of incubation, however, T7 ligase cannot efficiently barcode two shorter fragments (0.5 and 0.2 kbp) since no distinct bands were amplified even after incubation for 60 min.

Figure 25:
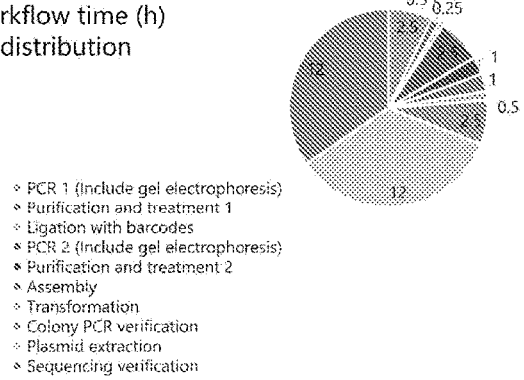
Figure 25:
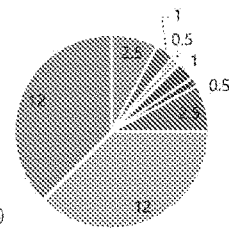
Figure 25:
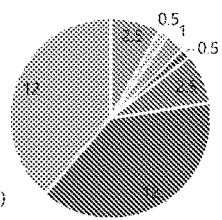

FIG. 25: Comparison of time distribution of three methods' workflow. (a) GTas-based workflow. (b) Restriction enzyme-based workflow. (c) Gibson assembly-based workflow. Cost time of each step of three workflows is calculated based on construction of one plasmid that is assembled with two fragments. We found that the time limiting steps in current cloning works are cell culture and sequencing, instead of PCR and assembly step.

DEFINITIONS

As used herein, the term "comprising" or "including" is to be interpreted as specifying the presence of the stated features, integers, steps or components as referred to, but does not preclude the presence or addition of one or more features, integers, steps or components, or groups thereof. However, in context with the present disclosure, the term "comprising" or "including" also includes "consisting of". The variations of the word "comprising", such as "comprise" and "comprises", and "including", such as "include" and "includes", have correspondingly varied meanings.

As used herein, a scar refers to additional nucleotide(s) left between joined nucleic acid molecules after ligation. For example, the scar is typically left over from the linking sequences. It will be appreciated that such scar(s) may affect biological function.

As used herein a "stem-loop structure" refers to a nucleic acid secondary structure that includes a region of nucleotides which are known or predicted to form a double strand (stem portion) that is linked on one side by a region of predominantly single-stranded nucleotides (loop portion). Stem-loop structures also include "hairpin" and "fold-back" structures. Such structures and terms are known in the art. The actual primary sequence of nucleotides within the stem-loop structure is not critical as long as the secondary structure is present. As is known in the art, the secondary structure does not require exact base-pairing. Thus, the stem may include one or more base mismatches. Alternatively, the base-pairing may not include any mismatches.

As used herein, a "tag" is a sequence of nucleic acid, called the "tag sequence," that permits identification, recognition, and/or molecular or biochemical manipulation of the DNA to which the tag is joined or attached. For example, a tag may provide a site for annealing a primer (i.e., a "priming site") for DNA sequencing or nucleic acid amplification reaction. The tag sequence may comprise non-coding sequences or coding sequences. With respect to non-coding sequences, the tag sequence includes but is not limited to promoter sequences, ribosome binding sequences, exonic sequences, regulatory sequences, termination sequences, origin of replication sequences or part thereof. With respect to coding sequences, the tag sequences may contain a complete coding sequence or open reading frame or part thereof. Examples of coding sequence include but are not limited to antibiotic resistance genes, gfp (which encodes green fluorescent protein).

The process of joining the tag to the nucleic acid molecule is sometimes referred to herein as "tagging" and the nucleic acid that undergoes tagging is referred to as "tagged" (e.g., "tagged nucleic acid"). The tag can comprise one or more "tag portions," which mean herein a portion of the tag that contains a sequence for a desired intended purpose or application. The names and descriptions of different tag portions used herein are for convenience, such as to make it easier to understand and discuss the intended purposes and applications of the different portions of the tag in different embodiments. When a tag is used for identification, it may be referred to as a barcode sequence. As used herein, a barcode sequence comprises a predefined sequence that can be used to identify a nucleic acid molecule or used for assembling nucleic acid molecules. For example, the barcode sequence may be ligated/joined to a nucleic acid molecule to tag; identify or assemble a nucleic acid molecule.

With respect to a tag sequence serving as a linking sequence, the tag sequence may include restriction enzyme sites; for example. Alternatively, compatible cohesive overhangs may be generated in the linking sequences using a chemical cleavage method. It will be appreciated that using a chemical cleavage method may reduce the size of the tag sequence since additional restriction site sequences need not be incorporated, which is an advantage. It will further be appreciated that by carefully designing suitable tag sequences and ligating such tag sequences to different nucleic acid molecules, different nucleic acid molecules may be assembled in any order and combination. It will be appreciated that such tag sequences may be used as the Universal DNA-assembly Standard-BPs.

For maximum efficiency, it will be appreciated that a tag sequence may serve several functions, such as serve as a primer binding site, a linking sequence, include a coding sequence or part thereof, a non-coding sequence or part thereof as well as a barcoding sequence. As will be appreciated, this also may reduce the size of the tag sequence which is an advantage.

In particular, linking sequences are used for the assembly of nucleic acid molecule and in joining a nucleic acid molecule tagged with a linking sequence to one or more tagged nucleic acids to form the assembly, each with a linking sequence may form a complete sequence (for example: a complete coding sequence, a complete promoter region). The further assembly method is very versatile and/or flexible and this versatility and/or flexibility will be more fully appreciated from this specification.

As used herein, a "barcode sequence" refers to a unique oligonucleotide sequence used to identify a nucleic acid base and/or nucleic acid sequence tagged with the barcode sequence.

DETAILED DESCRIPTION OF THE INVENTION

According to a first aspect, the present invention provides a method for ligating at least two nucleic acid molecules comprising:
  (i) providing a first nucleic acid molecule comprising a first overhang of at least one nucleotide in length at a first end;
  (ii) providing a second nucleic acid molecule capable of forming a stem-loop structure with an overhang of at least one nucleotide; wherein the overhang of the second nucleic acid molecule is substantially complementary to the first overhang of the first end of the first nucleic acid molecule; and
  (iii) ligating the first nucleic acid molecule to the second nucleic acid molecule at the complementary overhangs to form a single nucleic acid molecule.

In particular, the second nucleic acid molecule comprises a defined sequence. For example, the defined sequence of the second nucleic acid may further comprise a tag sequence, a barcode sequence and/or a linking sequence. It will be appreciated that the second nucleic acid molecule is useful for tagging the first nucleic acid molecule.

For the method according to the first aspect of the invention, step (i) may comprise the steps of:
  (i)(a) providing a double-stranded nucleic acid template comprising a first nucleic acid strand and a second nucleic acid strand substantially reverse complementary to the first nucleic acid strand;
  (i)(b) providing a first primer comprising a first sequence with at least one modified nucleotide upstream of a second sequence substantially complementary to the first strand of the nucleic acid template; and a second primer comprising a sequence substantially complementary to the second strand of the nucleic acid template;
  (i)(c) amplifying the nucleic acid template using the first and second primers in a polymerase chain reaction to produce an amplicon; and
  (i)(d) chemically cleaving the amplicon to produce the first nucleic acid molecule comprising a first overhang of at least one nucleotide in length at a first end; or
  (i)(a) providing a first single-stranded nucleic acid molecule;
  (i)(b) providing a second single-stranded nucleic acid molecule substantially complementary to the first single nucleic acid molecule; and
  (i)(c) allowing the first and second single-stranded nucleic acid molecule to anneal to produce the first nucleic acid molecule comprising a first overhang of at least one nucleotide in length at a first end.

The number of nucleotides in the first overhang of the first nucleic acid molecule and the number of nucleotides in the overhang of the second nucleic acid molecule may be 1, 2 or 3. It will be appreciated that the number of nucleotides in the first overhang of the first nucleic acid molecule and the overhang of the second nucleic acid molecule may be the same number. For example, the number of nucleotides in the first overhang of the first nucleic acid molecule is 1, and the number of nucleotides in the overhang of the second nucleic acid molecule is also 1.

According to a second aspect, the present invention provides a method for ligating three nucleic acid molecules comprising:
  (i) providing a first nucleic acid molecule comprising a first overhang of at least one nucleotide in length at a first end and a second overhang of at least one nucleotide of at least one nucleotide in length at its other (or second) end; wherein the first overhang and the second overhang have different sequences and/or are not complementary to each other;
  (ii) providing a second nucleic acid molecule capable of forming a stem-loop structure with an overhang of at least one nucleotide; wherein the overhang of the second nucleic acid molecule is substantially complementary to the first overhang of the first end of the first nucleic acid molecule; and also providing a third nucleic acid molecule capable of forming a stem-loop structure with an overhang of at least one nucleotide; wherein the overhang of the third nucleic acid molecule is substantially complementary to the second overhang of the second end of the first nucleic acid molecule; and wherein the overhang of the second nucleic acid molecule and the overhang of the third nucleic acid molecule have different sequences and/or are not complementary to each other; and
  (iii) ligating the first overhang at the first end of the first nucleic acid molecule to the overhang of the second nucleic acid molecule and also the second overhang of the second end of the first nucleic acid molecule to the overhang of the third nucleic acid molecule to form a single nucleic acid molecule.

In particular, the second nucleic acid molecule comprises a first defined sequence and the third nucleic acid molecule comprises a second defined sequence. The first defined sequences of the second nucleic acid molecule and the second defined sequences of the third nucleic acid molecule may be the same sequence, substantially the same sequence or may be different sequences. The first defined sequence of the second nucleic acid molecule may further comprise a first tag sequence, a first barcode sequence and/or a first linking sequence. The second defined sequence of the third nucleic acid molecule may comprise a second tag sequence, a second barcode sequence and/or a second linking sequence. It will be appreciated that the second nucleic acid molecule and/or the third nucleic acid molecules are useful for tagging the first nucleic acid molecule.

For the method according to the second aspect of the invention, step (i) may comprise the steps of:
- (i)(a) providing a double-stranded nucleic acid template comprising a first nucleic acid strand and a second nucleic acid strand substantially reverse complementary to the first nucleic acid strand;
- (i)(b) providing a first primer comprising a first sequence with at least one modified nucleotide upstream of a second sequence substantially complementary to the second strand of the nucleic acid template; and a second primer comprising a third sequence with at least one modified nucleotide upstream of a fourth sequence substantially complementary to the first strand of the nucleic acid template;
- (i)(c) amplifying the nucleic acid template using the first and second primers to produce an amplicon; and
- (i)(d) chemically cleaving the amplicon to produce the first nucleic acid molecule comprising a first overhang of at least one nucleotide in length at a first end and a second overhang of at least one nucleotide of at least one nucleotide in length at its other (or second) end; wherein the first overhang and the second overhang have different sequences and/or are not complementary to each other; or
- (i)(a) providing a first single-stranded nucleic acid molecule;
- (i)(b) providing a second single-stranded nucleic acid molecule substantially complementary to the first single nucleic acid molecule; and
- (i)(c) allowing the first and second single-stranded nucleic acid molecule to anneal to produce the first nucleic acid molecule comprising a first overhang of at least one nucleotide in length at a first end.

The number of nucleotides in the first overhang of the first nucleic acid and the overhang of the second nucleic acid molecule may be 1, 2 or 3. It will be appreciated that the number of nucleotides in the first overhang of the first nucleic acid and the overhang of the second nucleic acid molecule may be the same. For example, the number of nucleotides in the first overhang of the first nucleic and the number of nucleotides in the overhang of the second nucleic molecule are both 1.

Independently of the first overhang of the first nucleic acid and the overhang of the second nucleic acid molecule, the number of nucleotides in the second overhang of the first nucleic acid molecule and the overhang of the third nucleic acid molecule may be 1, 2 or 3. It will be appreciated that the number of nucleotides in the second overhang of the first nucleic acid and the overhang of the third nucleic acid molecule may be the same. For example, the number of nucleotides in the second overhang of the first nucleic and the number of nucleotides in the overhang of the third nucleic molecule are both 1. In a particular embodiment, the number of nucleotides in the first overhang of the first nucleic acid molecule and the number of nucleotides in the overhang of the second nucleic molecule are both 1 and the number of nucleotides in the second overhang of the first nucleic acid molecule and the number of nucleotides in the overhang of the third nucleic molecule are also both 1.

In one example, the method further comprises the steps of:
- iv) using the single nucleic acid molecule from step (iii) as a template for amplifying in a polymerase chain reaction with two amplification primers to produce an amplicon; and
- (v) performing a ligation to join the amplicon with at least one nucleic acid molecule to form an assembly comprising the ligated nucleic acid molecules.

In particular, step (iv) may comprise amplifying the template with an amplification primer comprising at least one modified nucleotide and another amplification primer comprising at least one modified nucleotide to produce the amplicon; chemically cleaving the amplicon to produce an end with a third overhang; and step (v) comprises ligating the amplicon to another nucleic acid molecule with an overhang substantially complementary to the third overhang. The at least one other nucleic acid molecule in step (v) may be an amplicon from step (iv) using another nucleic acid molecule from step (iii) as a template. It will be appreciated that in one embodiment, the amplicon and the at least one other nucleic acid molecule have different sequences.

It will be further appreciated that in another embodiment, step (v) may comprise ligating to form an assembly of ligated nucleic molecules comprising a concatemer of nucleic acid molecules, wherein each nucleic acid molecule of the concatemer comprises substantially the same sequence.

It will be appreciated that the assembly comprising the ligated nucleic acid molecules is circular. It will be appreciated that said circular assembly may comprise a plasmid.

In another example, the method further comprises the steps of:
- (iv) using the single nucleic acid molecule from step (iii) as a template for amplifying in a polymerase chain reaction with two amplification primers to produce an amplicon;
- (v) performing a ligation to join the amplicon to a plurality of nucleic acid molecules to form an assembly of joined plurality of nucleic acid molecules.

In particular, step (iv) comprises amplifying the template with an amplification primer comprising at least one modified nucleotide and another amplification primer comprising at least one modified nucleotide; further chemically cleaving the amplicon to produce a first end with a third overhang and a second end with a fourth overhang.

More in particular, each of the plurality of nucleic acid molecules is an amplicon from step (iv) using another single nucleic acid molecule from step (iii) as a template.

It will be appreciated that the amplicon and each of the plurality of nucleic acid molecules may have different sequences.

Alternatively, step (v) may comprise ligating to form a concatemer of nucleic acid molecules, each with substantially the same sequence.

The assembly of joined plurality of nucleic acid molecules may be circular. In particular, the circular assembly of joined plurality of nucleic acid molecules comprises a plasmid.

In an exemplfiication of the method according to the second aspect of the invention, the second nucleic acid molecule may comprise a first defined sequence and the second nucleic nucleic acid molecule may comprise a second defned sequence. In a further exemplification, the first defined sequence of the second nucleic acid molecule may comprise a first tag sequence, a first barcode sequence and/or a first linking sequence and the second defined sequence of the third nucleic acid molecule may comprise a second tag sequence, a second barcode sequence and/or a second linking sequence. In a further exemplification. It will be appreciated that for these exemplifications, the method may further comprise the steps of:

iv) using the single nucleic acid molecule from step (iii) as a template for amplifying in a polymerase chain reaction with an amplification primer having a sequence designed based on at least part or all of the first defined sequence and comprising at least one modified nucleotide and another amplification primer having a sequence designed based on at least part or all of the second defined sequence and comprising at least one modified nucleotide to produce an amplicon, chemically cleaving the amplicon to produce a first end with a third overhang and a second end with a fourth overhang; and (v) performing a ligation to join the amplicon to a plurality of nucleic acid molecules to form an assembly of joined plurality of nucleic acid molecules; wherein each of the plurality of nucleic acid molecules is an amplicon from step (iv).

It will be appreciated that each of the plurality of nucleic acid molecules is an amplicon from step (iv) using another single nucleic acid molecule from step (iii) as a template.

It will be further appreciated that the amplification primers designed based on the defined sequences of a said second nucleic acid molecule as applicable and these amplification primers may be used to order and/or arrange the plurality of nucleic acid molecules in the assembly of joined plurality of nucleic acid molecules.

It will be appreciated that each defined sequence of said second nucleic acid molecule as applicable may comprise a tag sequence, barcode sequence and/or a linking sequence. The barcode sequence may include a first linking sequence flanking the left side of the barcode sequence and/or a second linking sequence flanking the right side of the barcode sequence. It will be appreciated that the left side of the barcode sequence may be considered upstream of the barcode sequence. It will be appreciated that the right side of the barcode sequence may be considered the downstream of the barcode sequence. The It will be appreciated that in designing the amplification primers, an amplification primer may comprise a tag sequence comprising a first portion of a barcode sequence and either the left or right tag sequence from a said corresponding second nucleic acid molecule as applicable. It will be appreciated that another amplification primer may comprise a tag sequence comprising a second portion of a barcode sequence from another said corresponding second nucleic acid molecule as applicable. It will be appreciated that the first portion of the barcode sequence and the second portion of the barcode sequence when put together may also be considered a barcode sequence. It will be appreciated that a said second nucleic acid molecule comprising a stem-loop structure is used in to tag one end of a nucleic acid molecule from the plurality of nucleic acid molecules in the assembly. It will be appreciated that another said applicable corresponding second nucleic acid molecule comprising a stem-loop structure is used to tag one end of another nucleic acid molecule from the plurality of nucleic acid moelcules in the assembly. It will be appreciated that the order and arrangement of the plurality of nucleic acid molecules in the assembly may be determined from selecting applicable second nucleic acid molecules comprising a stem-loop structure for each of the plurality of nucleic acid moiecules in addition to the amplification primers. (Please refer to Example 7 and FIG. 12)

It will be appreciated that the amplicon and each of the plurality of nucleic acid molecules may have different sequences. The assembly of joined plurality of nucleic acid molecules may be circular. In particular, the circular assembly of joined plurality of nucleic acid molecules comprises a plasmid. It will be appreciated that the method may further comprise using polymerase chain reaction with amplification primers designed based on applicable defined sequences to implement a modification in the assembly of joined plurality of nucleic acid molecules, wherein the modification includes inserting at least one nucleic acid molecule in to the assembly, removing t least one joined nucleic acid molecule from the assembly or replacing at least one joined nucleic acid molecule in the assembly. It will be appreciated that the modification may be implemented to form a library of different plasmids.

The present method provides a lot of flexibility and versatility in the design of the nucleic acid molecules capable of forming a stem-loop structure with an overhang of at least one nucleotide. The design of the nucleic acid molecules may be computer-implemented. For any aspect of the invention, any of the overhangs may independently comprise any number of nucleotides. Overhangs that are for joining together will typically have the same number of nucleotides. It will be appreciated that the overhangs may not be additional nucleotide sequences which serve no purpose but form scars. As an illustration, the overhang may be part of a useful coding sequence, for example. This minimizes wastage as there are no scars. It will be appreciated that an overhang for any aspect of the invention may be a 5' or a 3' overhang. For the second aspect of the invention, the first overhang and the second overhang may independently be a 5' overhang or a 3' overhang.

It will also be appreciated that the number of nucleotides in any of the overhangs can be reduced to as small as possible, especially for standardized BPs. For example, the number of nucleotides in the overhang(s) may be 1, 2 or 3. In particular, the number of nucleotides in the overhang(s) is 1, such that the scar size is one nucleotide long.

It will be appreciated that the number of nucleotides for the first overhang and the overhang of the second nucleic acid molecule are independent of the number of nucleotides for the second overhang and the overhang of the third nucleic acid molecule.

For the second aspect of the invention, the first overhang and the second overhang may have different sequences and/or are not complementary to each other. For example, it will be appreciated that this helps to ensure the desired ligation occurs. If the number of nucleotides in the first and second overhang is 1, it will be appreciated that if the first overhang is a G or a C, the second overhang should be an A or a T and vice versa.

Theoretically, the minimal length of a sticky end is 1 nt, and even with 1 nt, there is still a large degree of freedom left in selecting amino acid codons. For example, we can define all fragments to start with 'G' and end with 'T'. Then, if this is a protein-coding sequence and we intend to express it as a standalone protein, we can choose barcodes to flank the fragment by 'ATG' and 'TGA', which are start and stop codons respectively; if we plan to fuse this protein to others, we could select barcodes to flank it by 'GGG' and 'TCT', which encode flexible amino acid glycine and serine respectively (FIG. 5). When a fragment is not a protein-coding sequence, one usually can easily find a 'G' and a 'T' in its natural sequence to define the beginning and the end of the fragment It will be appreciated that dephosphorylation of the 5' end(s) of nucleic acid molecules as appropriate may be utilised to increase the ligation of the desired nucleic acid molecules in any ligation and/or assembly molecule. For example, either the first nucleic acid molecule may be dephosphorylated or the nucleic acid molecule(s) capable of forming a stem-loop structure may be dephosphorylated. Similarly, for forming an assembly of a joined plurality of nucleic acid molecules, it is important to identify and select the nucleic acid molecules for dephosphorylation to increase the formation of the desired assembly.

It will be appreciated that chemical cleavage comprises non-enzymatic cleavage. Any suitable modified nucleotide may be utilised and an applicable cleavage method may be used. The modified nucleotides and cleavage method as described in WO 2000/18967[27] may be adapted for the present invention.

Having now generally described the invention, the same will be more readily understood through reference to the following examples which are provided by way of illustration, and are not intended to be limiting of the present invention.

The invention includes a nucleic acid molecule comprising of a defined sequence capable of forming a stem-loop structure with an overhang of one nucleotide. The invention includes a nucleic acid molecule comprising of a defined sequence capable of forming a stem-loop structure with an overhang of at least one nucleotide.

It will be appreciated that the defined sequence of a nucleic acid molecule according to the invention may comprise a tag sequence, a barcode sequence and/or a linking sequence. The tag sequence, barcode sequence and/or linking sequence may comprise a coding region or part thereof. Alternatively, the tag sequence, barcode sequence and/or linking sequence may comprise a non-coding region or part thereof. It will be appreciated that the tag sequence, barcode sequence and/or linking sequence may include but is not limited to a ribosomal binding stie or part thereof, a linker peptide sequence or part thereof, a 2a peptide sequence or part thereof, a protein tag sequence or part thereof, an untranslated sequence or part thereof, a promoter sequence or part thereof, The invention also includes a kit comprising a plurality of nucleic acid molecules; each with a defined sequence capable of forming a stem-loop structure with an overhang of at least one nucleotide. Each defined sequence may independent comprise a tag sequence, a barcode sequence and/or a linking sequence. Said tag sequence, bar code sequence and/or linking sequence may comprise a coding region or part thereof. Alternatively, said tag sequence, bar code sequence and/or linking sequence may comprise a non-coding region or part thereof.

The kit may further comprise one or a plurality of oligonucleotide(s). It will be appreciated that said one oligonucleotide or each oligonucletotide from the plurality of oligonucleotides is capable of annealing to a defined sequence of at least one of the plurality of nucleic acid molecules.

In a particular embodiment of the kit, the kit may further comprise a plurality of oligonucleotides, wherein each oligonucleotide is capable of annealing to a defined sequence of a corresponding nucleic acid molecule from the plurality of nucleic acid molecules in the kit.

It will be appreciated that the oligonucleotides can serve as (amplifying) primers in a polymerase chain reaction.

EXAMPLES

Standard molecular biology techniques known in the art and not specifically described were generally followed as described in Green and Sambrook, Molecular Cloning: A Laboratory Manual, Cold Springs Harbor Laboratory, New York (2012)[26].

Example 1: Development of a Universal DNA-Assembly Standard and the Enabling Technology For ease of understanding, we define two types of standardized biological parts (namely fragments and barcodes), and consider any DNA molecule to be made of fragments and barcodes appearing in alternating order (FIG. 1). The difference between fragments and barcodes is their length—barcode is less than 60 nt and fragment is longer than 60 nt in this first example. Both fragments and barcodes can be functional. To assemble standardized fragments and barcodes in a pre-defined order, we need to add one barcode onto each side of a fragment, and then use these barcodes to direct desired assembly of fragments (FIG. 1).

In this work, we developed a new BP standard (termed as Universal DNA-assembly Standard, UDS, FIG. 1) or GT Assembly Standard (GTas) and the technology needed to implement it. This method can assemble up to seven standardized BPs in any order without using any customized parts, does not leave any scar in final construct, does not need to avoid any forbidden restriction enzyme site, and is compatible with multi-tier DNA assembly. To demonstrate the usefulness of this method, we built a small UDS library of standardized BPs, and used it to construct a large panel of plasmids for producing isoprenoid and aromatic compounds in *Escherichia coli* (*E. coli*). These plasmids allowed us to fine tune expression of multiple genes and implement CRISPR-Cas9 based genome editing. With an expanded library of UDS BPs and more participations from the research community, this technology would substantially reduce the time needed, and cost incurred, in cell line development, in metabolic engineering, synthetic biology, and other biotechnological applications.

By using phosphorothioate oligos, PCR and a chemical cleavage method, we can control length of sticky end and create 1 nt sticky ends on fragments (FIG. 2a). Thereafter, two barcode oligos with a stem-loop structure was joined to a DNA fragment to form a closed DNA molecule with two stem-loop secondary structures (FIG. 2e). This strategy eliminated the addition of tandem barcodes to the fragment, because there was no free end for further ligation to occur after one fragment is flanked by two stem loops (FIG. 2e). When we used such stem-loop oligos to barcode five different fragments, we indeed managed to amplify all of them without any smear (FIG. 2e), and can accurately assemble these fragments into one functional plasmid (FIG. 2f) by using enhanced version of CLIVA method (Work Flow Diagram: FIG. 6, Plasmid verification results: FIG. 7).

For comparison, we also added barcodes to a common cloning vector (used as an entry vector) and create 1 nt sticky ends outside barcodes (FIG. 2b), however, it was very difficult to carry out the ligation based on such short sticky ends, due to high Gibbs free energy. We assessed the ligation efficiency by amplifying the barcoded fragment from the ligation product of the fragment and the vector via PCR.

Here, we attempted to barcode five fragments and we found all the PCR reactions had low yield and non-specific products (FIG. 2c), inferring low ligation efficiency in all cases.

For further comparison, we created barcodes by annealing two oligos, which were designed to produce the desired 1-nt SE after being annealed (FIG. 2d). After two barcodes produced this way were incubated with a fragment containing 1 nt sticky ends for a period, we attempted to amplify the barcoded fragment by using PCR (we tested the same set of fragments and barcodes). The results showed that the PCR yield was much higher than the previous case, but many non-specific products were still produced as evidenced by the heavy smear in the picture (FIG. 2d). From literature, such smears were attributed to presence of barcode oligos (those used to form the barcodes) in the PCR reaction, so we removed the excess oligos by using magnetic beads based purification before conducting PCR amplification, however, smears were not substantially reduced after this practice (data not shown).

To further understand the root cause of the heavy smear, we cloned some of the ligation products into vector and sequenced the obtained vector, whose data showed that some fragments had tandem barcodes on their sides. So, we hypothesized that the successfully barcoded fragments (with one barcode on each side) could be further linked to barcode oligos via blunt end like ligation, and such complex product mixture caused formation of the non-specific products in the subsequent PCR reactions.

To further validate the robustness and general applicability of the UDS BPs and the technologies that enable it, we designed a small library of UDS fragments and barcodes, and have used them to construct ~50 unique plasmids for various biotechnological applications. The statistics of these plasmid construction show that we have experimentally validated 200 plasmids (including replicates) and 90% of them were confirmed to be correct (Table 1). Most of these plasmids were created by assembling 5-7 fragments (Table 1), size of used fragments ranged from 53 bp to 5300 bp, and the largest plasmid we have constructed was more than 10 kb (data not shown), which together have covered the commonly used ranges in biotechnological applications.

require customized DNA oligos for each application, which is time-consuming and expensive. In this example, we optimized production of valencene, a fragrance molecule, from glucose in E. coli by systematically changing expression level of four genes in the biosynthetic pathway (dxs, idi, ispA and valC). Specifically, we arranged these four genes in an operon and shuffled their order, which would alter their expression level—genes closer to their promoter would be transcribed at a higher level in an operon. In total, there would be 24 (4!) variants, and they can be easily constructed by using five fragments (the four genes and one expression vector that contains T7 promoter, T7 terminator, LacI repressor module, p5 replication origin, spectinomycin antibiotic resistance), and five barcodes (RBS1, RBS2stop, RBS3stop, RBS4stop and 3UTR), which encode various ribosomal binding sites with or without stop codon and 3' untranslated region (FIG. 3a). We introduced each of these 24 plasmids into an E. coli strain, and cultured the production strains with three levels of IPTG concentration (0, 0.005 and 0.1 mM, IPTG: inducer of T7 promoter), which dictates the overall transcription level of the operon. Combining IPTG concentration with the gene order generated 72 conditions in total, covering a large search space, as evidenced by the fact that we detected a large range of valencene titer at these conditions (from 0.05 to 5 mg/L, FIG. 3b). Though the product titer is not yet impressive, this proof-of-concept study has proved that the UDS parts can be easily used to construct a large number of plasmids and to tune expression level of multiple genes.

The second application focuses on customizing expression vectors by using UDS BPs. Replication origin and promoter often need to be changed in biological applications to enable use of multiple plasmids and/or to optimize protein expression level. In this study, we have catered 16 plasmids for optimizing production of tyrosine, a useful amino acid, from glucose in E. coli (FIG. 4a). We have combined four replication origins (p5, p15, pMB1 and pMB1 mutant), two promoters (T7 and lac) and two gene orders (tyrA-aroG or aroG-tyrA). Each of these components is a standardized fragment in our small UDS library, so construction of the 16 plasmids was straightforward—six or seven fragments were

TABLE 1

Statistics of plasmid construction by using UDS biological parts

| Line | Method of adding barcodes | Number of fragments | Molar Ratio of fragments | CFU per transformation | Accuracy |
|---|---|---|---|---|---|
| 1 | Use standardized oligos | 3 | Equal | 100-200 | 6/6 |
| 2 | Use standardized oligos | 5 | Equal | 50-500 | 129/144 |
| 3 | Use standardized oligos | 6 | Equal | 50-500 | 43/48 |
| 4 | Use standardized oligos | 7 | Equal | 10-100 | 43/48 |

Example 2: Biotechnological Applications

We have completed a few applications to demonstrate the usefulness of UDS BPs and the plasmids derived from them.

The first application demonstrated that UDS BPs can be used to construct a panel of plasmids for fine-tuning expression level of multiple genes, which has been shown to be critical in many biotechnological applications. For example, in metabolic engineering, balancing expression level of multiple genes was crucial in optimizing production of value-added chemica. To date, constructing such plasmids assembled each time with proper barcodes to create one plasmid in one step. Again, E. coli strains with these plasmids were shown to have various abilities to produce tyrosine, whose titer ranged from 0.1 to 1.4 g/L (FIG. 4b). These data allowed us to swiftly identify the optimal condition and to learn that only medium copy number plasmid worked the best for tyrosine production. This information would be very useful to further develop this strain into an industrial workhorse.

The third application focused on constructing plasmids for CRISPR-Cas9, which has revolutionized how biotechnology is being done[11,12]. Even for *E. coli*, an organism that is considered to be easy-to-manipulate, CRISPR has made inserting a large number of genes into *E. coli* genome to be much easier, because CRISPR does not require marker recycle[11,13]. Based on a two-plasmid CRISPR system for *E. coli*[13], we designed some parts for genome editing of *E. coli*, and used them to perform two types of editing. First, we constructed plasmids for knocking out various genes, and optimized the genome-editing efficiency by tuning length of homologous arms (Table 2). We further constructed plasmids for inserting expression cassettes into *E. coli* genome via the CRISPR system. Here we defined each gene knock-out plasmid to be a new UDS BP and could combine it easily with any cassette to be inserted by using two barcodes (FIG. 8). We have experimentally verified that a short 300 bp demo fragment could be integrated into *E. coli* successfully (Table 2), and plasmids carrying larger size insertions (optimal operon) that had been identified from valencene and tyrosine screening are also being constructed, and will be tested.

TABLE 2

Characterization of CRISPR-Cas9 plasmids for *E. coli* gene deletion and insertion

| E. coli_Locus | gRNA | Homologues arm length (bp) | Gene deletion efficiency | Gene insertion efficiency |
| --- | --- | --- | --- | --- |
| nupG | Optimized | 500 | 6/6 | 6/6 |
| nupG | ... | 1000 | 8/8 | Undergoing |
| nupG | ... | 1500 | 6/8 | Undergoing |
| pheA | ... | 500 | 6/6 | N/A |
| tyrR | ... | 500 | 3/16 | N/A |
| tyrR | ... | 1000 | Undergoing | N/A |
| ptsH, ptsI and crr | ... | 700 | 4/4 | Undergoing |
| melB | ... | 1000 | 7/8 | Undergoing |
| rcsB | ... | 1000 | 8/8 | Undergoing |
| aslA | ... | 500 | Undergoing | N/A |
| aslA | ... | 1000 | Undergoing | N/A |

N/A: Not applicable

Example 3: Materials and Methods

UDS Fragment

UDS fragment oligos with one phosphorothioate bond modified after 'G' of forward primer and 'A' on the reverse primer (FIG. 2a) were synthesized from Integrated DNA Technologies (IDT, sequence of oligos and modifications can be found in Table 3, and all oligos used in this study are prepared to be 100 µM). Amplify template DNA by using the designed oligos in a PCR reaction (NEB Q5 Master Mix, M0494, is recommended, and regular volume of reaction is 50 microliters). Purify the obtained fragments by using column according to manufacture instructions, and add 40 microliters nuclease-free water (1st BASE Biochemicals, BUF-1180) in elution step. Add 5.5 microliters of 1 M Tris-HCl UDS fragments and oligosabove obtained elution, and incubate the mixture at 70° C. for 5 min in a 1.7 milliliter Eppendorf tube immersed in a water bath (Mix the components well before the 70° C. incubation). After chemical treatment, 1-mer sticky end-containing fragments were generated by cleaving specifically at the phosphorothioate positions[23]. Add 250 microliters of nuclease-free water to the treated mixture, and if Thermo-Scientific Gel Extraction Kit (K0692) is used, add 350 microliters of binding buffer, and mix and load the solution to the column, wash it by using 550 microliters of wash buffer twice, and elute the solution by using 30 microliters of nuclease-free water at room temperature.

TABLE 3

UDS fragments and oligos

| UDS fragments | Forward Oligos | Sequence (*: phosphorothioate bond) | Reverse oligos | Sequence (*: phosphorothioate bond) |
|---|---|---|---|---|
| gRNA-nupG | G-gRNA-nupG F | G*tacgagttaatcaatatcacagttttagagctagaaatag (SEQ ID NO: 1) | gRNA-T R | A*tctagagaattcaaaaaaag (SEQ ID NO: 2) |
| gRNA-aslA | G-gRNA-aslA F | G*tgcagaacttgagaaaaaaacgttttagagctagaaatag (SEQ ID NO: 3) | gRNA-T R | Same to gRNA-T R |
| gRNA-melB | G-gRNA-melB F | G*tctaccatttgttaattatgtgttttagagctagaaatag (SEQ ID NO: 4) | gRNA-T R | Same to gRNA-T R |
| gRNA-rcsB | G-gRNA-rcsB F | G*taatcacttgagcaaattgaggttttagagctagaaatag (SEQ ID NO: 5) | gRNA-T R | Same to gRNA-T R |
| gRNA-tyrR | G-gRNA-tyrR F | G*tttaataccgagcgttcaaaagttttagagctagaaatag (SEQ ID NO: 6) | gRNA-T R | Same to gRNA-T R |
| gRNA-pheA | G-gRNA-pheA F | G*ttttgagcaattcattgaaaggttttagagctagaaatag (SEQ ID NO: 7) | gRNA-T R | Same to gRNA-T R |
| gRNA-ptsI | G-gRNA-ptsI F | G*tgaagttgatttctttagtatgttttagagctagaaatag (SEQ ID NO: 8) | gRNA-T R | Same to gRNA-T R |
| nupG-HF0.5 | G-nupG-HF0.5 F | G*ttgatcctgccagcaata (SEQ ID NO: 9) | nupG-HF0.5-T R | A*catcgtgatgcggatgag (SEQ ID NO: 10) |
| nupG-HF1.0 | G-nupG-HF1.0 F | G*accatcgccgggacagaacc (SEQ ID NO: 11) | nupG-HF1.0-T R | Same to nupG-HF0.5-T R |
| nupG-HF1.5 | G-nupG-HF1.5 F | G*tgcaacgtgaagcagaaggt (SEQ ID NO: 12) | nupG-HF1.5-T R | Same to nupG-HF0.5-T R |
| aslA-HF0.5 | G-aslA-HF0.5 F | G*caccgtaaacggctctgc (SEQ ID NO: 13) | aslA-HF0.5-T R | A*gtttcatgtcatcaaaatg (SEQ ID NO: 14) |
| aslA-HF1.0 | G-aslA-HF1.0 F | G*ccagtacgacgatcgcct (SEQ ID NO: 15) | aslA-HF1.0-T R | Same to aslA-HF0.5-T R |
| melB-HF1.0 | G-melB-HF1.0 F | G*cccaatggcgatgaatacct (SEQ ID NO: 16) | melB-HF1.0-T R | A*gctgttaccaacgcccgcct (SEQ ID NO: 17) |
| rcsB-HF1.0 | G-rcsB-HF1.0 F | G*gttagcgaacatgcttgcgg (SEQ ID NO: 18) | rcsB-HF1.0-T R | A*ttgctacagcaagctcttga (SEQ ID NO: 19) |
| tyrR-HF0.5 | G-tyrR-HF0.5 F | G*cagcccgctggcgttggt (SEQ ID NO: 20) | tyrR-HF0.5-T R | A*gtcagcacccgatattgcat (SEQ ID NO: 21) |
| pheA-HF0.5 | G-pheA-HF0.5 F | G*catgtcgcagaccgtctcg (SEQ ID NO: 22) | pheA-HF0.5-T R | A*cgaaacgcctcccattcag (SEQ ID NO: 23) |
| ptsI-HF0.7 | G-ptsI-HF0.7 F | G*ccccgcataaaattcaggg (SEQ ID NO: 24) | ptsI-HF0.7-T R | A*ggaactaaagtctagcctgg (SEQ ID NO: 25) |
| nupG-HT0.5 | G-nupG-HT0.5 F | G*ttacgcaaagaaaaacgg (SEQ ID NO: 26) | nupG-HT0.5-T R | A*gccgctggttgaggtgtt (SEQ ID NO: 27) |
| nupG-HT1.0 | G-nupG-HT1.0 F | Same to G-nupG-HT0.5 F | nupG-HT1.0-T R | A*acgcctttatgctccatgct (SEQ ID NO: 28) |
| nupG-HT1.5 | G-nupG-HT1.5 F | Same to G-nupG-HT0.5 F | nupG-HT1.5-T R | A*gcgacgccggtctatctgga (SEQ ID NO: 29) |
| aslA-HT0.5 | G-aslA-HT0.5 F | G*gccggcgctatcgctgag (SEQ ID NO: 30) | aslA-HT0.5-T R | A*cactatgtttatccgcaa (SEQ ID NO: 31) |
| aslA-HT1.0 | G-aslA-HT1.0 F | Same to G-aslA-HT0.5 F | aslA-HT1.0-T R | A*gcccgcctgagatccaca (SEQ ID NO: 32) |

TABLE 3-continued

UDS fragments and oligos

| UDS fragments | Forward Oligos | Sequence (*: phosphorothioate bond) | Reverse oligos | Sequence (*: phosphorothioate bond) |
|---|---|---|---|---|
| melB-HT1.0 | G-melB-HT1.0 F | G*gtgcagtgagtgatgtgaaa (SEQ ID NO: 33) | melB-HT1.0-T R | A*gggtatggaagctatctgga (SEQ ID NO: 34) |
| rcsB-HT1.0 | G-rcsB-HT1.0 F | G*tcacctgtaggccagataag (SEQ ID NO: 35) | rcsB-HT1.0-T R | A*attcagaaccgggaatgggc (SEQ ID NO: 36) |
| tyrR-HT0.5 | G-tyrR-HT0.5 F | G*gcgcgaatatgcctgatg (SEQ ID NO: 37) | tyrR-HT0.5-T R | A*catcccgcaggcgggtag (SEQ ID NO: 38) |
| pheA-HT0.5 | G-pheA-HT0.5 F | G*ttactggcgattgtcattcg (SEQ ID NO: 39) | pheA-HT0.5-T R | A*aaatgggccattacaggcc (SEQ ID NO: 40) |
| ptsI-HT0.7 | G-ptsI-HT0.7 F | G*agcgcatcacttccagtac (SEQ ID NO: 41) | ptsI-HT0.7-T R | A*taacgataagagtagggcac (SEQ ID NO: 42) |
| aadA | G-spectR F | G*tcgacctgcagaagctt (SEQ ID NO: 43) | spectR-T R | A*cgttaagggattttggt (SEQ ID NO: 44) |
| bla | G-ampR F | G*tttctacaaactctttt (SEQ ID NO: 45) | G-ampR F | Same to spectR-T R |
| P5 | G-repA/p5 F | G*ccgttttcatctgtgcatat (SEQ ID NO: 46) | repA/p5-T R | A*tccttttgtaatactgcgga (SEQ ID NO: 47) |
| p15 | G-p15A F | G*tgttcagctactgacgg (SEQ ID NO: 48) | p15A-T R | A*gacatcaccgatgggga (SEQ ID NO: 49) |
| pMB1 | G-pMB1 F | G*agttttcgttccactga (SEQ ID NO: 50) | pMB1-T R | A*ggatccagcatatgcgg (SEQ ID NO: 51) |
| pMB1 mutant | G-pUC F | G*gctcactcaaaggcggta (SEQ ID NO: 52) | pUC-T R | A*attaccgcctttgagtga (SEQ ID NO: 53) |
| pLac | G-pLac F | G*caacgcaattaatgtgagt (SEQ ID NO: 54) | pLac-T R | A*ttgttatccgctcacaatt (SEQ ID NO: 55) |
| LacIT7 | G-lacIT7 F | G*gaaactacccataatacaag (SEQ ID NO: 56) | LacIT7-T R | A*gaggggaattgttatccgc tcacaattcccctatagtga (SEQ ID NO: 57) |
| t7t | G-t7t F | G*ggctgctaacaaagccc (SEQ ID NO: 58) | t7t-T R | A*ggcaccgtcaccctggat (SEQ ID NO: 59) |
| LacI | G-lacI F | Same to G-lacIT7 F | lacI-T R | A*tcccggacaccatcgaat (SEQ ID NO: 60) |
| dxs | G-dxs F | G*agttttgatattgccaaata (SEQ ID NO: 61) | dxs-T R | A*tgccagccaggccttg (SEQ ID NO: 62) |
| idi | G-idi F | G*caaacgaacacgtcatttt (SEQ ID NO: 63) | idi-T R | A*tttaagctgggtaaatgcag (SEQ ID NO: 64) |
| ispA | G-ispA F | G*gactttccgcagcaact (SEQ ID NO: 65) | ispA-T R | A*tttattacgctggatgatgt (SEQ ID NO: 66) |
| ValC | G-ValC F | G*gccgagatgttcaacgg (SEQ ID NO: 67) | ValC-T R | A*ggggatgatgggctcg (SEQ ID NO: 68) |
| tyrR mutant | G-tyrR mutant F | G*gttgctgaattgaccgcatt (SEQ ID NO: 69) | tyrR mutant-T R | A*ctggcgattgtcattcgc (SEQ ID NO: 70) |
| aroG mutant | G-aroG mutant F | G*aattatcagaacgacgattt (SEQ ID NO: 71) | aroG mutant-T R | A*cccgcgacgcgctttta (SEQ ID NO: 72) |

UDS Barcode

The sequence and annotation of UDS barcode are listed in Table 4, 3 types of UDS barcodes are prepared as following procedures:

Common cloning vectors (1.8 kb) containing replication origin (pMB1) and antibiotic resistance (spectinomycin) were amplified from template plasmid (pTarget), and barcodes were introduced during PCR by using oligos (one phosphorothioate bond were modified after T of forward primer and 'C' on the reverse primer as shown in FIG. 2b, details can be found in Table 5). For example, pT2-N21N22 can be amplified by using oligos of T-N22'_pT2 F and pT2_N21"-G R. Then, 1 nt sticky ends of 'A' and 'G' outside barcodes could be generated by using chemical treatment.

Five cloning plasmids with 1 nt SE-based barcodes obtained here are pT2-N21N22, pT2-N22pJ23119, pT2-pJ23119N23, pT2-N23N24 and pT2-N24N21, respectively, which are available to use for barcoding five 1 nt SE-based fragments to construct nupG knock out plasmid (FIG. 2f).

Two oligos that will be annealed to be barcodes were synthesised directly (Sequence of oligos and modifications can be found in Table 5), and the desired 1 nt SE of barcodes could be generated by simply mixing 50 microliters of forward and reverse oligos (Table 4 and FIG. 2d), and annealed by following PCR program in a PCR machine: 95° C. for 2 minutes, and gradually decrease temperature (0.1° C. per second) to 75° C., hold it for 2 minutes, then gradually decrease temperature (0.1° C. per second) to 4° C. For example, annealing oligos of N21s-Bff and N21s-Bfr to be prefix barcode N21-Bf, while suffix barcode N21-Br are obtained by annealing oligos of N21s-Brf and N21s-Brr. In the same way, five prefix barcodes and suffix barcodes are prepared for barcoding five 1 nt SE-based fragments to construct nupG knock out plasmid (FIG. 2d).

Stem-loop oligos used to create barcodes were synthesized directly (Sequence of barcode oligos and modifications can be found in Table 5), and 6 nucleotides loop sequence were generated randomly, and filtered subsequently by an algorithm to remove undesired interaction with stem region covering SE part and adjacent part of barcode. Phosphorylation of 1 microliter of barcode oligo was done by using T4 Polynucleotide Kinase (NBE, M0201) (Table 6), which can be omitted by directly using the phosphorylated oligos synthesized by oligo manufacturer. Folding the barcode oligos to be stem-loop structure was completed by identical PCR program used above to create annealed oligos-based barcode. For example, prefix barcode RBS1-Bf-SL will be generated after simply annealing barcode oligos of RBS1-Bf-SL (Table 4 and FIG. 2e).

TABLE 4

UDS Barcodes

| Barcodes | Sequence | Functionality |
|---|---|---|
| RBS1 | TagaaataattttgtttaactttaagaaggagatatacatatG (SEQ ID NO: 73) | Ribosome binding site |
| RBS2stop | TaaccgttcatttatcacaaaaggattgttcgatG (SEQ ID NO: 74) | Ribosome binding site with stop codon |
| RBS3stop | TgattcacacaggaaacagctatG (SEQ ID NO: 75) | Ribosome binding site with stop codon |
| RBS4stop | TaaattaattgttctttttttcaggtgaaggttcccatG (SEQ ID NO: 76) | Ribosome binding site with stop codon |
| pJ23119 | TtgacagctagctcagtcctaggtataatactaG (SEQ ID NO: 77) | Promoter |
| N21 | TtccctcgactcacacttggG (SEQ ID NO: 78) | Non-functional |
| N22 | TtcacacaacatagccacggG (SEQ ID NO: 79) | Non-functional |
| N23 | TtcaaacagaaaggccatggG (SEQ ID NO: 80) | Non-functional |
| N24 | TtcctcatggattctacgggG (SEQ ID NO: 81) | Non-functional |
| N31 | TgatgggctgaagggtttaaG (SEQ ID NO: 82) | Non-functional with stop codon |
| N32 | TgtcccatcacagcttacaaG (SEQ ID NO: 83) | Non-functional |
| LK3 | TcaggctcgtcttcttcaggG (SEQ ID NO: 84) | Linker used to create fusion protein |

TABLE 5

| Barcode oligos | | | |
|---|---|---|---|
| Forward Oligos (Cloning vectors) | Sequence (* phosphorothioate bond) | Reverse oligos (Cloning vectors) | Sequence (* phosphorothioate bond) |
| T-N2'_1pT2 F | T*tcctcgactcacttcgagtcatgtgcagctcc (SEQ ID NO: 85) | pT2_N21"-G R | C*ccaagtgagtcgagtcagctcactcaaaggcggt (SEQ ID NO: 86) |
| T-N22'_pT2 F | T*tcacacacatagccactcgagtcatgtgca gctcc (SEQ ID NO: 87) | pT2_N22"-G R | C*ccgtggctatgttgtgttcagctcactcaaaggcggt (SEQ ID NO: 88) |
| T-N23'_pT2 F | T*tcaaacagaaaggccattcgagtcatgtgca gctcc (SEQ ID NO: 89) | pT2_N23"-G R | C*catggcctttctgtttgtcagctcactcaaaggcggt (SEQ ID NO: 90) |
| T-N24'_pT2 F | T*tcctcatggattctacgtcgagtcatgtgcagctcc (SEQ ID NO: 91) | pT2_N24"-G R | C*cccgtagaatcatgagtcagctcactcaaaggcggt (SEQ ID NO: 92) |
| T-pJ23119'_pT2 F | T*tgacagctagtcctagtcgagttcatgtgcagctcc (SEQ ID NO: 93) | pT2_pJ23119"-G R | C*tagtattatacctaggactgagctatcagctcactcaaaggcggt (SEQ ID NO: 94) |
| Forward Oligos (Annealed Oligos) | Sequence (/5Phos/: 5'-end phosphorylation) | Reverse oligos (Annealed Oligos) | Sequence (/5Phos/: 5'-end phosphorylation) |
| N21s-Bff | cctcgactcacacttgG (SEQ ID NO: 95) | N21s-Bfr | /5Phos/caagtgtgagtcgagg (SEQ ID NO: 96) |
| N22s-Bff | acacaacatagccacgG (SEQ ID NO: 97) | N22s-Bfr | /5Phos/cgtggctatgttgtgt (SEQ ID NO: 98) |
| N23s-Bff | caaacagaaaggccatgG (SEQ ID NO: 99) | N23s-Bfr | /5Phos/catggcctttctgttg (SEQ ID NO: 100) |
| N24s-Bff | ctcatggattctacggG (SEQ ID NO: 101) | N24s-Bfr | /5Phos/ccgtagaatcatgag (SEQ ID NO: 102) |
| pJ23119s-Bff | tagctcagtcctagtataactaG (SEQ ID NO: 103) | pJ23119s-Bfr | /5Phos/tagtattacctaggactgagcta (SEQ ID NO: 104) |
| N21s-Brf | /5Phos/ccctcgactcacactt (SEQ ID NO: 105) | N21s-Brr | aagtgtgagtcgagggA (SEQ ID NO: 106) |
| N22s-Brf | /5Phos/cacacaacatagccac (SEQ ID NO: 107) | N22s-Brr | gtggctatgttgtgtgA (SEQ ID NO: 108) |
| N23s-Brf | /5Phos/caaacagaaaggccat (SEQ ID NO: 109) | N23s-Brr | atggcctttctgtttgA (SEQ ID NO: 110) |
| N24s-Brf | /5Phos/cctcatggattctacg (SEQ ID NO: 111) | N24s-Brr | cgtagaatccatgaggA (SEQ ID NO: 112) |
| pJ23119s-Brf | /5Phos/tgacagctagtcctagg | pJ23119s-Brr | cctaggactgagctagtgtcaA |

TABLE 5-continued

Barcode oligos

| Prefix barcode oligos (Stem-loop Oligos) | Sequence (upper case ones indicate loop region) (SEQ ID NO: 113) | Sufttx barcode oligos (Stem-loop Oligos ) | Sequence (upper case ones indicate loop region) (SEQ ID NO: 114) |
|---|---|---|---|
| RBS1-Bf-SL | atatgtatatctccttcttaaagttaaacaaTATG TTtgttttaacttaaggaggagatatacatatG (SEQ ID NO: 115) | RBS1-Br-SL | agaaataatttgttaacttgttaacttaagaaggTCTA CTccttcttaaagttaaacaaaattattctA (SEQ ID NO: 116) |
| RBS2stop-Bf-SL | atcgacaatacctttgtgataaatgaaTCGGT TttcattatcacaaaaggattgttcgatG (SEQ ID NO: 117) | RBS2stop-Br-SL | aaccgttcattatcacaaaaggaTATCACt cctttgataatgaacggttA (SEQ ID NO: 118) |
| RBS3stop-Bf-SL | gattcacacaggaaacagctTCTTCGagc atagctgttcctgtGCCTGGacacaggaa acagctatG (SEQ ID NO: 119) | RBS3stop-Br-SL | tgttccgtgtaatcA (SEQ ID NO: 120) |
| RBS4stop-Bf-SL | aaattaattgtctcttttttcaggtgaaggttcccT atgggaacttcacctgaAGTTAcaggtgaag gttcccatG (SEQ ID NOL 121) | RBS4stop-Br-SL | CACATggaacctttcacctgaaaaagaa caattaattA (SEQ ID NO: 122) |
| pJ23119-Bf-SL | tagtattataccctaggactgagctaAGAGGGta gctcagtcctaggtatatactaG (SEQ ID NO: 123) | pJ23119-Br-SL | tgacagctagctcagtcctaggGCACAGc ctaggactgagctagctgtcaA (SEQ ID NO: 124) |
| N21-Bf-SL | ccaagtgtgagtcgaggAAGGGcctcgact cacacttggG (SEQ ID NO: 125) | N21-Br-SL | tccctgactcacacttGCGAGAagtgtg agtcgagggaA (SEQ ID NO: 126) |
| N22-Bf-SL | ccgtggctatgtgtgtCGTATTacacacata gccacggG (SEQ ID NO: 127) | N22-Br-SL | tcacacaacatagccacTTGCTGtggct atgtgtgtgaA (SEQ ID NO: 128) |
| N23-Bf-SL | ccatggcctttctgttgACCATAcaaacagaa aggcatggG (SEQ ID NO: 129) | N23-Br-SL | tcaaacagaaaggccatCATTCAatggcc ttctgttttgaA (SEQ ID NO: 130) |
| N24-Bf-SL | cccgtagaatccatgagAACCCGctcatggat tctacgggG (SEQ ID NO: 131) | N24-Br-SL | tcctcatggattctacgACTATGcgtagaat ccatgaggaA (SEQ ID NO: 132) |
| N31-Bf-SL | ttaaaccctcagcccaCACACAtgggctgaa gggtttaaG (SEQ ID NO: 133) | N31-Br-SL | gatgggctgaagggtttCACACAaaaccct tcagcccaccA (SEQ ID NO: 134) |
| N32-Bf-SL | ttgtaagctgtgatgggGCCTGGcccatcaca gcttacaaG (SEQ ID NO: 135) | N32-Br-SL | gtccatcacagcttacGCTTCGgtaagct gtgatgggacA S (SEQ ID NO: 136) |
| LK3-Bf-SL | cctgaagaagacgagcCACACAggctcgt cttcttcaggG (SEQ ID NO: 137) | LK3-Br-SL | caggctcgtcttcttcaCACACAtgaagaa gacgagcctgA (SEQ ID NO: 138) |

TABLE 6

Phosphorylation of stem-loop barcode oligo

| Barcoding Oligos (100 μM stock solution) | T4 ligase Buffer (10X) | T4 Polynucleotide Kinase (NBE: M0201) | Nuclease-free Water |
|---|---|---|---|
| 1 microliters | 2 microliters | 0.5 microliter | 16.5 microliters |

Incubate the mixture in a PCR tube at 37° C. for 30 minutes, and 65° C. for 20 minutes for deactivation of kinase.
Stem-loop folding program: incubating at 98° C. for 2 minutes, and decrease to 75° C. (0.1° C. per second), hold it for 2 mins, then gradually decrease to 4° C. (0.1° C. per second).

Barcoding UDS Fragment

Ligation of 3 types of barcodes (cloning vector, annealed oligo and stem-loop oligo) with 1 nt SE-based UDS fragments was done at 25° C. for 5 to 10 minutes by using NEB Blunt/TA Ligase Master Mix (M0367) according to manufacture instructions, and molar ratio of barcodes and UDS fragments should be between 10:1 to 3:1 to reach maximum ligation efficiency (Table 7), but for cloning vector based barcoding, the molar ratio of insert and cloning vector should be 3:1. Amplify the barcoded UDS fragments in a 50 microliters PCR reaction by using 1 microliter of the ligation products as templates and UDS universal oligos that are corresponded to barcodes (FIG. 2c, indicated by black arrow, and sequence of oligos and modifications can be found in (Table 8). The barcoded UDS fragments were then digested chemically to create 10-20 bp SE (FIG. 6), and purified for downstream assembly. Barcoded UDS fragments used in three applications are listed in in Table 9 and the sequences are shown in Table 10.

TABLE 7

Barcoding ligation

| Prefix Barcode (5 μM) | Suffix Barcode (5 μM) | 1-mer based Fragments | Blunt/TA Ligase Master Mix (2X) (NEB: M0367) |
|---|---|---|---|
| 0.3 microliters | 0.3 microliters | 3 microliters | 3.6 microliters |

Incubate the mixture in PCR tube at 25° C. for 5 to 10 minutes. This step also can be done at room temperature and on the bench.
Note:
the volume of fragments used for barcoding depends on its concentration, usually, 10-200 ng (3 μL) of fragments with size less than 3 kb should be adequate, and the molar ratio of barcodes and fragments is recommended to be 10:1 to 3:1 as suggested form NEB protocol. For barcoding fragments with a size over 3 kb, it is better to calculate the molar ratio of barcodes and fragment and use higher concentration of fragments (over 100 ng/mL, the ligation volume also can be increased accordingly). The yield of ligation PCR can be improved by adding more ligation products (diluted 5-fold or not) in a certain degree.

TABLE 8

UDS universal oligos

| UDS forward universal oligos | Sequence (*: phosphorothioate bond) |
|---|---|
| RBS1-Bff | ttgtttaac*tttaagaagg*agatatacatatG (SEQ ID NO: 139) |
| RBS2stop-Bff | ttcatttat*cacaaaagga*ttgttcgatG (SEQ ID NO:140) |
| RBS3-Bff | acacagga*aacagct*atG (SEQ ID NO: 141) |
| RBS4-Bff | caggtgaa*ggttccc*atG (SEQ ID NO: 142) |
| pJ23119-Bff | tagctca*gtcctagg*tataatactaG (SEQ ID NO: 143) |
| N21-Bff | cctcgac*tcacactt*ggG (SEQ ID NO: 144) |
| N22-Bff | acacaac*atagccac*ggG (SEQ ID NO: 145) |
| N23-Bff | caaacaga*aaggccat*ggG (SEQ ID NO: 146) |
| N24-Bff | ctcatgg*attctacg*ggG (SEQ ID NO: 147) |
| N31-Bff | tgggctg*aagggttt*aaG (SEQ ID NO: 148) |
| N32-Bff | cccatcac*agcttac*aaG (SEQ ID NO: 149) |
| LK3-Bff | ggctcgt*cttcttca*ggG (SEQ ID NO: 150) |
| UDS reverse universal oligos | Sequence (*: phosphorothioate bond) |
| RBS1-Brr | ccttcttaa*agttaaacaa*aattatttctA (SEQ ID NO: 151) |
| RBS2stop-Brr | tccttttgt*gataaatgaa*cggttA (SEQ ID NO: 152) |
| RBS3stop-Brr | agctgttt*cctgtgt*gaatcA (SEQ ID NO: 153) |
| RBS4stop-Brr | gggaacct*tcacctg*aaaaagaacaatta atttA (SEQ ID NO: 154) |

TABLE 8-continued

UDS universal oligos

| | |
|---|---|
| pJ23119-Brr | cctagga*ctgagcta*gctgtcaA (SEQ ID NO: 155) |
| N21-Brr | aagtgtg*agtcgagg*gaA (SEQ ID NO: 156) |
| N22-Brr | gtggcta*tgttgtgt*gaA (SEQ ID NO:157) |
| N23-Brr | atggcctt*tctgtttg*aA (SEQ ID NO: 158) |
| N24-Brr | cgtagaa*tccatgag*gaA (SEQ ID NO:159) |
| N31-Brr | aaaccct*tcagccca*tcA (SEQ ID NO: 160) |
| N32-Brr | gtaagctg*tgatggg*acA (SEQ ID NO:161) |
| LK3-Brr | tgaagaa*gacgagcc*tgA (SEQ ID NO:162) |

TABLE 9

Barcoded UDS fragments

| Barcoded UDS fragments | Barcoded UDS fragments |
|---|---|
| (pJ23119)gRNA-nupG(N23) | (N31)t7t(LK3) |
| (pJ23119)gRNA-aslA(N23) | (LK3)LacI(N21) |
| (pJ23119)gRNA-melB(N23) | (RBS1)dxs(RBS2stop) |
| (pJ23119)gRNA-rcsB(N23) | (RBS2stop)idi(RBS3stop) |
| (pJ23119)gRNA-tyrR(N23) | (RBS3stop)valC(RBS4stop) |
| (pJ23119)gRNA-pheA(N23) | (RBS4stop)ispA(N31) |
| (pJ23119)gRNA-ptsI(N23) | (RBS1)idi(RBS2stop) |
| (N23)nupG-HF0.5(N24) | (RBS2stop)dxs(RBS3stop) |
| (N23)nupG-HF1.0(N24) | (RBS3stop)dxs(RBS4stop) |
| (N23)nupG-HF1.5(N24) | (RBS4stop)dxs(N31) |
| (N23)aslA-HF0.5(N24) | (RBS1)valC(RBS2stop) |
| (N23)aslA-HF1.0(N24) | (RBS2stop)valC(RBS3stop) |
| (N23)melB-HF1.0(N24) | (RBS3stop)idi(RBS4stop) |
| (N23)rcsB-HF1.0(N24) | (RBS4stop)idi(N31) |
| (N23)tyrR-HF0.5(N24) | (RBS1)ispA(RBS2stop) |
| (N23)pheA-HF0.5(N24) | (RBS2stop)ispA(RBS3stop) |
| (N23)ptsI-HF0.7(N24) | (RBS3stop)ispA(RBS4stop) |
| (N24)nupG-HT0.5(N21) | (RBS4stop)valC(N31) |
| (N24)nupG-HT1.0(N21) | (RBS1)aroG mutant(RBS4stop) |
| (N24)nupG-HT1.5(N21) | (RBS1)tyrA mutant(RBS4stop) |
| (N24)aslA-HT0.5(N21) | (RBS4stop)tyrA mutant(N31) |
| (N24)aslA-HT1.0(N21) | (RBS4stop)aroG mutant(N31) |
| (N24)melB-HT1.0(N21) | |
| (N24)rcsB-HT1.0(N21) | |
| (N24)tyrR-HT0.5(N21) | |
| (N24)pheA-HT0.5(N21) | |
| (N24)ptsI-HT0.7(N21) | |
| (N21)aadA(N22) | |
| (N21)bla(N22) | |
| (N22)p5(N23) | |
| (N22)p15(N23) | |
| (N22)pMB1(N23) | |
| (N22)pMB1 mutant(N23 | |
| (N23)pLac(RBS1) | |
| (N23)LacIT7(RBS1) | |
| (N31)t7t(N21) | |

TABLE 10

Sequences of barcoded fragments

| Barcoded UDS fragments | Sequence |
|---|---|
| (pJ23119)gRNA-nupG(N23) | ttgacagctagctcagtcctaggtataatactagtACGAGTTAATCAATATC ACAgttttagagctagaaatagcaagttaaaataaggctagtccgttatcaacttga aaaagtggcaccgagtcggtgcttttttgaattctctagaTtcaaacagaaaggcc atggG (SEQ ID NO: 163) |
| (pJ23119)gRNA-aslA(N23) | ttgacagctagctcagtcctaggtataatactagtTCCAGATCTTCCATATA TTTgttttagagctagaaatagcaagttaaaataaggctagtccgttatcaacttga aaaagtggcaccgagtcggtgcttttttgaattctctagaTtcaaacagaaaggcc atggG (SEQ ID NO: 164) |
| (pJ23119)gRNA-melB(N23) | ttgacagctagctcagtcctaggtataatactagtCTACCATTTGTTAATTA TGTgttttagagctagaaatagcaagttaaaataaggctagtccgttatcaacttga aaaagtggcaccgagtcggtgcttttttgaattctctagaTtcaaacagaaaggcc atggG (SEQ ID NO: 165) |
| (pJ23119)gRNA-rcsB(N23) | ttgacagctagctcagtcctaggtataatactagtAATCACTTGAGCAAATT GAGgttttagagctagaaatagcaagttaaaataaggctagtccgttatcaacttga aaaagtggcaccgagtcggtgcttttttgaattctctagaTtcaaacagaaaggcc atggG (SEQ ID NO: 166) |
| (pJ23119)gRNA-tyrR(N23) | ttgacagctagctcagtcctaggtataatactagtTTAATACCGAGCGTTC AAAAgttttagagctagaaatagcaagttaaaataaggctagtccgttatcaacttg aaaaagtggcaccgagtcggtgcttttttgaattctctagaTtcaaacagaaaggc catggG (SEQ ID NO: 167) |
| (pJ23119)gRNA-pheA(N23) | ttgacagctagctcagtcctaggtataatactagtTTTGAGCAATTCATTGA AAGgttttagagctagaaatagcaagttaaaataaggctagtccgttatcaacttga aaaagtggcaccgagtcggtgcttttttgaattctctagaTtcaaacagaaaggcc atggG (SEQ ID NO: 168) |
| (pJ23119)gRNA-ptsI(N23) | ttgacagctagctcagtcctaggtataatactagtGAAGTTGATTTCTTTAG TATgttttagagctagaaatagcaagttaaaataaggctagtccgttatcaacttga aaaagtggcaccgagtcggtgcttttttgaattctctagaTtcaaacagaaaggcc atggG (SEQ ID NO: 169) |

TABLE 10-continued

Sequences of barcoded fragments

| Barcoded UDS fragments | Sequence |
| --- | --- |
| (N23)nupG-HF0.5(N24) | TtcaaacagaaaggccatggGttgatcctgccagcaatattgataccggcaccgc gtatctggcgatgctgaacaatgtttatctcggcggaattgataacccaacatcgcgg cgttatgccgtcatcaccgcctataacggcggcgcaggcagcgtgctgcgagtcttttt cgaatgataagattcaggctgccaatattattaacaccatgacgccgggcgatgttta tcagacgctgacgacccgccatccctctgcggaatctcgccgttatctttataaagtg aataccgcgcaaaaatcctaccgccgccgataattccattaaccgcccctgacgat gctcaggggcaaaaatgttatccacatcacaatttcgttttgcaaattgggaatgtttgc aattatttgccacaggtaacaaaaaaccagtccgcgaagttgatagaatcccatcat ctcgcacggtcaaatgtgcttttcaaacactcatccgcatcacgatgTtcctcatgga ttctacgggG (SEQ ID NO: 170) |
| (N23)nupG-HF1.0(N24) | TtcaaacagaaaggccatggGaccatcgccgggacagaacctgccgcgcatttg cgccgggcaattatcaaaacgttattgatgggtgacgatccgagttcggtcgatctct attccgacgttgatgatattacgatttcgaaagaaccttcctttacggtcaggtggtgg acaacaccgggcagccgattcgctgggaaggtcgcgcaagcaacttcgcggatta tctgctgaaaaaccgtctgaagagccgcagcaacgggctgcgtatcatctacagcg tcaccattaacatggtgccgaaccaccttgataaacgtgcgcacaaatatctcggca tggtccgccaggcgtcacggaaatatggcgttgatgagtcgctgattctggcaattat gcagaccgaatcttcctttaacccgtatgcggtcagccgttccgatgcgctgggatta atgcaggtggtacaacatactgccgggaaagatgtgttccgctcgcaggggaaatc cggcacgccgagccgcagtttcttgtttgatcctgccagcaatattgataccggcacc gcgtatctggcgatgctgaacaatgtttatctcggcggaattgataacccaacatcgc ggcgttatgccgtcatcaccgcctataacggcggcgcaggcagcgtgctgcgagtc ttttcgaatgataagattcaggctgccaatattattaacaccatgacgccgggcgatgt ttatcagacgctgacgacccgccatccctctgcggaatctcgccgttatctttataaag tgaataccgcgcaaaaatcctaccgccgccgataattccattaaccgcccctgacg atgctcaggggcaaaaatgttatccacatcacaatttcgttttgcaaattgggaatgttt gcaattatttgccacaggtaacaaaaaaccagtccgcgaagttgatagaatcccat catctcgcacggtcaaatgtgcttttcaaacactcatccgcatcacgatgTtcctcat ggattctacgggG (SEQ ID NO: 171) |
| (N23)nupG-HF1.5(N24) | TtcaaacagaaaggccatggGtgcaacgtgaagcagaaggtcaggattttcagc tgtaccccggcgagctgggaaaacgcatctataacgagatctccaaagaagcctg ggcgcagtggcagcacaagcaaaccatgctgattaatgaaaagaaactcaacat gatgaatgccgagcaccgcaagctgcttgagcaggagatggtcaacttcctgttcg agggtaaagaggtgcatatcgagggctatacgccggaagataaaaaataaaaac agtgccggagcacgcctccggcaacttgcataaaaacaaacacaacacgcacc cggaatgatgaaaaaatatctcgcgctggctttgattgcgccgttgctcatctcctgttc gacgaccaaaaaaggcgatacctataacgaagcctgggtcaaagataccaacg gttttgatattctgatggggcaatttgcccacaatattgagaacatctggggcttcaaa gaggtggtgatcgctggtcctaaggacgtgaaatacaccgatcaatatcagac ccgcagccacatcaacttcgatgacggtacgattactatcgaaaccatcgccggga cagaacctgccgcgcatttgcgccgggcaattatcaaaacgttattgatgggtgacg atccgagttcggtcgatctctattccgacgttgatgatattacgatttcgaaagaaccttt cctttacggtcaggtggtggacaacaccgggcagccgattcgctgggaaggtcgc gcaagcaacttcgcggattatctgctgaaaaaccgtctgaagagccgcagcaacg ggctgcgtatcatctacagcgtcaccattaacatggtgccgaaccaccttgataaac gtgcgcacaaatatctcggcatggtccgccaggcgtcacggaaatatggcgttgat gagtcgctgattctggcaattatgcagaccgaatcttcctttaacccgtatgcggtcag ccgttccgatgcgctgggattaatgcaggtggtacaacatactgccgggaaagatgt gttccgctcgcaggggaaatccggcacgccgagccgcagtttcttgtttgatcctgcc agcaatattgataccggcaccgcgtatctggcgatgctgaacaatgtttatctcggcg gaattgataacccaacatcgcggcgttatgccgtcatcaccgcctataacggcggc gcaggcagcgtgctgcgagtcttttcgaatgataagattcaggctgccaatattattaa caccatgacgccgggcgatgtttatcagacgctgacgacccgccatccctctgcgg aatctcgccgttatctttataaagtgaataccgcgcaaaaatcctaccgccgccgata attccattaaccgcccctgacgatgctcaggggcaaaaatgttatccacatcacaatt tcgttttgcaaattgggaatgtttgcaattatttgccacaggtaacaaaaaaccagtcc gcgaagttgatagaatcccatcatctcgcacggtcaaatgtgcttttcaaacactcat ccgcatcacgatgTtcctcatggattctacgggG (SEQ ID NO: 172) |
| (N23)aslA-HF0.5(N24) | TtcaaacagaaaggccatggGcaccgtaaacggctctgcgtcattccggagtttat gaggcactaaggcgaacataagagatggaatgagcatctactcgtttattatgccac agagaatcgggaaataacatcccttaacacttgttatgagataattctgtaatcctcttt gcttcctgagtaataacttcctgagtgaatatttaacctgagcttgatcctacacatactt attatgaatgataaaattcattcaattaatacacatatattaattgccgttaaaactaa aaacagcatcaataatcaacgcgatataatcaaacctgccttacatatcaactgcgcc agaggtaggattgaaaacgctctcctgattttccaattcattttctggataaataaataa tttatttttgtcactattatttatgtaatcatcctgtcagggagagggatctcaattatcaat gcttaattacgtcatcattttgatgacatgaaacTtcctcatggattctacgggG (SEQ ID NO: 173) |
| (N23)aslA-HF1.0(N24) | TtcaaacagaaaggccatggGccagtacgacgatcgcctactgctgccgattcct cgactgaaaacaaacaatccggaacagctggaaaaagtgctgcgccagcaaat caaaaacgtcggcgatcgcccgctgttgtggagcacactgggccagtcactgatga |

TABLE 10-continued

Sequences of barcoded fragments

| Barcoded UDS fragments | Sequence |
|---|---|
| | agcacggagaatggcaggaagcatcgctcgccttccgcgcagcgctgaaacaac<br>gtccggacgcctacgattacgcatggcttgccgacgcgctggacagactgcacaa<br>gccggaagaagctgcagctatgcgtcgcgacggtttgatgttaacgttgcagaataa<br>cccgccacagtagttccttctcacccggaggcaagcacctccggggccttcctgata<br>cataaaaaaacgcctgctcttattacggagcaggcgttaaaacaggtctgtatgaca<br>acaagtgggtgcttcactcaacgttgtgtccatggtgtctgatgaggcataagcgaca<br>tctgtcagtggacgataagcaccgtaaacggctctgcgtcattccggagtttatgagg<br>cactaaggcgaacataagagatggaatgagcatctactcgtttattatgccacagag<br>aatcgggaaataacatcccttaacacttgttatgagataattctgtaatcctctttgcttc<br>ctgagtaataacttcctgagtgaatatttaacctgagcttgatcctacacatacttattat<br>gaatgataaaattcattcaattaataacacatatattaattgccgttaaaactaaaaac<br>agcatcaataatcaacgcgatataataaacctgccttacatatcaactgcgccaga<br>ggtaggattgaaaacgctctcctgattttccaattcattttctggataaataaataatttat<br>ttttgtcactattatttatgtaatcatcctgtcagggagagggatctcaattatcaatgctt<br>aattacgtcatcattttgatgacatgaaacTtcctcatggattctacgggG (SEQ<br>ID NO: 174) |
| (N23)melB-HF1.0(N24) | TtcaaacagaaaggccatggGcccaatggcgatgaatacctgggcgatgtatgc<br>ccgctatccgcatatcaaacaggtcgggcgtgccattcggtcagggaacggcgg<br>aagagttggcgcgtgacctcaatatcgacccagctacgctgcgttaccgttgcgcag<br>gtatcaaccatatggcgttttacctggagctggagcgcaaaaccgccgacggcagt<br>tatgtgaatctctacccggaactgctggcggcttatgaagcagggcaggcaccgaa<br>gccgaatattcatggcaatactcgctgccagaatattgtgcgctacgaaatgttcaaa<br>aagctgggctatttcgtcacggaatcgtcagaacattttgctgagtacacaccgtggtt<br>tattaagccaggtcgtgaggatttgattgagcgttataaagtaccgctggatgagtac<br>ccgaaacgtgcgtcgagcagctggcgaactggcataaagagctggaggagtat<br>aaaaaagcctcccggattgatattaaaccgtcacgggaatatgccagcacaatcat<br>gaacgctatctggactggcgagccgagtgtgatttacggcaacgtccgtaacgatg<br>gtttgattgataacctgccacaaggatgttgcgtggaagtagcctgtctggttgatgct<br>aatggcattcagccgaccaaagtcggtacgctaccttcgcatctggccgccctgatg<br>caaaccaacatcaacgtacagacgctgctgaccgaagctattcttacggaaaatcg<br>cgaccgtgtttaccacgccgcgatgatgaccccgcatactgccgccgtgctgggca<br>ttgacgaaatatatgctcttgttgacgacctgattgccgcccacggcgactggctgcc<br>aggctggttgcaccgttaaaacgcgactaaacgctactgcgccggggatttattcc<br>ggcgcacacctctgacgataccaataacagaaggcgggcgttggtaacagcTtc<br>ctcatggattctacgggG (SEQ ID NO: 175) |
| (N23)rcsB-HF1.0(N24) | TtcaaacagaaaggccatggGgttagcgaacatgcttgcggatgatagctggaa<br>aagtgagacggtgctgttctccgtgcaggatttaattgatgaagttgtgccttcagtgtt<br>gcctgccatcaagcgtaaaggtctgcaactgctgattaacaatcatctgaaagcac<br>acgatatgcgccgcggcgatcgcgatgccttacgacgtattttgctgctactgatgca<br>atatgccgtgacctcaacgcaattgggaaaaatcacccttgaggttgatcaggatga<br>gtcctccgaagaccgcctgacgttccgcattctggacacgggagaaggcgtaagta<br>ttcatgaaatggataatttgcacttcccgtttatcaaccagacccaaaacgatcgctat<br>ggcaaggcggaccgctggcattctggctgagcgatcaactggcacgtaaactgg<br>gcggtcatttaaacatcaaaacgcgggatgggcttggtacacgctactctgtgcatat<br>caaaatgctcgcagctgacccggaagttgaagaggaagaagagcgtttactggat<br>gatgtctgcgtaatggtggatgttacttcggcagaaattcggaatattgtcactcgcca<br>gttagaaaattggggtgcaacctgtatcacacccgatgaaagattaattagtcaaga<br>ttatgatatctttttaacggataatccgtctaatcttactgcctctggcttgcttttaagcgat<br>gatgagtctggcgtacgggaaattgggcctggtcaattgtgcgtcaacttcaatatga<br>gcaacgctatgcaggaagcggtcttacaattaattgaagtgcaactggcgcaggaa<br>gaggtgacagaatcgcctctgggcggagatgaaaatgcgcaactccatgccagc<br>ggctattatgcgctctttgtagacacagtaccggatgatgttaagaggctgtatactga<br>agcagcaaccagtgactttgctgcgttagcccaaacggctcatcgtcttaaaggcgt<br>atttgccatgctaaatctggtacccggcaagcagttatgtgaaacgctggaacatctg<br>attcgtgagaaggatgttccaggaatagaaaaatacatcagcgacattgacagttat<br>gtcaagagcttgctgtagcaaTtcctcatggattctacgggG<br>(SEQ ID NO: 176) |
| (N23)tyrR-HF0.5(N24) | Cagcccgctggcgttggtcgatatggcgtttatcgcctggcgcaatctgcgtttaatta<br>atcgcatcgccacgctgtatggcattgaactggggtattacagccgtttgcgtctgttta<br>agctggtattgctgaatatcgcttttgccggagccagcgaactggtgcgcgaagtgg<br>ggatggactggatgtcgcaagatctcgctgctcgtttgtctacccgcgcagctcaggg<br>gattggtgcaggacttctgacggcacgactcgggattaaagctatggagctttgccg<br>cccgctgccgtggattgacgatgacaaacctcgcctcggggatttccgtcgtcagctt<br>atcggtcaggtgaaagaaacgctgcaaaaaggcaaaacgcccagcgaaaaata<br>atgcaatatcgggtgctgacTtcctcatggattctacgggG<br>(SEQ ID NO: 177) |
| (N23)pheA-HF0.5(N24) | TtcaaacagaaaggccatggGcatgtcgcagaccgtctcgccaaactggaaaa<br>atggcaaacacatctgattaatccacatatcattctgtccaaagagccacaagggttt<br>gttgctgacgccacaatcaatacacctaacggcgttctggttgccagtggtaaacat<br>gaagatatgtacaccgcaattaacgaattgatcaacaagctggaacggcagctca<br>ataaactgcagcacaaaggcgaagcacgtcgtgccgcaacatcggtgaaagac<br>gccaacttcgtcgaagaagttgaagaagagtagtcctttatattgagtgtatcgccaa |

TABLE 10-continued

Sequences of barcoded fragments

| Barcoded UDS fragments | Sequence |
|---|---|
| | cgcgccttcgggcgcgttttttgttgacagcgtgaaaacagtacgggtactgtactaa<br>agtcacttaaggaaacaaacatgaaacataccgttttcttcgcattctttttacctt<br>cccctgaatgggaggcgtttcgTtcctcatggattctacgggG<br>(SEQ ID NO: 178) |
| (N23)ptsI-HF0.7(N24) | TtcaaacagaaaggccatggGcatgtcgcagaccgtctcgccaaactggaaaa<br>atggcaaacacatctgattaatccacatatcattctgtccaaagagccacaagggttt<br>gttgctgacgccacaatcaatacacctaacggcgttctggttgccagtggtaaacat<br>gaagatatgtacaccgcaattaacgaattgatcaacaagctggaacggcagctca<br>ataaactgcagcacaaaggcgaagcacgtcgtgccgcaacatcggtgaaagac<br>gccaacttcgtcgaagaagttgaagaagagtagtcctttatattgagtgtatcgccaa<br>cgcgccttcgggcgcgttttttgttgacagcgtgaaaacagtacgggtactgtactaa<br>agtcacttaaggaaacaaacatgaaacataccgttttcttcgcattctttttacctt<br>cccctgaatgggaggcgtttcgTtcctcatggattctacgggG<br>(SEQ ID NO: 179) |
| (N24)nupG-HT0.5(N21) | Ttcctcatggattctacgggttacgcaaagaaaaacgggtcgccagaaggtgac<br>ccgttttttttattcttacttcaacacataaccgtacaaccgtttcacgccatccgcatcg<br>gtttcgctataaacaccttgcagctccggcgaaaatcccggcaacaaattcacccct<br>tcttccagtgcaaggaaataacgttgaaccgccccaccccagacttccccgggtac<br>cacgcaaagcacgccaggtggataaggcaacgcccttctgccgcaattcgccctt<br>cggcatcacgaatccgcaccaactccacgtcaccgcgaatataagcgctatgcgc<br>atcctgggggttcatcaccactgacgggaaactctgctggcggaacatcgcttttttgt<br>aggtctttgacgtcgaaactgacatacagatcgtgcatctcctgacacaactggcgc<br>agggtgtagtcgcgatagcgcaccggatacttgttataaacgctcggcaacacctc<br>aaccagcggcTtccctcgactcacacttggG<br>(SEQ ID NO: 180) |
| (N24)nupG-HT1.0(N21) | Ttcctcatggattctacgggttacgcaaagaaaaacgggtcgccagaaggtgac<br>ccgttttttttattcttacttcaacacataaccgtacaaccgtttcacgccatccgcatcg<br>gtttcgctataaacaccttgcagctccggcgaaaatcccggcaacaaattcacccct<br>tcttccagtgcaaggaaataacgttgaaccgccccaccccagacttccccgggtac<br>cacgcaaagcacgccaggtggataaggcaacgcccttctgccgcaattcgccctt<br>cggcatcacgaatccgcaccaactccacgtcaccgcgaatataagcgctatgcgc<br>atcctgggggttcatcaccactgacgggaaactctgctggcggaacatcgcttttttgt<br>aggtctttgacgtcgaaactgacatacagatcgtgcatctcctgacacaactggcgc<br>agggtgtagtcgcgatagcgcaccggatacttgttataaacgctcggcaacacctc<br>aaccagcggcgagtcatcctcaatatgctgttcaaattgcgccagcatcgccacca<br>gttgtgccagcttctcgtggctttccgccggagttaataaaaacagaatggagttgag<br>atcgcacttctccggcacaatgccgttctcacgcagatagtgcgccagaatcgtcgc<br>cggaacgccaaagtcgctatattcgccggtttcggcatcgatacctggtgtagtgagt<br>aacagcttgcacggatcaacaaaatactgatccgcggcatatccttcaaagccgtg<br>ccacttcgccccccggctcaaaactgaaaaaacggccggtcgctggctaacactgat<br>gtcggataatcctgccacaatttgccatcaacaacgggcgggataaacgggcgga<br>acagcttacagcgcgcaagaatagccttgcgcgcttcaatccctatctcaacacact<br>cagcccacagccgacgcccactctcccccttcatgaattttggcgttaacatccagtgc<br>agcaaacagcggatagaaagggctggtagaagcatggagcataaaggcgtTtc<br>cctcgactcacacttggG (SEQ ID NO: 181) |
| (N24)nupG-HT1.5(N21) | Ttcctcatggattctacgggttacgcaaagaaaaacgggtcgccagaaggtgac<br>ccgttttttttattcttacttcaacacataaccgtacaaccgtttcacgccatccgcatcg<br>gtttcgctataaacaccttgcagctccggcgaaaatcccggcaacaaattcacccct<br>tcttccagtgcaaggaaataacgttgaaccgccccaccccagacttccccgggtac<br>cacgcaaagcacgccaggtggataaggcaacgcccttctgccgcaattcgccctt<br>cggcatcacgaatccgcaccaactccacgtcaccgcgaatataagcgctatgcgc<br>atcctgggggttcatcaccactgacgggaaactctgctggcggaacatcgcttttttgt<br>aggtctttgacgtcgaaactgacatacagatcgtgcatctcctgacacaactggcgc<br>agggtgtagtcgcgatagcgcaccggatacttgttataaacgctcggcaacacctc<br>aaccagcggcgagtcatcctcaatatgctgttcaaattgcgccagcatcgccacca<br>gttgtgccagcttctcgtggctttccgccggagttaataaaaacagaatggagttgag<br>atcgcacttctccggcacaatgccgttctcacgcagatagtgcgccagaatcgtcgc<br>cggaacgccaaagtcgctatattcgccggtttcggcatcgatacctggtgtagtgagt<br>aacagcttgcacggatcaacaaaatactgatccgcggcatatccttcaaagccgtg<br>ccacttcgccccccggctcaaaactgaaaaaacggccggtcgctggctaacactgat<br>gtcggataatcctgccacaatttgccatcaacaacgggcgggataaacgggcgga<br>acagcttacagcgcgcaagaatagccttgcgcgcttcaatccctatctcaacacact<br>cagcccacagccgacgcccactctcccccttcatgaattttggcgttaacatccagtgc<br>agcaaacagcggatagaaagggctggtagaagcatggagcataaaggcgttatt<br>caaccgcttatgcgggcaaaaacgcctgtccgcggatatggttatctttttatgga<br>tctgcgacgtctgtgagaatcccgcctgctgtttgtgcaccgactgagtcacaaagat<br>ccccggatcgttttcgttaagttctaacagcagcggcgagctatccgccatcatcggg<br>ataaattgttcataaccgacccacgcggaatcaaacagaatgtaatcacacagatg<br>cccaacggtatcgatcacctgacgggcgttatagacagtgccgtcataggttcccag<br>ctgaataatcgccaggcgatacgggcgcggcaggtcggcttttttctggcgcaacgtc |

TABLE 10-continued

Sequences of barcoded fragments

| Barcoded UDS fragments | Sequence |
|---|---|
| | gcgaatttgctggcgcagatactcttcattaaaacagtgcgcatcaataccgccaat gaaaccaaacgggttgcgtgaagcttccagatagaccggcgtcgcTtccctcgact cacacttggG (SEQ ID NO:182) |
| (N24)aslA-HT0.5(N21) | TtcctcatggattctacgggGgccggcgctatcgctgagatctgcctttgccggatgc gatgctgacgcatcttatccagcctacagaacgctgcaatttattgaatttgcacgatc atgtaggccggataaggcgtttacgccgcatccggcaatcaaccgcaggcggccg ccgatttctacttactcaccaccagcaaatgcgcatgcataatgtcgctggccgggc gaccgtgcgccagcaaatcagccattgctttaagatatggcggtagatggcggaaa taacgctgatacccggcacacaaataattcagtcccggtttgccgctggcatcgagc atgaagcggtgtttcgggcagcctccccagcacgcttttaacacgttacaactgcga cactgcgccggtaactgcttaaatttatcttcaccaaacgcctgctgttgcggggaatc gatcatttctgcaattgtttgctggtgcatattccccagccgatattgcggataaacata gtgTtccctcgactcacacttggG (SEQ ID NO: 183) |
| (N24)aslA-HT1.0(N21) | TtcctcatggattctacgggGcggtaaactcgctgctgtgcgtatggatgagttcaag tatcacgtcctgattcagcaaccttacgcttatacccagagcggatatcagggtggat tcaccggcacagtaatgcaaacggcgggatcgtcggtgtttaacctctacaccgatc cgcaggaaagcgactccatcggcgtgcgccatattccgatgggtgtaccgctacag accgaaatgcacgcgtatatggagatcctgaaaaaatatccaccacgcgcgcag attaaatctgactaagccggcgctatcgctgagatctgcctttgccggatgcgatgct gacgcatcttatccagcctacagaacgctgcaatttattgaatttgcacgatcatgtag gccggataaggcgtttacgccgcatccggcaatcaaccgcaggcggccgccgatt tctacttactcaccaccagcaaatgcgcatgcataatgtcgctggccgggcgaccgt gcgccagcaaatcagccattgctttaagatatggcggtagatggcggaaataacgc tgatacccggcacacaaataattcagtcccggtttgccgctggcatcgagcatgaag cggtgtttcgggcagcctccccagcacgcttttaacacgttacaactgcgacactgc gccggtaactgcttaaatttatcttcaccaaacgcctgctgttgcggggaatcgatcat ttctgcaattgtttgctggtgcatattccccagccgatattgcggataaacatagtgatc acaggcgtaaacgtcgccgttgtgctcaacaatcaccgagcgcccacaggttggct gatgatggcaaaccgcacccggcgcaccgacaaaattggcaaacgcccattcga tattcatcacgaaaatcttgccgacgtcgcgtttgatccagtggtcgaatatcgccacc agaaactcaccgaactcctcggggcgcaccgaccattccgttagctcacccTtccc tcgactcacacttggG (SEQ ID NO:184) |
| (N24)melB-HT1.0(N21) | TtcctcatggattctacgggGttacgcaaagaaaaacgggtcgccagaaggtgac ccgtttttttattcttacttcaacacataaccgtacaaccgtttcacgccatccgcatcg gtttcgctataaacaccttgcagctccggcgaaaatcccggcaacaaattcacccct tcttccagtgcaaggaaataacgttgaaccgccccacccccagacttccccgggtac cacgcaaagcacgccaggtggataaggcaacgccccttctgccgcaattcgcctt cggcatcacgaatccgcaccaactccacgtcaccgcgaatataagcgctatgcgc atcctgggggttcatcaccactgacgggaaactctgctggcggaacatcgcttttgt aggtctttgacgtcgaaactgacatacagatcgtgcatctcctgacacaactggcgc agggtgtagtcgcgatagcgcaccggatacttgttataaacgctcggcaacacctc aaccagcggcgagtcatcctcaatatgctgttcaaattgcgccagcatcgccacca gttgtgccagcttctcgtggctttccgccggagttaataaaaacagaatggagttgag atcgcacttctccggcacaatgccgttctcacgcagatagtgcgccagaatcgtcgc cggaacgccaaagtcgctatattcgccggtttcggcatcgataccggtgtagtgagt aacagcttgcacggatcaacaaaatactgatccgcggcatatccttcaaagccgtg ccacttcgcccccggctcaaaactgaaaaaacgcggtcgctggctaacactgat gtcggataatcctgccacaatttgccatcaacaacgggcgggataaacgggcgga acagcttacagcgcgcaagaatagccttgcgcgcttcaatccctatctcaacacact cagcccacagccgacgcccactctccccttcatgaattttggcgttaacatccagtgc agcaaacagcggatagaaagggctggtagaagcatggagcataaaggcgttatt caaccgcttatgcgggcaaaaacgcgcctgtccgcggatatggttatctttttttatgga tctgcgacgtctgtgagaatcccgcctgctgtttgtgcaccgactgagtcacaaagat ccccggatcgtttcgttaagttctaacagcagcggcgagctatccgccatcatcggg ataaattgttcataaccgacccacgcggaatcaaacagaatgtaatcacacagatg cccaacggtatcgatcacctgacgggcgttatagacagtgccgtcataggttcccag ctgaataatcgccaggcgatacgggcgcggcaggtcggcttttctggcgcaacgtc gcgaatttgctggcgcagatactcttcattaaaacagtgcgcatcaataccgccaat gaaaccaaacgggttgcgtgaagcttccagatagaccggcgtcgcTtccctcgact cacacttggG (SEQ ID NO: 185) |
| (N24)rcsB-HT1.0(N21) | TtcctcatggattctacgggGgccggcgctatcgctgagatctgcctttgccggatgc gatgctgacgcatcttatccagcctacagaacgctgcaatttattgaatttgcacgatc atgtaggccggataaggcgtttacgccgcatccggcaatcaaccgcaggcggccg ccgatttctacttactcaccaccagcaaatgcgcatgcataatgtcgctggccgggc gaccgtgcgccagcaaatcagccattgctttaagatatggcggtagatggcggaaa taacgctgatacccggcacacaaataattcagtcccggtttgccgctggcatcgagc atgaagcggtgtttcgggcagcctccccagcacgcttttaacacgttacaactgcga cactgcgccggtaactgcttaaatttatcttcaccaaacgcctgctgttgcggggaatc gatcatttctgcaattgtttgctggtgcatattccccagccgatattgcggataaacata gtgTtccctcgactcacacttggG (SEQ ID NO: 186) |

TABLE 10-continued

Sequences of barcoded fragments

| Barcoded UDS fragments | Sequence |
|---|---|
| (N24)tyrR-HT0.5(N21) | TtcctcatggattctacgggGttatgctttcagtacagccagagctgcttcgtaatccg<br>gctcggtggtgatttcatccaccagctggctgaaaatcacattgtcattttcgtcaataa<br>ccacaacggcacgcgctgccagacctttcagtgggccatcagcaattgccacacc<br>gtaagcttgcagaaattcagcgttacggaaagtgggagagggtgataacgttgttcag<br>accttctgcgccgcagaaacgagactgggcgaacggcagatcggcagagatac<br>acagcacaacggtgttgtcgatctcagttgccagttggttaaacttacgtactgatgcg<br>gcgcaaacaccggtatcaatactcgggaaaatgttcagcactttgcgtttacccgca<br>aactgaccgagggtgacgtcagacagatctttgccacgagagtaaaagtctgcgc<br>tttgctacccgcctgcgggatggaattggcgactgtaaccgggttgccctggaaatg<br>aacggtttgtgacatTtccctcgactcacacttggG (SEQ ID NO: 187) |
| (N24)pheA-HT0.5(N21) | TtcctcatggattctacgggGttactggcgattgtcattcgcctgacgcaataacacg<br>cggcttcactctgaaaacgctgtgcgtaatcgccgaaccagtgctccaccttgcgg<br>aaactgtcaataaacgcctgcttatcgccctgctccagcaactcaatcgcctcgccg<br>aaacgcttatagtaacgtttgattaacgccagattacgctctgacgacataatgatgtc<br>ggcataaagctgcggatcctgagcaaacagtcgcccgaccatcgccagctcaag<br>gcggtaaatcggcgaagagagcgccagaagttgctcaagctgaacattttcttctgc<br>caggtgcagcccgtaagcaaaagtagcaaagtggcgcagtgcctgaataaacgc<br>catattctgatcgtgctcgacggcgctaatacgatgcagccgagcgccccagacct<br>gaatttgctccagaaaccattggtatgcttccggtttacgtccatcacaccagaccac<br>aacttgctttgccaggctaccgctgtccggaccgaacatcgggtgtagccccagca<br>ccggaccatcatgcgccaccagcatggcctgtaatggcccattttTtccctcgactca<br>cacttggG (SEQ ID NO: 188) |
| (N24)ptsI-HT0.7(N21) | TtcctcatggattctacgggGagcgcatcacttccagtacgcgcaaccccgctcgg<br>tgcactgcatcggttaacgccttcccttcagcaagccactgatgagctgagcacaa<br>aacaggtcgccagtcccttcaggtcggtttttacccgtgaatgggaaatgacattca<br>cgctgtcggcagtgaccaccacaacctgcatctcctgattttcttcattaccggaggc<br>gctggtaaccaccaccattttaatgtgtctgaaagcagacttttttgcggcagcaatg<br>gcactgtcgagatcgcggcaattttaccggtcaggattcccaactcaaagatattgg<br>gggtaattccctgcgccagcggcagtaaatattgtcgatacgcttcgggaaggtcag<br>gtttgacataaattccgctatcaatatcgccaatcaccggatcgaccatgatcaatag<br>gtcaggatggtctttgcgtagcgcagtcagccactcggcaaggattttgatttgcgatg<br>ccgttcccatatagcccgtggttacagcacgaagttggcgcagcgcatcacgctcct<br>gaagcgcacgcaaatagccgctaaaccattcgtccggaatcgcaccaccgtaga<br>aagtgtcataatgcggcgtattgctcagcaataccgtcggcacggcaaagacattc<br>aggccgttctgtttgatagcaggcacggcaatgctgttgcccacgctgccgtaaacc<br>acctgcgactgcacggcgacgatatccgcctgcagtgccctactcttatcgttaTtcc<br>ctcgactcacacttggG<br>(SEQ ID NO: 189) |
| (N21)aadA(N22) | TtccctcgactcacacttggGtcgacctgcagaagcttagatctattaccctgttatcc<br>ctactcgagttcatgtgcagctccatcagcaaaaggggatgataagtttatcaccac<br>cgactatttgcaacagtgccgttgatcgtgctatgatcgactgatgtcatcagcggtgg<br>agtgcaatgtcatgaggaagcggtgatcgccgaagtatcgactcaactatcagag<br>gtagttggcgtcatcgagcgccatctcgaaccgacgttgctggccgtacatttgtacg<br>gctccgcagtggatggcggcctgaagccacacagtgatattgatttgctggttacggt<br>gaccgtaaggcttgatgaaacaacgcggcgagctttgatcaacgaccttttggaaa<br>cttcggcttcccctggagagagcgagattctccgcgctgtagaagtcaccattgttgtg<br>cacgacgacatcattccgtggcgttatccagctaagcgcgaactgcaatttggaga<br>atggcagcgcaatgacattcttgcaggtatcttcgagccagccacgatcgacattga<br>tctggctatcttgctgacaaaagcaagagaacatagcgttgccttggtaggtccagc<br>ggcggaggaactctttgatccggttcctgaacaggatctatttgaggcgctaaatgaa<br>accttaacgctatggaactcgccgcccgactgggctggcgatgagcgaaatgtagt<br>gcttacgttgtcccgcatttggtacagcgcagtaaccggcaaaatcgcgccgaagg<br>atgtcgctgccgactgggcaatggagcgcctgccggcccagtatcagcccgtcata<br>cttgaagctagacaggcttatcttggacaagaagaagatcgcttggcctcgcgcgc<br>agatcagttggaagaatttgtccactacgtgaaaggcgagatcaccaaggtagtcg<br>gcaaataagatgccgctcgccagtcgattggctgagctcatgaagttcctattccga<br>agttccgcgaacgcgtaaaggatctaggtgaagatcctttttgataatctcatgacca<br>aaatcccttaacgTtcacacaacatagccacggG (SEQ ID NO: 190) |
| (N21)bla(N22) | TtccctcgactcacacttggGtttctacaaactcttttgtttattttttctaaatacattcaaa<br>tatgtatccgctcatgagacaataaaccctgataaatgcttcaataatattgaaaaagg<br>aagagtatgagtattcaacatttccgtgtcgcccttattcccttttttgcggcatttttgcttc<br>ctgttttgctcacccagaaacgctggtgaaagtaaaagatgctgaagatcagttgg<br>gtgcacgagtgggttacatcgaactggatctcaacagcggtaagatccttgagagttt<br>tcgccccgaagaacgttttccaatgatgagcacttttaaagttctgctatgtggcgcgg<br>tattatcccgtgttgacgccgggcaagagcaactcggtcgccgcatacactattctca<br>gaatgacttggttgagtactcaccagtcacagaaaagcatcttacggatggcatgac<br>agtaagagaattatgcagtgctgccataaccatgagtgataacactgcggccaactt<br>acttctgacaacgatcggaggaccgaaggagctaaccgcttttttgcacaacatgg<br>gggatcatgtaactcgccttgatcgttgggaaccggagctgaatgaagccatacca<br>aacgacgagcgtgacaccacgatgcctgtagcaatggcaacaacgttgcgcaaa<br>ctattaactggcgaactacttactctagcttcccggcaacaattaatagactggatgg |

TABLE 10-continued

Sequences of barcoded fragments

| Barcoded UDS fragments | Sequence |
|---|---|
| | aggcggataaagttgcaggaccacttctgcgctcggcccttccggctggctggtttatt<br>gctgataaatctggagccggtgagcgtgggtctcgcggtatcattgcagcactgggg<br>ccagatggtaagccctcccgtatcgtagttatctacacgacggggagtcaggcaact<br>atggatgaacgaaatagacagatcgctgagataggtgcctcactgattaagcattg<br>gtaactgtcagaccaagtttactcatatatactttagattgatttaaaacttcattttttaattt<br>aaaaggatctaggtgaagatcctttttgataatctcatgaccaaaatcccttaacgTtc<br>acacaacatagccacggG (SEQ ID NO: 191) |
| (N22)p5(N23) | TtcacacaacatagccacggGccgttttcatctgtgcatatggacagttttccctttgat<br>atgtaacggtgaacagttgttctacttttgtttgttagtcttgatgcttcactgatagataca<br>agagccataagaacctcagatccttccgtatttagccagtatgttctctagtgtggttcg<br>ttgttttttgcgtgagccatgagaacgaaccattgagatcatacttactttgcatgtcactc<br>aaaaattttgcctcaaaactggtgagctgaattttttgcagttaaagcatcgtgtagtgttt<br>ttcttagtccgttatgtaggtaggaatctgatgtaatggttgttggtattttgtcaccattcat<br>tttttatctggttgttctcaagttcggttacgagatccatttgtctatctagttcaacttggaaa<br>atcaacgtatcagtcgggcggcctcgcttatcaaccaccaatttcatattgctgtaagt<br>gtttaaatctttacttattggttcaaaaccattggttaagccttttaaactcatggtagtt<br>attttcaagcattaacatgaacttaaattcatcaaggctaatctctatatttgccttgtgag<br>ttttctttttgtgttagttctttttaataaccactcataaatcctcatagagtatttgttttcaaaa<br>gacttaacatgttccagattatattttatgaattttttttaactggaaaagataaggcaatat<br>ctcttcactaaaaactaattctaattttttcgcttgagaacttggcatagtttgtccactgga<br>aaatctcaaagcctttaaccaaaggattcctgatttccacagttctcgtcatcagctctc<br>tggttgctttagctaatacaccataagcattttccctactgatgttcatcatctgagcgtat<br>tggtatagtgaacgataccgtccgttcttccttgtagggttttcaatcgtggggttga<br>gtagtgccacacagcataaaattagcttggtttcatgctccgttaagtcatagcgacta<br>atcgctagttcatttgctttgaaaacaactaattcagacatacatctcaattggtctaggt<br>gattttaatcactataccaattgagatgggctagtcaatgataattactagtcctttccttt<br>gagttgtgggtatctgtaaattctgctagaccttttgctggaaaacttgtaaattctgctag<br>accctctgtaaattccgctagaccttttgtgtgtttttttgtttatattcaagtggttataatttta<br>tagaataaagaaagaataaaaaaagataaaaagaatagatcccagccctgtgtat<br>aactcactactttagtcagttccgcagtattacaaaaggaTtcaaacagaaaggcc<br>atgg (SEQ ID NO: 192) |
| (N22)p15(N23) | TtcacacaacatagccacggGtgttcagctactgacggggtggtgcgtaacggca<br>aaagcaccgccggacatcagcgctagcggagtgtatactggcttactatgttggca<br>ctgatgagggtgtcagtgaagtgcttcatgtggcaggagaaaaaaggctgcaccg<br>gtgcgtcagcagaatatgtgatacaggatatattccgcttcctcgctcactgactcgct<br>acgctcggtcgttcgactgcggcgagcggaaatggcttacgaacggggcggagat<br>tcctggaagatgccaggaagatacttaacagggaagtgagagggccgcggcaa<br>agccgttttccataggctccgcccccctgacaagcatcacgaaatctgacgctcaa<br>atcagtggtggcgaaacccgacaggactataaagataccaggcgtttcccctggc<br>ggctccctcgtgcgctctcctgttcctgccctttccggttttaccggtgtcattccgctgttatgg<br>ccgcgtttgtctcattccacgcctgacactcagttccgggtaggcagttcgctccaagc<br>tggactgtatgcacgaaccccccgttcagtccgaccgctgcgccttatccggtaacta<br>tcgtcttgagtccaacccggaaagacatgcaaaagcaccactggcagcagccact<br>ggtaattgatttagaggagttagtcttgaagtcatgcgccggttaaggctaaactgaa<br>aggacaagttttggtgactgcgctcctccaagccagttacctcggttcaaagagttgg<br>tagctcagagaaccttcgaaaaaccgccctgcaaggcggtttttttcgttttcagagca<br>agagattacgcgcagaccaaaacgatctcaagaagatcatcttattaatcagataa<br>aatatttctagatttcagtgcaatttatctcttcaaatgtagcacctgaagtcagcccat<br>acgatataagttgtaattctcatgtttgacagcttatcacccagtcctgctcgcttcgcta<br>cttggccatacccacgccgaaacaagcgctcatgagcccgaagtggcgagcccg<br>atcttccccatcggtgatgtcTtcaaacagaaaggccatggG<br>(SEQ ID NO: 193) |
| (N22)pMB1(N23) | TtcacacaacatagccacggGagttttcgttccactgagcgtcagaccccgtagaa<br>aagatcaaaggatcttcttgagatcctttttttctgcgcgtaatctgctgcttgcaaacaa<br>aaaaaccaccgctaccagcggtggtttgtttgccggatcaagagctaccaactcttttt<br>ccgaaggtaactggcttcagcagagcgcagataccaaatactgtccttctagtgtag<br>ccgtagttaggccaccacttcaagaactctgtagcaccgcctacatacctcgctctgc<br>taatcctgttaccagtggctgctgccagtggcgataagtcgtgtcttaccgggttggac<br>tcaagacgatagttaccggataaggcgcagcggtcgggctgaacggggggttcgt<br>gcacacagcccagcttggagcgaacgacctacaccgaactgagatacctacagc<br>gtgagctatgagaaagcgccacgcttcccgaagggagaaaggcggacaggtatc<br>cggtaagcggcagggtcggaacaggagagcgcacgagggagcttccaggggg<br>aaacgcctggtatctttatagtcctgtcgggtttcgccacctctgacttgagcgtcgatttt<br>tgtgatgctcgtcagggggcggagcctatggaaaaacgccagcaacgcggcctt<br>tttacggttcctggccttttgctggccttttgctcacatgttctttcctgcgttatcccctgatt<br>ctgtggataaccgtattaccgcctttgagtgagctgataccgctcgccgcagccgaa<br>cgaccgagcgcagcgagtcagtgagcgaggaagcggaagagcgcctgatgcg<br>gtattttctccttacgcatctgtgcggtatttcacaccgcatatgctggatccttgacagct<br>agctcagtcctaggtataatactag<br>(SEQ ID NO: 194) |
| (N22)pMB1 mutant(N23) | TtcacacaacatagccacggGgctcactcaaaggcggtaatacggttatccacag<br>aatcaggggataacgcaggaaagaacatgtgagcaaaaggccagcaaaaggc |

TABLE 10-continued

Sequences of barcoded fragments

| Barcoded UDS fragments | Sequence |
|---|---|
| | caggaaccgtaaaaaggccgcgttgctggcgttttttccataggctccgccccctga<br>cgagcatcacaaaaatcgacgctcaagtcagaggtggcgaaacccgacaggac<br>tataaagataccaggcgtttccccctggaagctccctcgtgcgctctcctgttccgacc<br>ctgccgcttaccggatacctgtccgcctttctcccttcgggaagcgtggcgctttctcat<br>agctcacgctgtaggtatctcagttcggtgtaggtcgttcgctccaagctgggctgtgt<br>gcacgaaccccccgttcagcccgaccgctgcgccttatccggtaactatcgtcttga<br>gtccaacccggtaagacacgacttatcgccactggcagcagccactggtaacagg<br>attagcagagcgaggtatgtaggcggtgctacagagttcttgaagtggtggcctaac<br>tacggctacactagaagaacagtatttggtatctgcgctctgctgaagccagttaccttt<br>cggaaaaagagttggtagctcttgatccggcaaacaaaccaccgctggtagcggt<br>ggtttttttgtttgcaagcagcagattacgcgcagaaaaaaaggatctcaagaagat<br>cctttgatcttttctacggggtctgacgctcagtggaacgaaaactcacgttaagggat<br>tttggtcatgagattatcaaaaaggatcttcacctagatcctTtcaaacagaaaggcc<br>atggG (SEQ ID NO: 195) |
| (N23)pLac(RBS1) | TtcaaacagaaaggccatggGcaacgcaattaatgtgagttagctcactcattagg<br>caccccaggctttacactttatgcttccggctcgtatgttgtgtggaattgtgagcggat<br>aacaatttgaaataattttgtttaactttaagaaggagatatacatatg (SEQ ID<br>NO: 196) |
| (N23)LacIT7(RBS1) | tcaaacagaaaggccatggGgaaactacccataatacaagaaaagcccgtcac<br>gggcttctcagggcgtttatggcgggtctgctatgtggtgctatctgacttttttgctgttca<br>gcagttcctgccctctgattttccagtctgaccacttcggattatcccgtgacaggtcatt<br>cagactggctaatgcacccagtaaggcagcggtatcatcaacaggcttacccgtctt<br>actgtcgggaattcgcgttggccgattcattaatgcagctggcacgacaggtttcctct<br>agatttcagtgcaatttatctcttcaaatgtagcacctgaagtcagccccatacgatat<br>aagttgtaattctcatgttagtcatgccccgcgcccaccggaaggagctgactgggtt<br>gaaggctctcaagggcatcggtcgagatcccggtgcctaatgagtgagctaactta<br>cattaattgcgttgcgctcactgcccgctttccagtcgggaaacctgtcgtgccagctg<br>cattaatgaatcggccaacgcgcgggagaggcggtttgcgtattgggcgccagg<br>gtggtttttcttttcaccagtgagacgggcaacagctgattgcccttcaccgcctggcc<br>ctgagagagttgcagcaagcggtccacgctggtttgccccagcaggcgaaaatcct<br>gtttgatggtggttaacggcgggatataacatgagctgtcttcggtatcgtcgtatccca<br>ctaccgagatgtccgcaccaacgcgcagcccggactcggtaatggcgcgcattgc<br>gcccagcgccatctgatcgttggcaaccagcatcgcagtgggaacgatgccctcat<br>tcagcatttgcatggtttgttgaaaaccggacatggcactccagtcgccttcccgttcc<br>gctatcggctgaatttgattgcgagtgagatatttatgccagccagccagacgcaga<br>cgcgccgagacagaacttaatgggcccgctaacagcgcgatttgctggtgaccca<br>atgcgaccagatgctccacgcccagtcgcgtaccgtcttcatgggagaaaataata<br>ctgttgatgggtgtctggtcagagacatcaagaaataacgccggaacattagtgca<br>ggcagcttccacagcaatggcatcctggtcatccagcggatagttaatgatcagccc<br>actgacgcgttgcgcgagaagattgtgcaccgccgctttacaggcttcgacgccgct<br>tcgttctaccatcgacaccaccacgctggcacccagttgatcggcgcgagatttaat<br>cgccgcgacaatttgcgacggcgcgtgcagggccagactggaggtggcaacgcc<br>aatcagcaacgactgtttgcccgccagttgttgtgccacgcggttgggaatgtaattc<br>agctccgccatcgccgcttccacttttttccgcgcgttttcgcagaaacgtggctggcctg<br>gttcaccacgcgggaaacggtctgataagagacaccggcatactctgcgacatcgt<br>ataacgttactggtttcacattcaccaccctgaattgactctcttccgggcgctatcatg<br>ccataccgcgaaaggttttgcgccattcgatggtgtccgggatctcgacgctctccctt<br>atgcgactcctgcattaggaaattaatacgactcactatagggaattgtgagcgga<br>taacaattcccctctagaaataattttgtttaactttaagaaggagatatacatatg<br>(SEQ ID NO: 197) |
| (N31)t7t(N21) | TgatgggctgaagggtttaaGggctgctaacaaagcccgaaaggaagctgagtt<br>ggctgctgccaccgctgagcaataactagcataaccccttgggccctctaaacggg<br>tcttgaggggttttttgctgaaaggaggaactatatccggatatcccgcaagaggccc<br>ggcagtaccggcataaccaagcctatgcctacagcatccagggtgacggtgccT<br>TccctcgactcacacttgGG<br>(SEQ ID NO: 198 |
| (N31)t7t(LK3) | TgatgggctgaagggtttaaGggctgctaacaaagcccgaaaggaagctgagtt<br>ggctgctgccaccgctgagcaataactagcataaccccttgggccctctaaacggg<br>tcttgaggggttttttgctgaaaggaggaactatatccggatatcccgcaagaggccc<br>ggcagtaccggcataaccaagcctatgcctacagcatccagggtgacggtgccTc<br>aggctcgtcttcttcaggG<br>(SEQ ID NO: 199) |
| (LK3)LacI(N21) | TcaggctcgtcttcttcaggGgaaactacccataatacaagaaaagcccgtcacg<br>gcttctcagggcgtttatggcgggtctgctatgtggtgctatctgacttttttgctgttcag<br>cagttcctgccctctgattttccagtctgaccacttcggattatcccgtgacaggtcattc<br>agactggctaatgcacccagtaaggcagcggtatcatcaacaggcttacccgtctta<br>ctgtcgggaattcgcgttggccgattcattaatgcagctggcacgacaggtttcctcta<br>gatttcagtgcaatttatctcttcaaatgtagcacctgaagtcagccccatacgatata<br>agttgtaattctcatgttagtcatgccccgcgcccaccggaaggagctgactgggttg<br>aaggctctcaagggcatcggtcgagatcccggtgcctaatgagtgagctaacttac<br>attaattgcgttgcgctcactgcccgctttccagtcgggaaacctgtcgtgccagctgc |

TABLE 10-continued

Sequences of barcoded fragments

| Barcoded UDS fragments | Sequence |
|---|---|
| | attaatgaatcggccaacgcgcggggagaggcggtttgcgtattgggcgccagggt<br>ggttttctttttcaccagtgagacgggcaacagctgattgcccttcaccgcctggccct<br>gagagagttgcagcaagcggtccacgctggtttgcccagcaggcgaaaatcctg<br>tttgatggtggttaacggcgggatataacatgagctgtcttcggtatcgtcgtatcccac<br>taccgagatgtccgcaccaacgcgcagcccggactcggtaatggcgcgcattgcg<br>cccagcgccatctgatcgttggcaaccagcatcgcagtgggaacgatgccctcatt<br>cagcatttgcatggtttgttgaaaaccggacatggcactccagtcgccttcccgttccg<br>ctatcggctgaatttgattgcgagtgagatatttatgccagccagccagacgcagac<br>gcgccgagacagaacttaatgggcccgctaacagcgcgatttgctggtgacccaat<br>gcgaccagatgctccacgcccagtcgcgtaccgtcttcatgggagaaaataatact<br>gttgatgggtgtctggtcagagacatcaagaaataacgccggaacattagtgcagg<br>cagcttccacagcaatggcatcctggtcatccagcggatagttaatgatcagcccac<br>tgacgcgttgcgcgagaagattgtgcaccgccgctttacaggcttcgacgccgcttc<br>gttctaccatcgacaccaccacgctggcacccagttgatcggcgcgagatttaatcg<br>ccgcgacaatttgcgacggcgcgtgcagggccagactggaggtggcaacgccaa<br>tcagcaacgactgtttgcccgccagttgttgtgccacgcggttgggaatgtaattcag<br>ctccgccatcgccgcttccacttttttcccgcgttttcgcagaaacgtggctggctggtt<br>caccacgcgggaaacggtctgataagagacaccggcatactctgcgacatcgtat<br>aacgttactggtttcacattcaccaccctgaattgactctcttccgggcgctatcatgcc<br>ataccgcgaaaggttttgcgccattcgatggtgtccgggaTTccctcgactcacact<br>tgGG (SEQ ID NO: 200) |
| (RBS1)dxs(RBS2stop) | tagaaataattttgtttaactttaagaaggagatatacatatgagttttgatattgccaaa<br>tacccgaccctggcactggtcgactccacccaggagttacgactgttgccgaaaga<br>gagtttaccgaaactctgcgacgaactgcgccgctatttactcgacagcgtgagccg<br>ttccagcgggcacttcgcctccgggctgggcacggtcgaactgaccgtggcgctgc<br>actatgtctacaacaccccgtttgaccaattgatttgggatgtgggcatcaggcttat<br>ccgcataaaattttgaccggacgccgcgacaaaatcggcaccatccgtcagaaag<br>gcggtctgcacccgttcccgtggcgcggcgaaagcgaatatgacgtattaagcgtc<br>gggcattcatcaacctccatcagtgccggaattggtattgcggttgctgccgaaaaa<br>gaaggcaaaaatcgccgcaccgtctgtgtcattggcgatggcgcgattaccgcag<br>gcatggcgtttgaagcgatgaatcacgcgggcgatatccgtcctgatatgctggtgat<br>tctcaacgacaatgaaatgtcgatttccgaaaatgtcggcgcgctcaacaaccatct<br>ggcacagctgctttccggtaagctttactcttcactgcgcgaaggcgggaaaaaagt<br>tttctctggcgtgccgccaattaaagagctgctcaaacgcaccgaagaacatattaa<br>aggcatggtagtgcctggcacgttgtttgaagagctgggctttaactacatcggcccg<br>gtggacggtcacgatgtgctggggcttatcaccacgctaaagaacatgcgcgacct<br>gaaaggcccgcagttcctgcatatcatgaccaaaaaaggtcgtggttatgaaccgg<br>cagaaaaagacccgatcacttttccacgccgtgcctaaatttgatccctccagcggtt<br>gtttgccgaaaagtagcggcggtttgccgagctattcaaaaatctttggcgactggttg<br>tgcgaaacggcagcgaaagacaacaagctgatggcgattactccggcgatgcgt<br>gaaggttccggcatggtcgagttttcacgtaaattcccggatcgctacttcgacgtgg<br>caattgccgagcaacacgcggtgaccttttgctgcgggtctggcgattggtgggtaca<br>aacccattgtcgcgatttactccactttcctgcaacgcgcctatgatcaggtgctgcat<br>gacgtggcgattcaaaagcttccggtcctgttcgccatcgaccgcgcgggcattgttg<br>gtgctgacggtcaaacccatcagggtgcttttgatctctcttacctgcgctgcataccg<br>gaaatggtcattatgaccccgagcgatgaaaacgaatgtcgccagatgctctatac<br>cggctatcactataacgatggcccgtcagcggtgcgctaccgcgtggcaacgcg<br>gtcggcgtggaactgacgcgcgctggaaaaactaccaattggcaaaggcattgtga<br>agcgtcgtggcgagaaactggcgatccttaactttggtacgctgatgccagaagcg<br>gcgaaagtcgccgaatcgctgaacgccacgctggtcgatatgcgttttgtgaaacc<br>gcttgatgaagcgttaattctggaaatggccgccagccatgaagcgctggtcaccgt<br>agaagaaaacgccattatgggcggcgcaggcagcggcgtgaacgaagtgctgat<br>ggcccatcgtaaaccagtacccgtgctgaacattggcctgccggacttcttttattccg<br>caaggaactcaggaagaaatgcgcgcgaactcggcctcgatgccgctggtatg<br>gaagccaaaatcaaggcctggctggcaTaaccgttcatttatcacaaaaggattgtt<br>cgatG<br>(SEQ ID NO: 201) |
| (RBS2stop)idi(RBS3stop) | TaaccgttcatttatcacaaaaggattgttcgatGCAAACGGAACACGTC<br>ATTTTATTGAATGCACAGGGAGTTCCCACGGGTACGCTG<br>GAAAAGTATGCCGCACACACGGCAGACACCCGCTTACAT<br>CTCGCGTTCTCCAGTTGGCTGTTTAATGCCAAAGGACAA<br>TTATTAGTTACCCGCCGCGCACTGAGCAAAAAAGCATGG<br>CCTGGCGTGTGGACTAACTCGGTTTGTGGGCACCCACAA<br>CTGGGAGAAAGCAACGAAGACGCAGTGATCCGCCGTTG<br>CCGTTATGAGCTTGGCGTGGAAATTACGCCTCCTGAATC<br>TATCTATCCTGACTTTCGCTACCGCGCCACCGATCCGAG<br>TGGCATTGTGGAAAATGAAGTGTGTCCGGTATTTGCCGC<br>ACGCACCACTAGTGCGTTACAGATCAATGATGATGAAGT<br>GATGGATTATCAATGGTGTGATTTAGCAGATGTATTACAC<br>GGTATTGATGCCACGCCGTGGGCGTTCAGTCCGTGGAT<br>GGTGATGCAGGCGACAAATCGCGAAGCCAGAAAACGAT<br>TATCTGCATTTACCCAGCTTAAATgattcacacaggaaacagctat<br>G (SEQ ID NO: 202) |

TABLE 10-continued

Sequences of barcoded fragments

| Barcoded UDS fragments | Sequence |
|---|---|
| (RBS3stop)valC(RBS4stop) | TgattcacacaggaaacagctatGGCCGAGATGTTCAACGGCAAC<br>TCTTCTAACGACGGATCTTCTTGCATGCCCGTGAAGGAC<br>GCCCTGCGACGAACCGGCAACCACCACCCCAACCTGTG<br>GACCGACGACTTCATCCAGTCTCTGAACTCTCCCTACTC<br>TGACTCTTCTTACCACAAGCACCGAGAGATCCTGATCGA<br>CGAGATCCGAGACATGTTCTCTAACGGCGAGGGCGACG<br>AGTTCGGCGTGCTCGAGAACATCTGGTTCGTGGACGTG<br>GTGCAGCGACTGGGCATCGACCGACACTTCCAGGAGGA<br>GATCAAGACCGCCCTGGACTACATCTACAAGTTCTGGAA<br>CCACGACTCTATCTTCGGCGACCTGAACATGGTGGCCCT<br>GGGCTTCCGAATCCTGCGACTGAACCGATACGTGGCCT<br>CTTCTGACGTGTTCAAGAAGTTCAAGGGCGAGGAGGGC<br>CAGTTCTCTGGCTTCGAGTCCTCTGACCAGGACGCTAAG<br>CTCGAAATGATGCTGAACCTGTACAAGGCCTCTGAGCTG<br>GACTTCCCCGACGAGGACATCCTGAAGGAGGCCCGAGC<br>CTTCGCCTCTATGTACCTGAAGCACGTGATCAAGGAGTA<br>CGGCGACATCCAGGAGTCTAAGAACCCCCTGCTGATGG<br>AGATCGAGTACACCTTCAAGTACCCCTGGCGATGCCGAC<br>TGCCCCGACTCGAGGCCTGGAACTTCATCCACATCATGC<br>GACAGCAGGACTGCAACATCTCTCTGGCCAACAACCTCT<br>ACAAGATCCCCAAGATCTACATGAAGAAGATCCTCGAGC<br>TGGCCATCCTGGACTTCAACATCCTGCAGTCTCAGCACC<br>AGCACGAGATGAAGCTGATCTCTACCTGGTGGAAGAACT<br>CTTCTGCTATCCAGCTGGACTTCTTCCGACACCGACACA<br>TCGAGTCTTACTTTTGGTGGGCCTCGCCCCTGTTCGAGC<br>CCGAGTTCTCTACCTGCCGAATCAACTGCACCAAGCTGT<br>CTACCAAGATGTTCCTGCTGGACGACATCTACGACACCT<br>ACGGCACCGTCGAGGAGCTGAAGCCCTTCACCACCACC<br>CTGACCCGATGGGACGTGTCTACCGTGGACAACCACCC<br>CGACTACATGAAGATCGCCTTCAACTTCTCTTACGAGATC<br>TACAAGGAGATCGCCTCTGAGGCCGAGCGAAAGCACGG<br>CCCCTTCGTGTACAAGTACCTGCAGTCTTGCTGGAAGTC<br>TTACATCGAGGCCTACATGCAGGAGGCCGAGTGGATCG<br>CCTCTAACCACATCCCCGGCTTCGACGAGTACCTGATGA<br>ACGGCGTGAAGTCCTCTGGCATGCGAATCCTGATGATCC<br>ACGCCCTGATCCTGATGGACACCCCCCTGTCTGACGAGA<br>TTCTCGAGCAGCTGGACATCCCCTCGTCTAAGTCTCAGG<br>CCCTGCTGTCTCTGATCACCCGACTGGTGGACGACGTGA<br>AGGACTTCGAGGACGAGCAGGCCCACGGCGAGATGGCC<br>TCTTCTATCGAGTGCTACATGAAGGACAACCACGGCTCT<br>ACCCGAGAGGACGCCCTGAACTACCTGAAGATCCGAATC<br>GAGTCTTGCGTGCAGGAGCTGAACAAGGAGCTGCTCGA<br>GCCCTCTAACATGCACGGATCTTTCCGAAACCTGTACCT<br>GAACGTGGGAATGCGAGTGATTTTCTTCATGCTGAACGA<br>CGGCGACCTGTTCACCCACTCTAACCGAAAGGAGATCCA<br>GGACGCCATCACCAAGTTCTTCGTCGAGCCCATCATCCC<br>CTaaattaattgttcttttttcaggtgaaggttcccatG (SEQ ID NO: 203) |
| (RBS4stop)ispA(N31) | TaaattaattgttcttttttcaggtgaaggttcccatGGACTTTCCGCAGCAA<br>CTCGAAGCCTGCGTTAAGCAGGCCAACCAGGCGCTGAG<br>CCGTTTTATCGCCCCACTGCCCTTTCAGAACACTCCCGT<br>GGTCGAAACCATGCAGTATGGCGCATTATTAGGTGGTAA<br>GCGCCTGCGACCTTTCCTGGTTTATGCCACCGGTCATAT<br>GTTCGGCGTTAGCACAAACACGCTGGACGCACCCGCTG<br>CCGCCGTTGAGTGTATCCACGCTTACTCATTAATTCATGA<br>TGATTTACCGGCAATGGATGATGACGATCTGCGTCGCGG<br>TTTGCCAACCTGCCATGTGAAGTTTGGCGAAGCAAACGC<br>GATTCTCGCTGGCGACGCTTTACAAACGCTGGCGTTCTC<br>GATTTTAAGCGATGCCGATATGCCGGAAGTGTCGGACCG<br>CGACAGAATTTCGATGATTTCTGAACTGGCGAGCGCCAG<br>TGGTATTGCCGGAATGTGCGGTGGTCAGGCATTAGATTT<br>AGACGCGGAAGGCAAACACGTACCTCTGGACGCGCTTG<br>AGCGTATTCATCGTCATAAAACCGGCGCATTGATTCGCG<br>CCGCCGTTCGCCTTGGTGCATTAAGCGCCGGAGATAAA<br>GGACGTCGTGCTCTGCCGGTACTCGACAAGTATGCAGA<br>GAGCATCGGCCTTGCCTTCCAGGTTCAGGATGACATCCT<br>GGATGTGGTGGGAGATACTGCAACGTTGGGAAAACGCC<br>AGGGTGCCGACCAGCAACTTGGTAAAAGTACCTACCCTG<br>CACTTCTGGGTCTTGAGCAAGCCCGGAAGAAAGCCCGG<br>GATCTGATCGACGATGCCCGTCAGTCGCTGAAACAACTG<br>GCTGAACAGTCACTCGATACCTCGGCACTGGAAGCGCTA<br>GCGGACTACATCATCCAGCGTAATAAATgatgggctgaagggttt<br>aaG (SEQ ID NO: 204) |
| (RBS1)idi(RBS2stop) | tagaaataattttgtttaactttaagaaggagatatacatatgCAAACGGAACA<br>CGTCATTTTATTGAATGCACAGGGAGTTCCCACGGGTAC |

TABLE 10-continued

Sequences of barcoded fragments

| Barcoded UDS fragments | Sequence |
|---|---|
| | GCTGGAAAAGTATGCCGCACACACGGCAGACACCCGCT<br>TACATCTCGCGTTCTCCAGTTGGCTGTTTAATGCCAAAG<br>GACAATTATTAGTTACCCGCCGCGCACTGAGCAAAAAAG<br>CATGGCCTGGCGTGTGGACTAACTCGGTTTGTGGGCAC<br>CCACAACTGGGAGAAAGCAACGAAGACGCAGTGATCCG<br>CCGTTGCCGTTATGAGCTTGGCGTGGAAATTACGCCTCC<br>TGAATCTATCTATCCTGACTTTCGCTACCGCGCCACCGAT<br>CCGAGTGGCATTGTGGAAAATGAAGTGTGTCCGGTATTT<br>GCCGCACGCACCACTAGTGCGTTACAGATCAATGATGAT<br>GAAGTGATGGATTATCAATGGTGTGATTTAGCAGATGTAT<br>TACACGGTATTGATGCCACGCCGTGGGCGTTCAGTCCGT<br>GGATGGTGATGCAGGCGACAAATCGCGAAGCCAGAAAA<br>CGATTATCTGCATTTACCCAGCTTAAATaaccgttcatttatcacaa<br>aaggattgttcgatG (SEQ ID NO: 205) |
| (RBS2stop)dxs(RBS3stop) | TaaccgttcatttatcacaaaaggattgttcgatGagttttgatattgccaaatacccg<br>accctggcactggtcgactccacccaggagttacgactgttgccgaaagagagttta<br>ccgaaactctgcgacgaactgcgccgctatttactcgacagcgtgagccgttccag<br>cgggcacttcgcctccgggctgggcacggtcgaactgaccgtggcgctgcactatg<br>tctacaacaccccgtttgaccaattgatttgggatgtggggcatcaggcttatccgcat<br>aaaattttgaccggacgccgcgacaaaatcggcaccatccgtcagaaaggcggtc<br>tgcaccgttcccgtggcgcggcgaaagcgaatatgacgtattaagcgtcgggcat<br>tcatcaacctccatcagtgccggaattggtattgcggttgctgccgaaaaagaaggc<br>aaaaatcgccgcaccgtctgtgtcattggcgatggcgcgattaccgcaggcatggc<br>gtttgaagcgatgaatcacgcgggcgatatccgtcctgatatgctggtgattctcaac<br>gacaatgaaatgtcgatttccgaaaatgtcggcgcgctcaacaaccatctggcaca<br>gctgcttttccggtaagctttactcttcactgcgcgaaggcgggaaaaaagtttttctctg<br>gcgtgccgccaattaaagagctgctcaaacgcaccgaagaacatattaaaggcat<br>ggtagtgcctggcacgttgtttgaagagctgggctttaactacatcggcccggtggac<br>ggtcacgatgtgctggggcttatcaccacgctaaagaacatgcgcgacctgaaag<br>gcccgcagttcctgcatatcatgaccaaaaaaggtcgtggttatgaaccggcagaa<br>aaagacccgatcactttccacgccgtgcctaaatttgatccctccagcggttgtttgcc<br>gaaaagtagcggcggtttgccgagctattcaaaaatctttggcgactggttgtgcga<br>acggcagcgaaagacaacaagctgatggcgattactccggcgatgcgtgaagg<br>ttccggcatggtcgagttttcacgtaaatttcccggatcgctacttcgacgtggcaattgc<br>cgagcaacacgcggtgacctttgctgcgggtctggccgattggtgggtacaaaccca<br>ttgtcgcgatttactccactttcctgcaacgcgcctatgatcaggtgctgcatgacgtgg<br>cgattcaaaagcttccggtcctgttcgccatcgaccgcgcgggcattgttggtgctga<br>cggtcaaacccatcagggtgcttttgatctctcttacctgcgctgcataccggaaatgg<br>tcattatgaccccgagcgatgaaaacgaatgtcgccagatgctctataccggctatc<br>actataacgatggcccgtcagcggtgcgctacccgcgtggcaacgcggtcggcgt<br>ggaactgacgccgctggaaaaaactaccaattggcaaaggcattgtgaagcgtcgt<br>ggcgagaaactggcgatccttaactttggtacgctgatgccagaagcggcgaaagt<br>cgccgaatcgctgaacgccacgctggtcgatatgcgttttgtgaaaccgcttgatga<br>agcgttaattctggaaatggccgccagccatgaagcgctggtcaccgtagaagaa<br>aacgccattatgggcggcgcaggcagcggcgtgaacgaagtgctgatggcccat<br>cgtaaaccagtacccgtgctgaacattggcctgccggacttctttattccgcaaggaa<br>ctcaggaagaaatgcgcgccgaactcggcctcgatgccgctggtatggaagccaa<br>aatcaaggcctggctggcaTgattcacacaggaaacagctatG (SEQ ID<br>NO: 206) |
| (RBS3stop)dxs(RBS4stop) | TgattcacacaggaaacagctatGagttttgatattgccaaatacccgaccctggc<br>actggtcgactccacccaggagttacgactgttgccgaaagagagtttaccgaaac<br>tctgcgacgaactgcgccgctatttactcgacagcgtgagccgttccagcgggcact<br>tcgcctccgggctgggcacggtcgaactgaccgtggcgctgcactatgtctacaac<br>accccgtttgaccaattgatttgggatgtggggcatcaggcttatccgcataaaattttg<br>accggacgccgcgacaaaatcggcaccatccgtcagaaaggcggtctgcaccc<br>gttcccgtggcgcggcgaaagcgaatatgacgtattaagcgtcgggcattcatcaa<br>cctccatcagtgccggaattggtattgcggttgctgccgaaaaagaaggcaaaaat<br>cgccgcaccgtctgtgtcattggcgatggcgcgattaccgcaggcatggcgtttgaa<br>gcgatgaatcacgcgggcgatatccgtcctgatatgctggtgattctcaacgacaat<br>gaaatgtcgatttccgaaaatgtcggcgcgctcaacaaccatctggcacagctgcttt<br>ccggtaagctttactcttcactgcgcgaaggcgggaaaaaagtttttctctggcgtgcc<br>gccaattaaagagctgctcaaacgcaccgaagaacatattaaaggcatggtagtg<br>cctggcacgttgtttgaagagctgggctttaactacatcggcccggtggacggtcac<br>gatgtgctggggcttatcaccacgctaaagaacatgcgcgacctgaaaggcccgc<br>agttcctgcatatcatgaccaaaaaaggtcgtggttatgaaccggcagaaaaagac<br>ccgatcactttccacgccgtgcctaaatttgatccctccagcggttgtttgccgaaaag<br>tagcggcggtttgccgagctattcaaaaatctttggcgactggttgtgcgaaacggca<br>gcgaaagacaacaagctgatggcgattactccggcgatgcgtgaaggttccggca<br>tggtcgagttttcacgtaaatttcccggatcgctacttcgacgtggcaattgccgagca<br>acacgcggtgacctttgctgcgggtctggccgattggtgggtacaaaccccattgtcgc<br>gatttactccactttcctgcaacgcgcctatgatcaggtgctgcatgacgtggcgattc<br>aaaagcttccggtcctgttcgccatcgaccgcgcgggcattgttggtgctgacggtca<br>aacccatcagggtgcttttgatctctcttacctgcgctgcataccggaaatggtcattat<br>gaccccgagcgatgaaaacgaatgtcgccagatgctctataccggctatcactata |

TABLE 10-continued

Sequences of barcoded fragments

| Barcoded UDS fragments | Sequence |
|---|---|
| | acgatggcccgtcagcggtgcgctacccgcgtggcaacgcggtcggcgtggaact gacgccgctggaaaaactaccaattggcaaaggcattgtgaagcgtcgtggcgag aaactggcgatccttaactttggtacgctgatgccagaagcggcgaaagtcgccga atcgctgaacgccacgctggtcgatatgcgttttgtgaaaccgcttgatgaagcgtta attctggaaatggccgccagccatgaagcgctggtcaccgtagaagaaaacgcc attatgggcggcgcaggcagcggcgtgaacgaagtgctgatggcccatcgtaaac cagtacccgtgctgaacattggcctgccggacttctttattccgcaaggaactcagga agaaatgcgcgccgaactcggcctcgatgccgctggtatggaagccaaaatcaa ggcctggctggcaTaaattaattgttcttttttcaggtgaaggttcccatG (SEQ ID NO: 207) |
| (RBS4stop)dxs(N31) | TaaattaattgttcttttttcaggtgaaggttcccatGagttttgatattgccaaataccc gaccctggcactggtcgactccacccaggagttacgactgttgccgaaagagagttt accgaaactctgcgacgaactgcgccgctatttactcgacagcgtgagccgttcca gcgggcacttcgcctccgggctgggcacggtcgaactgaccgtggcgctgcactat gtctacaacaccccgtttgaccaattgatttgggatgtggggcatcaggcttatccgc ataaaattttgaccggacgccgcgacaaaatcggcaccatccgtcagaaaggcg gtctgcacccgttcccgtggcgcggcgaaagcgaatatgacgtattaagcgtcggg cattcatcaacctccatcagtgccggaattggtattgcggttgctgccgaaaaagaa ggcaaaaatcgccgcaccgtctgtgtcattggcgatggcgcgattaccgcaggcat ggcgtttgaagcgatgaatcacgcgggcgatatccgtcctgatatgctggtgattctc aacgacaatgaaatgtcgatttccgaaaatgtcggcgcgctcaacaaccatctggc acagctgctttccggtaagctttactcttcactgcgcgaaggcgggaaaaaagttttct ctggcgtgccgccaattaaagagctgctcaaacgcaccgaagaacatattaaagg catggtagtgcctggcacgttgtttgaagagctgggcttttaactacatcggcccggtg gacggtcacgatgtgctggggcttatcaccacgctaaagaacatgcgcgacctga aaggcccgcagttcctgcatatcatgaccaaaaaaggtcgtggttatgaaccggca gaaaaagacccgatcactttccacgcgtgcctaaatttgatccctccagcggttgttt gccgaaaagtagcggcggtttgccgagctattcaaaaatctttggcgactggttgtgc gaaacggcagcgaaagacaacaagctgatggcgattactccggcgatgcgtgaa ggttccggcatggtcgagttttcacgtaaattcccggatcgctacttcgacgtggcaat tgccgagcaacacgcggtgacctttgctgcgggtctggcgattggtgggtacaaac ccattgtcgcgatttactccactttcctgcaacgcgcctatgatcaggtgctgcatgac gtggcgattcaaaagcttccggtcctgttcgccatcgaccgcgcgggcattgttggtg ctgacggtcaaacccatcagggtgcttttgatctctcttacctgcgctgcataccggaa atggtcattatgaccccgagcgatgaaaacgaatgtcgccagatgctctataccgg ctatcactataacgatggcccgtcagcggtgcgctacccgcgtggcaacgcggtcg gcgtggaactgacgccgctggaaaaactaccaattggcaaaggcattgtgaagcg tcgtggcgagaaactggcgatccttaactttggtacgctgatgccagaagcggcga aagtcgccgaatcgctgaacgccacgctggtcgatatgcgttttgtgaaaccgcttg atgaagcgttaattctggaaatggccgccagccatgaagcgctggtcaccgtagaa gaaaacgccattatgggcggcgcaggcagcggcgtgaacgaagtgctgatggcc catcgtaaaccagtacccgtgctgaacattggcctgccggacttctttattccgcaag gaactcaggaagaaatgcgcgccgaactcggcctcgatgccgctggtatggaag ccaaaatcaaggcctggctggcaTgatgggctgaagggtttaaG (SEQ ID NO: 208) |
| (RBS1)valC(RBS2stop) | tagaaataattttgtttaactttaagaaggagatatacatatgGCCGAGATGTT CAACGGCAACTCTTCTAACGACGGATCTTCTTGCATGCC CGTGAAGGACGCCCTGCGACGAACCGGCAACCACCACC CCAACCTGTGGACCGACGACTTCATCCAGTCTCTGAACT CTCCCTACTCTGACTCTTCTTACCACAAGCACCGAGAGA TCCTGATCGACGAGATCCGAGACATGTTCTCTAACGGCG AGGGCGACGAGTTCGGCGTGCTCGAGAACATCTGGTTC GTGGACGTGGTGCAGCGACTGGGCATCGACCGACACTT CCAGGAGGAGATCAAGACCGCCCTGGACTACATCTACAA GTTCTGGAACCACGACTCTATCTTCGGCGACCTGAACAT GGTGGCCCTGGGCTTCCGAATCCTGCGACTGAACCGAT ACGTGGCCTCTTCTGACGTGTTCAAGAAGTTCAAGGGCG AGGAGGGCCAGTTCTCTGGCTTCGAGTCCTCTGACCAG GACGCTAAGCTCGAAATGATGCTGAACCTGTACAAGGCC TCTGAGCTGGACTTCCCCGACGAGGACATCCTGAAGGA GGCCCGAGCCTTCGCCTCTATGTACCTGAAGCACGTGAT CAAGGAGTACGGCGACATCCAGGAGTCTAAGAACCCCC TGCTGATGGAGATCGAGTACACCTTCAAGTACCCCTGGC GATGCCGACTGCCCCGACTCGAGGCCTGGAACTTCATC CACATCATGCGACAGCAGGACTGCAACATCTCTCTGGCC AACAACCTCTACAAGATCCCCAAGATCTACATGAAGAAG ATCCTCGAGCTGGCCATCCTGGACTTCAACATCCTGCAG TCTCAGCACCAGCACGAGATGAAGCTGATCTCTACCTGG TGGAAGAACTCTTCTGCTATCCAGCTGGACTTCTTCCGA CACCGACACATCGAGTCTTACTTTTGGTGGGCCTCGCCC CTGTTCGAGCCCGAGTTCTCTACCTGCCGAATCAACTGC ACCAAGCTGTCTACCAAGATGTTCCTGCTGGACGACATC TACGACACCTACGGCACCGTCGAGGAGCTGAAGCCCTT CACCACCACCCTGACCCGATGGGACGTGTCTACCGTGG |

TABLE 10-continued

Sequences of barcoded fragments

| Barcoded UDS fragments | Sequence |
|---|---|
| | ACAACCACCCCGACTACATGAAGATCGCCTTCAACTTCT<br>CTTACGAGATCTACAAGGAGATCGCCTCTGAGGCCGAGC<br>GAAAGCACGGCCCCTTCGTGTACAAGTACCTGCAGTCTT<br>GCTGGAAGTCTTACATCGAGGCCTACATGCAGGAGGCC<br>GAGTGGATCGCCTCTAACCACATCCCCGGCTTCGACGA<br>GTACCTGATGAACGGCGTGAAGTCCTCTGGCATGCGAAT<br>CCTGATGATCCACGCCCTGATCCTGATGGACACCCCCCT<br>GTCTGACGAGATTCTCGAGCAGCTGGACATCCCCTCGTC<br>TAAGTCTCAGGCCCTGCTGTCTCTGATCACCCGACTGGT<br>GGACGACGTGAAGGACTTCGAGGACGAGCAGGCCCACG<br>GCGAGATGGCCTCTTCTATCGAGTGCTACATGAAGGACA<br>ACCACGGCTCTACCCGAGAGGACGCCCTGAACTACCTG<br>AAGATCCGAATCGAGTCTTGCGTGCAGGAGCTGAACAAG<br>GAGCTGCTCGAGCCCTCTAACATGCACGGATCTTTCCGA<br>AACCTGTACCTGAACGTGGGAATGCGAGTGATTTTCTTC<br>ATGCTGAACGACGGCGACCTGTTCACCCACTCTAACCGA<br>AAGGAGATCCAGGACGCCATCACCAAGTTCTTCGTCGAG<br>CCCATCATCCCCTaaccgttcatttatcacaaaaggattgttcgatG (SEQ ID NO: 209) |
| (RBS2stop)valC(RBS3stop) | TaaccgttcatttatcacaaaaggattgttcgatGGCCGAGATGTTCAAC<br>GGCAACTCTTCTAACGACGGATCTTCTTGCATGCCCGTG<br>AAGGACGCCCTGCGACGAACCGGCAACCACCACCCCAA<br>CCTGTGGACCGACGACTTCATCCAGTCTCTGAACTCTCC<br>CTACTCTGACTCTTCTTACCACAAGCACCGAGAGATCCT<br>GATCGACGAGATCCGAGACATGTTCTCTAACGGCGAGG<br>GCGACGAGTTCGGCGTGCTCGAGAACATCTGGTTCGTG<br>GACGTGGTGCAGCGACTGGGCATCGACCGACACTTCCA<br>GGAGGAGATCAAGACCGCCCTGGACTACATCTACAAGTT<br>CTGGAACCACGACTCTATCTTCGGCGACCTGAACATGGT<br>GGCCCTGGGCTTCCGAATCCTGCGACTGAACCGATACG<br>TGGCCTCTTCTGACGTGTTCAAGAAGTTCAAGGGCGAGG<br>AGGGCCAGTTCTCTGGCTTCGAGTCCTCTGACCAGGAC<br>GCTAAGCTCGAAATGATGCTGAACCTGTACAAGGCCTCT<br>GAGCTGGACTTCCCCGACGAGGACATCCTGAAGGAGGC<br>CCGAGCCTTCGCCTCTATGTACCTGAAGCACGTGATCAA<br>GGAGTACGGCGACATCCAGGAGTCTAAGAACCCCCTGC<br>TGATGGAGATCGAGTACACCTTCAAGTACCCCTGGCGAT<br>GCCGACTGCCCCGACTCGAGGCCTGGAACTTCATCCAC<br>ATCATGCGACAGCAGGACTGCAACATCTCTCTGGCCAAC<br>AACCTCTACAAGATCCCCAAGATCTACATGAAGAAGATC<br>CTCGAGCTGGCCATCCTGGACTTCAACATCCTGCAGTCT<br>CAGCACCAGCACGAGATGAAGCTGATCTCTACCTGGTGG<br>AAGAACTCTTCTGCTATCCAGCTGGACTTCTTCCGACAC<br>CGACACATCGAGTCTTACTTTTGGTGGGCCTCGCCCCTG<br>TTCGAGCCCGAGTTCTCTACCTGCCGAATCAACTGCACC<br>AAGCTGTCTACCAAGATGTTCCTGCTGGACGACATCTAC<br>GACACCTACGGCACCGTCGAGGAGCTGAAGCCCTTCAC<br>CACCACCCTGACCCGATGGGACGTGTCTACCGTGGACA<br>ACCACCCCGACTACATGAAGATCGCCTTCAACTTCTCTTA<br>CGAGATCTACAAGGAGATCGCCTCTGAGGCCGAGCGAA<br>AGCACGGCCCCTTCGTGTACAAGTACCTGCAGTCTTGCT<br>GGAAGTCTTACATCGAGGCCTACATGCAGGAGGCCGAG<br>TGGATCGCCTCTAACCACATCCCCGGCTTCGACGAGTAC<br>CTGATGAACGGCGTGAAGTCCTCTGGCATGCGAATCCTG<br>ATGATCCACGCCCTGATCCTGATGGACACCCCCCTGTCT<br>GACGAGATTCTCGAGCAGCTGGACATCCCCTCGTCTAAG<br>TCTCAGGCCCTGCTGTCTCTGATCACCCGACTGGTGGAC<br>GACGTGAAGGACTTCGAGGACGAGCAGGCCCACGGCGA<br>GATGGCCTCTTCTATCGAGTGCTACATGAAGGACAACCA<br>CGGCTCTACCCGAGAGGACGCCCTGAACTACCTGAAGA<br>TCCGAATCGAGTCTTGCGTGCAGGAGCTGAACAAGGAG<br>CTGCTCGAGCCCTCTAACATGCACGGATCTTTCCGAAAC<br>CTGTACCTGAACGTGGGAATGCGAGTGATTTTCTTCATG<br>CTGAACGACGGCGACCTGTTCACCCACTCTAACCGAAAG<br>GAGATCCAGGACGCCATCACCAAGTTCTTCGTCGAGCCC<br>ATCATCCCCTgattcacacaggaaacagctatG (SEQ ID NO: 210) |
| (RBS3stop)idi(RBS4stop) | TgattcacacaggaaacagctatGCAAACGGAACACGTCATTTTAT<br>TGAATGCACAGGGAGTTCCCACGGGTACGCTGGAAAAG<br>TATGCCGCACACACGGCAGACACCCGCTTACATCTCGCG<br>TTCTCCAGTTGGCTGTTTAATGCCAAAGGACAATTATTAG<br>TTACCCGCCGCGCACTGAGCAAAAAGCATGGCCTGGC<br>GTGTGGACTAACTCGGTTTGTGGGCACCCACAACTGGGA<br>GAAAGCAACGAAGACGCAGTGATCCGCCGTTGCCGTTAT<br>GAGCTTGGCGTGGAAATTACGCCTCCTGAATCTATCTAT |

TABLE 10-continued

Sequences of barcoded fragments

| Barcoded UDS fragments | Sequence |
|---|---|
| | CCTGACTTTCGCTACCGCGCCACCGATCCGAGTGGCATT<br>GTGGAAAATGAAGTGTGTCCGGTATTTGCCGCACGCACC<br>ACTAGTGCGTTACAGATCAATGATGATGAAGTGATGGATT<br>ATCAATGGTGTGATTTAGCAGATGTATTACACGGTATTGA<br>TGCCACGCCGTGGGCGTTCAGTCCGTGGATGGTGATGC<br>AGGCGACAAATCGCGAAGCCAGAAAACGATTATCTGCAT<br>TTACCCAGCTTAAATaaattaattgttctttttcaggtgaaggttcccatG<br>(SEQ ID NO: 211) |
| (RBS4stop)idi(N31) | TaaattaattgttctttttcaggtgaaggttcccatGCAAACGGAACACGTC<br>ATTTTATTGAATGCACAGGGAGTTCCCACGGGTACGCTG<br>GAAAAGTATGCCGCACACACGGCAGACACCCGCTTACAT<br>CTCGCGTTCTCCAGTTGGCTGTTTAATGCCAAAGGACAA<br>TTATTAGTTACCCGCCGCGCACTGAGCAAAAAAGCATGG<br>CCTGGCGTGTGGACTAACTCGGTTTGTGGGCACCCACAA<br>CTGGGAGAAAGCAACGAAGACGCAGTGATCCGCCGTTG<br>CCGTTATGAGCTTGGCGTGGAAATTACGCCTCCTGAATC<br>TATCTATCCTGACTTTCGCTACCGCGCCACCGATCCGAG<br>TGGCATTGTGGAAAATGAAGTGTGTCCGGTATTTGCCGC<br>ACGCACCACTAGTGCGTTACAGATCAATGATGATGAAGT<br>GATGGATTATCAATGGTGTGATTTAGCAGATGTATTACAC<br>GGTATTGATGCCACGCCGTGGGCGTTCAGTCCGTGGAT<br>GGTGATGCAGGCGACAAATCGCGAAGCCAGAAAACGAT<br>TATCTGCATTTACCCAGCTTAAATgatgggctgaagggtttaaG<br>(SEQ ID NO: 212) |
| (RBS1)ispA(RBS2stop) | tagaaataattttgtttaactttaagaaggagatatacatatgGACTTTCCGCA<br>GCAACTCGAAGCCTGCGTTAAGCAGGCCAACCAGGCGC<br>TGAGCCGTTTTATCGCCCCACTGCCCTTTCAGAACACTC<br>CCGTGGTCGAAACCATGCAGTATGGCGCATTATTAGGTG<br>GTAAGCGCCTGCGACCTTTCCTGGTTTATGCCACCGGTC<br>ATATGTTCGGCGTTAGCACAAACACGCTGGACGCACCCG<br>CTGCCGCCGTTGAGTGTATCCACGCTTACTCATTAATTCA<br>TGATGATTTACCGGCAATGGATGATGACGATCTGCGTCG<br>CGGTTTGCCAACCTGCCATGTGAAGTTTGGCGAAGCAAA<br>CGCGATTCTCGCTGGCGACGCTTTACAAACGCTGGCGTT<br>CTCGATTTTAAGCGATGCCGATATGCCGGAAGTGTCGGA<br>CCGCGACAGAATTTCGATGATTTCTGAACTGGCGAGCGC<br>CAGTGGTATTGCCGGAATGTGCGGTGGTCAGGCATTAGA<br>TTTAGACGCGGAAGGCAAACACGTACCTCTGGACGCGCT<br>TGAGCGTATTCATCGTCATAAAACCGGCGCATTGATTCG<br>CGCCGCCGTTCGCCTTGGTGCATTAAGCGCCGGAGATA<br>AAGGACGTCGTGCTCTGCCGGTACTCGACAAGTATGCAG<br>AGAGCATCGGCCTTGCCTTCCAGGTTCAGGATGACATCC<br>TGGATGTGGTGGGAGATACTGCAACGTTGGGAAAACGC<br>CAGGGTGCCGACCAGCAACTTGGTAAAAGTACCTACCCT<br>GCACTTCTGGGTCTTGAGCAAGCCCGGAAGAAAGCCCG<br>GGATCTGATCGACGATGCCCGTCAGTCGCTGAAACAACT<br>GGCTGAACAGTCACTCGATACCTCGGCACTGGAAGCGC<br>TAGCGGACTACATCATCCAGCGTAATAAATaaccgttcatttatc<br>acaaaaggattgttcgatG (SEQ ID NO: 213) |
| (RBS2stop)ispA(RBS3stop) | TaaccgttcatttatcacaaaaggattgttcgatGGACTTTCCGCAGCAA<br>CTCGAAGCCTGCGTTAAGCAGGCCAACCAGGCGCTGAG<br>CCGTTTTATCGCCCCACTGCCCTTTCAGAACACTCCCGT<br>GGTCGAAACCATGCAGTATGGCGCATTATTAGGTGGTAA<br>GCGCCTGCGACCTTTCCTGGTTTATGCCACCGGTCATAT<br>GTTCGGCGTTAGCACAAACACGCTGGACGCACCCGCTG<br>CCGCCGTTGAGTGTATCCACGCTTACTCATTAATTCATGA<br>TGATTTACCGGCAATGGATGATGACGATCTGCGTCGCGG<br>TTTGCCAACCTGCCATGTGAAGTTTGGCGAAGCAAACGC<br>GATTCTCGCTGGCGACGCTTTACAAACGCTGGCGTTCTC<br>GATTTTAAGCGATGCCGATATGCCGGAAGTGTCGGACCG<br>CGACAGAATTTCGATGATTTCTGAACTGGCGAGCGCCAG<br>TGGTATTGCCGGAATGTGCGGTGGTCAGGCATTAGATTT<br>AGACGCGGAAGGCAAACACGTACCTCTGGACGCGCTTG<br>AGCGTATTCATCGTCATAAAACCGGCGCATTGATTCGCG<br>CCGCCGTTCGCCTTGGTGCATTAAGCGCCGGAGATAAA<br>GGACGTCGTGCTCTGCCGGTACTCGACAAGTATGCAGA<br>GAGCATCGGCCTTGCCTTCCAGGTTCAGGATGACATCCT<br>GGATGTGGTGGGAGATACTGCAACGTTGGGAAAACGCC<br>AGGGTGCCGACCAGCAACTTGGTAAAAGTACCTACCCTG<br>CACTTCTGGGTCTTGAGCAAGCCCGGAAGAAAGCCCGG |

TABLE 10-continued

Sequences of barcoded fragments

| Barcoded UDS fragments | Sequence |
|---|---|
| | GATCTGATCGACGATGCCCGTCAGTCGCTGAAACAACTG<br>GCTGAACAGTCACTCGATACCTCGGCACTGGAAGCGCTA<br>GCGGACTACATCATCCAGCGTAATAAATgattcacacaggaaac<br>agctatG (SEQ ID NO: 214) |
| (RBS3stop)ispA(RBS4stop) | TgattcacacaggaaacagctatGGACTTTCCGCAGCAACTCGAA<br>GCCTGCGTTAAGCAGGCCAACCAGGCGCTGAGCCGTTT<br>TATCGCCCCACTGCCCTTTCAGAACACTCCCGTGGTCGA<br>AACCATGCAGTATGGCGCATTATTAGGTGGTAAGCGCCT<br>GCGACCTTTCCTGGTTTATGCCACCGGTCATATGTTCGG<br>CGTTAGCACAAACACGCTGGACGCACCCGCTGCCGCCG<br>TTGAGTGTATCCACGCTTACTCATTAATTCATGATGATTTA<br>CCGGCAATGGATGATGACGATCTGCGTCGCGGTTTTGCC<br>AACCTGCCATGTGAAGTTTGGCGAAGCAAACGCGATTCT<br>CGCTGGCGACGCTTTACAAACGCTGGCGTTCTCGATTTT<br>AAGCGATGCCGATATGCCGGAAGTGTCGGACCGCGACA<br>GAATTTCGATGATTTCTGAACTGGCGAGCGCCAGTGGTA<br>TTGCCGGAATGTGCGGTGGTCAGGCATTAGATTTAGACG<br>CGGAAGGCAAACACGTACCTCTGGACGCGCTTGAGCGT<br>ATTCATCGTCATAAAACCGGCGCATTGATTCGCGCCGCC<br>GTTCGCCTTGGTGCATTAAGCGCCGGAGATAAAGGACGT<br>CGTGCTCTGCCGGTACTCGACAAGTATGCAGAGAGCATC<br>GGCCTTGCCTTCCAGGTTCAGGATGACATCCTGGATGTG<br>GTGGGAGATACTGCAACGTTGGGAAAACGCCAGGGTGC<br>CGACCAGCAACTTGGTAAAAGTACCTACCCTGCACTTCT<br>GGGTCTTGAGCAAGCCCGGAAGAAAGCCCGGGATCTGA<br>TCGACGATGCCCGTCAGTCGCTGAAACAACTGGCTGAAC<br>AGTCACTCGATACCTCGGCACTGGAAGCGCTAGCGGAC<br>TACATCATCCAGCGTAATAAATaaattaattgttctttttcaggtgaagg<br>ttcccatG (SEQ ID NO: 215) |
| (RBS4stop)valC(N31) | TaaattaattgttctttttcaggtgaaggttcccatGGCCGAGATGTTCAAC<br>GGCAACTCTTCTAACGACGGATCTTCTTGCATGCCCGTG<br>AAGGACGCCCTGCGACGAACCGGCAACCACCACCCCAA<br>CCTGTGGACCGACGACTTCATCCAGTCTCTGAACTCTCC<br>CTACTCTGACTCTTCTTACCACAAGCACCGAGAGATCCT<br>GATCGACGAGATCCGAGACATGTTCTCTAACGGCGAGG<br>GCGACGAGTTCGGCGTGCTCGAGAACATCTGGTTCGTG<br>GACGTGGTGCAGCGACTGGGCATCGACCGACACTTCCA<br>GGAGGAGATCAAGACCGCCCTGGACTACATCTACAAGTT<br>CTGGAACCACGACTCTATCTTCGGCGACCTGAACATGGT<br>GGGCCCTGGGCTTCCGAATCCTGCGACTGAACCGATACG<br>TGGCCTCTTCTGACGTGTTCAAGAAGTTCAAGGGCGAGG<br>AGGGCCAGTTCTCTGGCTTCGAGTCCTCTGACCAGGAC<br>GCTAAGCTCGAAATGATGCTGAACCTGTACAAGGCCTCT<br>GAGCTGGACTTCCCCGACGAGGACATCCTGAAGGAGGC<br>CCGAGCCTTCGCCTCTATGTACCTGAAGCACGTGATCAA<br>GGAGTACGGCGACATCCAGGAGTCTAAGAACCCCCTGC<br>TGATGGAGATCGAGTACACCTTCAAGTACCCCTGGCGAT<br>GCCGACTGCCCCGACTCGAGGCCTGGAACTTCATCCAC<br>ATCATGCGACAGCAGGACTGCAACATCTCTCTGGCCAAC<br>AACCTCTACAAGATCCCCAAGATCTACATGAAGAAGATC<br>CTCGAGCTGGCCATCCTGGACTTCAACATCCTGCAGTCT<br>CAGCACCAGCACGAGATGAAGCTGATCTCTACCTGGTGG<br>AAGAACTCTTCTGCTATCCAGCTGGACTTCTTCCGACAC<br>CGACACATCGAGTCTTACTTTTGGTGGGCCTCGCCCCTG<br>TTCGAGCCCGAGTTCTCTACCTGCCGAATCAACTGCACC<br>AAGCTGTCTACCAAGATGTTCCTGCTGGACGACATCTAC<br>GACACCTACGGCACCGTCGAGGAGCTGAAGCCCTTCAC<br>CACCACCCTGACCCGATGGGACGTGTCTACCGTGGACA<br>ACCACCCCGACTACATGAAGATCGCCTTCAACTTCTCTTA<br>CGAGATCTACAAGGAGATCGCCTCTGAGGCCGAGCGAA<br>AGCACGGCCCCTTCGTGTACAAGTACCTGCAGTCTTGCT<br>GGAAGTCTTACATCGAGGCCTACATGCAGGAGGCCGAG<br>TGGATCGCCTCTAACCACATCCCCGGCTTCGACGAGTAC<br>CTGATGAACGGCGTGAAGTCCTCTGGCATGCGAATCCTG<br>ATGATCCACGCCCTGATCCTGATGGACACCCCCCTGTCT<br>GACGAGATTCTCGAGCAGCTGGACATCCCCTCGTCTAAG<br>TCTCAGGCCCTGCTGTCTCTGATCACCCGACTGGTGGAC<br>GACGTGAAGGACTTCGAGGACGAGCAGGCCCACGGCGA<br>GATGGCCTCTTCTATCGAGTGCTACATGAAGGACAACCA<br>CGGCTCTACCCGAGAGGACGCCCTGAACTACCTGAAGA<br>TCCGAATCGAGTCTTGCGTGCAGGAGCTGAACAAGGAG<br>CTGCTCGAGCCCTCTAACATGCACGGATCTTTCCGAAAC<br>CTGTACCTGAACGTGGGAATGCGAGTGATTTTCTTCATG<br>CTGAACGACGGCGACCTGTTCACCCACTCTAACCGAAAG |

TABLE 10-continued

Sequences of barcoded fragments

| Barcoded UDS fragments | Sequence |
| --- | --- |
| | GAGATCCAGGACGCCATCACCAAGTTCTTCGTCGAGCCC<br>ATCATCCCCTgatgggctgaagggtttaaG (SEQ ID NO: 216) |
| (RBS1)aroG mutant(RBS4stop) | Tagaaataattttgtttaactttaagaaggagatatacatatgaattatcagaacgac<br>gattacgcatcaaagaaatcaaagagttacttcctcctgtcgcattgctggaaaaatt<br>ccccgctactgaaaatgccgcgaatacggttgcccatgcccgaaaagcgatccat<br>aagatcctgaaaggtaatgatgatcgcctgttggttgtgattggcccatgctcaattcat<br>gatcctgtcgcggcaaaagagtatgccactcgcttgctggcgctgcgtgaagagct<br>gaaagatgagctggaaatcgtaatgcgcgtctattttgaaaagccgcgtaccacggt<br>gggctggaaagggctgattaacgatccgcatatggataatagcttccagatcaacg<br>acggtctgcgtatagcccgtaaattgctgcttgatattaacgacagcggtctgccagc<br>ggcaggtgagtttctcaatatgatcaccccacaatatctcgctgacctgatgagctgg<br>ggcgcaattggcgcacgtaccaccgaatcgcaggtgcaccgcgaactggcatca<br>gggcttttcttgtccggtcggcttcaaaaatggcaccgacggtacgattaaagtggcta<br>tcgatgccattaatgccgccggtgcgccgcactgcttcctgtccgtaacgaaatggg<br>ggcattcggcgattgtgaataccagcggtaacggcgattgccatatcattctgcgcg<br>gcggtaaagagcctaactacagcgcgaagcacgttgctgaagtgaaagaagggc<br>tgaacaaagcaggcctgccagcacaggtgatgatcgatttcagccatgctaactcg<br>tccaaacaattcaaaaagcagatggatgtttgtgctgacgtttgccagcagattgccg<br>gtggcgaaaaggccattattggcgtgatggtggaaagccatctggtggaaggcaat<br>cagagcctcgagagcggggagccgctggcctacggtaagagcatcaccgatgcc<br>tgcatcggctgggagataccgatgctctgttacgtcaactggcgaatgcagtaaaa<br>gcgcgtcgcgggTaaattaattgttcttttttcaggtgaaggttcccatG<br>(SEQ ID NO: 217) |
| (RBS1)tyrA mutant(RBS4stop) | tagaaataattttgtttaactttaagaaggagatatacatatggttgctgaattgaccgc<br>attacgcgatcaaattgatgaagtcgataaagcgctgctgaatttattagcgaagcgt<br>ctggaactggttgctgaagtgggcgaggtgaaaagccgctttggactgcctatttatg<br>ttccggagcgcgaggcatctattttggcctcgcgtcgtgcagaggcggaagctctgg<br>gtgtaccgccagatctgattgaggatgttttgcgtcgggtgatgcgtgaatcttactcca<br>gtgaaaacgacaaaggatttaaaacactttgtccgtcactgcgtccggtggttatcgt<br>cggcggtggcggtcagatgggacgcctgttcgagaagatgctgaccctctcggggtt<br>atcaggtgcggattctggagcaacatgactgggatcgagcggctgatattgttgccg<br>atgccgaatggtgattgttagtgtgccaatccacgttactgagcaagttattggcaa<br>attaccgcctttacccgaaagattgtattctggtcgatctggcatcagtgaaaaatgggc<br>cattacaggccatgctggtggcgcatgatggtccggtgctggggctacacccgatgt<br>tcggtccggacagcggtagcctggcaaagcaagttgtggtctggtgtgatggacgta<br>aaccggaagcataccaatggtttctggagcaaattcaggtctgggggcgctcggctg<br>catcgtattagcgccgtcgagcacgatcagaatatggcgtttattcaggcactgcgcc<br>actttgctactttttgcttacgggctgcacctggcagaagaaaatgttcagcttgagcaa<br>cttctggcgctctcttcgccgatttaccgccttgagctggcgatggtcgggcgactgttt<br>gctcaggatccgcagctttatgccgacatcattatgtcgtcagagcgtaat ctggcgtt<br>aatcaaacgttactataagcgtttcggcgaggcgattgagttgctggagcagggcg<br>ataagcaggcgtttattgacagttttccgcaaggtggagcactggttcggcgattacgt<br>acagcgttttcagagtgaaagccgcgtgttattgcgtcaggcgaatgacaatcgcca<br>gTaaattaattgttcttttttcaggtgaaggttcccatG<br>(SEQ ID NO: 218) |
| (RBS4stop)tyrA mutant(N31) | TaaattaattgttcttttttcaggtgaaggttcccatGgttgctgaattgaccgcattacg<br>cgatcaaattgatgaagtcgataaagcgctgctgaatttattagcgaagcgtctgga<br>actggttgctgaagtgggcgaggtgaaaagccgctttggactgcctatttatgttccgg<br>agcgcgaggcatctattttggcctcgcgtcgtgcagaggcggaagctctgggtgtac<br>cgccagatctgattgaggatgttttgcgtcgggtgatgcgtgaatcttactccagtgaa<br>aacgacaaaggatttaaaacactttgtccgtcactgcgtccggtggttatcgtcggcg<br>gtggcggtcagatgggacgcctgttcgagaagatgctgaccctctcggggttatcagg<br>tgcggattctggagcaacatgactgggatcgagcggctgatattgttgccgatgccg<br>aatggtgattgttagtgtgccaatccacgttactgagcaagttattggcaaattaccg<br>cctttacccgaaagattgtattctggtcgatctggcatcagtgaaaaatgggccattaca<br>ggccatgctggtggcgcatgatggtccggtgctggggctacacccgatgttcggtcc<br>ggacagcggtagcctggcaaagcaagttgtggtctggtgtgatggacgtaaaccg<br>gaagcataccaatggtttctggagcaaattcaggtctgggggcgctcggctgcatcgt<br>attagcgccgtcgagcacgatcagaatatggcgtttattcaggcactgcgccactttg<br>ctactttttgcttacgggctgcacctggcagaagaaaatgttcagcttgagcaacttctg<br>gcgctctcttcgccgatttaccgccttgagctggcgatggtcgggcgactgtttgctca<br>ggatccgcagctttatgccgacatcattatgtcgtcagagcgtaatctggcgttaatca<br>aacgttactataagcgtttcggcgaggcgattgagttgctggagcagggcgataag<br>caggcgtttattgacagttttccgcaaggtggagcactggttcggcgattacgtacagc<br>gttttcagagtgaaagccgcgtgttattgcgtcaggcgaatgacaatcgccagTgat<br>gggctgaagggtttaaG<br>(SEQ ID NO: 219) |
| (RBS4stop)aroG mutant(N31) | TaaattaattgttcttttttcaggtgaaggttcccatGaattatcagaacgacgatttac<br>gcatcaaagaaatcaaagagttacttcctcctgtcgcattgctggaaaaattcccgc<br>tactgaaaatgccgcgaatacggttgcccatgcccgaaaagcgatccataagatcc<br>tgaaaggtaatgatgatcgcctgttggttgtgattggcccatgctcaattcatgatcctgt<br>cgcggcaaaagagtatgccactcgcttgctggcgctgcgtgaagagctgaaagat |

TABLE 10-continued

Sequences of barcoded fragments

| Barcoded UDS fragments | Sequence |
|---|---|
| | gagctggaaatcgtaatgcgcgtctattttgaaaagccgcgtaccacggtgggctgg |
| | aaagggctgattaacgatccgcatatggataatagcttccagatcaacgacggtctg |
| | cgtatagcccgtaaattgctgcttgatattaacgacagcggtctgccagcggcaggt |
| | gagtttctcaatatgatcaccccacaatatctcgctgacctgatgagctggggcgcaa |
| | ttggcgcacgtaccaccgaatcgcaggtgcaccgcgaactggcatcagggcttttctt |
| | gtccggtcggcttcaaaaatggcaccgacggtacgattaaagtggctatcgatgcc |
| | attaatgccgccggtgcgccgcactgcttcctgtccgtaacgaaatgggggcattcg |
| | gcgattgtgaataccagcggtaacggcgattgccatatcattctgcgcggcggtaaa |
| | gagcctaactacagcgcgaagcacgttgctgaagtgaaagaagggctgaacaaa |
| | gcaggcctgccagcacaggtgatgatcgatttcagccatgctaactcgtccaaaca |
| | attcaaaaagcagatggatgtttgtgctgacgtttgccagcagattgccggtggcga |
| | aaaggccattattggcgtgatggtggaaagccatctggtggaaggcaatcagagc |
| | ctcgagagcgggggagccgctggcctacggtaagagcatcaccgatgcctgcatcg |
| | gctgggaagataccgatgctctgttacgtcaactggcgaatgcagtaaaagcgcgt |
| | cgcgggTgatgggctgaagggtttaaG (SEQ ID NO: 220) |

Assembly of Barcoded UDS Fragment

Previously reported cross-lapping in vitro assembly (CLIVA) suffered low efficiency of DNA assembly (the success rate of assembling 7 fragments is less than 10%)[24], and we have demonstrated that it could be substantially improved by using a thermophilic Taq ligase with longer incubation time in vitro (Data not shown, termed as enhanced CLIVA). Mix each equimolar barcoded UDS fragments obtained from PCR by universal oligos, and add 0.5 microliters of Taq DNA ligase (NEB, M0208) and 0.5 microliters of 10× ligation buffer. Top up the reaction volume to 5 microliters by using nuclease-free water. Incubate the solution at 45° C. overnight in PCR tube that is heated up by using a PCR machine. Incubation time of assembly can be 1 to 6 hours for assembly of 2 to 5 fragments assembly which may reduce the efficiency of the DNA assembly, since overnight incubation time has been demonstrated to be more efficient (Data not shown), especially when the size of construct assembled by using 5-7 UDS barcoded fragments is over 10 kb.

Mix 1 to 2 microliters of ligation products with 17 microliters of DH5a heat-shock competent cells (NEB, C2987H), chill on ice for 5 min and incubate the mixture at 42° C. for 35 seconds (in a 1.7 milliliter Eppendorf tube immersed in a water bath), then place on ice for 2 minutes. Add 150 microliters of SOC medium and plate all of the cells on agar plate with proper selection antibiotics. Colony PCR (10 microliters volume) was performed to evaluate the efficiency of plasmid assembly, and all used oligos are list in Table 11. Sequencing confirmed plasmids with accurate barcode regions were transformed to corresponded E. coli MG1655 strains, and all constructed strains are listed in Tables 12 and 13.

TABLE 11

Plasmids and colony PCR

| Name | Plasmid constructed | Colony PCR forward oligos | Colony PCR reverse oligos | Colony number raised on the plate | Correct colony number out of tested |
|---|---|---|---|---|---|
| GE1 | (N21)aadA(N22)pMB1(pJ23119)gRNAaslA(N23)aslAHF0.5(N24)aslAHT0.5 | pJ23119-Bff | N21-Brr | Over 100 | 3 out of 3 |
| GE2 | (N21)aadA(N22)pMB1(pJ23119)gRNAaslA(N23)aslAHF1.0(N24)aslAHT1.0 | pJ23119-Bff | N21-Brr | Over 100 | 3 out of 3 |
| GE3 | (N21)aadA(N22)pMB1(pJ23119)gRNAnupG(N23)nupGHF0.5(N24)nupGHT0.5 | pJ23119-Bff | N21-Brr | Over 100 | 8 out of 3 |
| GE4 | (N21)bla(N22)pMB1(pJ23119)gRNAtyrR(N23)tyrRHF0.5(N24)tyrRHT0.5 | pJ23119-Bff | N21-Brr | Over 100 | 4 out of 4 |
| GE5 | (N21)aadA(N22)pMB1(pJ23119)gRNApheA(N23)pheAHF0.5(N24)pheA-HT0.5 | pJ23119-Bff | N21-Brr | Over 100 | 3 out of 3 |
| GE6 | (N21)aadA(N22)pMB1(pJ23119)gRNAnupG(N23)nupGHF1.0(N24)nupGHT1.0 | pJ23119-Bff | N21-Brr | 10 to 50 | 2 out of 3 |
| GE7 | (N21)aadA(N22)pMB1(pJ23119)gRNAnupG(N23)nupGHF1.5(N24)nupGHT1.5 | pJ23119-Bff | N21-Brr | 10 to 50 | 3 out of 3 |
| GE8 | (N21)aadA(N22)pMB1(pJ23119)gRNAmelB(N23)nupGHF1.0(N24)nupG-HT1.0 | pJ23119-Bff | N21-Brr | 10 to 50 | 3 out of 3 |
| GE9 | (N21)aadA(N22)pMB1(pJ23119)gRNArcsB(N23)nupGHF1.0(N24)nupGHT1.0 | pJ23119-Bff | N21-Brr | 2 | 1 out of 2 |
| GE10 | (N21)aadA(N22)pMB1(pJ23119)gRNAptsI(N23)ptsIHF0.7(N24)ptsIHT0.77 | pJ23119-Bff | N21-Brr | Over 100 | 1 out of 1 |
| IP1 | (N21)aadA(N22)p5(N23)lacIT7(RBS1)dxs(RBS2stop)idi(RBS3stop)ispA(RBS4stop)valC(N31)t7t | ACAY_ggatctcgacgctctccctt | N31-Brr | Over 100 | 5 out of 6 |
| IP2 | (N21)aadA(N22)p5(N23)lacIT7(RBS1)dxs(RBS2stop)idi(RBS3stop)valC(RBS4stop)ispA(N31)t7t | ACAY_ggatctcgacgctctccctt | N31-Brr | Over 100 | 6 out of 6 |

TABLE 11-continued

Plasmids and colony PCR

| Name | Plasmid constructed | Colony PCR forward oligos | Colony PCR reverse oligos | Colony number raised on the plate | Correct colony number out of tested |
|---|---|---|---|---|---|
| IP3 | (N21)aadA(N22)p5(N23)lacIT7(RBS1)dxs(RBS2stop)valC(RBS3stop)idi(RBS4stop)ispA(N31)t7t | ACAY__ggatctcgacgctctccctt | N31-Brr | Over 100 | 6 out of 6 |
| IP4 | (N21)aadA(N22)p5(N23)lacIT7(RBS1)dxs(RBS2stop)valC(RBS3stop)ispA(RBS4stop)idi(N31)t7t | ACAY__ggatctcgacgctctccctt | N31-Brr | Over 100 | 6 out of 6 |
| IP5 | (N21)aadA(N22)p5(N23)lacIT7(RBS1)dxs(RBS2stop)ispA(RBS3stop)valC(RBS4stop)idi(N31)t7t | ACAY__ggatctcgacgctctccctt | N31-Brr | Over 100 | 6 out of 6 |
| IP6 | (N21)aadA(N22)p5(N23)lacIT7(RBS1)dxs(RBS2stop)ispA(RBS3stop)idi(RBS4stop)valC(N31)t7t | ACAY__ggatctcgacgctctccctt | N31-Brr | Over 100 | 6 out of 6 |
| IP7 | (N21)aadA(N22)p5(N23)lacIT7(RBS1)idi(RBS2stop)dxs(RBS3stop)valC(RBS4stop)ispA(N31)t7t | ACAY__ggatctcgacgctctccctt | N31-Brr | Over 100 | 6 out of 6 |
| IP8 | (N21)aadA(N22)p5(N23)lacIT7(RBS1)idi(RBS2stop)dxs(RBS3stop)ispA(RBS4stop)valC(N31)t7t | G-idi F | N31-Brr | Over 100 | 5 out of 6 |
| IP9 | (N21)aadA(N22)p5(N23)lacIT7(RBS1)idi(RBS2stop)valC(RBS3stop)dxs(RBS4stop)ispA(N31)t7t | ACAY__ggatctcgacgctctccctt | N31-Brr | Over 100 | 6 out of 6 |
| IP10 | (N21)aadA(N22)p5(N23)lacIT7(RBS1)idi(RBS2stop)valC(RBS3stop)ispA(RBS4stop)dxs(N31)t7t | G-idi F | N31-Brr | Over 100 | 5 out of 6 |
| IP11 | (N21)aadA(N22)p5(N23)lacIT7(RBS1)idi(RBS2stop)ispA(RBS3stop)dxs(RBS4stop)valC(N31)t7t | G-idi F | ValC-R_tgtctcggatctcgtcgatc | Over 100 | 5 out of 6 |
| IP12 | (N21)aadA(N22)p5(N23)lacIT7(RBS1)idi(RBS2stop)ispA(RBS3stop)valC(RBS4stop)dxs(N31)t7t | G-idi F | N31-Brr | Over 100 | 5 out of 6 |
| IP13 | (N21)aadA(N22)p5(N23)lacIT7(RBS1)valC(RBS2stop)idi(RBS3stop)dxs(RBS4stop)ispA(N31)t7t | ValC-F_gaactacctgaagatccgaa | N31-Brr | Over 100 | 6 out of 6 |
| IP14 | (N21)aadA(N22)p5(N23)lacIT7(RBS1)valC(RBS2stop)idi(RBS3stop)ispA(RBS4stop)dxs(N31)t7t | ValC-F_gaactacctgaagatccgaa | N31-Brr | Over 100 | 4 out of 6 |
| IP15 | (N21)aadA(N22)p5(N23)lacIT7(RBS1)valC(RBS2stop)dxs(RBS3stop)idi(RBS4stop)ispA(N31)t7t | ValC-F_gaactacctgaagatccgaa | N31-Brr | Over 100 | 6 out of 6 |
| IP16 | (N21)aadA(N22)p5(N23)lacIT7(RBS1)valC(RBS2stop)dxs(RBS3stop)ispA RBS4stop)idi(N31)t7t | ACAY__ggatctcgacgctctccctt | N31-Brr | Over 100 | 6 out of 6 |
| IP17 | (N21)aadA(N22)p5(N23)lacIT7(RBS1)valC(RBS2stop)ispA(RBS3stop)dxs(RBS4stop)idi(N31)t7t | ValC-F_gaactacctgaagatccgaa | N31-Brr | Over 100 | 5 out of 6 |
| IP18 | (N21)aadA(N22)p5(N23)lacIT7(RBS1)valC(RBS2stop)ispA(RBS3stop)idi(RBS4stop)dxs(N31)t7t | ValC-F_gaactacctgaagatccgaa | N31-Brr | Over 100 | 3 out of 6 |
| IP19 | (N21)aadA(N22)p5(N23)lacIT7(RBS1)ispA(RBS2stop)idi(RB3stop)dxs(RBS4stop)valC(N31)t7t | ispA-F_atgacatcctggatgtggtg | N31-Brr | Over 100 | 5 out of 6 |
| IP20 | (N21)aadA(N22)p5(N23)lacIT7(RBS1)ispA(RBS2stop)idi(RBS3stop)valC(RBS4stop)dxs(N31)t7t | ACAY__ggatctcgacgctctccctt | N31-Brr | Over 100 | 6 out of 6 |
| IP21 | (N21)aadA(N22)p5(N23)lacIT7(RBS1)ispA(RBS2stop)dxs(RBS3stop)valC(RBS4stop)idi(N31)t7t | ACAY__ggatctcgacgctctccctt | N31-Brr | Over 100 | 6 out of 6 |
| IP22 | (N21)aadA(N22)p5(N23)lacIT7(RBS1)ispA(RBS2stop)dxs(RBS3stop)idi(RBS4stop)valC(N31)t7t | ispA-F_atgacatcctggatgtggtg | N31-Brr | Over 100 | 6 out of 6 |
| IP23 | (N21)aadA(N22)p5(N23)lacIT7(RBS1)ispA(RBS2stop)valC(RBS3stop)dxs(RBS4stop)idi(N31)t7t | ispA-F_atgacatcctggatgtggtg | N31-Brr | Over 100 | 4 out of 6 |
| IP24 | (N21)aadA(N22)p5(N23)lacIT7(RBS1)ispA(RBS2stop)valC(RBS3stop)idi(RBS4stop)dxs(N31)t7t | ValC-F_gaactacctgaagatccgaa | N31-Brr | Over 100 | 5 out of 6 |
| TP1 | (N21)aadA(N22)p5(N23)lacIT7(RBSB1)aroG mutant(RBS4stop)tyrA mutant(N31)t7t(N21) | RBS1-Bff | N31-Brr | Over 100 | 5 out of 6 |
| TP2 | (N21)aadA(N22)p15(N23)lacIT7(RBSB1)aroG mutant(RBS4stop)tyrA mutant(N31)t7t(N21) | RBS1-Bff | N31-Brr | Over 100 | 5 out of 6 |

TABLE 11-continued

Plasmids and colony PCR

| Name | Plasmid constructed | Colony PCR forward oligos | Colony PCR reverse oligos | Colony number raised on the plate | Correct colony number out of tested |
|---|---|---|---|---|---|
| TP3 | (N21)aadA(N22)pMB1(N23)lacIT7(RBSB1)aroG mutant(RBS4stop)tyrA mutant(N31)t7t(N21) | RBS1-Bff | N31-Brr | Over 100 | 6 out of 6 |
| TP4 | (N21)aadA(N22)pMB1 mutant(N23)lacIT7(RBSB1)aroG mutant(RBS4stop)tyrA mutant(N31)t7t(N21) | RBS1-Bff | N31-Brr | Over 100 | 5 out of 6 |
| TP5 | (N21)aadA(N22)p5(N23)pLac(RBSB1)aroG mutant RBS4stop)tyrA mutant(N31)t7t(LK3)LacI(N21) | G-pLac F | t7t-T R | 20 to 30 | 3 out of 6 |
| TP6 | (N21)aadA(N22)p15(N23)pLac(RBSB1)aroG mutant(RBS4stop)tyrA mutant(N31)t7t(LK3)LacI(N21) | G-pLac F | t7t-T R | 50 to 100 | 6 out of 6 |
| TP7 | (N21)aadA(N22)pMB1(N23)pLac(RBSB1)aroG mutant(RBS4stop)tyrA mutant(N31)t7t(LK3)LacI(N21) | G-pLac F | t7t-T R | 50 to 100 | 6 out of 6 |
| TP8 | (N21)aadA(N22)pMB1 mutant(N23)pLac(RBSB1)aroG mutant(RBS4stop)tyrA mutant(N31)t7t(LK3)LacI(N21) | G-pLac F | t7t-T R | 50 to 100 | 6 out of 6 |
| TP9 | (N21)aadA(N22)p5(N23)lacIT7(RBSB1)tyrA mutant(RBS4stop)aroG mutant(N31)t7t(N21) | RBS1-Bff | N31-Brr | Over 100 | 6 out of 6 |
| TP10 | (N21)aadA(N22)p15(N23)lacIT7(RBSB1)tyrA mutant(RBS4stop)aroG mutant(N31)t7t(N21) | RBS1-Bff | N31-Brr | Over 100 | 4 out of 6 |
| TP11 | (N21)aadA(N22)pMB1(N23)lacIT7(RBSB1)tyrA mutant(RBS4stop)aroG mutant(N31)t7t(N21) | RBS1-Bff | N31-Brr | Over 100 | 6 out of 6 |
| TP12 | (N21)aadA(N22)pMB1 mutant(N23)lacIT7(RBSB1)tyrA mutant(RBS4stop)aroG mutant(N31)t7t(N21) | RBS1-Bff | N31-Brr | Over 100 | 6 out of 6 |
| TP13 | (N21)aadA(N22)p5(N23)pLac(RBSB1)tyrA mutant(RBS4stop)aroG mutant(N31)t7t(LK3)LacI(N21) | G-pLac F | t7t-T R | 10 to 20 | 6 out of 6 |
| TP14 | (N21)aadA(N22)p15(N23)pLac(RBSB1)tyrA mutant(RBS4stop)aroG mutant(N31)t7t(LK3)LacI(N21) | G-pLac F | t7t-T R | 50 to 100 | 4 out of 6 |
| TP15 | (N21)aadA(N22)pMB1(N23)pLac(RBSB1)tyrA mutant(RBS4stop)aroG mutant(N31)t7t(LK3)LacI(N21) | G-pLac F | t7t-T R | 50 to 100 | 6 out of 6 |
| TP16 | (N21)aadA(N22)pMB1 mutant(N23)pLac(RBSB1)tyrA mutant(RBS4stop)aroG mutant(N31)t7t(LK3)LacI(N21) | G-pLac F | t7t-T R | 50 to 100 | 6 out of 6 |

TABLE 12

Transformed strains and introduced plasmids

| Name | Strains genotype | Plasmids |
|---|---|---|
| IPS1 | MG1655_ΔrecA_ΔendA_DE3 | IP1 |
| IPS2 | MG1655_ΔrecA_ΔendA_DE3 | IP2 |
| IPS3 | MG1655_ΔrecA_ΔendA_DE3 | IP3 |
| IPS4 | MG1655_ΔrecA_ΔendA_DE3 | IP4 |
| IPS5 | MG1655_ΔrecA_ΔendA_DE3 | IP5 |
| IPS6 | MG1655_ΔrecA_ΔendA_DE3 | IP6 |
| IPS7 | MG1655_ΔrecA_ΔendA_DE3 | IP7 |
| IPS8 | MG1655_ΔrecA_ΔendA_DE3 | IP8 |
| IPS9 | MG1655_ΔrecA_ΔendA_DE3 | IP9 |
| IPS10 | MG1655_ΔrecA_ΔendA_DE3 | IP10 |
| IPS11 | MG1655_ΔrecA_ΔendA_DE3 | IP11 |
| IPS12 | MG1655_ΔrecA_ΔendA_DE3 | IP12 |
| IPS13 | MG1655_ΔrecA_ΔendA_DE3 | IP13 |
| IPS14 | MG1655_ΔrecA_ΔendA_DE3 | IP14 |
| IPS15 | MG1655_ΔrecA_ΔendA_DE3 | IP15 |
| IPS16 | MG1655_ΔrecA_ΔendA_DE3 | IP16 |
| IPS17 | MG1655_ΔrecA_ΔendA_DE3 | IP17 |
| IPS18 | MG1655_ΔrecA_ΔendA_DE3 | IP18 |
| IPS19 | MG1655_ΔrecA_ΔendA_DE3 | IP19 |
| IPS20 | MG1655_ΔrecA_ΔendA_DE3 | IP20 |
| IPS21 | MG1655_ΔrecA_ΔendA_DE3 | IP21 |
| IPS22 | MG1655_ΔrecA_ΔendA_DE3 | IP22 |
| IPS23 | MG1655_ΔrecA_ΔendA_DE3 | IP23 |
| IPS24 | MG1655_ΔrecA_ΔendA_DE3 | IP24 |
| TPS1 | MG1655_ΔrecA_ΔendA_ΔpheA_ΔtyrR_DE3 | TP1 |
| TPS2 | MG1655_ΔrecA_ΔendA_ΔpheA_ΔtyrR_DE3 | TP2 |
| TPS3 | MG1655_ΔrecA_ΔendA_ΔpheA_ΔtyrR_DE3 | TP3 |
| TPS4 | MG1655_ΔrecA_ΔendA_ΔpheA_ΔtyrR_DE3 | TP4 |
| TPS5 | MG1655_ΔrecA_ΔendA_ΔpheA_ΔtyrR_DE3 | TP5 |
| TPS6 | MG1655_ΔrecA_ΔendA_ΔpheA_ΔtyrR_DE3 | TP6 |
| TPS7 | MG1655_ΔrecA_ΔendA_ΔpheA_ΔtyrR_DE3 | TP7 |
| TPS8 | MG1655_ΔrecA_ΔendA_ΔpheA_ΔtyrR_DE3 | TP8 |
| TPS9 | MG1655_ΔrecA_ΔendA_ΔpheA_ΔtyrR_DE3 | TP9 |
| TPS10 | MG1655_ΔrecA_ΔendA_ΔpheA_ΔtyrR_DE3 | TP10 |
| TPS11 | MG1655_ΔrecA_ΔendA_ΔpheA_ΔtyrR_DE3 | TP11 |
| TPS12 | MG1655_ΔrecA_ΔendA_ΔpheA_ΔtyrR_DE3 | TP12 |
| TPS13 | MG1655_ΔrecA_ΔendA_ΔpheA_ΔtyrR_DE3 | TP13 |
| TPS14 | MG1655_ΔrecA_ΔendA_ΔpheA_ΔtyrR_DE3 | TP14 |
| TPS15 | MG1655_ΔrecA_ΔendA_ΔpheA_ΔtyrR_DE3 | TP15 |
| TPS16 | MG1655_ΔrecA_ΔendA_ΔpheA_ΔtyrR_DE3 | TP16 |

TABLE 13

Transformed strains and introduced plasmids with PCR primers used for colony PCR

| E. coli strains with expected genotype modifications | Plasmids used | Colony PCR forward and reverse oligos | Sequence |
| --- | --- | --- | --- |
| MG1655_ΔrecA_ΔendA_ΔaslA_DE3 | GE1 | aslA screening 4F/4R | TGGAACAACAGGCATGGATT (SEQ ID NO: 221)/ ACAGGCGAAATATGGTGCT (SEQ ID NO: 222) |
| MG1655_ΔrecA_ΔendA_ΔaslA_DE3 | GE2 | aslA screening 4F/4R | TGGAACAACAGGCATGGATT (SEQ ID NO: 221/ ACAGGCGAAATATGGTGCT (SEQ ID NO: 222) |
| MG1655_ΔrecA_ΔendA_ΔnupG_DE3 | GE3 | nupG screening 2F/2R | GGAAATATGGCGTTGATGAG (SEQ ID NO: 223/ AGGATTATCCGACATCAGTG (SEQ ID NO: 224) |
| MG1655_ΔrecA_ΔendA_ΔpheA_DE3 | GE4 | pheA screening F/R | TCATCAAATATGGCTCGCTT (SEQ ID NO: 225)/ TCGAGCGGCTGATATTGTTG (SEQ ID NO: 226) |
| MG1655_ΔrecA_ΔendA_ΔpheA_ΔtyrR_DE3 | GE5 | tyrR screening F/R | AACGCTGGTATGCCTCAATC (SEQ ID NO: 227)/ AGGCTTCCTCGAATACCTTA (SEQ ID NO: 228) |
| MG1655_ΔrecA_ΔendA_ΔnupG_DE3 | GE6 | nupG screening 4F/4R | TATTGTGCCTATGTGGCTTC (SEQ ID NO: 229)/ CGAATAAAGTGGTGACGAATG (SEQ ID NO: 230) |
| MG1655_ΔrecA_ΔendA_ΔnupG_DE3 | GE7 | nupG screening 4F/4R | TATTGTGCCTATGTGGCTTC (SEQ ID NO: 229)/ CGAATAAAGTGGTGACGAATG (SEQ ID NO: 230) |
| MG1655_ΔrecA_ΔendA_ΔmelB_DE3 | GE8 | melB screening 2F/2R | GTAAGCGGCATGGTCTGGAAC (SEQ ID NO: 231)/ GCAGGCCGTATGGACTCCTA (SEQ ID NO: 232) |
| MG1655_ΔrecA_ΔendA_ΔrcsB_DE3 | GE9 | rcsB screening 3F/3R | AACTGGCGAATCAGGCAGA (SEQ ID NO: 233)/ GCGATTATCTCTCTATCCGT (SEQ ID NO: 234) |
| MG1655_ΔrecA_ΔendA_ΔptsH_ptsI_crr_DE3 | GE10 | ptsH/I_crr screening F/R | AGACCGATCTTATCTCTGTC (SEQ ID NO: 235)/ TAGTGTAATGACCAGACAAA (SEQ ID NO: 236) |

Cell Culture, GCMS and HPLC Measurement

Valencene-producing E. coli will be screened in test tubes. Single colony will be inoculated into LB medium, and cultured overnight at 37° C. and 250 rpm. The overnight grown cell suspension was diluted 100-fold by using K3 medium[25], and cultured at 30° C. and 250 rpm until cell density reached 0.5-1.0 (OD600), at which proper amount of inducers (IPTG, 100 mM) was added to final concentration to be 0, 0.005 and 0.1 mM. One milliliter of the induced cells will be transferred to a 14 mL round-bottom falcon tube, and 200 microliters of dodecane was added. The tube will be incubated at 30° C. and 250 rpm for 72 h. Spectinomycin was added to both seed culture to be 50 microgram per milliliter in seed medium (LB) and culture medium (K3 medium). At the end of incubation, 8 microliters of dodecane phase will be drawn and diluted with 800 microliters of ethyl acetate. One microliter of the mixture will be injected into GCMS for analysis of valencene. GCMS measurement condition: Agilent HP-5 ms column. The program for valencene is 100° C. for 1 min, ramping up to 190° C. at 110° C. per minute, ramping up to 220° C. at 5° C. per minute, ramping up to 280° C. at 60° C. per minute, and hold it for 2 minutes. Helium is used as carrier gas at 1 milliliter per minute. Mass spectrometry is operated at scan mode (40-400 m/z). Quantification of valencene with calibration was done by using standards.

Tyrosine-producing E. coli will be screened in test tubes. Single colony will be inoculated into LB medium, and cultured overnight at 37° C. and 250 rpm. The overnight grown cell suspension was diluted 100-fold by using K3 medium, and cultured at 30° C. and 250 rpm until cell density reached 0.5-1.0 (OD600), at which proper inducers (IPTG, 100 mM) was added to final concentration to be 0.1 mM. One milliliter of the induced cells will be transferred to a 14 mL round-bottom falcon tube. The tube will be incubated at 30° C. and 250 rpm for 84 h. Spectinomycin was added to both seed culture to be 50 microgram per milliliter in seed medium (LB) and culture medium (K3 medium). At the end of incubation, 100 microliters of 6 M HCl will be added to 1 milliliter cell culture broth to dissolve precipitation of tyrosine at 37° C. and 250 rpm for 30 minutes, then 150 microliters obtained cell suspension was diluted with 450 microliters of 0.1 M HCl, and centrifuged at 12,000 rpm for 5 minutes. 2 microliter of the supernatant will be injected into HPLC for analysis of tyrosine. HPLC measurement condition: Agilent C18 column. The mobile phase is 10% (v/v) of acetonitrile and 90% (v/v) of 0.1% (v/v) trifluoroacetic acid, a flow rate of mobile phase is 0.4 milliliter per minute and column temperature is set at 30° C., and run for 15 minutes. Detector sets as UV absorbance at 254 nm.

Genome Editing of E. coli

Based on a two-plasmid CRISPR system for E. coli[13], the procedure from reported method was further simplified. An isolated colony from plate, which was prepared from glycerol stock of E. coli MG1655_DE3 cell carrying plasmid of pCAS, was inoculated to 5 milliliters of LB at 30° C. and 200 rpm for overnight, and 50 microgram per milliliter kanamycin was added to maintain the plasmid of pCAS. Transfer 100 microliters overnight grown cell suspension to 10 milliliters LB with 150 mM L-arabinose and 50 microgram per milliliter kanamycin at 30° C. and 200 rpm to OD600 of 0.55 (approximately 2.5-3 h), then spin at 6,000 rpm for 10 minutes at room temperature. Resuspend the cell pellet with 1 milliliter of ice-cold ultrapure water, and transfer to a chilled 1.5 milliliters Eppendorf tube and incubated at ice for 5 minutes. Spin at 10,000 g for 15 seconds at room temperature, resuspend and wash the cells twice with 1 milliliter of ice-cold ultrapure water. Resuspend the cell pellet in a final volume of 100 microliters as electrocompetent cells. Mix 100 to 200 nanogram of plasmids with 50 microliters of electrocompetent cells, and chill on ice for 5 minutes. Electroporation was operated at 1.8 kV. Immediately add 600 microliters of SOC medium after electroporation, and transfer the cells to a 1.7 milliliters Eppendorf tube. Incubate cell resuspension at 30° C. for 2 hours. Spread all recovered cells onto LB plate containing double antibiotics (100 microgram per milliliter ampicillin plus 50 microgram per milliliter kanamycin, or 50 microgram per milliliter spectinomycin plus 50 microgram per milliliter kanamycin), then incubated at 30° C. for 48 hours. Colony PCR was performed to evaluate the efficiency of gene deletion and insertion, and all used strains and oligos are list in Tables 12 and 13.

Example 4: Discussion

A critical step in adding barcodes to sides of fragment is to ensure that any standardized barcode can be added to side of any standardized fragment. Theoretically, blunt end ligation could be used to add two barcodes to sides of any fragment, but it may be difficult to control to which side of fragment a barcode will be added. As a result, in an existing DNA assembly standard (BASIC[8]), barcodes were added to fragments by using sticky end ligation to gain the specificity. However, use of sticky end based ligation required both barcodes and fragments to have conserved sticky end sequences on their sides, to ensure compatibility between any barcode-fragment pair. And, such conserved sequences remained in the final construct and became scars, which may be 4-6 nt long. Such scar would result in extra amino in protein if it exists in protein-coding sequence; it would also make function of nearby BPs to be less predictable when it is in non-coding sequence[9].

With sticky end ligation, the traditional DNA assembly is dependent upon restriction enzyme digestion to generate SE (BioBricks assembly[4], Golden gate[15] and BASIC[7])—their length is usually 4 nt—resulting in an at least 4 bp scar left between BPs. These scars would introduce extra amino acids to proteins' and extra nucleotides to transcription regulatory regions[16]. For example, BASIC method[7] leaves scar 'GTCC' in front of, and scar 'GGCTCG' behind, protein-coding sequence (FIG. 9), i.e. an extra serine will be added to the N terminus ('TCC' encodes serine), and an extra glycine and serine will be added to the C terminus ('GGC' and 'TCG' encode glycine and serine respectively). Recently, an automatic design algorithm for DNA assembly, called J5, was invented to reduce scar in combinatorial DNA assembly[6], in which several DNA assembly methods were combined systematically, but it still left scar in final construct and also needed to avoid forbidden sequence, because they used type II restriction enzymes. Here, the UDS BPs and the innovative barcoding method has managed to avoid scars in most cases.

An important feature of UDS is that a new fragment formed by assembly of existing fragments and barcodes (we term them as composite fragments) can be readily used in a new round of plasmid construction (FIG. 1). In fact, they can just be treated as regular fragments, providing maximal flexibility in reusing composite fragments. On the contrary, existing multi-tier standards always have strict hierarchy: there are a few tiers of parts and parts in a tier can only be assembled with the ones in the same tier[17].

We foresee the method developed here to be a powerful tool in biotechnology. With a small library of UDS BPs, we have demonstrated three applications and the possibility of creating versatile plasmids from standardized BPs. The impact of UDS will become much larger when the size of UDS library increases and the population of researchers using it grows. UDS fragments, once barcoded, can also be assembled by any assembly method, including but not limited to SLIC[18], Gibson[19], USER[20], MODAL and DNA assembler[22]. This feature reduces the activation energy for researchers to adopt UDS BPs, because they can continue to use the DNA assembly method they are familiar with.

Example 5: The Three Rules and Workflow of GTas

In this example, GTas has three rules: (1) any DNA sequence longer than 35 nucleotides (nt), starting with 'G' and ending with 'T' can be defined as a fragment; (2) any DNA sequence longer than 20 nt and shorter than 80 nt can be defined as a barcode; (3) in plasmid construction any fragment must be placed after a barcode, and any barcode must be placed after a fragment. Because the first two rules are very easy to satisfy, most functional DNA sequences can be defined as fragment and/or barcode (examples are provided in FIG. 10a). To construct a plasmid, each end of a fragment is first connected to half of a barcode, which has a complementary half that is connected to another fragment. The barcoded fragments are then assembled into a plasmid in a specific order based on pairing of barcode halves (FIG. 10a). This workflow always satisfies the third rule.

A basic requirement of any standard system is compatibility. In this context, it means any barcode can be placed after any fragment, which enables arrangement of fragments and barcodes in any order as long as the third rule is met. To have such compatibility, one has to conserve nucleotides at fragment ends to ensure their standard connections to any barcodes. A key innovation of this work is that we managed to minimize the length of conserved sequence at each end to be one nt, which is the minimal length of any conserved sequence.

Having longer conserved sequence constrains flexible use of fragments. For example, if a fragment is a protein coding sequence and the conserved sequence at its 3' end is 'TAG' (a stop codon), it is impossible to fuse a fluorescence protein to its C-terminus to study its cellular localization, because translation terminates at the stop codon; in GTas, the conserved sequence at 3' end is 'T', which can be used to create 16 codons (including stop and nonstop codons) by connecting different barcodes to this end (FIG. 10b). This example also explains why we selected 'T' as conserved sequence at 3' end of fragment. Similarly, we chose 'G' as conserved sequence at 5' end of fragment, because it can be used to encode 'ATG' (a start codon) or another 15 codons that end with 'G' (FIG. 10b). An experimental validation of this flexibility is provided in FIG. 16. Because of this flexibility, GTas almost eliminates scars, which often interfere with function of DNA parts by adding extra, undesired codons to coding sequence and/or incurring undesired DNA-protein interaction[31].

To connect halves of two barcodes to designated ends of a fragment (this process is defined as barcoding), one needs to use DNA ligation techniques based on sticky DNA ends, which on fragment are derived from the conserved DNA sequences, and which on barcodes are added as standard connectors (FIG. 10c). Since the conserved sequence length is one nt in GTas, the corresponding sticky end length is one nt. A major challenge we faced was that DNA ligation based on such short sticky ends was inefficient, if we used the conventional method, in which two oligos were annealed to form one barcode half with a one nt overhang (FIG. 11a and FIG. 17). We assessed ligation efficiency by using PCR: we attempted to amplify the barcoded fragments from the ligation product by using two oligos that only bind the barcode halves—PCR would only be successful if enough sticky ends are ligated. In a test run with barcoding five fragments (FIG. 11e), although correct PCR products were observed on agarose gel after electrophoresis, undesired PCR products (in the form of smear) were also observed (FIG. 11c). When we further attempted to assemble the five barcoded fragments (each of which was excised from the gel to remove as much undesired products as possible) into a plasmid, we only obtained a few colonies and sequencing the plasmids they contained also revealed that a large fraction of the plasmids had duplication of some barcode halves (FIGS. 11f and 11g). We tried the same procedure with another two plasmids, each of which was also assembled from five fragments, and we obtained similar, negative results (FIG. 11g and FIG. 18b).

The duplication of barcode halves suggested that two barcode halves were ligated to one side of some fragments in a tandem manner. We hypothesized that if we sealed the blunt end of each barcode halve by connecting the two strands with a few extra nucleotides, this problem could be solved, because the barcoded fragments would be circular DNA molecule, leaving no end for additional barcode halve to attach (FIG. 11b). Essentially, each barcode half would be created by using one oligo that has a stem-loop secondary structure (such oligo is termed as Boligo, barcoding oligo). With this new design, we repeated construction of the same plasmids. We found that most undesired PCR products were eliminated (FIG. 11d). More importantly, the number of colonies we obtained from the subsequent plasmid construction was ~100 fold higher than that from the conventional method (FIG. 11f), and the plasmids these colonies contained were confirmed to be correct by sequencing in all our tests (FIG. 11g and FIG. 18b).

In this workflow, fragment was usually generated by amplifying a template DNA by using two oligos that had phosphorothioate (PS) bond after their first nucleotide at 5' end (FIG. 10c and FIG. 11b, design principle: FIG. 12f). The PS bonds were incorporated into fragment after PCR and can be cleaved by using a simple chemical reaction to generate the one nt sticky ends (FIG. 10c). The oligo used in this step is termed as Foligo (fragment-creating oligo). Fragments less than 90 nt can also be generated by annealing two oligos, and this process also added the sticky ends to fragments because of the oligo design (FIG. 19). These oligos are termed as Noligos (Non-modified oligos for creating fragments). Barcoded fragments can be activated by introducing PS bonds to specific locations of barcodes through PCR (FIG. 10c, this is the PCR that we used to assess ligation efficiency). PS oligos are needed in this process, but they are standard parts—each oligo is associated with a barcode and can be used to amplify any fragment flanked by the barcode. Chemically cleaving the PS bonds in the PCR products generates long sticky ends (15 to 20 nt), which can be accurately annealed and ligated at elevated temperature by using thermophilic ligase (FIG. 10c and FIG. 20). Such PS oligo is termed as Aoligo (Assembling oligo, FIG. 12c).

Example 6: Construction of Plasmids

We have successfully constructed 370 plasmids (P1 to P370) by using this workflow (FIG. 21) for various projects from an expanding library of fragments and barcodes (Table 14 and 15). The accuracy was 86% based on Sanger sequencing, and the accuracy did not substantially change when plasmid length (2.43-13.04 kb) and the number of fragments used in plasmid construction (2-7) varied (FIG. 10d). This large set of validation data proved that this workflow of GTas is reliable and robust. In comparison, the averaged accuracy of BASIC method was only 50% when six fragments were assembled and one antibiotic was used[7].

TABLE 14

List of fragments, Foligos and Noligos used in this study

| SN Foligos | Fragment | Forward Foligo name | Forward Foligo sequence (*: phosphorothioate bond) | Reverse Foligo name | Reverse Foligo sequence (*: phosphorothioate bond) | Templates | Annotation |
|---|---|---|---|---|---|---|---|
| 1 | gRNA-nupG | G-gRNA-nupG F | G*tacgagttaatcaatatcacattttagagctagaaatag (SEQ ID NO: 1) | gRNA-T R | A*tctagagaattcaaaaaag (SEQ ID NO: 2) | pTarget from Addgene | guide RNA_Spacer is indicaed as bold |
| 2 | gRNA-aslA | G-gRNA-as A F | G*tgcagaacttgagaaaaaaacttttagagctagaaatag (SEQ ID NO: 3) | gRNA-T R | A*tctagagaattcaaaaaag (SEQ ID NO: 2) | pTarget from Addgene | guide RNA_Spacer is indicaed as bold |
| 3 | gRNA-melB | G-gRNA-me B F | G*tctaccatttgttaattatgtttttagagctagaaatag (SEQ ID NO: 4) | gRNA-T R | A*tctagagaattcaaaaaag (SEQ ID NO: 2) | pTarget from Addgene | guide RNA_Spacer is indicaed as bold |
| 4 | gRNA-rcsB | G-gRNA-rcsB F | G*taatcacttgagcaaattgagttttagagctagaaatag (SEQ ID NO: 5) | gRNA-T R | A*tctagagaattcaaaaaag (SEQ ID NO: 2) | pTarget from Addgene | guide RNA_Spacer is indicaed as bold |
| 5 | gRNA-tyrR | G-gRNA-tyrR F | G*ttttaataccgagcgttcaaaattttagagctagaaatag (SEQ ID NO: 6) | gRNA-T R | A*tctagagaattcaaaaaag (SEQ ID NO: 2) | pTarget from Addgene | guide RNA_Spacer is indicaed as bold |

TABLE 14-continued

List of fragments, Foligos and Noligos used in this study

| | | | | | | | |
|---|---|---|---|---|---|---|---|
| 6 | gRNA-pheA | G-gRNA-pheA F | G*ttttgagcaattcattgaaagttttagagctagaaatag (SEQ ID NO: 7) | gRNA-T R | A*tctagagaattcaaaaaaag (SEQ ID NO: 2) | pTarget from Addgene | guide RNA_Spacer is indicaed as bold |
| 7 | gRNA-ptsI | G-gRNA-ptsI F | G*tgaagttgatttctttagtatttttagagctagaaatag (SEQ ID NO: 8) | gRNA-T R | A*tctagagaattcaaaaaaag (SEQ ID NO: 2) | pTarget from Addgene | guide RNA_Spacer is indicaed as bold |
| 8 | gRNA-xylB | G-gRNA-xylB F | G*tataatactttgtcgatttgattttagagctagaaatag (SEQ ID NO: 237) | gRNA-T R | A*tctagagaattcaaaaaaag (SEQ ID NO: 2) | pTarget from Addgene | guide RNA_Spacer as bold |
| 9 | gRNA-manZ | G-gRNA-manZ F | G*ttttaacgatatcgataccttttttagagctagaaatag (SEQ ID NO: 238) | gRNA-T R | A*tctagagaattcaaaaaaag (SEQ ID NO: 2) | pTarget from Addgene | guide RNA_Spacer is indicaed as bold |
| 10 | gRNA-glk | G-gRNA-glk F | G*taatcgttaataatttccagattttagagctagaaatag (SEQ ID NO: 239) | gRNA-T R | A*tctagagaattcaaaaaaag (SEQ ID NO: 2) | pTarget from Addgene | guide RNA_Spacer is indcaed as bold |
| 11 | nupG-HF0.5 | G-nupG-HF0.5 F | G*ttgatcctgccagcaata (SEQ ID NO: 1) | nupG-HF0.5-T R | A*catcgtgatgcggatgag (SEQ ID NO: 10) | E. coli genomic DNA | Upstream homologous sequence |
| 12 | nupG-HF1.0 | G-nupG-HF1.0 F | G*accatcgccgggacagaacc (SEQ ID NO: 250) | nupG-HF1.0-T R | Same to nupG-HF0.5-T R | E. coli genomic DNA | Upstream homologous sequence |
| 13 | nupG-HF1.5 | G-nupG-HF1.5 F | G*tgcaacgtgaagcagaaggt SEQ ID NO: 12) | nupG-HF1.5-T R | Same to nupG-HF0.5-T R | E. coli genomic DNA | Upstream homologous sequence |
| 14 | aslA-HF0.5 | G-aslA-HF0.5 F | G*caccgtaaacggctctgc (SEQ ID NO: 13) | aslA-HF0.5-T R | A*gtttcatgtcatcaaatg (SEQ ID NO: 14) | E. coli genomic DNA | Upstream homologous sequence |
| 15 | aslA-HF1.0 | G-aslA-HF1.0 F | G*ccagtacgacgatcgcct (SEQ ID NO: 15) | aslA-HF1.0-T R | Same to aslA-HF0.5-T R | E. coli genomic DNA | Upstream homologous sequence |
| 16 | melB-HF1.0 | G-melB-HF1.0 | G*cccaatggcgatgaatacct (SEQ ID NO: 16) | melB-HF1.0-T R | A*gctgttaccaacgcccgcct (SEQ ID NO: 17) | E. coli genomic DNA | Upstream homologous sequence |
| 17 | rcsB-HF1.0 | G-rcsB-HF1.0 F | G*gttagcgaacatgcttgcgg (SEQ ID NO: 18) | rcsB-HF1.0-T R | A*ttgctacagcaagctcttga (SEQ ID NO: 19) | E. coli genomic DNA | Upstream homologous sequence |
| 18 | tyrR-HF0.5 | G-tyrR-HF0.5 F | G*cagcccgctggcgttggt (SEQ ID NO: 20) | tyrR-HF0.5-T R | A*gtcagcacccgatattgcat (SEQ ID NO: 21) | E. coli genomic DNA | Upstream homologous sequence |
| 19 | pheA-HF0.5 | G-pheA-HF0.5 F | G*catgtcgcagaccgtctcg (SEQ ID NO: 22) | pheA-HF0.5-T R | A*cgaaacgcctcccattcag (SEQ ID NO: 23) | E. coli genomic DNA | Upstream homologous sequence |
| 20 | ptsI-HF0.7 | G-ptsI-HF0.7 F | G*gcccgcataaaattcaggg (SEQ ID NO: 24) | ptsI-HF0.7-T R | A*ggaactaaagtctagcctgg (SEQ ID NO: 25) | E. coli genomic DNA | Upstream homologous sequence |
| 21 | manZ-HF0.5 | G-manZ-HF0.5 F | G*cgggccaggtactgaccatc (SEQ ID NO: 240) | manZ-HF0.5-T R | A*tagtccagttcgttatcgag (SEQ ID NO: 241) | E. coli genomic DNA | Upstream homologous sequence |
| 22 | glk-HF0.5 | G-glk-HF0.5 F | G*cgcagagggcggaaccggtg (SEQ ID NO: 242) | glk-HF0.5-T R | A*cgctaaagtcaaataattc (SEQ ID NO: 243) | E. coli genomic DNA | Upstream homologous sequence |
| 23 | xylB-HF0.5 | G-xylB-HF0.5 F | G*cgtggcgatgcgcaactg (SEQ ID NO: 244) | xylB-HF0.5-T R | A*agatctatcccgatatacat (SEQ ID NO: 245) | E. coli genomic DNA | Upstream homologous sequence |

TABLE 14-continued

List of fragments, Foligos and Noligos used in this study

| | | | | | | | |
|---|---|---|---|---|---|---|---|
| 24 | nupG-HT0.5 | G-nupG-HT0.5 F | G*ttacgcaaagaaaaacgg (SEQ ID NO: 26) | nupG-HT0.5-T R | A*gccgctggttgaggtgtt (SEQ ID NO: 27) | E. coli genomic DNA | Downstream homologous sequence |
| 25 | nupG-HT1.0 | G-nupG-HT1.0 F | Same to G-nupG-HT0.5 F | nupG-HT1.0-T R | A*acgcctttatgctccatgct (SEQ ID NO: 28) | E. coli genomic DNA | Downstream homologous sequence |
| 26 | nupG-HT1.5 | G-nupG-HT1.5 F | Same to G-nupG-HT0.5 F | nupG-HT1.5-T R | A*gcgacgccggtctatctga (SEQ ID NO: 29) | E. coli genomic DNA | Downstream homologous sequence |
| 27 | aslA-HT0.5 | G-aslA-HT0.5 F | G*ccggcgctatcgctgag (SEQ ID NO: 30) | aslA-HT0.5-T R | A*cactatgtttatccgcaa (SEQ ID NO: 31) | E. coli genomic DNA | Downstream homologous sequence |
| 28 | aslA-HT1.0 | G-aslA-HT1.0 F | Same to G-aslA-HT0.5 F | aslA-HT1.0-T R | A*gcccgcctgagatccaca (SEQ ID NO: 32) | E. coli genomic DNA | Downstream homologous sequence |
| 29 | melB-HT1.0 | G-melB-HT1.0 F | G*gtgcagtgagtgatgtgaaa (SEQ ID NO: 33) | melB-HT1.0-T R | A*gggtatggaagctatctga (SEQ ID NO: 34) | E. coli genomic DNA | Downstream homologous sequence |
| 30 | rcsB-HT1.0 | G-rcsB-HT1.0 F | G*tcacctgtaggccagataag (SEQ ID NO: 35) | rcsB-HT1.0-T R | A*attcagaaccgggaatgggc (SEQ ID NO: 36) | E. coli genomic DNA | Downstream homologous sequence |
| 31 | tyrR-HT0.5 | G-tyrR-HT0.5 F | G*gcgcgaatatgcctgatg (SEQ ID NO: 37) | tyrR-HT0.5-T R | A*catcccgcaggcgggtag (SEQ ID NO: 38) | E. coli genomic DNA | Downstream homologous sequence |
| 32 | pheA-HT0.5 | G-pheA-HT0.5 F | G*ttactggcgattgtcattcg (SEQ ID NO: 39) | pheA-HT0.5-T R | A*aaatgggccattacaggcc (SEQ ID NO: 40) | E. coli genomic DNA | Downstream homologous sequence |
| 33 | ptsI-HT0.7 | G-ptsI-HT0.7 F | G*agcgcatcacttccagtac (SEQ ID NO: 41) | ptsI-HT0.7-T R | A*taacgataagagtagggcac (SEQ ID NO: 42) | E. coli genomic DNA | Downstream homologous sequence |
| 34 | manZ-HT0.5 | G-manZ-HT0.5 F | G*gactgttgtacactaccggg (SEQ ID NO: 246) | manZ-HT0.5-T R | A*acgagaagcttataaatttt (SEQ ID NO: 247) | E. coli genomic DNA | Downstream homologous sequence |
| 35 | glk-HT0.5 | G-glk-HT0.5 F | G*atccttcctttttatatcggg (SEQ ID NO: 248) | glk-HT0.7-T R | A*gcccgcagcgttttttaattg (SEQ ID NO: 249) | E. coli DNA | Downstream homologus sequence |
| 36 | xylB-HT0.5 | G-xylB-HT0.5 F | G*acgttatcccctgcctga (SEQ ID NO: 250) | xylB-HT0.5-T R | A*cgaaacaaacgcatttga (SEQ ID NO: 251) | E. coli genomic DNA | Downstream homologous sequence |
| 37 | SpectR | G-spectR F | G*tcgacctgcagaagctt (SEQ ID NO: 43) | spectR-T R | A*cgttaagggattttggt (SEQ ID NO: 44) | pTarget from Addgene | Antibiotic resistance gene |
| 38 | AmpR | G-ampR F | G*tttctacaaactctttt (SEQ ID NO: 45) | G-ampR F | Same to spectR-T R | p5T7-eGFP from this lab | Antibiotic resistance gene |
| 39 | pSC101 | G-repA/p5 F | G*ccgttttcatctgtgcatat (SEQ ID NO: 46) | repA/p5-T R | A*tccttttgtaatactgcgga (SEQ ID NO: 47) | p5T7-eGFP from this lab | Replication origin-low copy number |
| 40 | pAC | G-p15A F | G*tgttcagctactgacgg (SEQ ID NO: 48) | p15A-T R | A*gacatcaccgatgggga (SEQ ID NO: 49) | pACmini-B2B3 from this lab | Replication origin-medium copy number |

TABLE 14-continued

List of fragments, Foligos and Noligos used in this study

| | | | | | | |
|---|---|---|---|---|---|---|
| 41 | pMB1 | G-pMB1 F | G*agttttcgttccactga (SEQ ID NO: 50) | pMB1-T R | A*ggatccagcatatgcgg (SEQ ID NO: 51) | pTarget from Addgene | Replication origin-medium copy number |
| 42 | pUC | G-pUC F | G*gctcactcaaaggcggta (SEQ ID NO: 52) | pUC-T R | A*attaccgcctttgagtga (SEQ ID NO: 53) | pUC19 from NEB | Replication origin-high copy number |
| 43 | pLac | G-pLac F | G*caacgcaattaatgtgagt (SEQ ID NO: 54) | pLac-T R | A*tttgttatccgctcacaatt (SEQ ID NO: 55) | pUC19 from NEB | Promoter |
| 44 | pthrC3 | G-pthrC3 F | G*agcttttcattctgactgcaa (SEQ ID NO: 252) | pthrC3-T R | A*ggttgttacctcgttacctt (SEQ ID NO: 253) | E.coli genomic DNA | Promoter |
| 45 | LacIPT7 | G-lacIT7 F | G*gaaactacccataatacaag (SEQ ID NO: 56) | LacIT7-T R | A*gagggaattgttatccgct cacaattcccctatagtga (SEQ ID NO: 57) | pET11a-eGFP from this lab | Promoter with LacI repressor coding sequence |
| 46 | t7t | G-t7t F | G*ggctgctaacaaagccc (SEQ ID NO: 58) | t7t-T R | A*ggcaccgtcaccctggat (SEQ ID NO: 59) | pET11a-eGFP from this lab | Terminator |
| 47 | LacI | G-lacI F | Same to G-lacIT7 F | lacI-T R | A*tcccggacaccatcgaat (SEQ ID NO: 60) | pET11a-eGFP from this lab | Coding sequence |
| 48 | tyrR mutant | G-tyrR mutant F | G*gttgctgaattgaccgcatt (SEQ ID NO: 69) | tyrR mutant-T R | A*ctggcgattgtcattcgc (SEQ ID NO: 70) | pACmini-tyrR mutant/ met5 3-Ile_ Ala354-Val from this lab | Coding sequence |
| 49 | aroG mutant | G-aroG mutant F | G*aattatcagaacgacgattt (SEQ ID NO: 71) | aroG mutant-T R | A*cccgcgacgcgctttta (SEQ ID NO: 72) | pACmini-aroG mutant/ aroG Asp146-Asn from this lab | Coding sequence |
| 50 | tal | G-tal F | G*acccaggttgttgaacgtca (SEQ ID NO: 254) | tal-T R | A*gccaaaatctttaccatc tgcttc (SEQ ID NO: 255) | Synthetic DNA from IDT | Coding sequence |
| 51 | eGFP | G-eGFP F | G*agcaaggcgaggagctgtt (SEQ ID NO: 256) | eGFP-T R | 3A*cttgtacagctcgtccatgc (SEQ ID NO: 257) | pET11a-eGFP from this lab | Coding sequence |
| 52 | ppsA | G-ppsA F | G*tccaacaatggctcgtca (SEQ ID NO: 258) | ppsA-T R | A*ttatttcttcagttcagcca gg (SEQ ID NO: 259) | E. coli genomic DNA | Coding sequence |
| 53 | tktA | G-tktA F | G*tcctcacgtaaagagcttg (SEQ ID NO: 260) | tktA-T R | A*cagcagttcttttgctttc (SEQ ID NO: 261) | E. coli DNA | Coding |
| 54 | aroE | G-aroE F | G*gaaacctatgctgtttttg gta (SEQ ID NO: 262) | aroE-T R | A*cgcggacaattcctcctgc (SEQ ID NO: 263) | E. coli genomic DNA | Coding sequence |

| SN_Noligos | Fragment | Forward Noligo | Sequence | Reverse Noligo | Sequence | Source | Annotation |
|---|---|---|---|---|---|---|---|
| 1 | CelN20 | CelN20-Noligo F | Gagggtaatacacgcgaagac aactttaagcacttattggt aacgacaacgttaagcgct (SEQ ID NO: 264) | CelN20-Noligo R | gcgcttaacgttgtcgttacc aataagtgcttaaagttgtctt cgcgtgtattaccctc (SEQ ID NO: 265) | Synthetic oligo from IDT | E. coli secretion signal peptide |

TABLE 14-continued

List of fragments, Foligos and Noligos used in this study

| | | | | | | |
|---|---|---|---|---|---|---|
| 2 | AS | AS-Noligo F | agtcgacctgcaggtatgtta atatggactact (SEQ ID NO: 266) | AS-Noligo R | gtagtccatattaacatacctg caggtcgactc (SEQ ID NO: 267) | Synthetic oligo from IDT | Antisense RNA in yeast |

TABLE 15

List of barcode in our GTas-based library

| SN | Barcode | Left | Sticky end | Right | Complete sequence | Annotation |
|---|---|---|---|---|---|---|
| 1 | N21 | tc | cctcgactcacactt (SEQ ID NO: 268) | gg | tccctcgactcacacttgg (SEQ ID NO: 269) | Non-functional |
| 2 | N22 | tc | Acacaacatagccac (SEQ ID NO: 270) | gg | tcacacaacatagccacgg (SEQ ID NO: 271) | Non-functional |
| 3 | N23 | t | caaacagaaaggccat (SEQ ID NO: 272) | gg | tcaaacagaaaggccatgg (SEQ ID NO: 273) | Non-functional |
| 4 | N24 | tc | ctcatggattctacg (SEQ ID NO: 274) | gg | tcctcatggattctacggg (SEQ ID NO: 275) | Non-functional |
| 5 | 3UTR1 | ga | tgggctgaagggttt (SEQ ID NO: 276) | aa | gatgggctgaagggtttaa (SEQ ID NO: 277) | 3' end untranslated region with stop codon |
| 6 | N32 | gt | cccatcacagcttac (SEQ ID NO: 278) | aa | gtcccatcacagcttacaa (SEQ ID NO: 279) | Non-functional |
| 7 | N36 | ac | taagggcgaatgtac (SEQ ID NO: 280) | ag | actaagggcgaatgtacag (SEQ ID NO: 281) | Non-functional |
| 8 | N37 | aa | ctttgggtcatgtgc (SEQ ID NO: 282) | tg | aactttgggtcatgtgctg (SEQ ID NO: 283) | 3' end untranslated region with stop codon |
| 9 | N38 | tc | actaaaccacagcct (SEQ ID NO: 284) | ac | tcactaaaccacagcctac (SEQ ID NO: 285) | Non-functional |
| 10 | N39 | ac | gtgggacatctgttt (SEQ ID NO: 286) | cg | acgtgggacatctgtttcg (SEQ ID NO: 287) | Non-functional |
| 11 | N40 | gtgc | gcggaaccccttattt (SEQ ID NO: 288) | | gtgcgcggaaccccttattt (SEQ ID NO: 289) | Non-functional |
| 12 | pJ23119 | tgacagc | tagctcagtcctagg (SEQ ID NO: 290) | tataatacta (SEQ ID NO: 291) | tgacagctagctcagtcctagg tataatacta (SEQ ID NO: 292) | Promtor_E. coli |
| 13 | SRBS2 | aaccg | ttcatttatcacaaa agga (SEQ ID NO: 293) | ttgttcgat | Aaccgttcatttatcacaaaag gattgttcgat (SEQ ID NO: 294) | Ribosome binding site with stop codon_E. coli |
| 14 | SRBS3 | gattc | acacaggaaacagct (SEQ ID NO: 295) | at | gattcacacaggaaacagctat (SEQ ID NO: 296) | Ribosome binding site with stop codon_E. coli |
| 15 | SRBS4 | aaattaat tgttcttt ttt (SEQ ID NO: 297) | caggtgaaggttccc (SEQ ID NO: 298) | at | aaattaattgttcttttttcag gtgaaggttcccat (SEQ ID NO: 299) | Ribosome binding site with stop codon_E. coli |
| 16 | SRBS5 | gactccat acccgtt (SEQ ID NO: 300) | ttttgggctaacagg (SEQ ID NO: 301) | aggaggaatt aaccat (SEQ ID NO: 302) | Gactccatacccgttttttggg ctaacaggaggaggaattaaccat (SEQ ID NO: 303) | Ribosome binding site with stop codon_E. coli |
| 17 | T2A | caggaagc ggagaggg cagaggaa gtctgc (SEQ ID NO: 304) | taacatgcggtgacg (SEQ ID NO: 305) | tcgaggagaa tcctggtcct gg (SEQ ID NO: 306) | Caggaagcggagagggcagaggaa gtctgctaacatgcggtgacgtcg aggagaatcctggtcctgg (SEQ ID NO: 307) | 2A peptide_Yeast |

TABLE 15-continued

List of barcode in our GTas-based library

| SN | Barcode | Left | Sticky end | Right | Complete sequence | Annotation |
|---|---|---|---|---|---|---|
| 18 | F2A | caggaagc ggagtgaa acagactt tgaatt (SEQ ID NO: 308) | tcgaccttctcaagt (SEQ ID NO: 309) | Tccaaggcgg gagacgccct ggttggagtc c (SEQ ID NO: 310) | Caggaagcggagtgaaacagactt tgaatttcgaccttctcaagttgg cgggagacgtggagtccaaccctg gtcc (SEQ ID NO: 311) | 2A peptide_Yeast |
| 19 | LK3 | ca | ggctcgtcttatca (SEQ ID NO: 312) | gg | caggctcgtcttcttcagg (SEQ ID NO: 313) | Linker used to create fusion protein |
| 20 | LK5 | cc | tcatcgtcaggcacc (SEQ ID NO: 314) | tc | cctcatcgtcaggcacctc (SEQ ID NO: 315) | Linker used to create fusion protein |
| 21 | LK6 | ataag | gacaacctgtatttcc (SEQ ID NO: 316) | aggg | ataaggacaacctgtatttccaggg (SEQ ID NO: 317) | Linker used to create fusion protein |
| 22 | LK7 | cagc | agcaggagcacacat (SEQ ID NO: 318) | | cagcagcaggagcacacat (SEQ ID NO: 319) | Linker used to create fusion protein |
| 23 | Shistag | ct | catcatcatcaccatc (SEQ ID NO: 320) | actga | ctcatcatcatcaccatcactga (SEQ ID NO: 321) | histag plus stop codon |
| 24 | 5UTR | a | gcaatctaatctaa gtt (SEQ ID NO: 322) | ttctagaaaa at (SEQ ID NO: 323) | agcaatctaatctaagttttcta gaaaaat (SEQ ID NO: 324) | 5' end untranslated region_Yeast |
| 25 | 5UTR2 | | Tcgacggattctagta (SEQ ID NO: 325) | aaatcat | tcgacggattctagtaaaatcat (SEQ ID NO: 326) | 5' end untranslated region_Yeast |
| 26 | 5UTR3 | tgaa | caactatcaaaacacaa (SEQ ID NO: 327) | tgat | tgaacaactatcaaaacacaatgat (SEQ ID NO: 328) | 5' end untranslated region_Yeast |
| 27 | 5UTR4 | a | gcaatctaatctaagtt (SEQ ID NO: 329) | ttaattacaa atctagaat (SEQ ID NO: 330) | agcaatctaatctaagttttaatta caaatctagaat (SEQ ID NO: 331) | 5' end untranslated region_Yeast |
| 28 | 5UTR5 | a | gcaatctaatctaagtt (SEQ ID NO: 332) | ttaattacaa aat (SEQ ID NO: 333) | agcaatctaatctaagttttaatta tcaaaa (SEQ ID NO: 334) | 5' end untranslated region_Yeast |
| 29 | 5UTR6 | a | gcaatctaatctaagtt (SEQ ID NO: 335) | taccccat | agcaatctaatctaagtttaccccat (SEQ ID NO: 336) | 5' end untranslated region_Yeast |
| 30 | 5UTR7 | a | gcaatctaatctaagtt (SEQ ID NO: 337) | taaaat | agcaatctaatctaagtttaaaat (SEQ ID NO: 338) | 5' end untranslated region_Yeast |
| 31 | 3UTR2 | aa | catcatcatcaccatca (SEQ ID NO: 339) | ctaaaa | aacatcatcatcaccatcactaaaa (SEQ ID NO: 340) | 3' end untranslated region_Yeast |
| 32 | 3UTR3 | ctcaaaaat | tgatttctgaagaa gatt (SEQ ID NO: 341) | tgtaatga | ctcaaaaattgatttctgaagaaga tttgtaatga (SEQ ID NO: 342) | 3' end untranslated region_Yeast |
| 33 | 3UTR4 | ctctcgag | catcatcaccatcac (SEQ ID NO: 343) | catcatcatt aatga (SEQ ID NO: 344) | ctctcgagcatcatcaccatccat catcattaatga (SEQ ID NO: 345) | 3' end untranslated region_Yeast |
| 34 | 3UTR5 | gacgg | gcaatcgcatcacatt (SEQ ID NO: 346) | caaga | gacgggcaatcgcatcacattcaaga (SEQ ID NO: 347) | 3' end untranslated region_Yeast |
| 35 | 3UTR6 | attag | ttatgtcacgcttaca (SEQ ID NO: 348) | ttcac | attagttatgtcacgcttacattcac (SEQ ID NO: 349) | 3' end untranslated region_Yeast |
| 36 | 3UTR7 | ct | catcatcatcatcacc (SEQ ID NO: 350) | atg | ctcatcatcatcatcaccatg (SEQ ID NO: 351) | 3' end untranslated region_Yeast |
| 37 | ICeuI | aact | ataacggtcctaa ggta (SEQ ID NO: 352) | gcgaa | aactataacggtcctaaggtagcgaa (SEQ ID NO: 353) | Homing endonuclease cutting site |

TABLE 15-continued

List of barcode in our GTas-based library

| SN | Barcode | Left | Sticky end | Right | Complete sequence | Annotation |
|----|---------|------|------------|-------|-------------------|------------|
| 38 | SEC17_L |      | atgtagtagggaaatata (SEQ ID NO: 354) | tcaaa | atgtagtagggaaatatatcaaa (SEQ ID NO: 355) | Yeast intron sequence |
| 39 | SEC17_R | t    | gatatttcccgttgtg (SEQ ID NO: 356) | ttaa | tgatatttcccgttgtgttaa (SEQ ID NO: 357) | Yeast intron sequence |
| 40 | EFB1_L  |      | atgttccgatttagttta (SEQ ID NO: 358) | ctttata | atgttccgatttagtttactttata (SEQ ID NO: 359) | Yeast intron sequence |
| 41 | EFB1_R  |      | gttttgtttctcctttta (SEQ ID NO: 360) | aaata | gttttgtttctcctttaaaata (SEQ ID NO: 361) | Yeast intron sequence |

Example 7: Feature of GTas—Flipping Standard Parts in Plasmid Constructions

A unique feature of GTas is that any fragment and barcode can be flipped in plasmid by using standard parts (Boligos and Aoligos). There are eight possible ways to link two fragments through one barcode, as each fragment and the barcode can be flipped independently (FIG. 12d). Each barcode in GTas has the following structure: L-SE-R (FIG. 12a). SE is the region that encodes the long (15 to 20 nt) Sticky End; L and R are the regions flanking Left and Right side of SE, and both are allowed to be empty. The two halves of each barcode have the following structures: L-SE and SE-R. Each Boligo encodes one barcode half. Because each barcode half may be connected to either end of a fragment, there are two Boligos for each barcode half, carrying 'G' or 'A' overhang (FIG. 12b). Each barcode thus has four Boligos in total. The combinations of Boligos to implement the eight connection types are listed in FIG. 12d.

We experimentally demonstrated the eight connection types by flipping replication origin (RO), antibiotic resistance marker (AR) and the barcode connecting them in a plasmid that can express green fluorescence protein (GFP, FIG. 12e) in Escherichia coli (E. coli). The plasmids were sequenced to ensure that the desired arrangements were achieved. Interestingly, expression level of GFP varied substantially (up to close to four-fold change) among the eight constructs, proving the importance of being able to flip elements of plasmid. The difference could be caused by the presence of known and hidden promoters in AR and RO, collision of DNA polymerase (used for plasmid replication) and RNA polymerase (used for transcription) on plasmid[32], or the local structure of RO (it could be affected by flipping the barcode). These hypotheses are good topics for future studies for better controlling protein expression. Flipping parts also allows arranging standard parts in ways that are more complex and are more similar to how DNA parts are naturally arranged in genome[33], e.g. arranging two operons on sense and antisense strands to avoid transcriptional crosstalk, and placing two repeated sequences on the two strands to avoid undesired homologous recombination.

Example 8: Feature of GTas—Flexible Editing Constructed Plasmids

One initial demonstration involved construction of 16 plasmids for engineering E. coli to overproduce tyrosine (FIGS. 13a and 13b), a valuable aromatic amino acid[34]. Each plasmid was assembled from six fragments, which are promoter, gene 1, gene 2, terminator, AR and RO. Sixteen plasmids are full combinations of four RO, two promoters, and two operon structures (4×2×2, elaborated in FIGS. 13a and 4c). Six barcodes were used. Three of them were functional—two containing ribosomal binding sites (RBSs) and one providing stop codon—and the rest merely served as connectors. The cells harboring the 16 plasmids exhibited a wide range of abilities in producing tyrosine (FIG. 13c). These plasmids provide a basis for further plasmid construction.

GTas allows flexible reuse of constructed plasmids. By using standard parts, we can replace fragments in, remove fragments from, and add fragments to any plasmid constructed under GTas (FIGS. 13d, 13e and 13f). Below are three demonstrations. Our lab had developed a short auto-inducible promoter[35] (PthrC3), and we were interested in replacing the promoter (PT7) of the best performing plasmid (among the 16 plasmids; plasmid name: TPP2) with PthrC3. We amplified the whole plasmid except PT7 by using two Aoligos of the barcodes that flanked PT7, barcoded PthrC3 with the same barcodes, and assembled them into one plasmid (FIG. 13d). The new plasmid (TPP17) led to slightly higher tyrosine titer than the one with PT7 (FIGS. 13c and 13h), and simplified the fermentation process by eliminating addition of inducer (PT7 requires addition of Isopropyl β-D-1-thiogalactopyranoside as an inducer). To test if there is any hidden promoter upstream of PT7, we needed to remove PT7 from plasmid TPP2 (FIG. 13e). We amplified the plasmid except PT7 and an adjacent fragment (RO) by using two Aoligos of the barcodes that flanked them, barcoded the adjacent fragment (RO) with the same barcodes, and assembled them (FIG. 13e). Surprisingly, the constructed plasmid still led to production of 1 g/L of tyrosine (FIG. 13h), indicating presence of hidden promoter(s) in the upstream sequence. We had the parental strain without any plasmid as the negative control, which was confirmed not to produce tyrosine (detection limit: 61 mg/L). Tyrosine can be deaminated into coumaric acid, precursor of many valuable flavonoids[4,12], when gene tal (encoding tyrosine ammonia-lyase) was expressed[37] (FIG. 13b). When we added tal into TPP17 by using standard oligos as described in FIG. 13f, E. coli with this new plasmid readily produced 22 mg/L of coumaric acid (FIG. 13i).

As shown in the above mini project, plasmids were often improved through multiple rounds of modifications, because plasmid performance needed to be assessed experimentally and used as feedback to direct the next round of plasmid construction. New parts and ideas from peers also drive many researchers to improve their plasmids in such iterative manner, so being able to edit constructed plasmids by using standard parts would help many researchers to move their project forward faster at lower cost.

Example 9: Feature of GTas—Easily Constructing Plasmid Library for Combinatorial Optimization If a barcoded fragment in plasmid construction was replaced by a mixture of fragments that were barcoded in the same way, a mixture of plasmids would be obtained. If two barcoded fragments were replaced this way, a more diverse mixture of plasmids would be obtained. Such plasmid mixture is termed as plasmid library, and can be used for combinatorial optimization of strains. To demonstrate this concept (FIG. 14), a small plasmid library was built for improving E. coli's ability of producing coumaric acid (FIG. 14a). We first constructed six plasmids that covered all possible ways of shuffling aroG, tyrA and tal (the three genes we used for coumaric acid production) in an operon (FIGS. 14a and 14b). The operon together with its promoter and terminator is termed as Module 1 (M1). We further selected another three genes that were reported to improve production of aromatic compounds (tktA, aroE and ppsA, FIG. 14b), and constructed six plasmids to shuffle them in an operon, which together with its promoter and terminator is termed as Module 2 (M2). Variants of M1 and M2 can be easily amplified from the 12 plasmids and combined into new plasmids (FIG. 14a). Two libraries were created. Each contained full combinations of six variants of M1 and M2 (36 possibilities). The difference between the two libraries was the plasmid backbone type (FIG. 14c). To simplify the workflow, we picked 72 colonies (2 times the size of the library) after transformation of E. coli with each plasmid library, and screened them by using coumaric acid titer. In general, the library with higher copy number replication origin (Library 2) produced more coumaric acid, and the top performer produced 263 mg/L of coumaric acid, which was more than 10 times higher than that before this combinatorial optimization (FIG. 13i). We can easily determine the identity of the plasmids responsible for the higher coumaric acid production by using sequencing (FIG. 14d).

In many biotechnology applications, due to lack of accurate in silico models and/or in-depth understanding of mechanisms of the biological systems, combinatorial optimizations have been widely used and proven to be effective[38, 39]. In this study, we did not intend to achieve highest tyrosine and coumaric acid titer (reports with higher values are available[40, 41]), instead we used these optimization exercises to demonstrate the unique features of GTas, and to provide a relevant context. As demonstration in this example, for the first time GTas allowed construction of plasmid library from.

Example 10: Feature of GTas—being Able to Handle Short Fragments

GTas has also been used to construct plasmids from standard parts for various applications that need to use short genetic elements (including E. coli gene editing through CRISPR/Cas9 system), which are described in FIG. 19 and FIG. 21.

Example 10: Other Materials and Methods

Chemicals

All the chemicals were purchased from Sigma-Aldrich unless otherwise stated. All DNA oligos used in this work were synthesized by Integrated DNA Technologies and Guangzhou IGE Biotechnology LTD, and the DNA oligo sequence information is provided in Table 14, 16, 17, 19 and 21.

TABLE 16

List of oligos used to prepare Boligos in this study

| RG-f (Conventional oligo) | Sequence | RG-r (Conventional oligo) | Sequence (/5Phos/: 5'-end phosphorylation) |
|---|---|---|---|
| N21 | cctcgactcacacttg (SEQ ID NO: 362) | N21 | /5Phos/ccaagtgtgagtcgagg (SEQ ID NO: 363) |
| N22 | acacaacatagccacggG (SEQ ID NO: 364) | N22 | /5Phos/ccgtggctatgttgtgt (SEQ ID NO: 365) |
| N23 | caaacagaaaggccatggG (SEQ ID NO: 366) | N23 | /5Phos/ccatggcctttctgtttg (SEQ ID NO: 367) |
| N24 | ctcatggattctacgggG (SEQ ID NO: 368) | N24 | /5Phos/cccgtagaatccatgag (SEQ ID NO: 369) |
| pJ23119 | tagctcagtcctaggtataatactaG (SEQ ID NO: 370) | pJ23119 | /5Phos/tagtattatacctaggactgagcta (SEQ ID NO: 371) |
| LG-f (Conventional oligo) | Sequence (/5Phos/: 5'-end phosphorylation | LG-r (Conventional oligo) | Sequence |
| N21 | /5Phos/tccctcgactcacactt (SEQ ID NO: 372) | N21 | aagtgtgagtcgagggaA (SEQ ID NO: 373) |
| N22 | /5Phos/tcacacaacatagccac (SEQ ID NO: 374) | N22 | gtggctatgttgtgtgaA (SEQ ID NO: 375) |

TABLE 16-continued

List of oligos used to prepare Boligos in this study

| | | | |
|---|---|---|---|
| N23 | /5Phos/tcaaacagaaagg ccat (SEQ ID NO: 376) | N23 | atggcctttctgtttgaA (SEQ ID NO: 377) |
| N24 | /5Phos/tcctcatggattctacg (SEQ ID NO: 378) | N24 | cgtagaatccatgaggaA (SEQ ID NO: 379) |
| pJ23119 | /5Phos/tgacagctagctca gtcctagg (SEQ ID NO: 380) | pJ23119 | cctaggactgagctagctgtcaA (SEQ ID NO: 381) |

| RG-Boligo (Novel oligo) | Sequence (blue and red highlighted sequences are stem regions that are complementary to each other, and there is a 6 bp loop (upper case) region between them) | LA-Boligo (Novel oligo) | Sequence (blue and red highlighted sequences are stem regions that are complementary to each other, and there is a 6 bp loop (upper case) region between them) |
|---|---|---|---|
| RBS1 | Atatgtatatctccttcttaaagt taaacaaTATGTTtgttta actttaagaaggagatataca tatG (SEQ ID NO: 382) | RBS1 | agaaataattttgtttaactttaag aaggTCTACTccttcttaaa gttaaacaaaattatttctA (SEQ ID NO: 383) |
| SRBS2 | atcgaacaatccttttgtgata aatgaaTCGGTTttcattta tc acaaaaggattgttcgatG (SEQ ID NO: 384) | SRBS2 | aaccgttcatttatcacaaaag gaTATCACTccttttgtgtga aatgaacggttA (SEQ ID NO: 385) |
| SRBS3 | atagctgtttcctgtgtGCCT GGacacaggaaacagct atG (SEQ ID NO: 386) | SRBS3 | gattcacacaggaaacagctT CTTCGagctgtttcctgtgtga atcA (SEQ ID NO: 387) |
| SRBS4 | atgggaaccttcacctgAAG TTAcaggtgaaggttccc atG (SEQ ID NO: 388) | SRBS4 | aaattaattgttctttttttcaggtga aggtcccTCACATgggaa ccttcacctgaaaaaagaaca attaatttA (SEQ ID NO: 389) |
| pJ23119 | tagtattataccctaggactgag ctaAGAGGGtagctca gtcctaggtataatactaG (SEQ ID NO: 390) | pJ23119 | tgacagctagctcagtcctagg GCACAGcctaggactgagc tagctgtcaA (SEQ ID NO: 391) |
| N21 | ccaagtgtgagtcgaggAA GGGCcctcgactcacac ttggG (SEQ ID NO: 392) | N21 | tccctcgactcacacttGCGA GAaagtgtgagtcgagggaA (SEQ ID NO: 393) |
| N22 | ccgtggctatgttgtgtCGTA TTacacaacatagccac ggG (SEQ ID NO: 394) | N22 | tcacacaacatagccacTTG CTGgtggctatgttgtgtgaA (SEQ ID NO: 395) |
| N23 | ccatggcctttctgtttgACCA TAcaaacagaaaggcca tggG (SEQ ID NO: 396) | N23 | tcaaacagaaaggccatCAT TCAatggcctttctgtttgaA (SEQ ID NO: 397) |
| N24 | cccgtagaatccatgagAA CCCGctcatggattcta cgggG (SEQ ID NO: 398) | N24 | tcctcatggattctacgACTAT Gcgtagaatccatgaggaa (SEQ ID NO: 399) |
| 3UTR1 | ttaaacccttcagcccaCAC ACAtgggctgaaggg tttaaG (SEQ ID NO: 400) | 3UTR1 | gatgggctgaagggtttCACA CAaaacccttcagcccatcA (SEQ ID NO: 401) |
| N32 | ttgtaagctgtgatgggGCC TGGcccatcacagcttaca aG (SEQ ID NO: 402) | N32 | gtccatcacagcttacGCTT CGgtaagctgtgatgggacA (SEQ ID NO: 403) |

TABLE 16-continued

List of oligos used to prepare Boligos in this study

| | | | |
|---|---|---|---|
| LK3 | cctgaagaagacgagccCA CACAggctcgtcttcttcagg G (SEQ ID NO: 404) | LK3 | caggctcgtcttcttcaCACA CAtgaagaagacgagcctgA (SEQ ID NO: 405) |
| 5UTR | atttttctagaaaacttagatta gattgcAAGTTAgcaatct aatctaagttttctagaaaaat G (SEQ ID NO: 406) | 5UTR | agcaatctaatctaagttGCA CATaacttagattagattgctA (SEQ ID NO: 407) |
| 3UTR2 | ttttagtgatggtgatgatgatg GGCAATcatcatcatcacc atcactaaaaG (SEQ ID NO: 408) | 3UTR2 | aacatcatcatcaccatcaAT GTACtgatggtgatgatgatg ttA (SEQ ID NO: 409) |
| RA-Boligo (Novel oligo) | Sequence (blue and red highlighted sequences are stem regions that are complementary to each other, and there is a 6 bp loop (upper case) region between them) | LG-Boligo (Novel oligo) | Sequence (blue and red highlighted sequences are stem regions that are complementary to each other, and there is a 6 bp loop (upper case) region between them) |
| N36 | ctgtacattcgcccttaAGCT TGtaagggcgaatgtacag A (SEQ ID NO: 410) | N36 | actaagggcgaatgtacAGC TTGgtacattcgcccttagtG (SEQ ID NO: 411) |
| ICeuI | ttcgctaccttaggaccgttat AGCTTGataacggtccta aggtagcgaaA (SEQ ID NO: 412) | ICeuI | aactataacggtcctaaggtaA GCTTGtaccttaggaccgtta tagttG (SEQ ID NO: 413) |
| N22 | ccgtggctatgttgtgtAGCT TGacacaacatagccacgg (SEQ ID NO: 414) | N22 | tcacacaacatagccacAGC TTGgtggctatgttgtgtgaG (SEQ ID NO: 415) |
| 3UTR2 | ttttagtgatggtgatgatgatg GGCAATcatcatcatcacc atcactaaaaA (SEQ ID NO: 416) | 3UTR2 | aacatcarcatcaccatcaAT GTACtgatggtgatgatgatg ttG (SEQ ID NO: 417) |
| N21 | ccaagtgtgagtcgaaggAA GGGCcctcgactcaacactt ggA (SEQ ID NO: 418) | N21 | tccctcgactcacacttGCGA GAaagtgtgagtcgagggaG (SEQ ID NO: 419) |
| N23 | ccatggcctttctgtttgACCA TAcaaacagaaaggccatg gA (SEQ ID NO: 420) | N23 | tcaaacagaaaggccatCAT TCAatggcctttctgtttgaG (SEQ ID NO: 421) |

PCR

PCR reaction solution in this work contained 1-5 µL of template DNA, 0.3 µL of 100 µM forward oligo, 0.3 µL of 100 µM reverse oligo, 25 µL of Q5® Hot Start High-Fidelity 2× Master Mix (M0494, New England Biolabs [NEB]), and ultrapure water to top up to 50 µL. The cycling condition was based on the manufacturer's instruction. All amplified DNA fragments were separated by standard gel electrophoresis and then purified by using commercial column according to manufacturer's instructions (GeneJET Gel Extraction Kit, K0691, Thermo Fisher Scientific). At the end of the purification, DNA was eluted from the column by using 40 µL of nuclease-free water (BUF-1180, 1st BASE Biochemicals [1st BASE]) in 1.7 mL Eppendorf tube.

Chemical Cleavage of Phosphorothioate (PS)-Modified DNA

To cleave PS bond in DNA molecules (FIG. 1c), forty microliters of purified DNA solution was mixed with 5.5 µL of 1 M Tris solution (3021, 1st BASE, pH adjusted to 9) and 10 µL of 30 g/L iodine solution (iodine: 207772, Sigma-Aldrich; solvent: ethanol), and was incubated at 70° C. for 5 min in a water bath. The solution was diluted with 250 µL of nuclease-free water, and purified by using commercial DNA purification column as described above.

Preparation of Fragment

Fragments can be amplified from various sources (plasmid, synthetic DNA, genomic DNA etc.) by using PCR and Foligos (FIG. 10c and FIG. 21). Chemical treatment of the PS bond left 'C' or 'T' sticky end on one end of fragment which could be paired with a Boligo that has the compatible sticky end (FIG. 1c, FIGS. 2a and 2b). Note that the chemically treated fragments must be purified by using column (GeneJET Gel Extraction Kit, K0691, Thermo Fisher Scientific). Short fragments can be directly created by annealing Noligos (FIG. 20). The annealing reaction solution contained 50 µL of 100 µM G-Noligo and 50 µL of 100 µM A-Noligo. The annealing was done by using the following program in a thermo cycler: 98° C. for 2 min, 98 to 75° C. at rate of 0.1° C./s, 75° C. for 2 min, 75 to 45° C. at rate of 0.1° C./s, 45° C. for 2 min, 45° C. to 4° C. at rate of 0.1° C./s and hold at 4° C. The fragments prepared by using Noligos were diluted with nuclease-free water to 10-20 ng/µL for barcoding, and did not require purification. All the fragments used in this study are listed in Table 14.

Phosphorylation and Folding of Boligos

Boligos need to have phosphate group at 5' end and properly folded. To reduce oligo synthesis cost, we ordered regular oligos and used T4 kinase to add phosphate group. The phosphorylation reaction solution contained 1 µL of 100 µM Boligo, 2 µL of 10× T4 ligase buffer (B0202, NEB), 0.5 µL of T4 kinase (B0201, NEB) and 16.5 µL of nuclease-free water. Phosphorylation and folding of Boligo were done by using the following condition in a thermo cycler: 37° C. for 30 min (phosphorylation), 65° C. for 20 min (inactivation of T4 kinase), 98° C. for 2 min (DNA denaturing), 98 to 45° C. at rate of 0.1° C./s, 45° C. for 2 min, 45° C. to 4° C. at rate of 0.1° C./s, and hold at 4° C. The prepared Boligos (diluted properly by using ultrapure water) can be directly used in subsequent reactions without purification. All the Boligos (conventional and novel oligo design) used in this study are listed in Table 16. The workflow for creating conventional Boligos is elaborated in FIG. 17.

Barcoding

Prepared fragments and barcodes were ligated by using a commercial kit (Blunt/TA Ligase Master Mix, M0367, New England Biolabs). The type of ligase was critical in this step (results from using different ligases are provided in FIG. 24). The ligation reaction solution contained 3 µL of fragment, 0.3 µL of 1.25 µM L(G/A)-Boligo, 0.3 µL of 1.25 µM R(G/A)-Boligo, and 3.6 µL of Blunt/TA Ligase Master Mix. The ligation reaction was done by using the following program in a thermo cycler: 25° C. for 5 min, and hold at 4° C. It is critical to have sufficient amount of high quality fragment in the ligation reaction. The recommended minimal fragment concentration is 10 ng/µL for fragment no longer than 1 kb. The concentration refers to that of fragment with one-nt sticky ends. If fragment is larger than 1 kb, we recommend to use at least 100 ng/µL; if fragment is larger than 2 kb, we recommend to use at least 200 ng/µL. We used Vacufuge (Eppendorf™ Vacufuge™ Concentrator) to concentrate fragment solution when its concentration was too low. Absorbance spectrum (200-300 nm) of each fragment solution should be examined by using Nanodrop (NanoDrop™ 2000/2000c Spectrophotometers, Thermo Fisher Scientific) or a similar device to ensure there is a peak at 260 nm before its fragment concentration data can be used in the calculation. We have successfully barcoded fragments between 0.035 kb to 5.259 kb.

After ligation, corresponding Aoligos (FIG. 12c) were used to amplify correctly barcoded fragments by using PCR. This step was termed as ligation PCR. The ligation product was directly used as template DNA in PCR without purification/dilution. PCR product was purified and chemically cleaved as specified in PCR and Chemical Cleavage of phosphorothioate (PS)-modified DNA. All Aoligos used in this study are listed in Table 17. All barcoded fragments used in this study are listed in Table 18.

TABLE 17

List of Aoligos used in this study

| RG-Aoligo | Sequence (*: phosphorothioate bond) | LA-Aoligo | Sequence (*: phosphorothioate bond) |
| --- | --- | --- | --- |
| RBS1-G-Assemble | ttgtttaac*tttaagaagg*agatatacatatG (SEQ ID NO: 422) | RBS1-T-Assemble | ccttcttaa*agttaaacaa*aattatttctA (SEQ ID NO: 423) |
| SRBS2-G-Assemble | ttcatttat*cacaaaagga*ttgttcgatG (SEQ ID NO: 424) | SRBS2-T-Assemble | tcctttttgt*gataaatgaa*cggttA (SEQ ID NO: 425) |
| SRBS3-G-Assemble | acacagga*aacagct*atG (SEQ ID NO: 426) | SRBS3-T-Assemble | agctgttt*cctgtgt*gaatcA (SEQ ID NO: 427) |
| SRBS4-G-Assemble | caggtgaa*ggttccc*atG (SEQ ID NO: 428) | SRBS4-T-Assemble | gggaacct*tcacctg*aaaaagaacaattaatttA (SEQ ID NO: 429) |
| pJ23119-G-Assemble | tagctca*gtcctagg*tataatactaG (SEQ ID NO: 430) | pJ23119-T-Assemble | cctagga*ctgagcta*gctgtcaA (SEQ ID NO: 431) |
| N21-G-Assemble | cctcgac*tcacactt*ggG (SEQ ID NO: 432) | N21-T-Assemble | aagtgtg*agtcgagg*gaA (SEQ ID NO: 433) |
| N22-G-Assemble | acacaac*atagccac*ggG (SEQ ID NO: 434) | N22T-T-Assemble | gtggcta*tgttgtgt*gaA (SEQ ID NO: 435) |
| N23-G-Assemble | caaacaga*aaggccat*ggG (SEQ ID NO: 436) | N23-T-Assemble | atggcctt*tctgtttg*aA (SEQ ID NO: 437) |
| N24-G-Assemble | ctcatgg*attctacg*ggG (SEQ ID NO: 438) | N24-T-Assemble | cgtagaa*tccatgag*gaA (SEQ ID NO: 439) |
| 3UTR1-G-Assemble | tgggctg*aagggttt*aaG (SEQ ID NO: 440) | 3UTR1-T-Assemble | aaaccct*tcagccca*tcA (SEQ ID NO: 441) |
| N32-G-Assemble | cccatcac*agcttac*aaG (SEQ ID NO: 442) | N32T-Assemble | gtaagctg*tgatggg*acA (SEQ ID NO: 443) |

TABLE 17-continued

List of Aoligos used in this study

| RG-Aoligo | Sequence (*: phosphorothioate bond) | LA-Aoligo | Sequence (*: phosphorothioate bond) |
|---|---|---|---|
| LK3-G-Assemble | ggctcgt*cttcttca*ggG (SEQ ID NO: 444) | LK3-T-Assemble | tgaagaa*gacgagcc*tgA (SEQ ID NO: 445) |
| fiveUTR-G-Assemble | gcaatctaa*tctaagtt*ttctagaaaaatG (SEQ ID NO: 446) | fiveUTR-T Assemble | aacttagat*tagattgc*tA (SEQ ID NO: 447) |
| 3UTR2-G-Assemble | catcatcat*caccatca*ctaaaaG (SEQ ID NO: 448) | 3UTR2-T-Assemble | tgatggtga*tgatgatg*ttA (SEQ ID NO: 449) |
| N36-A-Assemble | taagggcg*aatgtac*agA (SEQ ID NO: 450) | N36-C-Assemble | gtacattc*gcctta*gtG (SEQ ID NO: 451) |
| ICeuI-A-Assemble | ataacggtc*ctaaggta*gcgaaA (SEQ ID NO: 452) | ICeuI-C-Assemble | taccttagg*accgttat*agttG (SEQ ID NO: 453) |
| N22-A-Assemble | acacaaca*tagccac*ggA (SEQ ID NO: 454) | N22-C-Assemble | gtggctat*gttgtgt*gaG (SEQ ID NO: 455) |
| 3UTR2-A-Assemble | catcatcat*caccatca*ctaaaaA (SEQ ID NO: 456) | 3UTR2-C-Assemble | tgatggtga*tgatgatg*ttG (SEQ ID NO: 457) |
| N21-A-Assemble | cctcgac*tcacactt*ggA (SEQ ID NO: 458) | N21-C-Assemble | aagtgtg*agtcgagg*gaG (SEQ ID NO: 459) |
| N23-A-Assemble | caaacaga*aaggccat*ggA (SEQ ID NO: 460) | N23C-Assemble | atggcctt*tctgtttg*aG (SEQ ID NO: 461) |

TABLE 18

List of barcoded fragments used in this study

| SN | Barcoded fragment | Annotation |
|---|---|---|
| 1 | (pJ23119-RG-Boligo)gRNA-nupG(N23-LA-Boligo) | guide RNA with promoter |
| 2 | (pJ23119-RG-Boligo)gRNA-aslA(N23-LA-Boligo) | guide RNA with promoter |
| 3 | (pJ23119-RG-Boligo)gRNA-melB(N23-LA-Boligo) | guide RNA with promoter |
| 4 | (pJ23119-RG-Boligo)gRNA-rcsB(N23-LA-Boligo) | guide RNA with promoter |
| 5 | (pJ23119-RG-Boligo)gRNA-tyrR(N23-LA-Boligo) | guide RNA with promoter |
| 6 | (pJ23119-RG-Boligo)gRNA-pheA(N23-LA-Boligo) | guide RNA with promoter |
| 7 | (pJ23119-RG-Boligo)gRNA-ptsI(N23-LA-Boligo) | guide RNA with promoter |
| 8 | (pJ23119-RG-Boligo)gRNA-manZ(N23-LA-Boligo) | guide RNA with promoter |
| 9 | (pJ23119-RG-Boligo)gRNA-glk(N23-LA-Boligo) | guide RNA with promoter |
| 10 | (pJ23119-RG-Boligo)gRNA-xylB(N23-LA-Boligo) | guide RNA with promoter |
| 11 | (N23-RG-Boligo)nupG-HF0.5(N24-LA-Boligo) | Upstream homologous sequence |
| 12 | (N23-RG-Boligo)nupG-HF1.0(N24-LA-Boligo) | Upstream homologous sequence |
| 13 | (N23-RG-Boligo)nupG-HF1.5(N24-LA-Boligo) | Upstream homologous sequence |
| 14 | (N23-RG-Boligo)aslA-HF0.5(N24-LA-Boligo) | Upstream homologous sequence |
| 15 | (N23-RG-Boligo)aslA-HF1.0(N24-LA-Boligo) | Upstream homologous sequence |
| 16 | (N23-RG-Boligo)melB-HF1.0(N24-LA-Boligo) | Upstream homologous sequence |
| 17 | (N23-RG-Boligo)rcsB-HF1.0(N24-LA-Boligo) | Upstream homologous sequence |
| 18 | (N23-RG-Boligo)tyrR-HF0.5(N24-LA-Boligo) | Upstream homologous sequence |

TABLE 18-continued

List of barcoded fragments used in this study

| SN | Barcoded fragment | Annotation |
|---|---|---|
| 19 | (N23-RG-Boligo)pheA-HF0.5(N24-LA-Boligo) | Upstream homologous sequence |
| 20 | (N23-RG-Boligo)ptsI-HF0.7(N24-LA-Boligo) | Upstream homologous sequence |
| 21 | (N23-RG-Boligo)manZ-HF0.5(N24-LA-Boligo) | Upstream homologous sequence |
| 22 | (N23-RG-Boligo)glk-HF0.5(N24-LA-Boligo) | Upstream homologous sequence |
| 23 | (N23-RG-Boligo)xylB-HF0.7(N24-LA-Boligo) | Upstream homologous sequence |
| 24 | (N24-RG-Boligo)nupG-HT0.5(N21-LA-Boligo) | Downstream homologous sequence |
| 25 | (N24-RG-Boligo)nupG-HT1.0(N21-LA-Boligo) | Downstream homologous sequence |
| 26 | (N24-RG-Boligo)nupG-HT1.5(N21-LA-Boligo) | Downstream homologous sequence |
| 27 | (N24-RG-Boligo)aslA-HT0.5(N21-LA-Boligo) | Downstream homologous sequence |
| 28 | (N24-RG-Boligo)aslA-HT1.0(N21-LA-Boligo) | Downstream homologous sequence |
| 29 | (N24-RG-Boligo)melB-HT1.0(N21-LA-Boligo) | Downstream homologous sequence |
| 30 | (N24-RG-Boligo)rcsB-HT1.0(N21-LA-Boligo) | Downstream homologous sequence |
| 31 | (N24-RG-Boligo)tyrR-HT0.5(N21-LA-Boligo) | Downstream homologous sequence |
| 32 | (N24-RG-Boligo)pheA-HT0.5(N21-LA-Boligo) | Downstream homologous sequence |
| 33 | (N24-RG-Boligo)ptsI-HT0.7(N21-LA-Boligo) | Downstream homologous sequence |
| 34 | (N24-RG-Boligo)manZ-HT0.5(N21-LA-Boligo) | Downstream homologous sequence |
| 35 | (N24-RG-Boligo)glk-HT0.5(N21-LA-Boligo) | Downstream homologous sequence |
| 36 | (N24-RG-Boligo)xylB-HT0.7(N21-LA-Boligo) | Downstream homologous sequence |
| 37 | (N21-RG-Boligo)aadA(N22-LA-Boligo) | Antibiotic resistance gene expression cassette (spectinomycin) |
| 38 | (N21-RG-Boligo)bla(N22-LA-Boligo) | Antibiotic resistance gene expression cassette (ampicillin) |
| 39 | (N22-RG-Boligo)pSC101(pJ23119-LA-Boligo) | Replication origin-low copy number |
| 40 | (N22-RG-Boligo)pAC(pJ23119-LA-Boligo) | Replication origin-medium copy number |
| 41 | (N22-RG-Boligo)pMB1(pJ23119-LA-Boligo) | Replication origin-medium copy number |
| 42 | (N22-RG-Boligo)pUC(pJ23119-LA-Boligo) | Replication origin-high copy number |
| 43 | (N23-RG-Boligo)pLac(RBS1-LA-Boligo) | Promoter |
| 44 | (N23-RG-Boligo)LacIPT7(RBS1-LA-Boligo) | Promoter with LacI repressor coding sequence |
| 45 | (3UTR1-RG-Boligo)t7t(N21-LA-Boligo) | Terminator |
| 46 | (3UTR1-RG-Boligo)t7t(LK3-LA-Boligo) | Terminator |
| 47 | (LK3-RG-Boligo)LacI(LacI-LA-Boligo) | LacI repressor expression cassette |
| 48 | (RBS1-RG-Boligo)LacI(SRBS4-LA-Boligo) | Coding sequence |
| 49 | (RBS1-RG-Boligo)tyrA mutant(SRBS4-LA-Boligo) | Coding sequence |
| 50 | (SRBS4-RG-Boligo)tyrA mutant(3UTR1-LA-Boligo) | Coding sequence |
| 51 | (SRBS4-RG-Boligo)aroG mutant(3UTR1-LA-Boligo) | Coding sequence |
| 52 | (N23-RG-Boligo)pthrC3(RBS1-LA-Boligo) | Promoter |
| 53 | (N22-RG-Boligo)pAC(RBS1-LA-Boligo) | Replication origin-medium copy number |
| 54 | (SRBS2-RG-Boligo)tal(3UTR1-LA-Boligo) | Coding sequence |
| 55 | (SRBS4-RG-Boligo)aroG mutant(SRBS2-LA-Boligo) | Coding sequence |
| 56 | (SRBS4-RG-Boligo)tyrA mutant(SRBS2-LA-Boligo) | Coding sequence |

TABLE 18-continued

List of barcoded fragments used in this study

| SN | Barcoded fragment | Annotation |
|---|---|---|
| 57 | (SRBS2-RG-Boligo)aroG mutant(3UTR1-LA-Boligo) | Coding sequence |
| 58 | (SRBS2-RG-Boligo)tyrA mutant(3UTR1-LA-Boligo) | Coding sequence |
| 59 | (RBS1-RG-Boligo)SeSam8_tal(SRBS4-LA-Boligo) | Coding sequence |
| 60 | (SRBS4-RG-Boligo)SeSam8_tal(SRBS2-LA-Boligo) | Coding sequence |
| 61 | (SRBS2-RG-Boligo)SeSam8_tal(3UTR1-LA-Boligo) | Coding sequence |
| 62 | (RBS1-RG-Boligo)ppsA(SRBS4-LA-Boligo) | Coding sequence |
| 63 | (RBS1-RG-Boligo)tktA(SRBS4-LA-Boligo) | Coding sequence |
| 64 | (RBS1-RG-Boligo)aroE(SRBS4-LA-Boligo) | Coding sequence |
| 65 | (SRBS4-RG-Boligo)ppsA(SRBS2-LA-Boligo) | Coding sequence |
| 66 | (SRBS4-RG-Boligo)tktA(SRBS2-LA-Boligo) | Coding sequence |
| 67 | (SRBS4-RG-Boligo)aroE(SRBS2-LA-Boligo) | Coding sequence |
| 68 | (SRBS2-RG-Boligo)ppsA(3UTR1-LA-Boligo) | Coding sequence |
| 69 | (SRBS2-RG-Boligo)tktA(3UTR1-LA-Boligo) | Coding sequence |
| 70 | (SRBS2-RG-Boligo)aroE(3UTR1-LA-Boligo) | Coding sequence |
| 71 | (N36-RG-Boligo)SpecR(ICeul-LA-Boligo) | Antibiotic resistance gene expression cassette (spectinomycin) |
| 72 | (N36-RA-Boligo)SpecR-flipped(ICeul-LG-Boligo) | Antibiotic resistance gene expression cassette (spectinomycin) |
| 73 | (N36-LG-Boligo)SpecR(ICeul-LA-Boligo) | Antibiotic resistance gene expression cassette (spectinomycin) |
| 74 | (N36-RA-Boligo)SpecR-flipped(ICeul-RG-Boligo) | Antibiotic resistance gene expression cassette (spectinomycin) |
| 75 | (ICeul-RG-Boligo)pMB1(N22-RA-Boligo) | Replication origin-medium copy number |
| 76 | (ICeul-LA-Boligo)pMB1-flipped(N22-LG-Boligo) | Replication origin-medium copy number |
| 77 | (ICeul-LG-Boligo)pMB1(N22-LA-Boligo) | Replication origin-medium copy number |
| 78 | (ICeul-RA-Boligo)pMB1-flipped(N22-RG-Boligo) | Replication origin-medium copy number |
| 79 | (N22-RG-Boligo)P-gfp-T(N36-LA-Boligo) | GFP expression cassette |
| 80 | (N22-LG-Boligo)P-gfp-T(N36-LA-Boligo) | GFP expression cassette |

Direct Amplification of Barcoded Fragment from Constructed Plasmids

Barcoded fragments can also be directly amplified by using Aoligos from a plasmid if this plasmid contains the barcoded fragment (FIGS. 13d, 13e and 13f, FIG. 14a and FIG. 21). In such case, barcoding was not needed. The PCR product can be chemically cleaved and used in DNA assembly.

DNA Assembly

We revised the CLIVA method to develop a new DNA assembly method that is highly efficient (FIG. 20). The assembly reaction solution contained 0.5 µL of Taq DNA ligase (M0208, NEB), 0.5 µL of the 10× buffer for the Taq DNA ligase, and 4 µL of mixture containing the barcoded fragments (they must have close to the same molar concentration). The recommended minimal molar concentration of barcoded fragment is 10 nM. The ligation reaction was done 45° C. for 12 h by using thermo cycler.

One microliter of ligation product was mixed with 17 µL of E. coli Dh5a heat-shock competent cell solution (C2987H, NEB) in a pre-chilled 1.7 mL tube on ice (Axygen). The tube was heat-shocked in a 42° C. water bath for exactly 35 s and was quenched on ice. The cell solution was mixed with 150 µL of SOC medium (NEB) and directly plated on LB Agar plate that contained a proper antibiotic.

The plate was incubated temperature required by specific applications. Usually colony appeared after 12 h when incubated at 37° C.

Colony PCR and Sanger sequencing were carried out to determine accuracy of each DNA assembly. The accuracy was product of colony PCR accuracy and sequencing accuracy. Colony PCR accuracy was the ratio of the number of positive colonies (determined by colony PCR) to that of all the tested colonies. For each DNA assembly, one or more positive colonie(s) were cultured in LB with proper antibiotics overnight and the plasmids extracted from them were further tested by Sanger sequencing (Service provider: Axil Scientific, AITbiotech, and BioBasic). Sequencing accuracy was the ratio of the number of positive plasmids (free of mutation/deletion/insertion in sequenced region) to that of all the sequenced plasmids. Colony PCR reaction solution contained 1 μL of colony suspension (one single colony was re-suspended in 100 μL of ultrapure water), 0.15 μL of 100 μM forward oligo, 0.15 μL of 100 μM reverse oligo, 5 μL of Q5 Hot Start High-Fidelity 2× Master Mix, and 3.7 μL of ultrapure water.

Genome editing of E. coli.

For genome editing of E. coli MG1655_ΔrecA_ΔendA_DE3, we utilized a two-plasmid CRISPR/Cas9 system[2] and constructed a few plasmids targeting varied loci (Table 19). Colony PCR verification was performed to evaluate the efficiency of gene deletion at the selected locus, and a full list of the targeted locus and oligos used in colony PCR are provided in Table 19.

Strains

A list of strains used and constructed in this study is provided in Table 20. Each strain was derived from its parental strain through plasmid transformation done by using the standard electroporation protocol.

List of the efficiency of gene deletion at the targeted locus and oligos used to colony PCR in this study

| Plasmids name | Parental strain | Locus | Upstream homologous sequence length/ Downstream homologous sequence length (bp) | Gene deletion efficiency (Correct colony number/ Tested colony number) | Colony PCR forward oligo name | Colony PCR forward oligo sequence | Colony PCR reverse oligo name | Colony PCR reverse oligo sequence |
|---|---|---|---|---|---|---|---|---|
| GE1 | MG1655_ ΔrecA_ ΔendA_ DE3 | aslA | 487/500 | 0/6 | aslA screening 4F | TGGAACAAC AGGCATGGATT (SEQ ID NO: 221) | aslA screening 4R | ACAGGCGAAA TATGGTGCT (SEQ ID NO: 222) |
| GE2 | MG1655_ ΔrecA_ ΔendA_ DE3 | aslA | 987/1000 | 1/6 | aslA screening 4F | TGGAACAACA GGCATGGATT (SEQ ID NO: 221) | aslA screening 4R | ACAGGCGAAA TATGGTGCT (SEQ ID NO: 222) |
| GE3 | MG1655_ ΔrecA_ ΔendA_ DE3 | nupG | 4887/500 | 6/6 | nupG screening 2F | GGAAATATGG CGTTGATGAG (SEQ ID NO: 223) | nupG screening 2R | AGGATTATCCG ACATCAGTG (SEQ ID NO: 224) |
| GE4 | MG1655_ ΔrecA_ ΔendA_ DE3 | tyrR | 422/507 | 3/16 | tyrR screening F | AACGCTGGTA TGCCTCAATC (SEQ ID NO: 227) | tyrR screening R | AGGCTTCCTC GAATACCTTA (SEQ ID NO: 228) |
| GE5 | MG1655_ ΔrecA_ ΔendA_ ΔtyrR_ DE3 | pheA | 454/589 | 6/6 | pheA screening F | TCATCAAATA TGGCTCGCTT (SEQ ID NO: 225) | pheA screening R | TCGAGCGGCT GATATTGTTG (SEQ ID NO: 226) |
| GE6 | MG1655_ ΔrecA_ ΔendA_ DE3 | nupG | 1004/1050 | 8/8 | nupG screening 4F | TATTGTGCCT ATGTGGCCTTC (SEQ ID NO: 227) | nupG screening 4R | CGAATAAAGTG GTGACGAATG (SEQ ID NO: 228) |
| GE7 | MG1655_ ΔrecA_ ΔendA_ DE3 | nupG | 1580/1501 | 6/8 | nipG screening 4F | TATTGTGCCT ATGTGGCTTC (SEQ ID NO: 229) | nupG screening 4R | CGAATAAAGTGG TGACGAATG (SEQ ID NO: 230) |
| GE8 | MG1655_ ΔrecA_ ΔendA_ DE3 | melB | 993/1039 | 7/8 | melB screening 2F | GTAAGCGGC ATGGTCTGGAAC (SEQ ID NO: 231) | melB screening 2R | GCAGGCCGT ATGGACTCCTA (SEQ ID NO: 232) |
| GE9 | MG1655_ ΔrecA_ ΔendA_ DE3 | rcsB | 1147/1026 | 8/8 | rcsB screening 3F | AACTGGCGAA TCAGGCAGA (SEQ ID NO: 233) | rcsB screening 3R | GCGATTATCT CTCTATCCGT (SEQ ID NO: 234) |

List of the efficiency of gene deletion at the targeted locus and oligos used to colony PCR in this study

| Plasmids name | Parental strain | Locus | Upstream homologous sequence length/ Downstream homologous sequence length (bp) | Gene deletion efficiency (Correct colony number/ Tested colony number) | Colony PCR forward oligo name | Colony PCR forward oligo sequence | Colony PCR reverse oligo name | Colony PCR reverse oligo sequence |
|---|---|---|---|---|---|---|---|---|
| GE10 | MG1655_ ΔrecA_ ΔendA_ | ptsHIcrr | 656/776 | 0/4 | ptsH/I_crr screening F | AGACCGATCTT (SEQ ID NO: 235) | ptsH/I_crr | TAGTGTAATGA (SEQ ID NO: 236) |
| GE18 | MG1655_ ΔrecA_ ΔendA_ DE3 | xylB | 512/500 | 7/8 | xylB screening F | TCCTGAAACAG TTTGGTCTGGA (SEQ ID NO: 462) | xylB screening R | CATGGATAGCT CTCGTTGGT (SEQ ID NO: 463) |

TABLE 20

List of strains constructed in this study

| Strain name | E. coli strain genotype | Plasmid genotype (Barcodes used in one plasmid are placed into brackets between fragments) | Application in this study |
|---|---|---|---|
| A0 | BL21(DE3) | (N21)SpecR(N22)pMB1(N23)t7t | Empty plasmid_FIG. 3e |
| A1 | BL21(DE3) | SpecR(Ceul)pMB1(N22)pthrC3_gfp_t7t(N36) | Empty plasmid_FIG. 3e |
| A2 | BL21(DE3) | SpecR flippedICeul)pMB1(N22)pthrC3_gfp_t7t(N36) | Empty plasmid_FIG. 3e |
| A3 | BL21(DE3) | SpecR(Ceul)pMB1 flipped(N22)pthrC3_gfp_t7t(N36) | Empty plasmid_FIG. 3e |
| A4 | BL21(DE3) | SpecR flipped(Ceul)pMB1 flipped(N22)pthrC3_gfp_t7t(N36) | Empty plasmid_FIG. 3e |
| A5 | BL21(DE3) | SpecR(Ceul flipped)pMB1(N22)pthrC3_gfp_t7t(N36) | Empty plasmid_FIG. 3e |
| A6 | BL21(DE3) | SpecR flipped(Ceul flipped)pMB1(N22)pthrC3_gfp_t7t(N36) | Empty plasmid_FIG. 3e |
| A7 | BL21(DE3) | SpecR(Ceul flipped)pMB1 flipped(N22)pthrC3_gfp_t7t(N36) | Empty plasmid_FIG. 3e |
| A8 | BL21(DE3) | SpecR flipped(Ceul flipped)pMB1 flipped(N22)pthrC3_gfp_t7t(N36) | Empty plasmid_FIG. 3e |
| TPP0 | MG1655_ΔrecA_ΔendA_ΔpheA_ΔtyrR_DE3 | (N21)SpecR(N22)pAC(N23)t7t | Empty plasmid_FIG. 4a |
| TPP1 | MG1655_ΔrecA_ΔendA_ΔpheA_ΔtyrR_DE3 | (N21)SpecR(N22)pSC101(N23)lacIT7(RBS1)aroG mutant(SRBS4)tyrA mutant(3UTR1)t7t(N21) | Tyrosine production_FIG. 4c |
| TPP2 | MG1655_ΔrecA_ΔendA_ΔpheA_ΔtyrR_DE3 | (N21)SpecR(N22)pAC(N23)lacIT7(RBS1)aroG mutant(SRBS4)tyrA mutant(3UTR1)t7t(N21) | Tyrosine production_FIG. 4c |
| TPP3 | MG1655_ΔrecA_ΔendA_ΔpheA_ΔtyrR_DE3 | (N21)SpecR(N22)pMB1(N23)lacIT7(RBS1)aroG mutant(SRBS4)tyrA mutant(3UTR1)t7t(N21) | Tyrosine production_FIG. 4c |
| TPP4 | MG1655_ΔrecA_ΔendA_ΔpheA_ΔtyrR_DE3 | (N21)SpecR(N22)pUC((N23)lacIT7(RBS1)aroG mutant(SRBS4)tyrA mutant(3UTR1)t7t(N21) | Tyrosine production_FIG. 4c |
| TPP5 | MG1655_ΔrecA_ΔendA_ΔpheA_ΔtyrR_DE3 | (N21)SpecR(N22)pSC101(N23)pLac(RBS1)aroG mutant(SRBS4)tyrA mutant(3UTR1)t7t(LK3)LacI(N21) | Tyrosine production_FIG. 4c |
| TPP6 | MG1655_ΔrecA_ΔendA_ΔpheA_ΔtyrR_DE3 | (N21)SpecR(N22)pAC(N23)pLac(RBS1)aroG mutant(SRBS4)tyrA mutant(3UTR1)t7t(LK3)LacI(N21) | Tyrosine production_FIG. 4c |
| TPP7 | MG1655_ΔrecA_ΔendA_ΔpheA_ΔtyrR_DE3 | (N21)SpecR(N22)pMB1(N23)pLac(RBS1)aroG mutant(SRBS4)tyrA mutant(3UTR1)t7t(LK3)LacI(N21) | Tyrosine production_FIG. 4c |
| TPP8 | MG1655_ΔrecA_ΔendA_ΔpheA_ΔtyrR_DE3 | (N21)SpecR(N22)pUC((N23)pLac(RBS1)aroG mutant(SRBS4)tyrA mutant(3UTR1)t7t(LK3)LacI(N21) | Tyrosine production_FIG. 4c |
| TPP9 | MG1655_ΔrecA_ΔendA_ΔpheA_ΔtyrR_DE3 | (N21)SpecR(N22)pSC101(N23)lacIT7(RBS1) tyrA mutant(SRBS4)aroG mutant(3UTR1)t7t(N21) | Tyrosine production_FIG. 4c |

TABLE 20-continued

List of strains constructed in this study

| Strain name | E. coli strain genotype | Plasmid genotype (Barcodes used in one plasmid are placed into brackets between fragments) | Application in this study |
|---|---|---|---|
| TPP10 | MG1655_ΔrecA_ΔendA_ΔpheA_ΔtyrR_DE3 | (N21)SpecR(N22)pAC(N23)lacIT7(RBS1) tyrA mutant(SRBS4)aroG mutant(3UTR1)t7t(N21) | Tyrosine production_FIG. 4c |
| TPP11 | MG1655_ΔrecA_ΔendA_ΔpheA_ΔtyrR_DE3 | (N21)SpecR(N22)pMB1(N23)lacIT7(RBS1)tyrA mutant(SRBS4)aroG mutant(3UTR1)t7t(N21) | Tyrosine production_FIG. 4c |
| TPP12 | MG1655_ΔrecA_ΔendA_ΔpheA_ΔtyrR_DE3 | (N21)SpecR(N22)pUC((N23)lacIT7(RBS1) tyrA mutant(SRBS4)aroG mutant(3UTR1)t7t(N21) | Tyrosine production_FIG. 4c |
| TPP13 | MG1655_ΔrecA_ΔendA_ΔpheA_ΔtyrR_DE3 | (N21)SpecR(N22)pSC101(N23)pLac(RBS1)tyrA mutant(SRBS4)aroG mutant(3UTR1)t7t(LK3)LacI(N21) | Tyrosine production_FIG. 4c |
| TPP14 | MG1655_ΔrecA_ΔendA_ΔpheA_ΔtyrR_DE3 | (N21)SpecR(N22)pAC(N23)pLac(RBS1) tyrA mutant(SRBS4)aroG mutant(3UTR1)t7t(LK3)LacI(N21) | Tyrosine production_FIG. 4c |
| TPP15 | MG1655_ΔrecA_ΔendA_ΔpheA_ΔtyrR_DE3 | (N21)SpecR(N22)pMB1(N23)pLac(RBS1) aroG mutant(SRBS4)tyrA mutant(3UTR1)t7t(LK3)LacI(N21) | Tyrosine production_FIG. 4c |
| TPP16 | MG1655_ΔrecA_ΔendA_ΔpheA_ΔtyrR_DE3 | (N21)SpecR(N22)pUC(N23)pLac(RBS1) tyrA mutant(SRBS4)aroG mutant(3UTR1)t7t(LK3)LacI(N21) | Tyrosine production_FIG. 4c |
| TPP17 | MG1655_ΔrecA_ΔendA_ΔpheA_ΔtyrR_DE3 | (N21)SpecR(N22)pAC(N23)PthrC3(RBS1) aroG mutant(SRBS4)tyrA mutant(3UTR1)t7t | Tyrosine production_FIG. 4d |
| TPP18 | MG1655_ΔrecA_ΔendA_ΔpheA_ΔtyrR_DE3 | (N21)SpecR(N22)pAC(RBS1)aroG mutant(SRBS4)tyrA mutant(3UTR1)t7t | Tyrosine production_FIG. 4e |
| PCAP1 | MG1655_ΔrecA_ΔendA_ΔpheA_ΔtyrR_DE3 | (N21)SpecR(N22)pAC(N23)PthrC3(RBS1) aroG mutant(SRBS4)tyrA mutant(RBS2stop)tal(3UTR1)t7t | Coumaric acid production_FIG. 4f |
| Library 1_M1_Plasmid 1 | Dh5α | (5UTR)pthrC3(RBS1)ppsA(SRBS4)aroE(SRBS2)tktA(3UTR1)t7t(3UTR2)SpecR(N22)pAC | Construct M1 variant 1_FIG. 5a |
| Library 1_M1_Plasmid 2 | Dh5α | (5UTR)pthrC3(RBS1)ppsA(SRBS4)tktA(SRBS2)aroE(3UTR1)t7t(3UTR2)SpecR(N22)pAC | Construct M1 variant 2_FIG. 5a |
| Library 1_M1_Plasmid 3 | Dh5α | (5UTR)pthrC3(RBS1)tktA(SRBS4)aroE(SRBS2)ppsA(3UTR1)t7t(3UTR2)SpecR(N22)pAC | Construct M1 variant 3_FIG. 5a |
| Library 1_M1_Plasmid 4 | Dh5α | (5UTR)pthrC3(RBS1)tktA(SRBS4)ppsA(SRBS2)aroE(3UTR1)t7t(3UTR2)SpecR(N22)pAC | Construct M1 variant 4_FIG. 5a |
| Library 1_M1_Plasmid 5 | Dh5α | (5UTR)pthrC3(RBS1)aroE(SRBS4)ppsA(SRBS2)tktA(3UTR1)t7t(3UTR2)SpecR(N22)pAC | Construct M1 variant 5_FIG. 5a |
| Library 1_M1_Plasmid 6 | Dh5α | (5UTR)pthrC3(RBS1)aroE(SRBS4)tktA(SRBS2)ppsA(3UTR1)t7t(3UTR2)SpecR(N22)pAC | Construct M1 variant 6_FIG. 5a |
| Library 2_M2_Plasmid 1 | Dh5α | (3UTR2)pthrC3(RBS1)aroG mutant(SRBS4)tal(SRBS2)tyrA mutant(3UTR1)t7t(N36)SpecR(N22)pAC | Construct M2 variant 1_FIG. 5a |
| Library 2_M2_Plasmid 2 | Dh5α | (3UTR2)pthrC3(RBS1)aroG mutant(SRBS4)tyrA mutant(SRBS2)tal(3UTR1)t7t(N36)SpecR(N22)pAC | Construct M2 varient 2_FIG. 5a |
| Library 2_M2_Plasmid 3 | Dh5α | (3UTR2)pthrC3(RBS1)tyrA mutant(SRBS4)tal(SRBS2)aroG mutant 3UTR1)t7t(N36)SpecR(N22)pAC | Construct M2 variant 3_FIG. 5a |
| Library 2_M2_Plasmid 4 | Dh5α | (3UTR2)pthrC3(RBS1)tyrA mutant(SRBS4)aroG mutant(SRBS2)tal(3UTR1)t7t(N36)SpecR(N22)pAC | Construct M2 varient 4_FIG. 5a |
| Library 2_M2_Plasmid 5 | Dh5α | (3UTR2)pthrC3(RBS1)tal(SRBS4)tyrA mutant(SRBS2)aroG mutant(3UTR1)t7t(N36)SpecR(N22)pAC | Construct M2 variant 5_FIG. 5a |
| Library 2_M2_Plasmid 6 | Dh5α | (3UTR2)pthrC3(RBS1)tal(SRBS4)aroG mutant(SRBS2)tyrA mutant(3UTR1)t7t(N36)SpecR(N22)pAC | Construct M2 varient 6_FIG. 5a |
| Library 1_M1 + M2 | MG1655_ΔrecA_ΔendA_ΔpheA_ΔtyrR_DE3 | pSC101(5UTR)Module 1 fragment mixture(3UTR2) Module 2 fragmentmixture (N36)AmpR(N22) | Screening plasmids library 1_FIG. 5c |
| Library 2_M1 + M2 | MG1655_ΔrecA_ΔendA_ΔpheA_ΔtyrR_DE3 | pAC(5UTR)Module 1 fragment mixture(3UTR2) Module 2 fragment mixture(N36)SpecR(N22) | Screening plasmids library 2_FIG. 5c |

Construction of Combinatorial Plasmid Library

To construct variants of M1 or M2 in the first-tier construction (FIG. 14a), each fragment (ppsA, aroE, tktA, aroG, tal or tyrA) was barcoded by three sets of RG-Boligo/LA-Boligo: RBS1/SRBS4, SRBS4/SRBS2 and SRBS2/3UTR1. The barcoded fragments can be assembled into the 12 plasmids when they were properly combined (FIG. 23a). Each plasmid was verified by colony PCR and Sanger sequencing (data not shown). Each M1 plasmid (~1 ng/uL) was used as template to amplify one M1 fragment (FIG. 23a) by using RG-Aoligo (5UTR) and LA-Aoligo (3UTR2). Each M2 plasmid (~1 ng/uL) was used as template to amplify one M2 fragment (FIG. 23a) by using RG-Aoligo (3UTR2) and LA-Aoligo (N36). These M1 and M2 fragments were considered to be barcoded because Aoligos were used in the PCR, and thus can be directly assembled following our workflow (FIG. 10c). Six M1 fragments, six M2 fragments were equimolarly assembled with one plasmid backbone (barcoded) in one reaction to create a mixture of 36 plasmids (a plasmid library). Technical details in this step: the chemically cleaved fragments were ligated, and 2 µL of the ligation product was used to transform 34 µL of competent cells, which were spread on 90 mm LB agar with a proper antibiotic; all the obtained colonies were resuspended in 6 mL of LB medium, and the mixed plasmids were extracted directly from this suspension. Two plasmid libraries were prepared, and each library had a different plasmid backbone (pSC101+Amp$^R$ or pAC+Spec$^R$).

The quality of each plasmid library was checked by using colony PCR. In the above step, colonies were randomly picked after competent cells were transformed with the ligation product (a mixture). Each colony was tested by using two pairs of oligos. The first pair targeted RO and ppsA (M1), and it would generate amplicons with varied lengths when the colonies contained plasmids that had ppsA at different positions of the operon (FIG. 23b). Similarly, the second pair targeted tal (M2) and AR. The expected amplicon's length is listed in FIG. 23c. Six colonies were tested for each plasmid library, and colony PCR results showed that each plasmid library indeed contained various plasmids (FIG. 23b). The oligos used for colony PCR verification are listed in Table 21.

Two microliters of plasmid mixture from each library were used to transform E. coli MG1655 ΔrecA_ΔendA_ΔpheA_ΔtyrR_DE3 through the standard electroporation procedure. Seventy-two colonies were randomly picked for each library, and each colony was screened to determine its ability of producing coumaric acid (see the next section for how to culture the cells and determine coumaric acid concentration). After the screening, the top two coumaric acid-producing strains of each library were selected and the plasmids they harbor were sequenced to elucidate the responsible arrangement of the genetic parts.

TABLE 21

List of oligos used to colony PCR of quality control of plasmid library in this study

| Strain and library | Plasmids | Colony PCR Forward oligo name | Colony PCR forward oligo sequence | Colony PCR reverse oligo name | Colony PCR reverse oligo sequence |
|---|---|---|---|---|---|
| Dh5α_ Library 1 | pSC101(5UTR) Module 1 fragment mixture (3UTR2) Module 2 fragment mixture (N36)AmpR(N22) | RO1-f (p5_library_f) tal-f | TAGACCCTCTGTAAAT TCCG (SEQ ID NO: 464) TGAACTGGCAGGTATT TGTCC (SEQ ID NO: 466) | ppsA-r (ppsA_ library_r) AR1-r (AmpR_ library_r) | AAGCTGAGTAACATC GTCAATA (SEQ ID NO: 465) TAAGGGCGACACGGA AATGT (SEQ ID NO: 467) |
| Dh5α_ Library 2 | pAC(5UTR)Module 1 fragment mixture (3UTR2) Module 2 fragment mixture(N36)SpecR (N22) | RO2-f (p15_library_f) tal-f | CAAGAGATTACGCGCA GACC (SEQ ID NO: 468) TGAACTGGCAGGTATT TGTCC (SEQ ID NO: 466) | ppsA-r AR2-r (SpecR_ library_r) | AAGCTGAGTAACATC GTCAATA (SEQ ID NO: 469) AGCCGTACAAATGTA CGGCC (SEQ ID NO: 470) |

Culture and analysis of tyrosine/coumaric acid-producing E. coli Each of plasmid TPP1-16 was used to transform E. coli TPSO (genotype: MG1655 ΔrecA_ΔendA_ΔpheA_ΔtyrR_DE3) by using standard electroporation protocol. The resulting strains were named as TPS1-16. To test these strains, single colony was inoculated into LB with 50 μg/mL of spectinomycin, and cultured at 37° C./250 rpm overnight. One hundred microliters of the overnight grown cell suspension was inoculated into 10 mL of K3 medium (composition specified below) with 50 μg/mL of spectinomycin, and the culture was incubated at 30° C./250 rpm until cell density reached 0.5-1.0 (OD600), at which the culture was induced by 0.1 mM of isopropyl β-D-1-thiogalactopyranoside (IPTG). One milliliter of the induced cells was transferred to a 14 mL round-bottom Falcon tube. If PthrC3 was used, IPTG induction was skipped. The cell culture was started in the 14 mL tube. The tube was incubated at 30° C./250 rpm for 84 h.

At the end of incubation, one hundred microliters of 6 M HCl was added to 1 mL of cell culture broth for dissolving tyrosine crystals. The mixture was incubated at 37° C./250 rpm for 30 min, and then centrifuged at 13,500 g for 5 min. The supernatant was filtered by using 13 mm, 0.2 μm Nylon filter.

To measure tyrosine titer, two microliters of the filtered supernatant prepared according to the above protocol was analyzed by high-performance liquid chromatography (HPLC, Shimadzu LC-10). The HPLC conditions are as follows: the column was Agilent ZORBAX Eclipse Plus C18 100 mm, an isocratic flow was used (the flow rate was 0.7 mL/min and the mobile phase consists of 10% [v/v] acetonitrile and 90% [v/v] aqueous solution containing 0.1% [v/v] trifluoroacetic acid), the column temperature was 30° C., and the detector was UV detector (wavelength: 254 nm).

To measure coumaric acid titer, three hundred microliters of acidified medium (without centrifugation) was mixed with 700 μL of acetonitrile, the mixture was incubated at 30° C. for 1 h, the mixture was centrifuged at 13,500 g for 5 min, and two microliters of the supernatant was analyzed by HPLC (Shimadzu LC-10). The HPLC conditions are as follows: the column was Agilent ZORBAX Eclipse Plus C18 100 mm, an isocratic flow was used (the flow rate was 1 mL/min and the mobile phase consists of 35% [v/v] acetonitrile and 65% [v/v] aqueous solution containing 0.1% [v/v] trifluoroacetic acid), the column temperature was 30° C., and the detector was UV detector (wavelength: 285 nm).

K3 medium consisted of 89.8% (v/v) of K3 basal medium, 10% (v/v) carbon source stock solution and 0.17% (v/v) K3 master mix. K3 basal medium was prepared by dissolving 4 g of $(NH_4)_2HPO_4$ and 13.3 g of $KH_2PO_4$ in 1 L of deionized water, and autoclaving the solution. The carbon source stock solution was 200 g/L glucose solution (autoclaved). K3 master mix was prepared by mixing 2.5 mL of 0.1 M ferric citrate solution (autoclaved), 1 mL of 4.5 g/L thiamine solution (filtrated through 0.2 μm filter), 3 mL of 4 mM $Na_2MoO_3$ (autoclaved), 1 mL of 1000× K3 trace elements stock solution (autoclaved) and 1 mL of 1 M $MgSO_4$ solution (autoclaved). We prepared 1000× K3 trace elements stock solution by dissolving 5 g of $CaCl_2.2H_2O$, 1.6 g of $MnCl_2.4H_2O$, 0.38 g of $CuCl_2.4H_2O$, 0.5 g of $CoCl_2.2H_2O$, 0.94 g of $ZnCl_2$, 0.0311 g of $H_3BO_3$ and 0.4 g of $Na_2EDTA.2H_2O$ in 1 L of deionized water, and autoclaved this solution.

Culture and Analysis of GFP-Expressing E. coli

Each of plasmid A0-8 was used to transform E. coli BL21 (DE3) (C2527H, NEB). Single colony was inoculated into LB with 50 μg/mL of spectinomycin and cultured at 37° C./250 rpm overnight. Fifty microliters of the overnight grown cell suspension was inoculated into 5 mL of K3 medium with 50 μg/mL of spectinomycin, and the culture was incubated in 50 mL Falcon tube at 37° C./250 rpm for 24 h. Optical density 600 (OD600) of cell suspensions was determined by using a microplate reader (Varioskan LUX Multimode Microplate Reader, Thermo Fisher Scientific). For each sample, two hundred microliters of cell suspension was loaded into a well of 96-well optical plate and assayed with the following parameter setting: excitation wavelength was 483 nm, emission wavelength is 535 nm, measurement time was 100 ms, and the bandwidth of excitation and emission light was 12 nm. Fluorescence signal was normalized by OD600 of cell suspension to calculate specific fluorescence signal.

Example 11: Further Discussion

Biotechnology is transforming how humans generate fuels, produce chemicals, and treat diseases. Developing the needed technologies often requires construction of plasmid, a vector for carrying genetic information. Currently, most researchers construct plasmids in a highly inefficient way—they customize genetic materials, pay commercial companies to synthesize the materials, wait for many days, and often only use them once. In this study, we report a standard (GT assembly standard [GTas]) under which most functional DNA sequences (including very short and long ones) can be defined as standard parts, and a method that can assemble up to 14 of them into one plasmid in one round of operation. Based on 370 plasmids we have constructed, the averaged accuracy of this plasmid construction method is 86%. The standard parts can be flipped and arranged in any order as long as a simple rule is followed, and there is no scar (junk DNA sequences) in most junctions of the parts, making it possible to standardize construction of almost any plasmid. Plasmids constructed under this standard can also be easily edited, and/or be further assembled into more complex plasmids by using standard oligonucleotides. GTas may lead to commercial standard DNA parts sold as catalogued chemicals and/or in research kit, which would lower cost of acquiring these materials for researchers, and enable our community to utilize its limited DNA synthesis power more efficiently.

Researchers working on biotechnology projects often order customized DNA oligonucleotides (oligos), which can only be used by the lab that placed the order because the oligos are tailored for their specific applications. The labs usually can only consume less than 1% of each oligo they order even when the minimal quantity is requested—the supplier has difficulty or has no incentive in scaling down synthesis scale. Because there is no mechanism for sharing oligos, many identical oligos are being repeatedly synthesized. These together lead to suboptimal use of the society's DNA synthesis power, which has already substantially lagged behind the DNA reading capability[28].

A solution to this problem is use of standard DNA parts, which has been explored but has yet been adopted widely by the whole biotechnology community, possibly due to flaws in the previous designs. The most well-known standard of biological parts is BioBricks[14], which has been used since 2003 mainly by international Genetically Engineered Machine (iGEM)[29], a student competition in synthetic biology. Through the competition, BioBricks Foundation collects and distributes plasmids that carry standard parts, which can be combined to produce new standard parts with the help of restriction enzymes. This system is slow in combining parts together—every round only two parts can be combined. So, soon after the technologies that can assemble multiple DNA parts were developed around 2009, including Gibson[19] and Golden Gate[30] methods, research labs swiftly adopted them to speed up projects, and have, unfortunately, mostly used customized parts till to date.

In 2015, BASIC standard was developed[7], which allowed use of standard parts in multi-pieces DNA assembly, but it has so far not been used globally possibly due to some of its limitations, including low accuracy, difficulty in reuse of constructed plasmids, and leaving large scars.

Here, we report a new plasmid construction standard (GTas) and development of new technologies for implementing it, which together overcome all the limitations of existing standards and allow much more flexible arrangement of standard parts. GTas has the potential to substantially reduce the cost and time of plasmid construction in biotechnological applications, and to improve the efficiency of utilizing our DNA synthesis power.

Perspective on Transforming Plasmid Construction Practices in Global Biotechnology Community GTas may lead to new and cheaper distribution mechanisms for sharing standard parts in the global biotechnology community (FIG. 15a). As full information of a barcode is coded in a set of DNA oligos, a large library of barcodes can be easily provided by service providers at low cost to individual researchers through commercial kits, which contain a large number of standard oligos. There would be incentive for companies to develop such kits, because one oligo they synthesize/order in its minimal scale can be used for preparing at least 100 kits, making the cost of each oligo in a kit to be low and the profit margin of the kit to be reasonable. A kit can be optimized and developed for a popular application, such as "Engineering metabolism of E. coli", or could be customized by allowing users to choose oligos from a large library of a company.

Distributing physical copy of a fragment requires two oligos and one template DNA. The oligos may be distributed in a way similar to those of barcodes, though the number of oligos is large as fragments are diverse. The template DNA could be genomic DNA, complementary DNA, synthetic DNA or plasmid, which can also be included in commercial kits or sold as catalogued chemicals.

The DNA sequence of these standard parts may be patented, but the parts can still be sold if a licensing clause is included in the sales agreement, which protects intellectual properties and streamlines the licensing process. Plasmids constructed under GTas together with related oligos and other materials can also be shared among users directly or through service-providers (FIG. 15a), such as Addgene. In such case, licensing terms need to be customized ("Free to use" or "Open access" is also a customized term). These shareable materials from peers could be conveniently assimilated into any plasmid construction when GTas was used. PCR products created by using Aoligos should also be assembled by using some existing assembly methods, including Gibson[46] and In-Fusion (Clontech) methods.

Through these new mechanisms, repeatedly synthesizing the same oligos and longer DNA molecules (e.g. genes) can be reduced, utilization rate of any synthesized DNA oligos may be maximized, and waiting time for customer would be shorten (standard parts are ready to ship when they are in stock unlike customized parts that need manufacturing). As a supporting evidence, after we surveyed the 370 plasmids we have constructed so far in our lab under GTas, we found oligos associated with eleven barcodes have been reused for more than 50 times (FIG. 15b). Oligos associated with the most frequently used barcode (RBS1) have been used for up to 262 times. If this practice is adopted by a community, we would expect much more frequent reuse of standard parts.

REFERENCES

Any listing or discussion of an apparently prior-published document in this specification should not necessarily be taken as an acknowledgement that such document is part of the state of the art or is common general knowledge.

1. Fernandez-Rodriguez, J., Moser, F., Song, M. & Voigt, C. A. Engineering RGB color vision into *Escherichia coli*. *Nat. Chem. Biol.* (2017). doi:10.1038/nchembio.2390
2. Yim, H. et al. Metabolic engineering of *Escherichia coli* for direct production of 1,4-butanediol. *Nat Chem Biol* 7, 445-452 (2011).
3. Danino, T. et al. Programmable probiotics for detection of cancer in urine. *Sci. Transl. Med.* 7, 289ra84 (2015).
4. Eisenstein, M. Living factories of the future. *Nature* 531, 401-403 (2016).
5. Check Hayden, E. Synthetic biology called to order. *Nature* 141-142 (2015). doi:10.1038/520141a
6. Hillson, N. J., Rosengarten, R. D. & Keasling, J. D. J5 DNA assembly design automation software. *ACS Synth. Biol.* 1, 14-21 (2012).
7. Storch, M. et al. BASIC: A New Biopart Assembly Standard for Idempotent Cloning Provides Accurate, Single-Tier DNA Assembly for Synthetic Biology. *ACS Synth. Biol.* 4, 781-787 (2015).
8. Ngo, A. H., Ibáñez, M. & Do, L. H. Catalytic Hydrogenation of Cytotoxic Aldehydes Using Nicotinamide Adenine Dinucleotide (NADH) in Cell Growth Media. *ACS Catal.* 6, 2637-2641 (2016).
9. Salis, H. M., Mirsky, E. A. & Voigt, C. A. Automated design of synthetic ribosome binding sites to control protein expression. *Nat. Biotechnol.* 27, 946-50 (2009).
10. Ajikumar, P. K. et al. Isoprenoid pathway optimization for Taxol precursor overproduction in *Escherichia coli*. *Science (80-.).* 330, 70-74 (2010).
11. Bassalo, M. C. et al. Rapid and Efficient One-Step Metabolic Pathway Integration in *E. coli*. *ACS Synth. Biol.* 5, 561-568 (2016).
12. Jinek, M. et al. A Programmable Dual-RNA—Guided DNA Endonuclease in Adaptive Bacterial Immunity. *Science (80-.).* 337, 816-822 (2012).
13. Jiang, Y. et al. Multigene editing in the *Escherichia coli* genome via the CRISPR-Cas9. *Appl. Environ. Microbiol.* 81, 2506-2514 (2015).
14. Shetty, R. P., Endy, D. & Knight Jr., T. F. Engineering BioBrick vectors from BioBrick parts. *J Biol Eng* 2, 5 (2008).
15. Engler, C., Gruetzner, R., Kandzia, R. & Marillonnet, S. Golden gate shuffling: A one-pot DNA shuffling method based on type ils restriction enzymes. *PLoS One* 4, (2009).
16. Crook, N. C., Freeman, E. S. & Alper, H. S. Re-engineering multicloning sites for function and convenience. *Nucleic Acids Res.* 39, (2011).
17. Casini, A., Storch, M., Baldwin, G. S. & Ellis, T. Bricks and blueprints: methods and standards for DNA assembly. *Nat. Rev. Mol. Cell Biol.* 16, 568-576 (2015).
18. Li, M. Z. & Elledge, S. J. Harnessing homologous recombination in vitro to generate recombinant DNA via SLIC. *Nat Methods* 4, 251-256 (2007).
19. Gibson, D. G. et al. Enzymatic assembly of DNA molecules up to several hundred kilobases. *Nat Methods* 6, 343-345 (2009).

20. Bitinaite, J. et al. USER™ friendly DNA engineering and cloning method by uracil excision. *Nucleic Acids Res.* 35, 1992-2002 (2007).
21. Casini, A. et al. One-pot DNA construction for synthetic biology: the Modular Overlap-Directed Assembly with Linkers (MODAL) strategy. *Nucleic Acids Res.* 42, e7 (2014).
22. Shao, Z., Zhao, H. & Zhao, H. DNA assembler, an in vivo genetic method for rapid construction of biochemical pathways. *Nucleic Acids Res.* 37, 1-10 (2009).
23. Nakamaye, K. L., Gish, G., Eckstein, F. & Vosberg, H. P. Direct sequencing of polymerase chain reaction amplified DNA fragments through the incorporation of deoxynucleoside alpha-thiotriphosphates. *Nucleic Acids Res.* 16, 9947-59 (1988).
24. Zou, R., Zhou, K., Stephanopoulos, G. & Too, H. P. Combinatorial engineering of 1-deoxy-D-xylulose 5-phosphate pathway using cross-lapping in vitro assembly (CLIVA) method. *PLoS One* 8, e79557 (2013).
25. Zhou, K., Edgar, S. & Stephanopoulos, G. *Engineering Microbes to Synthesize Plant Isoprenoids. Methods in Enzymology* 575, (Elsevier Inc., 2016).
26. Green and Sambrook, *Molecular Cloning: A Laboratory Manual*, Cold Springs Harbor Laboratory, New York (2012).
27. WO 2000/018967.
28. Kosuri, S. & Church, G. M. Large-scale de novo DNA synthesis: technologies and applications. *Nat. Methods.* 11, 499-499 (2014).
29. Smolke, C. D. Building outside of the box: iGEM and the BioBricks Foundation. *Nat. Biotechnol.* 27, 1099-1102 (2009).
30. Engler, C., Kandzia, R. & Marillonnet, S. A one pot, one step, precision cloning method with high throughput capability. *PLoS. One.* 3, e3647 (2008).
31. Banks, C. A. at al. Proteins interacting with cloning scars: a source of false positive protein-protein interactions. *Sci. Rep.* 5, 8530 (2015).
32. Chen, X. & Zhang, J. Why are genes encoded on the lagging strand of the bacterial genome? *Genome. Biol. Evol.* 5, 2436-2439 (2013).
33. Smanski, M. J. et al. Functional optimization of gene clusters by combinatorial design and assembly. *Nat. Biotechnol.* 32, 1241-1249 (2014).
34. Santos, C. N., Xiao, W. & Stephanopoulos, G. Rational, combinatorial, and genomic approaches for engineering L-tyrosine production in *Escherichia coli*. *Proc. Natl. Acad. Sci. USA.* 109, 13538-13543 (2012).
35. Anilionyte, O. at al. Short, auto-inducible promoters for well-controlled protein expression in *Escherichia coli*. *Appl. Microbiol. Biotechnol.* 102, 7007-7015 (2018).
36. Fowler, Z. L. & Koffas, M. A. Biosynthesis and biotechnological production of flavanones: current state and perspectives. *Appl. Microbiol. Biotechnol.* 83, 799-808 (2009).
37. Jendresen, C. B. et al. Highly Active and specific tyrosine ammonia-lyases from diverse origins enable enhanced production of aromatic compounds in Bacteria and *Saccharomyces cerevisiae*. *Appl. Environ. Microbiol.* 81, 4458-4476 (2015).
38. Zhou, Y. et al. MiYA, an efficient machine-learning workflow in conjunction with the YeastFab assembly strategy for combinatorial optimization of heterologous metabolic pathways in *Saccharomyces cerevisiae*. *Metab. Eng.* 47, 294-302 (2018).
39. Coussement, P. et al. One step DNA assembly for combinatorial metabolic engineering. *Metab. Eng.* 23, 70-77 (2014).
40. Kang, S. Y. et al. Artificial biosynthesis of phenylpropanoic acids in a tyrosine overproducing *Escherichia coli* strain. *Microb. Cell. Fact.* 11, 153 (2012).
41. Kim, B. et al. Metabolic engineering of *Escherichia coli* for the enhanced production of L-tyrosine. *Biotechnol. Bioeng.* 1-11. https://doi.org/10.1002/bit.26797 (2018).
42. Gao, D. et al. Identification of a heterologous cellulase and its N-terminus that can guide recombinant proteins out of *Escherichia coli*. *Microb. Cell. Fact.* 14, 49 (2015).

The invention claimed is:

1. A method for ligating three nucleic acid molecules comprising:
   (i) providing a first nucleic acid molecule comprising a first overhang of one nucleotide in length at a first end and a second overhang of one nucleotide of in length at its other (or second) end; wherein the first overhang and the second overhang are different nucleotides and are not complementary to each other, wherein the first overhang is a 3' C overhang and the second overhang is a 3' T overhang, wherein the first nucleic acid molecule is a double-stranded nucleic acid molecule comprising a coding sequence strand and a substantially complementary strand, and wherein the 3' C overhang is on the substantially complementary strand and the 3' T overhang is on the coding sequence strand;
   (ii) providing a second nucleic acid molecule capable of forming a stem-loop structure with an overhang of one nucleotide; wherein the overhang of the second nucleic acid molecule is substantially complementary to the first overhang of the first end of the first nucleic acid molecule, wherein the overhang of the second nucleic acid molecule is a 3' G overhang; and also providing a third nucleic acid molecule capable of forming a stem-loop structure with an overhang of one nucleotide; wherein the overhang of the third nucleic acid molecule is substantially complementary to the second overhang of the second end of the first nucleic acid molecule, wherein the overhang of the third nucleic acid molecule is a 3' A overhang; and wherein the overhang of the second nucleic acid molecule and the overhang of the third nucleic acid molecule are different nucleotides and are not complementary to each other; and (iii) ligating the first overhang at the first end of the first nucleic acid molecule to the overhang of the second nucleic acid molecule and also the second overhang of the second end of the first nucleic acid molecule to the overhang of the third nucleic acid molecule to form a single nucleic acid molecule.

2. The method according to claim 1; wherein the second nucleic acid comprises a first defined sequence and the third nucleic acid comprises a second defined sequence.

3. The method according to claim 2; wherein the first defined sequence of the second nucleic acid molecule comprises a first tag sequence, a first barcode sequence and/or a first linking sequence and the second defined sequence of the third nucleic acid molecule comprises a second tag sequence; a second barcode sequence and/or a second linking sequence.

4. The method according to claim 1; wherein step (i) comprises:
(i)(a) providing a double-stranded nucleic acid template comprising a first nucleic acid strand and a second nucleic acid strand substantially reverse complementary to the first nucleic acid strand;
(i)(b) providing a first primer comprising a first sequence with at least one modified nucleotide upstream of a second sequence substantially complementary to the second strand of the nucleic acid template; and a second primer comprising a third sequence with at least one modified nucleotide upstream of a fourth sequence substantially complementary to the first strand of the nucleic acid template;
(i)(c) amplifying the nucleic acid template using the first and second primers to produce an amplicon; and
(i)(d) chemically cleaving the amplicon to produce the first nucleic acid molecule comprising a first overhang of one nucleotide in length at a first end and a second overhang of at least one nucleotide of one nucleotide in length at its other (or second) end; wherein the first overhang and the second overhang are different nucleotides and are not complementary to each other; or
(i)(a) providing a first single-stranded nucleic acid molecule;
(i)(b) providing a second single-stranded nucleic acid molecule substantially complementary to the first single nucleic acid molecule; and
(i)(c) allowing the first and second single-stranded nucleic acid molecule to anneal to produce the first nucleic acid molecule comprising a first overhang of one nucleotide in length at a first end and a second overhang of one nucleotide in length at its other (or second) end; wherein the first overhang and the second overhang are different nucleotides and are not complementary to each other.

5. The method according to claim 1, further comprising the steps of:
(iv) using the single nucleic acid molecule as a template from step (iii) for amplifying in a polymerase chain reaction with two amplification primers to produce an amplicon;

(v) performing a ligation to join the amplicon to a plurality of nucleic acid molecules to form an assembly of joined plurality of nucleic acid molecules.

6. The method according to claim 5; wherein step (iv) comprises amplifying the template with a first amplification primer comprising at least one modified nucleotide and a second amplification primer comprising at least one modified nucleotide; further chemically cleaving the amplicon to produce a first end with a third overhang and a second end with a fourth overhang.

7. The method according to claim 5; wherein each of the plurality of nucleic acid molecules is an amplicon from step (iv) using another single nucleic acid molecule from step (iii) as a template.

8. The method according to claim 5, wherein the amplicon and each of the plurality of nucleic acid molecules have different sequences.

9. The method according to claim 5, wherein step (v) comprises ligating to form a concatemer of nucleic acid molecules, each with substantially the same sequence.

10. The method according to claim 5, wherein the assembly of joined plurality of nucleic acid molecules is circular.

11. The method according to claim 2, further comprising the steps of:
(iv) using the single nucleic acid molecule from step (iii) as a template for amplifying in a polymerase chain reaction with an amplification primer having a sequence designed based on at least part or all of the first defined sequence and comprising at least one modified nucleotide and another amplification primer having a sequence designed based on at least part or all of the second defined sequence and comprising at least one modified nucleotide to produce an amplicon, chemically cleaving the amplicon to produce a first end with a third overhang and a second end with a fourth overhang; and
(v) performing a ligation to join the amplicon to a plurality of nucleic acid molecules to form an assembly of joined plurality of nucleic acid molecules; wherein each of the plurality of nucleic acid molecules is an amplicon from step (iv).

12. The method according to claim 11, wherein each of the plurality of nucleic acid molecules is an amplicon from step (iv) using another single nucleic acid molecule from step (iii) as a template.

13. The method according to claim 11, wherein amplification primers designed based on defined sequences of a said second nucleic acid molecules comprising a stem-loop structure as applicable are used to order and/or arrange the plurality of nucleic acid molecules in the assembly.

14. The method according to claim 11, wherein the amplicon and each of the plurality of nucleic acid molecules have different sequences.

15. The method according to claim 11, wherein the assembly of joined plurality of nucleic acid molecules is circular.

16. The method according to claim 15, wherein the method further comprises using polymerase chain reaction with amplification primers designed based on applicable defined sequences to implement a modification in the assembly of joined plurality of nucleic acid molecules, wherein the modification comprises inserting at least one nucleic acid molecule into the assembly, removing at least one joined nucleic acid molecule from the assembly or replacing at least one joined nucleic acid molecule in the assembly.

17. The method according to claim 16, comprising implementing the modification to form a library of different plasmids.

* * * * *